United States Patent
Reczek et al.

(10) Patent No.: US 8,962,273 B2
(45) Date of Patent: Feb. 24, 2015

(54) METHODS OF PRODUCING A SECRETED PROTEIN

(75) Inventors: David J. Reczek, Sudbury, MA (US); Paul Saftig, Gettorf (DE); Christine T. DeMaria, Franklin, MA (US)

(73) Assignees: Genzyme Corporation, Cambridge, MA (US); Biochemical Institute, Christian-Albrechts University Kiel, Kiel (DE)

( * ) Notice: Subject to any disclaimer, the term of this patent is extended or adjusted under 35 U.S.C. 154(b) by 1081 days.

(21) Appl. No.: 12/599,393

(22) PCT Filed: May 9, 2008

(86) PCT No.: PCT/US2008/005942
§ 371 (c)(1),
(2), (4) Date: Sep. 13, 2010

(87) PCT Pub. No.: WO2008/143797
PCT Pub. Date: Nov. 27, 2008

(65) Prior Publication Data
US 2010/0330617 A1 Dec. 30, 2010

Related U.S. Application Data

(60) Provisional application No. 60/967,415, filed on Sep. 4, 2007, provisional application No. 60/928,907, filed on May 11, 2007.

(51) Int. Cl.
| | | |
|---|---|---|
| C12P 21/06 | (2006.01) | |
| C12N 9/24 | (2006.01) | |
| C12N 15/00 | (2006.01) | |
| C12N 5/00 | (2006.01) | |
| C07H 21/02 | (2006.01) | |
| C07H 21/04 | (2006.01) | |
| C12P 21/02 | (2006.01) | |
| C12N 15/113 | (2010.01) | |

(52) U.S. Cl.
CPC .............. *C12P 21/02* (2013.01); *C12N 15/1138* (2013.01); *C12Y 302/01045* (2013.01); *C12N 9/2402* (2013.01); *C12N 2310/14* (2013.01)
USPC ....... 435/69.1; 435/200; 435/320.1; 435/325; 435/375; 530/350; 536/23.2

(58) Field of Classification Search
None
See application file for complete search history.

(56) References Cited

U.S. PATENT DOCUMENTS

| | | |
|---|---|---|
| 5,236,838 A | 8/1993 | Rasmussen et al. |
| 5,846,534 A | 12/1998 | Waldmann et al. |
| 6,120,766 A | 9/2000 | Hale et al. |

FOREIGN PATENT DOCUMENTS

| | | |
|---|---|---|
| AR | 066530 A1 | 8/2009 |
| WO | WO 92/13067 | 8/1992 |
| WO | WO-01-77307 | * 10/2001 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Dec. 17, 2010, Response to Office Action., 08754289.0.
Apr. 20, 2011, Communication Pursuant to Article 94(3)., 08754289.0.
Reczek, D., et al., "LIMP-2 is a Receptor for Lysosomal Mannose-6-Phosphate-Independent Targeting of β-Glucocerebrosidase", *Cell*, 131(4):770-783 (Nov. 16, 2007).
Jun. 15, 2010, Office Action, 08754289.0.
Aerts, J.M., et al., "Glucocerebrosidase, a Lysosomal Enzyme That Does Not Undergo Oligosaccharide Phosphorylation," *Biochim Biophys Acta* 964, 303-308 (1988).
Ahn, K., et al., "An Alternate Targeting Pathway for Procathepsin L in Mouse Fibroblasts," *Traffic*, 3, 147-159 (2002).
Asch, A.S., et al., "Isolation of the Thrombospondin Membrane Receptor," *J Clin Invest* 79, 1054-1061 (1987).
Beutler, E., "Gaucher's Disease," *N Engl J Med* 325, 1354-1360 (1991).
Beutler, E., "Gaucher Disease: Multiple Lessons From a Single Gene Disorder," *Acta Paediatr Suppl* 95, 103-109 (2006).
Beutler, E., and Kuhl, W., "Glucocerebrosidase Processing in Normal Fibroblasts and in Fibroblasts From Patients With Type I, Type II, and Type III Gaucher Disease," *Proc Natl Acad Sci U S A* 83, 7472-7474 (1986).
Brady, R.O., et al., "Metabolism of Glucocerebrosides. Ii. Evidence of an Enzymatic Deficiency in Gaucher's Disease," *Biochem Biophys Res Commun* 18, 221-225 (1965).
Calvo, D., and Vega, M.A., "Identification, Primary Structure, and Distribution of CLA-1, a Novel Member of the CD36/LIMPII Gene Family," *J Biol Chem* 268, 18929-18935 (1993).
Crombie, R., and Silverstein, R. "Lysosomal Integral Membrane Protein II Binds Thrombospondin-1. Structure-Function Homology With the Cell Adhesion Molecule CD36 Defines a Conserved Recognition Motif," *J Biol Chem* 273, 4855-4863 (1998).
Dittmer, F.D., et al., "Alternative Mechanisms for Trafficking of Lysosomal Enzymes in Mannose 6-Phosphate Receptor-Deficient Mice Are Cell Type-Specific," *J Cell Sci* 112, 1591-1597 (1999).
Febbraio, M., et al, "CD36: A Class B Scavenger Receptor Involved in Angiogenesis, Atherosclerosis, Inflammation, and Lipid Metabolism." *J Clin Invest* 108, 785-791 (2001).
Franc, N.C., et al., "Croquemort, a Novel *Drosophila* Hemocyte/Macrophage Receptor That Recognizes Apoptotic Cells," *Immunity* 4, 431-443 (1996).

(Continued)

*Primary Examiner* — Iqbal H Chowdhury
(74) *Attorney, Agent, or Firm* — Hamilton, Brook, Smith & Reynolds, P.C.

(57) ABSTRACT

The invention is directed to methods of producing a polypeptide or a variant thereof, wherein the polypeptide or variant thereof is dependent on LIMP-2 for trafficking, localization, stabilization and/or sorting of the polypeptide in the cell. In general, the methods comprise culturing a lysosomal integral membrane protein II (LIMP-2) deficient cell which expresses the polypeptide or the variant thereof under conditions in which the polypeptide or the variant thereof is produced.

14 Claims, 64 Drawing Sheets

(56) References Cited

OTHER PUBLICATIONS

Fujita, H., et al., "Isolation and Sequencing of a Cdna Clone Encoding 85kda Sialoglycoprotein in Rat Liver Lysosomal Membranes," *Biochem Biophys Res Commun* 178, 444-452 (1991).

Fujita, H., et al., "In Vitro Binding Study of Adaptor Protein Complex (AP-1) to Lysosomal Targeting Motif (L1-Motif)," *Biochem Biophys Res Commun* 255, 54-58 (1999).

Furbish, et al., "Uptake and Distribution of Placental Glucocerebrosidase in Rat Hepatic Cells and Effects of Sequential Deglycosylation," *Biochim. Biophys. Acta* 673:425-434 (1981).

Gamp, A., et al. "LIMP-2/LGP85 Deficiency Causes Ureteric Pelvic Junction Obstruction, Deafness and Peripheral Neuropathy in Mice," *Hum Mol Genet* 12, 631-646 (2003).

Ge, Y., and Elghetany, M.T. "CD36: A Multiligand Molecule," *Lab Hematol* 11, 31-37 (2005).

Ginsel, L.A., and Fransen, J.A. "Mannose 6-Phosphate Receptor Independent Targeting of Lysosomal Enzymes (A Mini-Review)," *Cell Biol Int Rep* 15, 1167-1173 (1991).

Glickman, J.N., and Kornfeld, S. "Mannose 6-Phosphate-Independent Targeting of Lysosomal Enzymes in I-Cell Disease B Lymphoblasts," *J Cell Biol* 123, 99-108 (1993).

Gunther, W., et al., "Clc-5, the Chloride Channel Mutated in Dent's Disease, Colocalizes With the Proton Pump in Endocytotically Active Kidney Cells," *Proc Natl Acad Sci U S A* 95, 8075-8080 (1998).

Hart, K., and Wilcox, M., "A *Drosophila* Gene Encoding an Epithelial Membrane Protein with Homology to CD36/LIMP II," *J Mol Biol* 234, 249-253 (1993).

Honing, S., et al., "A Di-Leucine-Based Motif in the Cytoplasmic Tail of LIMP-II and Tyrosinase Mediates Selective Binding of AP-3," *Embo J* 17, 1304-1314 (1998).

Huynh, K.K., et al., "LAMP Proteins Are Required for Fusion of Lysosomes With Phagosomes," *Embo J* 26, 313-324 (2007).

Imai, K. "A Macrophage Receptor for Liver Lysosomal Beta-Glucosidase," *Cell Struct Funct* 13, 325-332 (1988).

Knipper, M., et al., "Deafness in LIMP2-Deficient Mice Due to Early Loss of the Potassium Channel KCNQ1/KCNE1 in Marginal Cells of the Stria Vascularis," *J Physiol* 576, 73-86 (2006).

Kornfeld, S., "Trafficking of Lysosomal Enzymes in Normal and Disease States," *J Clin Invest* 77, 1-6 (1986).

Kornfeld, S. "Structure and Function of the Mannose 6-Phosphate/Insulinlike Growth Factor II Receptors," *Annu Rev Biochem* 61, 307-330 (1992).

Kornfeld, S., and Mellman, I., "The Biogenesis of Lysosomes," *Annu Rev Cell Biol* 5, 483-525 (1989).

Kornfeld, S., and Sly, W.S. "Lysosomal Storage Defects," *Hosp Pract (Off Ed)* 20, 71-75, 78-82 (1985).

Krieger, M., "Scavenger Receptor Class B Type I Is a Multiligand HDL Receptor That Influences Diverse Physiologic Systems," *J Clin Invest* 108, 793-797 (2001).

Kuronita, T. et al., "A Role for the Lysosomal Membrane Protein LGP85 in the Biogenesis and Maintenance of Endosomal and Lysosomal Morphology," *J Cell Sci* 115, 4117-4131 (2002).

Kuronita, T., et al., "The NH(2)-Terminal Transmembrane and Lumenal Domains of LGP85 Are Needed for the Formation of Enlarged Endosomes/Lysosomes," *Traffic* 6, 895-906 (2005).

Le Borgne, et al., "The Mammalian AP-3 Adaptor-Like Complex Mediates the Intracellular Transport of Lysosomal Membrane Glycoproteins," *J Biol Chem* 273, 29451-29461 (1998).

Leonova, T., and Grabowski, G.A. "Fate and Sorting of Acid Beta-Glucosidase in Transgenic Mammalian Cells," *Mol Genet Metab* 70, 281-294 (2000).

Liou, B., et al., "Analyses of Variant Acid Beta-Glucosidases: Effects of Gaucher Disease Mutations," *J Biol Chem* 281, 4242-4253 (2006).

Ludwig, T., et al., "Roles for Mannose-6-Phosphate Receptors in Lysosomal Enzyme Sorting, IGF-II Binding and Clathrin-Coat Assembly," *Trends Cell Biol* 5, 202-206 (1995).

Maeda, H., et al., "Limited and Selective Localization of the Lysosomal Membrane Glycoproteins LGP85 and LGP96 in Rat Osteoclasts," *Histochem Cell Biol* 111, 245-251 (1999).

Marshall, J., et al. "Demonstration of Feasibility of In Vivo Gene Therapy for Gaucher Disease Using a Chemically Induced Mouse Model," *Mol. Ther.* 6, 179-189 (2002).

Müller, W.E.G., et al., "Matrix-Mediated Canal Formation in Primmorphs from the Sponge *Suberites domuncula* Involves the Expression of a CD36 Receptor-Ligand System", *J. Cell Sci.*, 117(12):2579-2590 (2004).

Murao, K., et al., "Characterization of CLA-1, a Human Homologue of Rodent Scavenger Receptor B1, as a Receptor for High Density Lipoprotein and Apoptotic Thymocytes," *J Biol Chem* 272, 17551-17557 (1997).

Neufeld, E.F., "Lysosomal Storage Diseases," *Annu Rev Biochem* 60, 257-280 (1991).

Nilsson, O., et al., "Glycosphingolipid Studies of Visceral Tissues and Brain From Type 1 Gaucher Disease Variants," Clin Genet 27, 443-450 (1985).

Nilsson, O., and Svennerholm, L. "Accumulation of Glucosylceramide and Glucosylsphingosine (Psychosine) in Cerebrum and Cerebellum in Infantile and Juvenile Gaucher Disease," *J Neurochem* 39, 709-718 (1982).

Ogata, S., and Fukuda, M. "Lysosomal Targeting of Limp II Membrane Glycoprotein Requires a Novel Leu-Ile Motif at a Particular Position in Its Cytoplasmic Tail," *J Biol Chem* 269, 5210-5217 (1994).

Okazaki, I., et al., "Purification and Characterization of an 85 Kda Sialoglycoprotein in Rat Liver Lysosomal Membranes," *J Biochem (Tokyo)* 111, 763-769 (1992).

Pohlmann, R., et al., "The Two Mannose 6-Phosphate Receptors Transport Distinct Complements of Lysosomal Proteins," *J Biol Chem* 270, 27311-27318 (1995).

Reczek, D., et al., "Identification of EBP50: A PDZ-Containing Phosphoprotein That Associates With Members of the Ezrin-Radixin-Moesin Family," *J Cell Biol* 139, 169-179 (1997).

Rezaie, A.R., et al., "Expression and Purification of a Soluble Tissue Factor Fusion Protein With an Epitope for an Unusual Calcium-Dependent Antibody," *Protein Expr Purif* 3, 453-460 (1992).

Rijnboutt, S., et al., "Mannose 6-Phosphate-Independent Membrane Association of Cathepsin D, Glucocerebrosidase, and Sphingolipid-Activating Protein in Hepg2 Cells," *J Biol Chem* 266, 4862-4868 (1991).

Ron, I., et al.,"ER Retention and Degradation as the Molecular Basis Underlying Gaucher Disease Heterogeneity," *Hum. Mol. Genet.* 14:2387-2398 (2005).

Sandoval, I.V., et al., "The Residues Leu(Ile)475-Ile(Leu, Val, Ala)476, Contained in the Extended Carboxyl Cytoplasmic Tail, Are Critical for Targeting of the Resident Lysosomal Membrane Protein LIMP II to Lysosomes," *J Biol Chem* 269, 6622-6631 (1994).

Sasagasako, N., et al., "Glucosylceramide and Glucosylsphingosine Metabolism in Cultured Fibroblasts Deficient in Acid Beta-Glucosidase Activity," *J Biochem (Tokyo)* 115, 113-119 (1994).

Sawkar, A., et al., "Chemical Chaperones and Permissive Temperatures Alter Localization of Gaucher Disease Associated Glucocerebrosidase Variants," *ACS Chem Biol* 1, 235-251 (2006).

Schueler, U.H., et al., "Correlation between enzyme activity and substrate storage in a cell culture model system for Gaucher disease," *J Inherit Metab Dis* 27, 649-658 (2004).

Sidransky, E., "Gaucher Disease: Complexity in a "Simple" Disorder," *Mol Genet Metab* 83, 6-15 (2004).

Suarez-Quian, C.A., "The Distribution of Four Lysosomal Integral Membrane Proteins (Limps) in Rat Basophilic Leukemia Cells," *Tissue Cell* 19, 495-504 (1987).

Suarez-Quian, C.A., "Differential Cell Surface Expression of Four Lysosomal Integral Membrane Proteins (Limps) in Normal Rat Kidney Cells," *Tissue Cell* 20, 35-46 (1988).

Tabuchi, N., et al., "Ile (476), a Constituent of Di-Leucine-Based Motif of a Major Lysosomal Membrane Protein, LGP85/LIMP II, Is Important for Its Proper Distribution in Late Endosomes and Lysosomes," *Biochem Biophys Res Commun* 295, 149-156 (2002).

Tabuchi, N., et al., "Identification and Characterization of a Major Lysosomal Membrane Glycoprotein, LGP85/MILP II in Mouse Liver," *J. Biochem.*, 122(4):756-763 (1997).

(56) References Cited

OTHER PUBLICATIONS

Tanaka, Y., et al., "Lysosomal Cysteine Protease, Cathepsin H, Is Targeted to Lysosomes by the Mannose 6-Phosphate-Independent System in Rat Hepatocytes," *Biol Pharm Bull* 23, 805-809 (2000).

van Dongen, J.M., et al., "The Subcellular Localization of Soluble and Membrane-Bound Lysosomal Enzymes in I-Cell Fibroblasts: A Comparative Immunocytochemical Study," *Eur J Cell Biol* 39, 179-189 (1985).

Vega, M.A., et al., "Targeting of Lysosomal Integral Membrane Protein LIMP II. The Tyrosine-Lacking Carboxyl Cytoplasmic Tail of LIMP II Is Sufficient for Direct Targeting to Lysosomes," *J Biol Chem* 266, 16269-16272 (1991).

Vega, M.A., et al., "Cloning, Sequencing, and Expression of a Cdna Encoding Rat LIMP II, a Novel 74-Kda Lysosomal Membrane Protein Related to the Surface Adhesion Protein CD36," *J Biol Chem* 266, 16818-16824 (1991).

Zerangue, N., et al., "An Artificial Tetramerization Domain Restores Efficient Assembly of Functional Shaker Channels Lacking T1," *Proc Natl Acad Sci U S A* 97, 3591-3595 (2000).

Zimmer, K.P., et al., "Intracellular Transport of Acid Beta-Glucosidase and Lysosome-Associated Membrane Proteins Is Affected in Gaucher's Disease (G202R Mutation)," *J Pathol* 188, 407-414 (1999).

Fujita, H., et al., "Isolation and Sequencing of a cDNA Clone Encoding the 85 kDa Human Lysosomal Sialoglycoprotein (hLGP85) in Human Metastatic Pancreas Islet Tumor Cells," *Biochem. and Biophys. Research Comm.*, 184(2):604-611 (Apr. 30, 1992).

Nov. 26, 2009, Notification Concerning Transmittal of Copy of International Preliminary Report on Patentability (Chapter 1 of the Patent Cooperation Treaty), PCT/US2008/005942.

Oct. 31, 2008, Notification of Transmittal of the International Search Report and the Written Opinion of the International Searching Authority, or the Declaration, PCT/US2008/005942.

\* cited by examiner

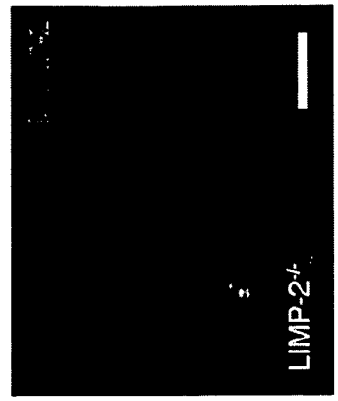
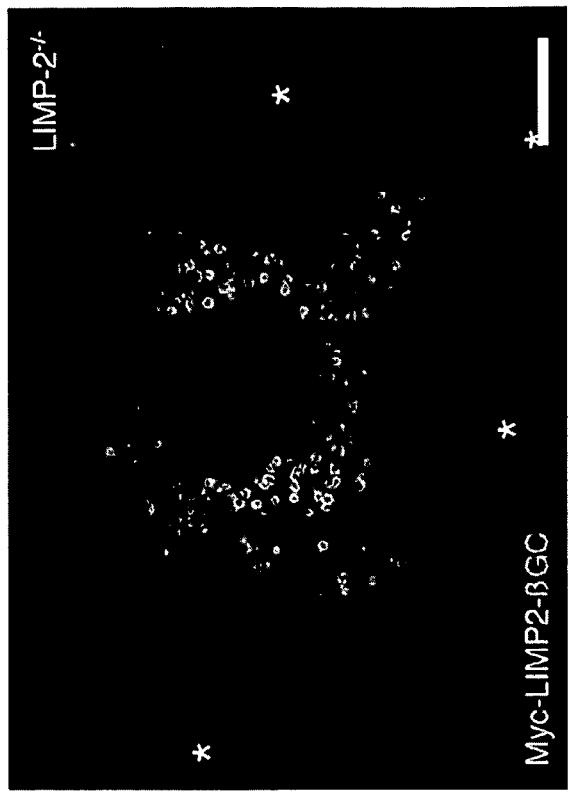
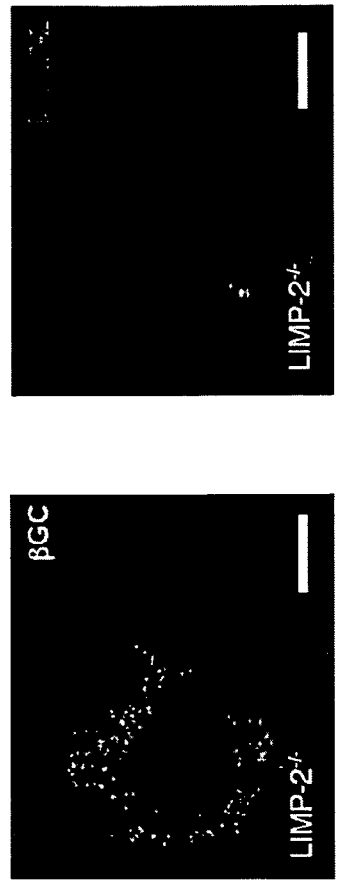
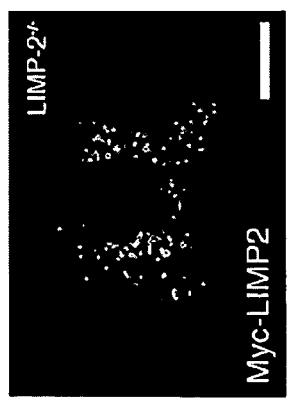
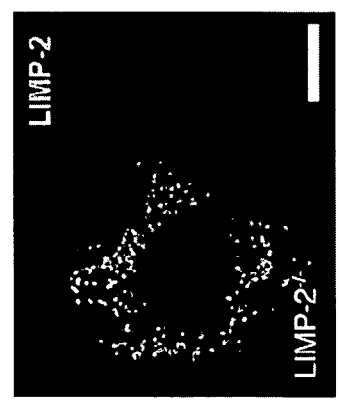

(d)
LIMP2, hβGC, DAPI
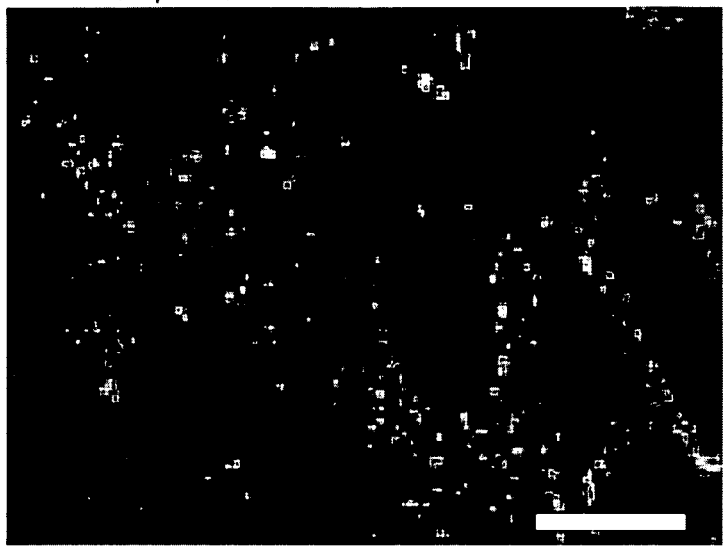
untreated
LIMP-2 siRNA
(e)
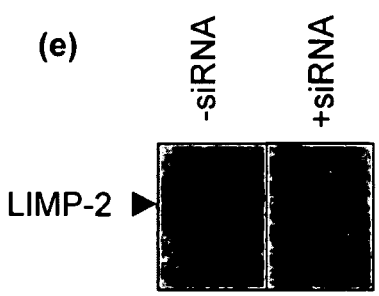
LIMP-2 ▶
FIG. 5F-2 scrambled siRNA

LIMP-2 siRNA

LIMP-2

LIMP-2

βGC

βGC

DAPI

DAPI

LIMP-2/βGC/DAPI

LIMP-2/βGC/DAPI

Hela cells

FIG. 10A  β-GC
FIG. 10D  LAMP-2
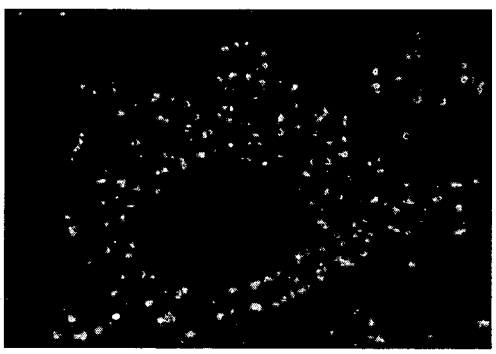
FIG. 10G  βGC /LAMP-2
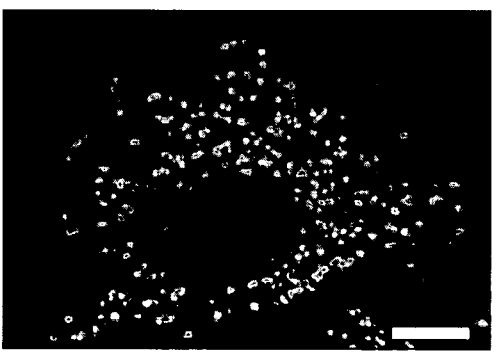
*Hela cells*

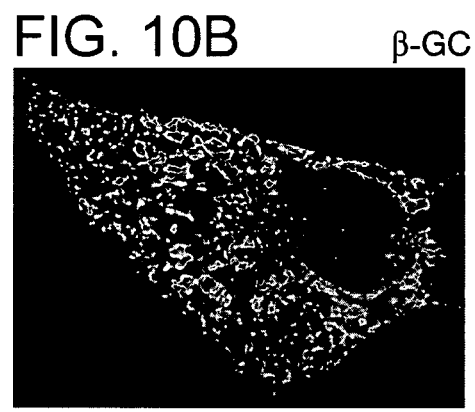
FIG. 10B β-GC
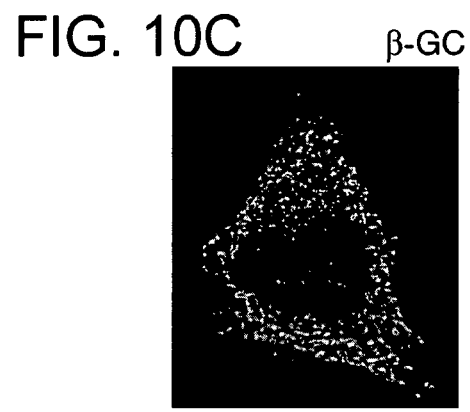
FIG. 10C β-GC
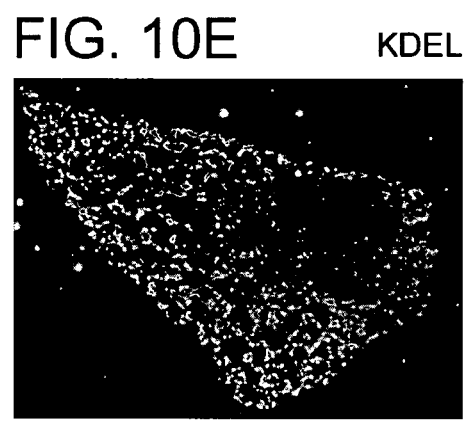
FIG. 10E KDEL
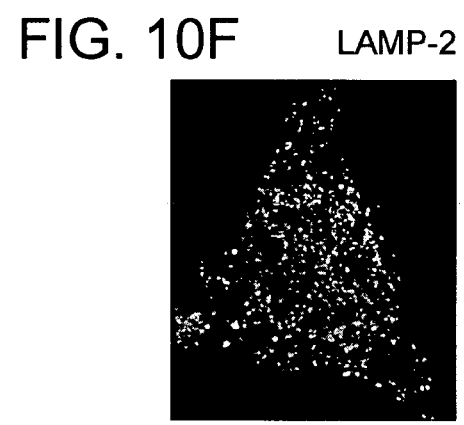
FIG. 10F LAMP-2
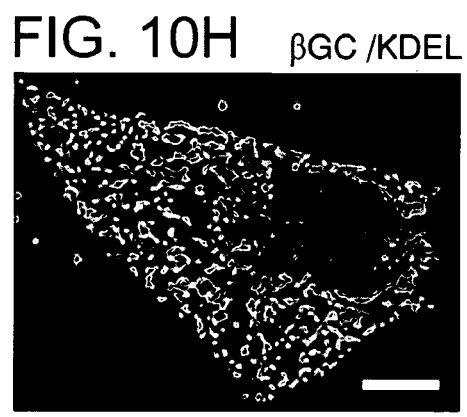
FIG. 10H βGC/KDEL
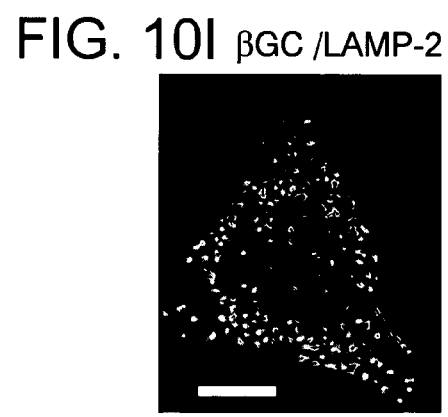
FIG. 10I βGC/LAMP-2
*LIMP-2-/-MEF cells*

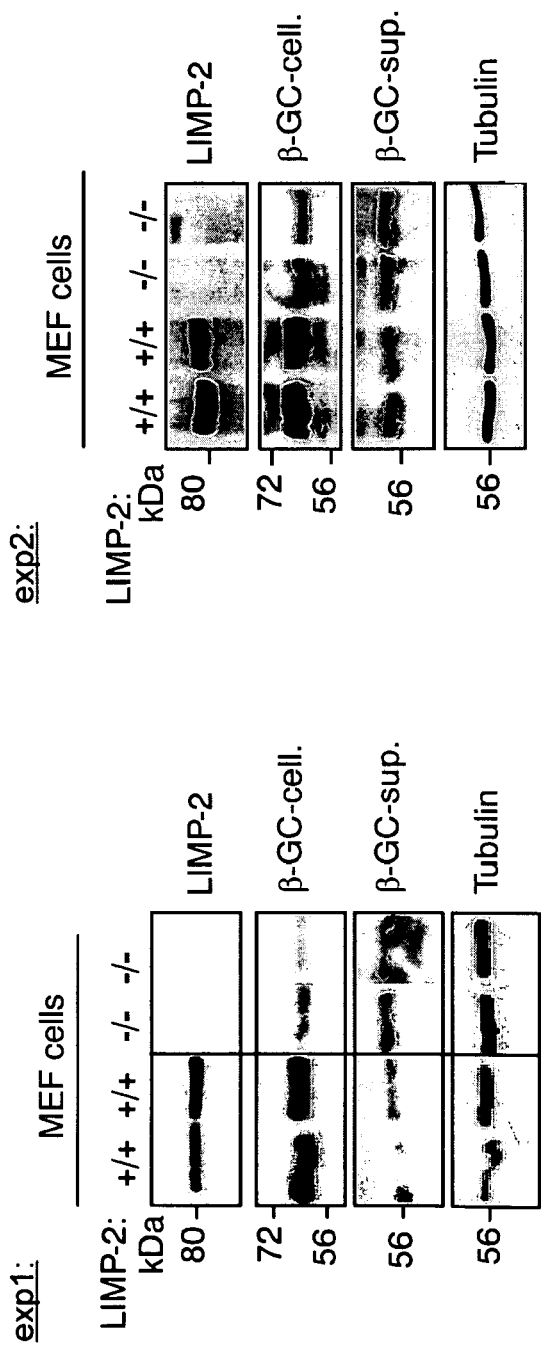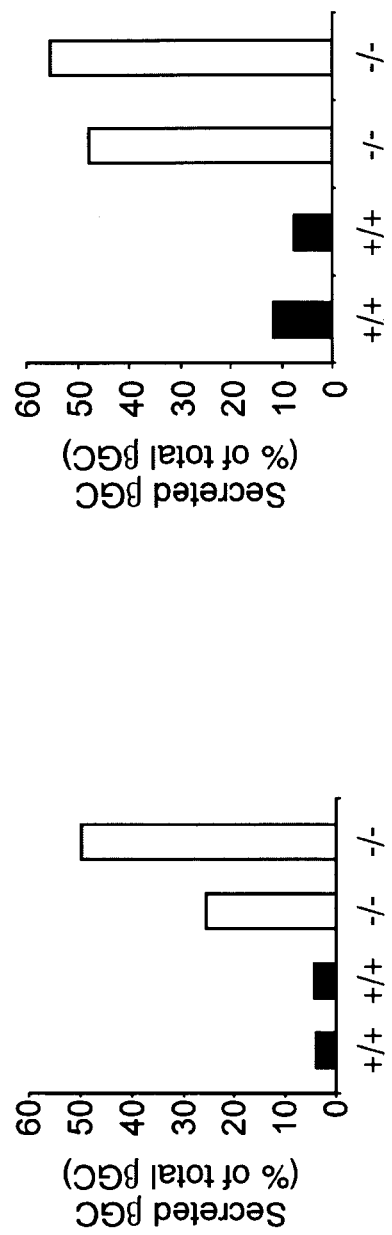
FIG. 12 mRNA (ORF) nucleotide alignment
Nucleotide Alignment of ORF (open reading frame):

```
                        1                                                    50
     hamster_LIMP-2_ORF ATGGGCAGAT GTTGCTTCTA CACGGCGGGG ACACTGTCCC TGCTGCTGCT
       human_LIMP-2_ORF ATGGGCCGAT GCTGCTTCTA CACGGCGGGG ACGTTGTCCC TGCTCCTGCT
       Mouse_LIMP-2_ORF ATGGGCAGAT GCTGCTTCTA CACGGCGGGG ACGCTGTCTC TGCTGCTGCT
         Rat_LIMP-2_ORF ATGGCCCGAT GCTGCTTCTA CACGGCGGGG ACACTGTCTC TGCTGCTGCT 51                                                   100
     hamster_LIMP-2_ORF GGTGGCTAGT GTCACGCTGC TGGTGGCTCG AGTCTTCCAG AAGGCGGTGG
       human_LIMP-2_ORF GGTGACCAGC GTCACGCTGC TGGTGGCCCG GGTCTTCCAG AAGGCTGTAG
       Mouse_LIMP-2_ORF GGTGACCAGC GTCACGCTGC TAGTGGCTCG AGTCTTTCAG AAGGCGGTAG
         Rat_LIMP-2_ORF GGTGACCAGT GTCACGCTGC TAGTGGCTCG AGTCTTTCAG AAGGCAGTGG 101                                                  150
     hamster_LIMP-2_ORF ACCAGACGAT CGAGAAGAGT ATGGTGTTAA GAAATGGTAC TGAGGTCTTT
       human_LIMP-2_ORF ACCAGAGTAT CGAGAAGAAA ATTGTGTTAA GGAATGGTAC TGAGGCATTT
       Mouse_LIMP-2_ORF ACCAGACGAT CGAGAAGAAT ATGGTATTAC AAAATGGCAC CAAGGTCTTT
         Rat_LIMP-2_ORF ACCAGACGAT CGAGAAGAAT ATGGTATTAC AAAATGGTAC CAAGGTCTTT 151                                                  200
     hamster_LIMP-2_ORF GACTCCTGGG AGAAACCCCC TCTACCTGTG TACACCCAGT TCTACTTCTT
       human_LIMP-2_ORF GACTCCTGGG AGAAGCCCCC TCTGCCTGTG TATACTCAGT TCTATTTCTT
       Mouse_LIMP-2_ORF AATTCCTGGG AGAAGCCCCC TCTACCTGTG TACATCCAGT TTTATTTCTT
         Rat_LIMP-2_ORF GATTCCTGGG AGAAGCCCCC TCTACCTGTG TACATCCAGT TTTATTTCTT 201                                                  250
     hamster_LIMP-2_ORF CAATGTCACC AATCCAGAGG AGATCCTCCA AGGAGAAATT CCCATACTTC
       human_LIMP-2_ORF CAATGTCACC AATCCAGAGG AGATCCTCAG AGGGGAGACC CCTCGGGTGG
       Mouse_LIMP-2_ORF CAATGTCACC AATCCTGAGG AGATCCTCCA AGGAGAAATC CCCCTACTAG
         Rat_LIMP-2_ORF CAATGTCACC AATCCAGAGG AGATCCTCCA AGGAGAAATC CCCCTGCTAG 251                                                  300
     hamster_LIMP-2_ORF AAGAAGTGGG ACCATACACA TACAGGGAAA TCAGGAACAA GGCAAACATC
       human_LIMP-2_ORF AAGAAGTGGG GCCATACACC TACAGGGAAC TCAGAAACAA AGCAAATATT
       Mouse_LIMP-2_ORF AAGAAGTGGG GCCATACACC TACAGGGAGC TCCGGAACAA GGCAAATATT
         Rat_LIMP-2_ORF AAGAAGTGGG GCCGTACACC TACAGGGAGC TCAGGAACAA GGCAAACGTT 301                                                  350
     hamster_LIMP-2_ORF CAATTTGGAG AGAATGGAAC AACCATATCG GCTGTTAGCA ATAAGGCATA
       human_LIMP-2_ORF CAATTTGGAG ATAATGGAAC AACAATATCT GCTGTTAGCA ACAAGGCCTA
       Mouse_LIMP-2_ORF CAGTTTGGAG AAAATGGAAC AACTATATCT GCTGTCACCA ATAAGGCATA
         Rat_LIMP-2_ORF CAGTTTGGAG AAAATGGAAC AACCATATCT GCCGTCACCA ATAAGGCATA 351                                                  400
     hamster_LIMP-2_ORF TGTTTTTGAA CGAAACCAAT CTGTTGGCGA CACTAATGTT GACTTGATTA
       human_LIMP-2_ORF TGTTTTTGAA CGAGACCAAT CTGTTGGAGA CCCTAAAATT GACTTAATTA
       Mouse_LIMP-2_ORF TGTTTTTGAA CGAAACCAAT CTGTTGGAGA TCCTAACGTT GACTTGATTA
         Rat_LIMP-2_ORF TATTTTTGAA CGAAACCAGT CTGTTGGAGA CCCTACCGTT GACTTGATTA 401                                                  450
     hamster_LIMP-2_ORF GAACGATAAA TATTCCTCTG TTGACTGTTG TGGAACTGAC CCAGCTGCCC
       human_LIMP-2_ORF GAACATTAAA TATTCCTGTA TTGACTGTCA TAGAGTGGTC CCAGGTGCAC
       Mouse_LIMP-2_ORF GAACAATAAA TATTCCTCTG TTGACTGTCG TGGATCTGGC CCAGCTGACC
         Rat_LIMP-2_ORF GAACAATAAA TATTCCTCTG TTGACTGTTG TGGAAATGGC CCAGCAGCCC 451                                                  500
     hamster_LIMP-2_ORF CTGCTTAAGG AAATCATTGA GGCCATGCTG AAAACCTACC AGCAGAAGCT
       human_LIMP-2_ORF TTCCTCAGGG AGATCATCGA GGCCATGTTG AAAGCCTATC AGCAGAAGCT
       Mouse_LIMP-2_ORF CTGCTCAGGG AGCTTATCGA AGCCATGCTG AAAGCCTATC AGCAGAAGTT
         Rat_LIMP-2_ORF TTCCTCAGGG AGATCATCGA GGCCATGCTG AAAGCTTATC AGCAGACGCT
```

FIG. 15A mRNA (ORF) nucleotide alignment

```
                         501                                                      550
     hamster_LIMP-2_ORF  GTTTGTGACT CACACAGTGC ACGAGCTGCT CTGGGGCTAT AAAGATGAGA
       human_LIMP-2_ORF  CTTTGTGACT CACACAGTTG ACGAATTGCT CTGGGGCTAC AAAGATGAAA
       Mouse_LIMP-2_ORF  GTTTGTGATT CACACCGTGC ACGAACTGCT CTGGGGCTAC AAAGATGAGA
         Rat_LIMP-2_ORF  GTTTGTCACT CACACTGTAC ATGAACTGCT CTGGGGCTAC AAAGATGAGG 551                                                      600
     hamster_LIMP-2_ORF  TCTTGTCCCT CGTCCATGTT TTCAAGCCTG GAATCTCCCC TAACTTTGGC
       human_LIMP-2_ORF  TCTTGTCCCT TATCCATGTT TTCAGGCCCG ATATCTCTCC CTATTTTGGC
       Mouse_LIMP-2_ORF  TCTTGTCCCT CGTCCATATT TTCAAACCTG ACGTCTCCCC GAATTTCGGC
         Rat_LIMP-2_ORF  TCTTGTCGCT CGTCCATATT TTCAGACCTG ACGTCTCCCC TAACTTTGGC 601                                                      650
     hamster_LIMP-2_ORF  CTGTTCTACG AAAAAAATGG AACTAATGAT GGAGATTATG TTTTCCTAAC
       human_LIMP-2_ORF  CTATTCTATG AGAAAAATGG GACTAATGAT GGAGACTATG TTTTTCTAAC
       Mouse_LIMP-2_ORF  CTGTTCTATG AGAGAAATGG AACGAATGAC GGGGAGTACG TGTTTCTGAC
         Rat_LIMP-2_ORF  CTGTTCTATG AGAGAAATGG AACTAATGAT GGGGAGTATG TTTTTCTGAC 651                                                      700
     hamster_LIMP-2_ORF  TGGAGAAGAC AATTACCTCA ACTTTACAAA AATTGTGGAG TGGAATGGTA
       human_LIMP-2_ORF  TGGAGAAGAC AGTTACCTTA ACTTTACAAA AATTGTGGAA TGGAATGGGA
       Mouse_LIMP-2_ORF  TGGAGAGGAC AATTACCTTA ACTTTTCAAA AATCGTGGAG TGGAATGGAA
         Rat_LIMP-2_ORF  TGGAGAGGAC AATTACCTGA ACTTTACAAA AATTGTGGAG TGGAATGGAA 701                                                      750
     hamster_LIMP-2_ORF  AAACGTCACT GGACTGGTGG ACCACAGACG AATGCAATAT GATTAACGGG
       human_LIMP-2_ORF  AAACGTCACT TGACTGGTGG ATAACAGACA AGTGCAATAT GATTAATGGA
       Mouse_LIMP-2_ORF  AAACGTCGCT GGACTGGTGG ACCACAGACA CATGCAATAT GATTAACGGG
         Rat_LIMP-2_ORF  AAACGTCGCT GGACTGGTGG ACGACGGACA CGTGCAATAT GATCAACGGG 751                                                      800
     hamster_LIMP-2_ORF  ACAGATGGAG ATTCTTTTCA TCCACTGATA ACCAAGGATG AAGTCCTCTA
       human_LIMP-2_ORF  ACAGATGGAG ATTCTTTTCA CCCACTAATA ACCAAAGATG AGGTCCTTTA
       Mouse_LIMP-2_ORF  ACAGACGGAG ACTCTTTTCA TCCGCTGATA AGCAAGGATG AGGTCCTGTA
         Rat_LIMP-2_ORF  ACAGACGGAG ATTCTTTTCA CCCATTAATA AGCAAGGATG AGACCCTGTA 801                                                      850
     hamster_LIMP-2_ORF  TGTGTTCCCG TCTGACTTCT GCAGGTCAGT ACATATAACT TTCAGTGGTT
       human_LIMP-2_ORF  TGTCTTCCCA TCTGACTTTT GCAGGTCAGT GTATATTACT TTCAGTGACT
       Mouse_LIMP-2_ORF  CCTCTTCCCG TCAGACTTGT GCAGGTCAGT ACATATCACT TTCAGCAGCT
         Rat_LIMP-2_ORF  CATCTTCCCA TCTGACTTCT GCAGGTCCGT CTATATAACT TTCAGTAGCT 851                                                      900
     hamster_LIMP-2_ORF  TTGAGACTGT GGAGGGTTTG CCTGCTTTTC GGTATAAGGT GCCTGCAGAA
       human_LIMP-2_ORF  ATGAGAGTGT ACAGGGACTG CCTGCCTTTC GGTATAAAGT TCCTGCAGAA
       Mouse_LIMP-2_ORF  TTGAGAACGT AGAAGGACTG CCTGCTTTTC GGTATAAGGT GCCTGCAGAA
         Rat_LIMP-2_ORF  TTGAGAACGT AGAAGGACTG CCTGCTTTTC GGTATAAGGT GCCTGCAGAA 901                                                      950
     hamster_LIMP-2_ORF  ATACTAGCCA ACACCTCTGA AAATGCAGGC TTCTGCATCC CTGAAGGAAA
       human_LIMP-2_ORF  ATATTAGCCA ATACGTCAGA CAATGCCGGC TTCTGTATAC CTGAGGGAAA
       Mouse_LIMP-2_ORF  ATACTAGCCA ACACCTCCGA AAACGCTGGC TTCTGTATAC CCGAGGGAAA
         Rat_LIMP-2_ORF  ATACTAGCCA ATTCCTCCGA AAACGCTGGC TTCTGTATAC CCGAGGGAAA 951                                                     1000
     hamster_LIMP-2_ORF  CTGCATGGAC TCGGGAGTGT TGAATGTCAG CATCTGCAAG AACGGTGTAC
       human_LIMP-2_ORF  CTGCCTGGGC TCAGGAGTTC TGAATGTCAG CATCTGCAAG AATGGTGCAC
       Mouse_LIMP-2_ORF  CTGCATGGAC TCAGGGGTGT TGAACATCAG CATCTGCAAG AATGGTGCAC
         Rat_LIMP-2_ORF  CTGCATGGAC GCGGGAGTGC TGAACGTCAG CATTTGCAAG AATGGTGCGC
```

FIG. 15B mRNA (ORF) nucleotide alignment

```
                        1001                                               1050
hamster_LIMP-2_ORF      CGATTATCAT GTCTTTCCCA CACTTTTACC AAGCTGATGA AAAGTTCGTT
  human_LIMP-2_ORF      CCATCATTAT GTCTTTCCCA CACTTTTACC AAGCAGATGA GAGGTTTGTT
  Mouse_LIMP-2_ORF      CCATTATCAT GTCTTTCCCA CACTTTTACC AAGCCGACGA GAAGTTCGTT
    Rat_LIMP-2_ORF      CCATTATCAT GTCTTTCCCA CACTTTTACC AAGCCGACGA GAAGTTCGTT 1051                                               1100
hamster_LIMP-2_ORF      TCTGCCATAA AAGGCATGCA CCCAAACAAG GAAGAGCATG AGACATTTGT
  human_LIMP-2_ORF      TCTGCCATAG AAGGCATGCA CCCAAATCAG GAAGACCATG AGACATTTGT
  Mouse_LIMP-2_ORF      TCTGCCATAA AAGGCATGCA TCCCAACAAG GAAGAGCATG AGTCGTTTGT
    Rat_LIMP-2_ORF      TCGGCCATAA AAGGCATGCG TCCAAACAAG GAAGAACATG AGTCATTTGT 1101                                               1150
hamster_LIMP-2_ORF      GGACATTAAT CCTTTGACTG GAATTATTTT AAGAGCAGCC AAGAGATTCC
  human_LIMP-2_ORF      GGACATTAAT CCTTTGACTG GAATAATCCT AAAAGCAGCC AAGAGGTTCC
  Mouse_LIMP-2_ORF      GGACATTAAT CCCTTGACTG GAATTATTTT GAGAGGGGCC AAGAGATTCC
    Rat_LIMP-2_ORF      GGACATTAAT CCTTTGACAG GAATTATTTT AAGAGGGGCC AAGAGATTCC 1151                                               1200
hamster_LIMP-2_ORF      AAATCAACAC TTATGTTAAA AAAATAGATG GCTTTGTTGA AATGGGAAAC
  human_LIMP-2_ORF      AAATCAACAT TTATGTCAAA AAATTAGATG ACTTTGTTGA ACGGGAGAC
  Mouse_LIMP-2_ORF      AGATCAACAC TTACGTTAGG AAACTGGATG ACTTTGTTGA ACGGGAGAC
    Rat_LIMP-2_ORF      AAATCAACAC GTACGTTAAG AAGCTGGATG ACTTTGTGGA ACGGGAAAC 1201                                               1250
hamster_LIMP-2_ORF      ATTAGGACTA TGGTTTTCCC AGTGATGTAT CTCAATGAGA GTGTTCTCAT
  human_LIMP-2_ORF      ATTAGAACCA TGGTTTTCCC AGTGATGTAC CTCAATGAGA GTGTTCACAT
  Mouse_LIMP-2_ORF      ATCAGGACTA TGGTTTTCCC AGTGATGTAT CTCAATGAGA GTGTCCTCAT
    Rat_LIMP-2_ORF      ATTAGGACTA TGGTTTTCCC AGTGATGTAT CTCAATGAGA GTGTTCTCAT 1251                                               1300
hamster_LIMP-2_ORF      TGACAAAGAG ACTGCAAGTC GATTGAAGTC CGTGACTAAC ACGACTTTGA
  human_LIMP-2_ORF      TGATAAAGAG ACGGCGAGTC GACTGAAGTC TATGATTAAC ACTACTTTGA
  Mouse_LIMP-2_ORF      TGACAAAGAG ACCGCAAATC AACTGAAGTC TGTGATTAAC ACGACTTTGG
    Rat_LIMP-2_ORF      TGACAAAGAG ACTGCAAGTC AACTGAAGTC TGTGATTAAC ACAACTTTGA 1301                                               1350
hamster_LIMP-2_ORF      TAGTCACCAA CATACCCTAC ATCATCATGG CATTGGGAGT GTTCTTTGGC
  human_LIMP-2_ORF      TCATCACCAA CATACCCTAC ATCATCATGG CGCTGGGTGT GTTCTTTGGT
  Mouse_LIMP-2_ORF      TTGTCACCAA CATACCCTAC ATCATTATGG CACTGGGTGT GTTCTTTGGC
    Rat_LIMP-2_ORF      TTGTCACCAA CATACCCTAC ATCATCATGG CACTGGGCGT GTTCTTTGGC 1351                                               1400
hamster_LIMP-2_ORF      TTGGTTTTCA CATGGCTTGC ATGCCGAGGA CAGGGGCCCA TGGATGAGGG
  human_LIMP-2_ORF      TTGGTTTTTA CCTGGCTTGC ATGCAAAGGA CAGGGATCCA TGGATGAGGG
  Mouse_LIMP-2_ORF      TTGGTTTTCA CGTGGCTGGC GTGTCGAGGA CAGGGGTCTA TGGATGAGGG
    Rat_LIMP-2_ORF      TTGATTTTCA CGTGGCTGGC GTGTCGAGGA CAGGGGTCTA CGGATGAGGG 1401            1437
hamster_LIMP-2_ORF      AACGGCAGAT GAAAGAGCAC CCCTCATACG AACCTAA
  human_LIMP-2_ORF      AACAGCGGAT GAAAGAGCAC CCCTCATTCG AACCTAA
  Mouse_LIMP-2_ORF      AACTGCAGAT GAAAGAGCAC CCCTCATACG AACCTAA
    Rat_LIMP-2_ORF      AACTGCAGAT GAAAGGGCAC CCCTCATACG GACCTAA
```

Section 1

```
                               (1) 1        10        20        30      42
hamster LIMP-2 lumenal domain  (1) RVFQKAVDQTIEKSMVLNGTEVFDSWEKPPLPVYQFYFFN
human LIMP-2 lumenal domain    (1) RVFQKAVDQIEKKVLNGTEAFDSWEKPPLPVYQFYFFN
mouse LIMP_2 lumenal domain    (1) RVFQKAVDQTIEKNMVLQNGTVFNSWEKPPLPVYTQFYFFN
rat LIMP-2 lumenal domain      (1) RVFQKAVDQTIEKNMVLQNGTVFDSWEKPPLPVYTQFYFFN
Consensus                      (1) RVFQKAVDQTIEKNMVLRNGTKVFDSWEKPPLPVYTQFYFFN
```

Section 2

```
                              (43) 43       50        60        70      84
hamster LIMP-2 lumenal domain (43) VTNPEEILQGEIPLQEVGPYTYRERNKANIQFGENGTTIS
human LIMP-2 lumenal domain   (43) VTNPEEILRGETPREEVGPYTYRELRNKANIQFGNGTTIS
mouse LIMP_2 lumenal domain   (43) VTNPEEILQGEIPLLEEVGPYTYRELRNKANIQFGENGTTIS
rat LIMP-2 lumenal domain     (43) VTNPEEILQGEIPLLEEVGPYTYRELRNKANQFGENGTTIS
Consensus                     (43) VTNPEEILQGEIPLLEEVGPYTYRELRNKANIQFGENGTTIS
```

Section 3

```
                              (85) 85       90       100       110     126
hamster LIMP-2 lumenal domain (85) AVNKAYVFERNQSVGDTNVDLIRTINIPLLTVVELTQLPL
human LIMP-2 lumenal domain   (85) AVNKAYVFERDQSVGDEKDLIRTNIPLTVEWSQHFL
mouse LIMP_2 lumenal domain   (85) AVNKAYVFERNQSVGDPNVDLIRTINIPLLTVLAQLTL
rat LIMP-2 lumenal domain     (85) AVNKAYFERNQSVGDPTVDLIRTINIPLLTVVEAQQPFL
Consensus                     (85) AVSNKAYVFERNQSVGDPNVDLIRTINIPLLTVVELAQLPLL
```

Section 4

```
                             (127) 127      140       150      168
hamster LIMP-2 lumenal domain (127) EIIEAMLKTYQQKLFVTHTVHELLWGYKDEILSLVHFPG
human LIMP-2 lumenal domain   (127) REIIEAMLKAYQQKLFVTHTVDELLWGYKDEILSLHVFPD
mouse LIMP_2 lumenal domain   (127) REIIEAMLKAYQQKLFVIHTVHELLWGYKDEILSLVHFPD
rat LIMP-2 lumenal domain     (127) REIIEAMLKAYQQTLFVTHTVHELLWGYKDELSLVHFPD
Consensus                    (127) REIIEAMLKAYQQKLFVTHTVHELLWGYKDEILSLVHIFKPD
```

Section 5

```
                             (169) 169      180       190      200     210
hamster LIMP-2 lumenal domain (169) SPNFGLFYENGTNDGYVFLTGEDNYLNFTKIVEWNGKTS
human LIMP-2 lumenal domain   (169) SPYFGLFYENGTNDGYVFLTGEDSYLNFTKIVEWNGKTS
mouse LIMP_2 lumenal domain   (169) SPNFGLFYENGTNDGYVFLTGEDNYLNFKIVEWNGKTS
rat LIMP-2 lumenal domain     (169) SPNFGLFYENGTNDGYVFLTGEDNYLNFTKIVEWNGKTS
Consensus                    (169) ISPNFGLFYEKNGTNDGDYVFLTGEDNYLNFTKIVEWNGKTS
```

Section 6

```
                             (211) 211      220       230      240     252
hamster LIMP-2 lumenal domain (211) LDWWITDECNMINGTDGDSFHPLIKDEVLYVFPSDFCRSV
human LIMP-2 lumenal domain   (211) LDWWITDKCNMINGTDGDSFHPLIKDEVLYVFPSDFCRSV
mouse LIMP_2 lumenal domain   (211) LDWWTDTCNMINGTDGDSFHPLIKDEVLYFPSDLCRSV
rat LIMP-2 lumenal domain     (211) LDWWTDTCNMINGTDGDSFHPLIKDETLYFPSDFCRSV
Consensus                    (211) LDWWTTDTCNMINGTDGDSFHPLISKDEVLYVFPSDFCRSVH
```

FIG. 16B

Section 7

|  | (253) | 253　　　260　　　270　　　280　　　294 |
|---|---|---|
| hamster LIMP-2 lumenal domain | (253) | ITFSGFETVEGLPAFRYKVPAEILANTSENAGFCIPEGNCMD |
| human LIMP-2 lumenal domain | (253) | ITFSDESVQGLPAFRYKVPAEILANTSNAGFCIPEGNCG |
| mouse LIMP_2 lumenal domain | (253) | ITFSSFENVEGLPAFRYKVPAEILANTSENAGFCIPEGNCMD |
| rat LIMP-2 lumenal domain | (253) | ITFSSFENVEGLPAFRYKVPAEILANSENAGFCIPEGNCMD |
| Consensus | (253) | ITFSSFENVEGLPAFRYKVPAEILANTSENAGFCIPEGNCMD |

Section 8

|  | (295) | 295　　300　　　310　　　320　　　336 |
|---|---|---|
| hamster LIMP-2 lumenal domain | (295) | SGVLNVSICKNGVPIIMSFPHFYQADEKFVSAIKGMHPNKEE |
| human LIMP-2 lumenal domain | (295) | SGVLNVSICKNGAPIIMSFPHFYQADEFVSAIEGMHPNQE |
| mouse LIMP_2 lumenal domain | (295) | SGVLNSICKNGAPIIMSFPHFYQADEKFVSAIKGMHPNKEE |
| rat LIMP-2 lumenal domain | (295) | GVLNVSICKNGAPIIMSFPHFYQADEKFVSAIKGMRPNKEE |
| Consensus | (295) | SGVLNVSICKNGAPIIMSFPHFYQADEKFVSAIKGMHPNKEE |

Section 9

|  | (337) | 337　　　350　　　360　　　378 |
|---|---|---|
| hamster LIMP-2 lumenal domain | (337) | HEFVDINPLTGIILRAKRFQINTYVKKDGFVEMGIRTM |
| human LIMP-2 lumenal domain | (337) | HEFVDINPLTGIILAKRFQINIYVKKLDDFVETGDIRTM |
| mouse LIMP_2 lumenal domain | (337) | HEFVDINPLTGIILRAKRFQINTYVKLDDFVETGDIRTM |
| rat LIMP-2 lumenal domain | (337) | HEFVDINPLTGIILRAKRFQINTYVKKLDDFVETGIRTM |
| Consensus | (337) | HESFVDINPLTGIILRAAKRFQINTYVKKLDDFVETGNIRTM |

Section 10

|  | (379) | 379　　　390　　　406 |
|---|---|---|
| hamster LIMP-2 lumenal domain | (379) | VFPVMYLNESVLIDKETASLKSVTNTT |
| human LIMP-2 lumenal domain | (379) | VFPVMYLNESVHIDKETASLKSINTT |
| mouse LIMP_2 lumenal domain | (379) | VFPVMYLNESVLIDKETANQLKSVINTT |
| rat LIMP-2 lumenal domain | (379) | VFPVMYLNESVLIDKETASQLKSVINTT |
| Consensus | (379) | VFPVMYLNESVLIDKETASRLKSVINTT |

FIG. 16C

Section 1

```
                                    (1)  1         10        20         39
hamster LIMP-2                (1)  MGRCCFYTAGTLSLLLLVASVTLLVARVFQKAVDQTIEK
Human LIMP-2 protein NM_005506 (1)  MGRCCFYTAGTLSLLLLVTSVTLLVARVFQKAVDQTIEK
Mouse LIMP-2 protein NM_007644 (1)  MGRCCFYTAGTLSLLLLVTSVTLLVARVFQKAVDQTIEK
Rat LIMP2 protein NM_054001    (1)  M RCCFYTAGTLSLLLLVTSVTLLVARVFQKAVDQTIEK
Consensus                      (1)  MGRCCFYTAGTLSLLLLVTSVTLLVARVFQKAVDQTIEK
```

Section 2

```
                                    (40) 40        50        60         78
hamster LIMP-2                (40) SMVL NGTEVFDSWEKPPLPVY QFYFFNVTNPEEILQG
Human LIMP-2 protein NM_005506 (40) K VL NGTEAFDSWEKPPLPVY QFYFFNVTNPEEILRG
Mouse LIMP-2 protein NM_007644 (40) NMVLQNGT VFNSWEKPPLPVYIQFYFFNVTNPEEILQG
Rat LIMP2 protein NM_054001    (40) NMVLQNGT VFDSWEKPPLPVYIQFYFFNVTNPEEILQG
Consensus                     (40) NMVLRNGTKVFDSWEKPPLPVYTQFYFFNVTNPEEILQG
```

Section 3

```
                                    (79) 79        90       100        117
hamster LIMP-2                (79) EIP LQEVGPYTYRE RNKANIQFGENGTTISAVSNKAY
Human LIMP-2 protein NM_005506 (79) ETPR EEVGPYTYRELRNKANIQFG NGTTISAV NKAY
Mouse LIMP-2 protein NM_007644 (79) EIPLLEEVGPYTYRELRNKANIQFGENGTTISAV NKAY
Rat LIMP2 protein NM_054001    (79) EIPLLEEVGPYTYRELRNKAN QFGENGTTISAV NKAY
Consensus                     (79) EIPLLEEVGPYTYRELRNKANIQFGENGTTISAVSNKAY
```

Section 4

```
                                   (118) 118       130       140        156
hamster LIMP-2               (118) VFERNQSVGDTNVDLIRTINIPLLTVVELTQLPLLAEII
Human LIMP-2 protein NM_005506(118) VFERDQSVGDPK DLIRT NIP LTV EW Q HFLREII
Mouse LIMP-2 protein NM_007644(118) VFERNQSVGDPNVDLIRTINIPLLTVV LAQLT LRE I
Rat LIMP2 protein NM_054001   (118)  FERNQSVGDPTVDLIRTINIPLLTVVE AQQPFLREII
Consensus                    (118) VFERNQSVGDPNVDLIRTINIPLLTVVELAQLPLLREII
```

Section 5

```
                                   (157) 157       170       180        195
hamster LIMP-2               (157) EAMLKTYQQKLFVTHTVHELLWGYKDEILSLVH F PG
Human LIMP-2 protein NM_005506(157) EAMLKAYQQKLFVTHTVDELLWGYKDEILSL H F PD
Mouse LIMP-2 protein NM_007644(157) EAMLKAYQQKLFVIHTVHELLWGYKDEILSLVH F PD
Rat LIMP2 protein NM_054001   (157) EAMLKAYQQTLFVTHTVHELLWGYKDE LSLVH F PD
Consensus                    (157) EAMLKAYQQKLFVTHTVHELLWGYKDEILSLVHIFKPDI
```

Section 6

```
                                   (196) 196       210       220        234
hamster LIMP-2               (196) SPNFGLFYE NGTNDG YVFLTGEDNYLNFTKIVEWNGK
Human LIMP-2 protein NM_005506(196) SPYFGLFYE NGTNDG YVFLTGEDSYLNFTKIVEWNGK
Mouse LIMP-2 protein NM_007644(196) SPNFGLFYE NGTNDG YVFLTGEDNYLNF KIVEWNGK
Rat LIMP2 protein NM_054001   (196) SPNFGLFYE NGTNDG YVFLTGEDNYLNFTKIVEWNGK
Consensus                    (196) SPNFGLFYEKNGTNDGDYVFLTGEDNYLNFTKIVEWNGK
```

FIG. 16D

Section 7

|  | (235) | 235 | 240 | 250 | 260 | 273 |
|---|---|---|---|---|---|---|
| hamster LIMP-2 | (235) | TSLDWWTTDECNMINGTDGDSFHPLIKDEVLYVFPSDF |
| Human LIMP-2 protein NM_005506 | (235) | TSLDWWITDKCNMINGTDGDSFHPLIKDEVLYVFPSDF |
| Mouse LIMP-2 protein NM_007644 | (235) | TSLDWWTTDTCNMINGTDGDSFHPLIKDEVLYVFPSDL |
| Rat LIMP2 protein NM_054001 | (235) | TSLDWWTTDTCNMINGTDGDSFHPLIKDETLYVFPSDF |
| Consensus | (235) | TSLDWWTTDTCNMINGTDGDSFHPLISKDEVLYVFPSDF |

Section 8

|  | (274) | 274 | 280 | 290 | 300 | 312 |
|---|---|---|---|---|---|---|
| hamster LIMP-2 | (274) | CRSVHITFSGFETVEGLPAFRYKVPAEILANTSENAGFC |
| Human LIMP-2 protein NM_005506 | (274) | CRSVHITFSDESVQGLPAFRYKVPAEILANTSENAGFC |
| Mouse LIMP-2 protein NM_007644 | (274) | CRSVHITFSSFENVEGLPAFRYKVPAEILANTSENAGFC |
| Rat LIMP2 protein NM_054001 | (274) | CRSVHITFSSFENVEGLPAFRYKVPAEILANSSENAGFC |
| Consensus | (274) | CRSVHITFSSFENVEGLPAFRYKVPAEILANTSENAGFC |

Section 9

|  | (313) | 313 | 320 | 330 | 340 | 351 |
|---|---|---|---|---|---|---|
| hamster LIMP-2 | (313) | IPEGNCMDSGVLNVSICKNGVPIIMSFPHFYQADEKFVS |
| Human LIMP-2 protein NM_005506 | (313) | IPEGNCGSGVLNVSICKNGAPIIMSFPHFYQADERFVS |
| Mouse LIMP-2 protein NM_007644 | (313) | IPEGNCMDSGVLNSICKNGAPIIMSFPHFYQADEKFVS |
| Rat LIMP2 protein NM_054001 | (313) | IPEGNCMDGVLNVSICKNGAPIIMSFPHFYQADEKFVS |
| Consensus | (313) | IPEGNCMDSGVLNVSICKNGAPIIMSFPHFYQADEKFVS |

Section 10

|  | (352) | 352 | 360 | 370 | 380 | 390 |
|---|---|---|---|---|---|---|
| hamster LIMP-2 | (352) | AIKGMHPNKEEHESFVDINPLTGIILRAAKRFQINTYVK |
| Human LIMP-2 protein NM_005506 | (352) | AIEGMHPNQEEHESFVDINPLTGIILRAAKRFQINIYVK |
| Mouse LIMP-2 protein NM_007644 | (352) | AIKGMHPNKEEHESFVDINPLTGIILRAAKRFQINTYVK |
| Rat LIMP2 protein NM_054001 | (352) | AIKGMRPNKEEHESFVDINPLTGIILRAAKRFQINTYVK |
| Consensus | (352) | AIKGMHPNKEEHESFVDINPLTGIILRAAKRFQINTYVK |

Section 11

|  | (391) | 391 | 400 | 410 | 429 |
|---|---|---|---|---|---|
| hamster LIMP-2 | (391) | KLDGFVEMGDIRTMVFPVMYLNESVLIDKETASLKSVT |
| Human LIMP-2 protein NM_005506 | (391) | KLDDFVETGDIRTMVFPVMYLNESVHIDKETASLKSI |
| Mouse LIMP-2 protein NM_007644 | (391) | KLDDFVETGDIRTMVFPVMYLNESVLIDKETANQLKSVI |
| Rat LIMP2 protein NM_054001 | (391) | KLDDFVETGDIRTMVFPVMYLNESVLIDKETASQLKSVI |
| Consensus | (391) | KLDDFVETGNIRTMVFPVMYLNESVLIDKETASRLKSVI |

Section 12

|  | (430) | 430 | 440 | 450 | 468 |
|---|---|---|---|---|---|
| hamster LIMP-2 | (430) | NTTLIVTNIPYIIMALGVFFGLVFTWLACRGQGPMDEGT |
| Human LIMP-2 protein NM_005506 | (430) | NTTLIVTNIPYIIMALGVFFGLVFTWLACGQGSMDEGT |
| Mouse LIMP-2 protein NM_007644 | (430) | NTTLVTNIPYIIMALGVFFGLVFTWLACRGQGSMDEGT |
| Rat LIMP2 protein NM_054001 | (430) | NTTLIVTNIPYIIMALGVFFGLVFTWLACRGQGSTDEGT |
| Consensus | (430) | NTTLIVTNIPYIIMALGVFFGLVFTWLACRGQGSMDEGT |

FIG. 16E ─────────────────────────────────── Section 13

|  | | 469 | 478 |
|---|---|---|---|
| hamster LIMP-2 | (469) | ADERAPLIRT | |
| Human LIMP-2 protein NM_005506 | (469) | ADERAPLIRT | |
| Mouse LIMP-2 protein NM_007644 | (469) | ADERAPLIRT | |
| Rat LIMP2 protein NM_054001 | (469) | ADERAPLIRT | |
| Consensus | (469) | ADERAPLIRT | |

HAMSTER LIMP-2 LUMENAL DOMAIN PROTEIN SEQUENCE: (AMINO ACIDS R27-T432)
[406AA TOTAL]

RVFQKAVDQTIEKSMVLRNGTEVFDSWEKPPLPVYTQFYFFNVTNPEEILQGEIPILQEVGPYT
YREIRNKANIQFGENGTTISAVSNKAYVFERNQSVGDTNVDLIRTINIPLLTVVELTQLPLLKEII
EAMLKTYQQKLFVTHTVHELLWGYKDEILSLVHVFKPGISPNFGLFYEKNGTNDGDYVFLTG
EDNYLNFTKIVEWNGKTSLDWWTTDECNMINGTDGDSFHPLITKDEVLYVFPSDFCRSVHITF
SGFETVEGLPAFRYKVPAEILANTSENAGFCIPEGNCMDSGVLNVSICKNGVPIIMSFPHFYQAD
EKFVSAIKGMHPNKEEHETFVDINPLTGIILRAAKRFQINTYVKKIDGFVEMGNIRTMVFPVMY
LNESVLIDKETASRLKSVTNTT

FIG. 17A

HAMSTER LIMP-2 LUMENAL DOMAIN NUCLEOTIDE SEQUENCE: (BASE PAIRS 79-1296)
[1218 TOTAL]

CGAGTCTTCCAGAAGGCGGTGGACCAGACGATCGAGAAGAGTATGGTGTTAAGAAATGGT
ACTGAGGTCTTTGACTCCTGGGAGAAACCCCCTCTACCTGTGTACACCCAGTTCTACTTCT
TCAATGTCACCAATCCAGAGGAGATCCTCCAAGGAGAAATTCCCATACTTCAAGAAGTGG
GACCATACACATACAGGGAAATCAGGAACAAGGCAAACATCCAATTTGGAGAGAATGGA
ACAACCATATCGGCTGTTAGCAATAAGGCATATGTTTTGAACGAAACCAATCTGTTGGCG
ACACTAATGTTGACTTGATTAGAACGATAAATATTCCTCTGTTGACTGTTGTGGAACTGAC
CCAGCTGCCCCTGCTTAAGGAAATCATTGAGGCCATGCTGAAAACCTACCAGCAGAAGCT
GTTTGTGACTCACACAGTGCACGAGCTGCTCTGGGGCTATAAAGATGAGATCTTGTCCCTC
GTCCATGTTTTCAAGCCTGGAATCTCCCCTAACTTTGGCCTGTTCTACGAAAAAAATGGAA
CTAATGATGGAGATTATGTTTTCCTAACTGGAGAAGACAATTACCTCAACTTTACAAAAAT
TGTGGAGTGGAATGGTAAAACGTCACTGGACTGGTGGACCACAGACGAATGCAATATGAT
TAACGGGACAGATGGAGATTCTTTTCATCCACTGATAACCAAGGATGAAGTCCTCTATGTG
TTCCCCGTCTGACTTCTGCAGGTCAGTACATATAACTTTCAGTGGTTTTGAGACTGTGGAGG
GTTTGCCTGCTTTTCGGTATAAGGTGCCTGCAGAAATACTAGCCAACACCTCTGAAAATGC
AGGCTTCTGCATCCCTGAAGGAAACTGCATGGACTCGGGAGTGTTAATGTCAGCATCTG
CAAGAACGGTGTACCGATTATCATGTCTTTCCCACACTTTTACCAAGCTGATGAAAAGTTC
GTTTCTGCCATAAAAGGCATGCACCCAAACAAGGAAGAGCATGAGACATTTGTGGACATT
AATCCTTTGACTGGAATTATTTTAAGAGCAGCCAAGAGATTCCAAATCAACACTTATGTTA
AAAAAATAGATGGCTTTGTTGAAATGGGAAACATTAGGACTATGGTTTTCCCAGTGATGT
ATCTCAATGAGAGTGTTCTCATTGACAAAGAGACTGCAAGTCGATTGAAGTCCGTGACTA
ACACGACT

FIG. 17B

```
  1    MEFSSPSREE   CPKPLSRVSI   MAGSLTGLLL   LQAVSWASGA   RPCIPKSFGY   SSVVCVCNAT
 61    YCDSFDPPTF   PALGTFSRYE   STRSGRRMEL   SMGPIQANNT   GTGLLLTLQP   EQKFQKVKGF
121    GGAMTDAAAL   NILALSPPAQ   NLLLKSYFSE   EGIGYNIIRY   PMASCDFSIR   TYTYADTPDD
181    FQLHNFSLPE   EDTKLKIPLI   HRALQLAQRP   VSLLASPWTS   PTWLKTNGAV   NGKGSLKGQP
241    GDIYHQTWAR   YFVKFLDAYA   EHKLQFWAVT   AENEPSAGLL   SGYPFGCLGF   TPEHQRDFIA
301    RDLGPTLANS   THHNVRLLML   DDQRLLLPHW   AKVVLTDPEA   AKYVHGIAVH   WYLDFLAPAK
361    ATLGETHRLF   PNTMLFASEA   CVGSKFWEGS   VRLGSWDRGM   QYSHSIITNL   LYHVVGWTDW
421    NLALNPEGGP   NWVRNFVDSP   IIVDITKDTF   YKQPMFYHLG   HFSKFIPEGS   QRVGLVASQK
481    NDLDAVALMH   PDGSAVVVVL   NRSSKDVPLT   IKDPAVGFLE   TISPGYSIHT   YLWRRQ
```

FIG. 23

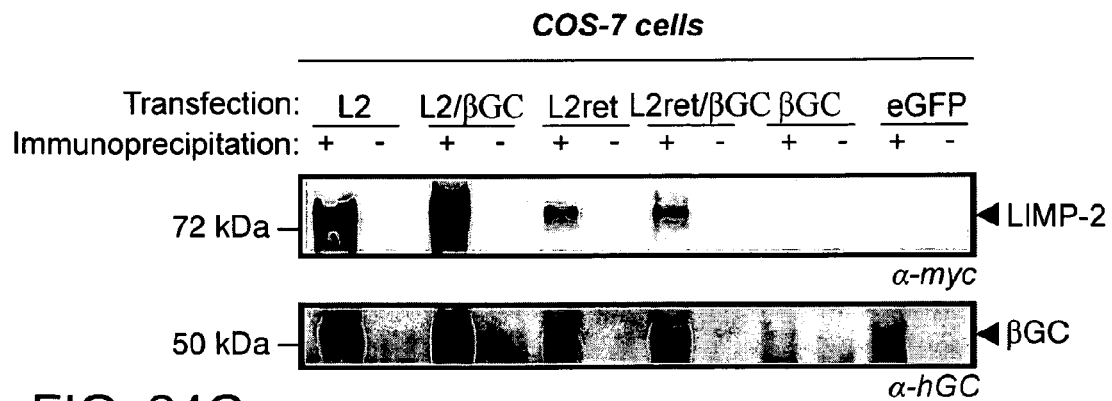

FIG. 24G  co-immunoprecipitation (LIMP-2 pull down)

```
Human       VLTVIEWSQVHFLREIIEAMLKAYQQKLFVTHTVDELLWGY 180
Macaca      VLTVIEWSQVHFLREIIEAMLKAYQQKLFVTHTVDELLWGY 180
Chimpanzee  VLTVIEWSQVRFLREIIEAMLKAYQQKLFVTHTVDELLWGY 180
Dog         VTAMEWAHLHFFRELIEALLKAYQQTLFVTHTVDELLWGY  149
Cattle      LTAMEWTQLFLLRDIIEALLKAYRQKLFVTHTVDELLWGY  391
Rat         LLTVVEMAQQPFLREIIEAMLKAYQQTLFVTHTVHELLWGY 180
Mouse       LLTVVDLAQLTLLRELIEAMLKAYQQKLFVTHTVHELLWGY 180
                        abcdefgabcdefga
```

FIG. 25B

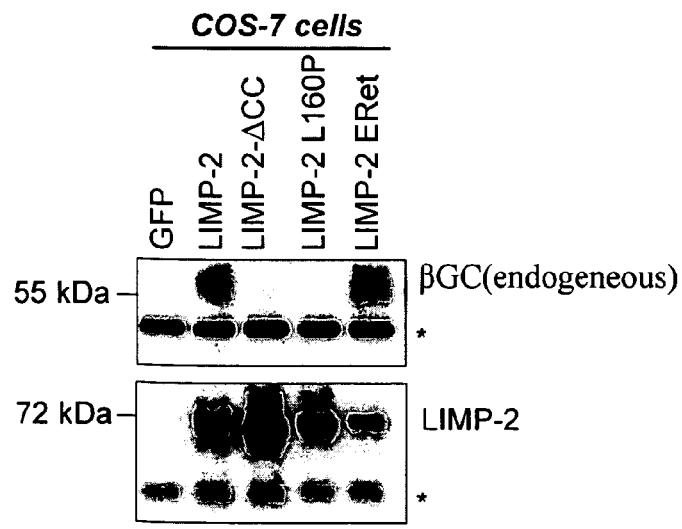

FIG. 25E  co-immuniprecipitation (LIMP-2 pull down)

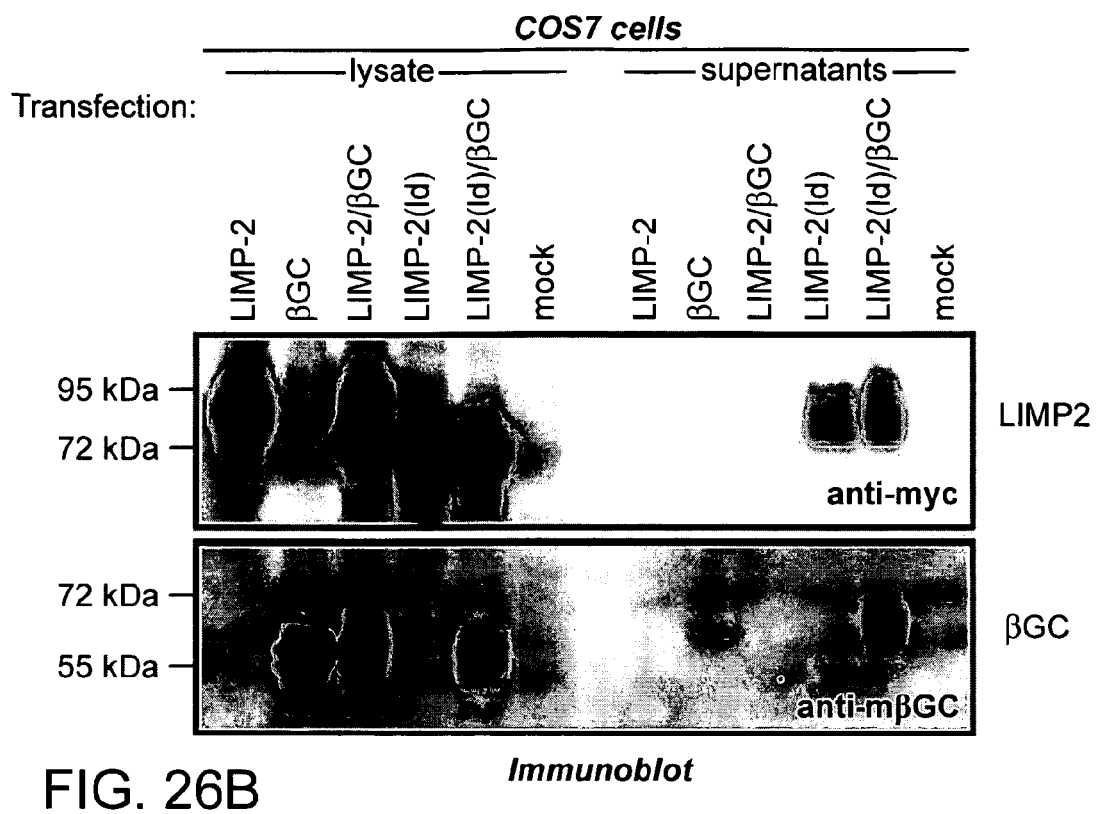
FIG. 26B
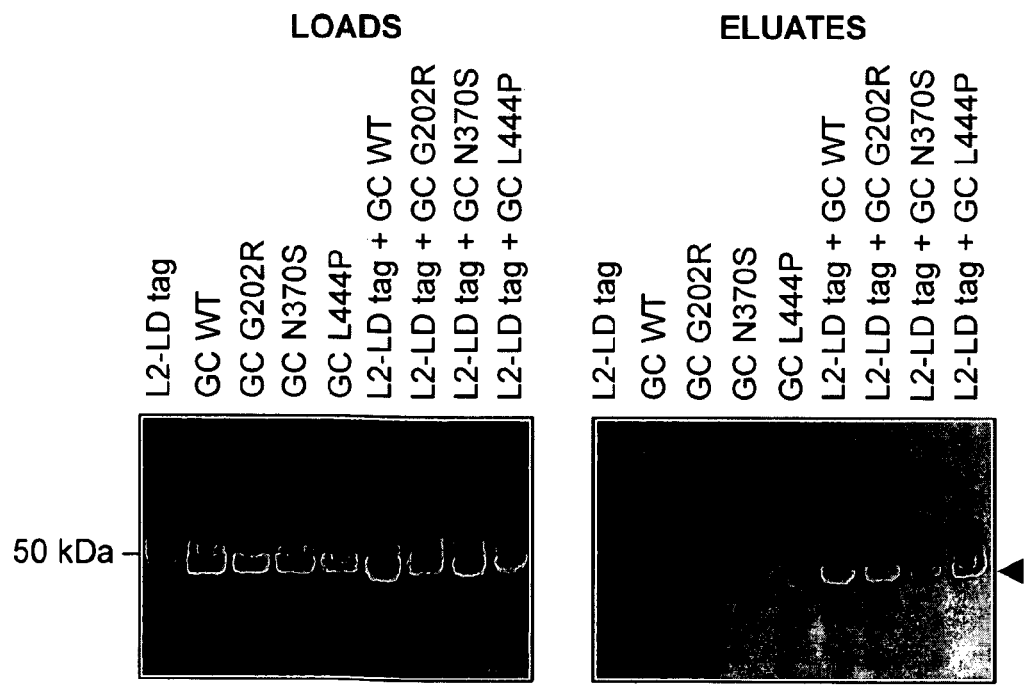
FIG. 27A  SDS-PAGE & Coomassie

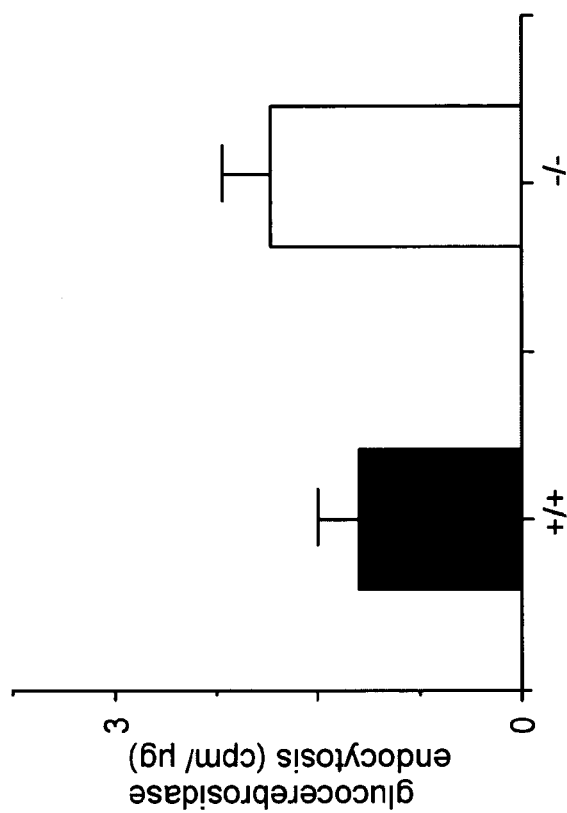
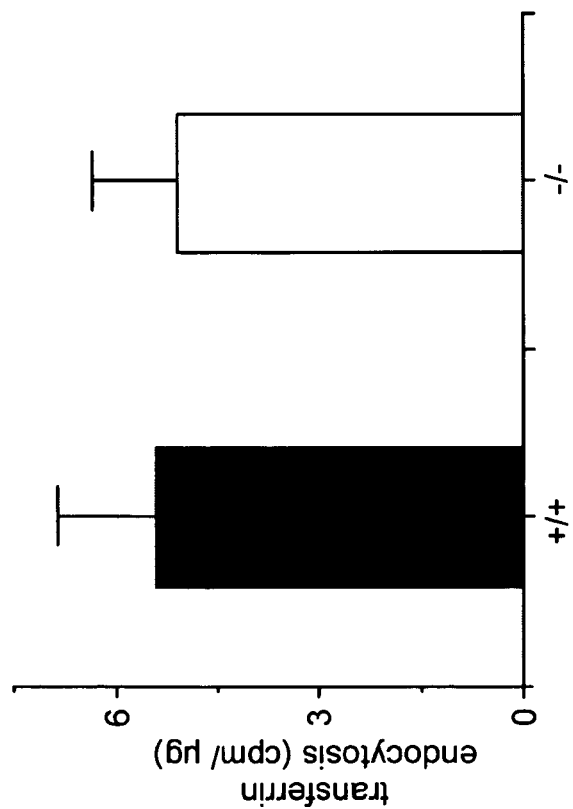
FIG. 34A
FIG. 34B

SEQUENCE LISTING

```
<160> NUMBER OF SEQ ID NOS: 35

<210> SEQ ID NO 1
<211> LENGTH: 1437
<212> TYPE: DNA
<213> ORGANISM: Unknown
<220> FEATURE:
<223> OTHER INFORMATION: hamster Limp-2

<400> SEQUENCE: 1
atgggcagat gttgcttcta cacggcgggg acactgtccc tgctgctgct ggtggctagt      60
gtcacgctgc tggtggctcg agtcttccag aaggcggtgg accagacgat cgagaagagt     120
atggtgttaa gaaatggtac tgaggtcttt gactcctggg agaaaccccc tctacctgtg     180
tacacccagt tctacttctt caatgtcacc aatccagagg agatcctcca aggagaaatt     240
cccatacttc aagaagtggg accatacaca tacagggaaa tcaggaacaa ggcaaacatc     300
```

```
caatttggag agaatggaac aaccatatcg gctgttagca ataaggcata tgtttttgaa    360
cgaaaccaat ctgttggcga cactaatgtt gacttgatta gaacgataaa tattcctctg    420
ttgactgttg tggaactgac ccagctgccc ctgcttaagg aaatcattga ggccatgctg    480
aaaacctacc agcagaagct gtttgtgact cacacagtgc acgagctgct ctggggctat    540
aaagatgaga tcttgtccct cgtccatgtt ttcaagcctg gaatctcccc taactttggc    600
ctgttctacg aaaaaaatgg aactaatgat ggagattatg ttttcctaac tggagaagac    660
aattacctca actttacaaa aattgtggag tggaatggta aaacgtcact ggactggtgg    720
accacagacg aatgcaatat gattaacggg acagatggag attcttttca tccactgata    780
accaaggatg aagtcctcta tgtgttcccg tctgacttct gcaggtcagt acatataact    840
ttcagtggtt ttgagactgt ggaggggtttg cctgcttttc ggtataaggt gcctgcagaa    900
atactagcca acacctctga aaatgcaggc ttctgcatcc ctgaaggaaa ctgcatggac    960
tcgggagtgt tgaatgtcag catctgcaag aacggtgtac cgattatcat gtctttccca   1020
cacttttacc aagctgatga aaagttcgtt tctgccataa aaggcatgca cccaaacaag   1080
gaagagcatg agacatttgt ggacattaat cctttgactg gaattatttt aagagcagcc   1140
aagagattcc aaatcaacac ttatgttaaa aaaatagatg gctttgttga atgggaaac    1200
attaggacta tggttttccc agtgatgtat ctcaatgaga gtgttctcat tgacaaagag   1260
actgcaagtc gattgaagtc cgtgactaac acgactttga tagtcaccaa catacccta    1320
atcatcatgg cattgggagt gttctttggc ttggttttca catggcttgc atgccgagga   1380
caggggccca tggatgaggg aacggcagat gaaagagcac ccctcatacg aacctaa     1437
```

<210> SEQ ID NO 2
<211> LENGTH: 406
<212> TYPE: PRT
<213> ORGANISM: Unknown
<220> FEATURE:
<223> OTHER INFORMATION: hamster Limp-2 lumenal domain

<400> SEQUENCE: 2

```
Arg Val Phe Gln Lys Ala Val Asp Gln Thr Ile Glu Lys Ser Met Val
 1               5                  10                  15
Leu Arg Asn Gly Thr Glu Val Phe Asp Ser Trp Glu Lys Pro Pro Leu
             20                  25                  30
Pro Val Tyr Thr Gln Phe Tyr Phe Asn Val Thr Asn Pro Glu Glu
         35                  40                  45
Ile Leu Gln Gly Glu Ile Pro Ile Leu Gln Glu Val Gly Pro Tyr Thr
     50                  55                  60
Tyr Arg Glu Ile Arg Asn Lys Ala Asn Ile Gln Phe Gly Glu Asn Gly
 65                  70                  75                  80
Thr Thr Ile Ser Ala Val Ser Asn Lys Ala Tyr Val Phe Glu Arg Asn
                 85                  90                  95
Gln Ser Val Gly Asp Thr Asn Val Asp Leu Ile Arg Thr Ile Asn Ile
            100                 105                 110
Pro Leu Leu Thr Val Val Glu Leu Thr Gln Leu Pro Leu Leu Lys Glu
        115                 120                 125
Ile Ile Glu Ala Met Leu Lys Thr Tyr Gln Gln Lys Leu Phe Val Thr
    130                 135                 140
His Thr Val His Glu Leu Leu Trp Gly Tyr Lys Asp Glu Ile Leu Ser
145                 150                 155                 160
Leu Val His Val Phe Lys Pro Gly Ile Ser Pro Asn Phe Gly Leu Phe
```

165                 170                 175
Tyr Glu Lys Asn Gly Thr Asn Asp Gly Asp Tyr Val Phe Leu Thr Gly
            180                 185                 190

Glu Asp Asn Tyr Leu Asn Phe Thr Lys Ile Val Glu Trp Asn Gly Lys
        195                 200                 205

Thr Ser Leu Asp Trp Trp Thr Thr Asp Glu Cys Asn Met Ile Asn Gly
    210                 215                 220

Thr Asp Gly Asp Ser Phe His Pro Leu Ile Thr Lys Asp Glu Val Leu
225                 230                 235                 240

Tyr Val Phe Pro Ser Asp Phe Cys Arg Ser Val His Ile Thr Phe Ser
                245                 250                 255

Gly Phe Glu Thr Val Glu Gly Leu Pro Ala Phe Arg Tyr Lys Val Pro
            260                 265                 270

Ala Glu Ile Leu Ala Asn Thr Ser Glu Asn Ala Gly Phe Cys Ile Pro
        275                 280                 285

Glu Gly Asn Cys Met Asp Ser Gly Val Leu Asn Val Ser Ile Cys Lys
    290                 295                 300

Asn Gly Val Pro Ile Ile Met Ser Phe Pro His Phe Tyr Gln Ala Asp
305                 310                 315                 320

Glu Lys Phe Val Ser Ala Ile Lys Gly Met His Pro Asn Lys Glu Glu
                325                 330                 335

His Glu Thr Phe Val Asp Ile Asn Pro Leu Thr Gly Ile Ile Leu Arg
            340                 345                 350

Ala Ala Lys Arg Phe Gln Ile Asn Thr Tyr Val Lys Lys Ile Asp Gly
        355                 360                 365

Phe Val Glu Met Gly Asn Ile Arg Thr Met Val Phe Pro Val Met Tyr
    370                 375                 380

Leu Asn Glu Ser Val Leu Ile Asp Lys Glu Thr Ala Ser Arg Leu Lys
385                 390                 395                 400

Ser Val Thr Asn Thr Thr
                405

<210> SEQ ID NO 3
<211> LENGTH: 1437
<212> TYPE: DNA
<213> ORGANISM: Unknown
<220> FEATURE:
<223> OTHER INFORMATION: human Limp-2

<400> SEQUENCE: 3
atgggccgat gctgcttcta cacggcgggg acgttgtccc tgctcctgct ggtgaccagc     60
gtcacgctgc tggtggcccg ggtcttccag aaggctgtag accagagtat cgagaagaaa    120
attgtgttaa ggaatggtac tgaggcattt gactcctggg agaagccccc tctgcctgtg    180
tatactcagt tctatttctt caatgtcacc aatccagagg agatcctcag aggggagacc    240
cctcgggtgg aagaagtggg gccatacacc tacagggaac tcagaaacaa agcaaatatt    300
caatttggag ataatggaac aacaatatct gctgttagca acaaggccta tgttttgaa    360 cgagaccaat ctgttggaga ccctaaaatt gacttaatta gaacattaaa tattcctgta    420
ttgactgtca tagagtggtc ccaggtgcac ttcctcaggg agatcatcga ggccatgttg    480
aaagcctatc agcagaagct ctttgtgact cacacagttg acgaattgct ctggggctac    540
aaagatgaaa tcttgtccct tatccatgtt tcaggcccg atatctctcc tatttggc    600 ctattctatg agaaaaatgg gactaatgat ggagactatg ttttctaac tggagaagac    660

```
agttacctta actttacaaa aattgtggaa tggaatggga aaacgtcact tgactggtgg    720
ataacagaca agtgcaatat gattaatgga acagatggag attcttttca cccactaata    780
accaaagatg aggtccttta tgtcttccca tctgactttt gcaggtcagt gtatattact    840
ttcagtgact atgagagtgt acagggactg cctgcctttc ggtataaagt tcctgcagaa    900
atattagcca atacgtcaga caatgccggc ttctgtatac ctgagggaaa ctgcctgggc    960
tcaggagttc tgaatgtcag catctgcaag aatggtgcac ccatcattat gtctttccca   1020
cactttttacc aagcagatga gaggtttgtt tctgccatag aaggcatgca cccaaatcag   1080
gaagaccatg agacatttgt ggacattaat cctttgactg aataatcct aaaagcagcc    1140
aagaggttcc aaatcaacat ttatgtcaaa aaattagatg actttgttga acgggagac    1200
attgaaacca tggttttccc agtgatgtac ctcaatgaga gtgttcacat tgataaagag   1260
acggcgagtc gactgaagtc tatgattaac actactttga tcatcaccaa catacctac   1320
atcatcatgg cgctgggtgt gttctttggt ttggtttttta cctggcttgc atgcaaagga   1380
cagggatcca tggatgaggg aacagcggat gaaagagcac ccctcattcg aacctaa     1437
```

<210> SEQ ID NO 4
<211> LENGTH: 406
<212> TYPE: PRT
<213> ORGANISM: Unknown
<220> FEATURE:
<223> OTHER INFORMATION: human Limp-2 lumenal domain

<400> SEQUENCE: 4

```
Arg Val Phe Gln Lys Ala Val Asp Gln Ser Ile Glu Lys Lys Ile Val
  1               5                  10                  15

Leu Arg Asn Gly Thr Glu Ala Phe Asp Ser Trp Glu Lys Pro Pro Leu
                 20                  25                  30

Pro Val Tyr Thr Gln Phe Tyr Phe Asn Val Thr Asn Pro Glu Glu
             35                  40                  45

Ile Leu Arg Gly Glu Thr Pro Arg Val Glu Val Gly Pro Tyr Thr
         50                  55                  60

Tyr Arg Glu Leu Arg Asn Lys Ala Asn Ile Gln Phe Gly Asp Asn Gly
 65                  70                  75                  80

Thr Thr Ile Ser Ala Val Ser Asn Lys Ala Tyr Val Phe Glu Arg Asp
                 85                  90                  95

Gln Ser Val Gly Asp Pro Lys Ile Asp Leu Ile Arg Thr Leu Asn Ile
            100                 105                 110

Pro Val Leu Thr Val Ile Glu Trp Ser Gln Val His Phe Leu Arg Glu
        115                 120                 125

Ile Ile Glu Ala Met Leu Lys Ala Tyr Gln Gln Lys Leu Phe Val Thr
    130                 135                 140

His Thr Val Asp Glu Leu Leu Trp Gly Tyr Lys Asp Glu Ile Leu Ser
145                 150                 155                 160

Leu Ile His Val Phe Arg Pro Asp Ile Ser Pro Tyr Phe Gly Leu Phe
                165                 170                 175

Tyr Glu Lys Asn Gly Thr Asn Asp Gly Asp Tyr Val Phe Leu Thr Gly
            180                 185                 190

Glu Asp Ser Tyr Leu Asn Phe Thr Lys Ile Val Glu Trp Asn Gly Lys
        195                 200                 205

Thr Ser Leu Asp Trp Trp Ile Thr Asp Lys Cys Asn Met Ile Asn Gly
    210                 215                 220

Thr Asp Gly Asp Ser Phe His Pro Leu Ile Thr Lys Asp Glu Val Leu
```

```
                225                 230                 235                 240
        Tyr Val Phe Pro Ser Asp Phe Cys Arg Ser Val Tyr Ile Thr Phe Ser
                            245                 250                 255
        Asp Tyr Glu Ser Val Gln Gly Leu Pro Ala Phe Arg Tyr Lys Val Pro
                        260                 265                 270
        Ala Glu Ile Leu Ala Asn Thr Ser Asp Asn Ala Gly Phe Cys Ile Pro
                    275                 280                 285
        Glu Gly Asn Cys Leu Gly Ser Gly Val Leu Asn Val Ser Ile Cys Lys
                290                 295                 300
        Asn Gly Ala Pro Ile Ile Met Ser Phe Pro His Phe Tyr Gln Ala Asp
        305                 310                 315                 320
        Glu Arg Phe Val Ser Ala Ile Glu Gly Met His Pro Asn Gln Glu Asp
                            325                 330                 335
        His Glu Thr Phe Val Asp Ile Asn Pro Leu Thr Gly Ile Ile Leu Lys
                        340                 345                 350
        Ala Ala Lys Arg Phe Gln Ile Asn Ile Tyr Val Lys Lys Leu Asp Asp
                    355                 360                 365
        Phe Val Glu Thr Gly Asp Ile Arg Thr Met Val Phe Pro Val Met Tyr
                370                 375                 380
        Leu Asn Glu Ser Val His Ile Asp Lys Glu Thr Ala Ser Arg Leu Lys
        385                 390                 395                 400
        Ser Met Ile Asn Thr Thr
                    405

<210> SEQ ID NO 5
<211> LENGTH: 1437
<212> TYPE: DNA
<213> ORGANISM: Unknown
<220> FEATURE:
<223> OTHER INFORMATION: mouse Limp-2

<400> SEQUENCE: 5
atgggcagat gctgcttcta cacggcgggg acgctgtctc tgctgctgct ggtgaccagc      60
gtcacgctgc tagtggctcg agtctttcag aaggcggtag accagacgat cgagaagaat     120
atggtattac aaaatggcac caaggtcttt aattcctggg agaagccccc tctacctgtg     180
tacatccagt tttatttctt caatgtcacc aatcctgagg gatcctcca aggagaaatc      240 cccctactag aagaagtggg gccatacacc tacagggagc tccggaacaa ggcaaatatt     300
cagtttggag aaaatggaac aactatatct gctgtcacca taaggcata tgttttgaa      360 cgaaaccaat ctgttggaga tcctaacgtt gacttgatta gaacaataaa tattcctctg     420
ttgactgtcg tggatctggc ccagctgacc ctgctcaggg agcttatcga agccatgctg     480
aaagcctatc agcagaagtt gtttgtgatt cacaccgtgc acgaactgct ctggggctac     540
aaagatgaga tcttgtccct cgtccatatt ttcaaacctg acgtctcccc gaatttcggc     600
ctgttctatg agagaaatgg aacgaatgac ggggagtacg tgtttctgac tggagaggac     660
aattacctta acttttcaaa atcgtggag tggaatggaa aaacgtcgct ggactggtgg     720
accacagaca catgcaatat gattaacggg acagacggag actcttttca tccgctgata     780
agcaaggatg aggtcctgta cctcttcccg tcagacttgt gcaggtcagt acatatcact     840
ttcagcagct ttgagaacgt agaaggactg cctgcttttc ggtataaggt gcctgcagaa     900
atactagcca cacctccga aaacgctggc ttctgtatac ccgagggaaa ctgcatggac      960
tcaggggtgt tgaacatcag catctgcaag aatggtgcac ccattatcat gtctttccca    1020
```

-continued

```
cacttttacc aagccgacga gaagttcgtt tctgccataa aaggcatgca tcccaacaag    1080
gaagagcatg agtcgtttgt ggacattaat cccttgactg gaattatttt gagaggggcc    1140
aagagattcc agatcaacac ttacgttagg aaactggatg actttgttga aacgggagac    1200
atcaggacta tggttttccc agtgatgtat ctcaatgaga gtgtcctcat tgacaaagag    1260
accgcaaatc aactgaagtc tgtgattaac acgactttgg ttgtcaccaa atacccctac    1320
atcattatgg cactgggtgt gttctttggc ttggttttca cgtggctggc gtgtcgagga    1380 cagggtgtcta tggatgaggg aactgcagat gaaagagcac ccctcatacg aacctaa      1437
```

<210> SEQ ID NO 6
<211> LENGTH: 406
<212> TYPE: PRT
<213> ORGANISM: Unknown
<220> FEATURE:
<223> OTHER INFORMATION: mouse Limp-2 lumenal domain

<400> SEQUENCE: 6

```
Arg Val Phe Gln Lys Ala Val Asp Gln Thr Ile Glu Lys Asn Met Val
 1               5                   10                  15

Leu Gln Asn Gly Thr Lys Val Phe Asn Ser Trp Glu Lys Pro Pro Leu
             20                  25                  30

Pro Val Tyr Ile Gln Phe Tyr Phe Asn Val Thr Asn Pro Glu Glu
         35                  40                  45

Ile Leu Gln Gly Glu Ile Pro Leu Leu Glu Glu Val Gly Pro Tyr Thr
     50                  55                  60

Tyr Arg Glu Leu Arg Asn Lys Ala Asn Ile Gln Phe Gly Glu Asn Gly
 65                  70                  75                  80

Thr Thr Ile Ser Ala Val Thr Asn Lys Ala Tyr Val Phe Glu Arg Asn
                 85                  90                  95

Gln Ser Val Gly Asp Pro Asn Val Asp Leu Ile Arg Thr Ile Asn Ile
            100                 105                 110

Pro Leu Leu Thr Val Val Asp Leu Ala Gln Leu Thr Leu Leu Arg Glu
        115                 120                 125

Leu Ile Glu Ala Met Leu Lys Ala Tyr Gln Gln Lys Leu Phe Val Ile
    130                 135                 140

His Thr Val His Glu Leu Leu Trp Gly Tyr Lys Asp Glu Ile Leu Ser
145                 150                 155                 160

Leu Val His Ile Phe Lys Pro Asp Val Ser Pro Asn Phe Gly Leu Phe
                165                 170                 175

Tyr Glu Arg Asn Gly Thr Asn Asp Gly Glu Tyr Val Phe Leu Thr Gly
            180                 185                 190

Glu Asp Asn Tyr Leu Asn Phe Ser Lys Ile Val Glu Trp Asn Gly Lys
        195                 200                 205

Thr Ser Leu Asp Trp Trp Thr Thr Asp Thr Cys Asn Met Ile Asn Gly
    210                 215                 220

Thr Asp Gly Asp Ser Phe His Pro Leu Ile Ser Lys Asp Glu Val Leu
225                 230                 235                 240

Tyr Leu Phe Pro Ser Asp Leu Cys Arg Ser Val His Ile Thr Phe Ser
                245                 250                 255

Ser Phe Glu Asn Val Glu Gly Leu Pro Ala Phe Arg Tyr Lys Val Pro
            260                 265                 270

Ala Glu Ile Leu Ala Asn Thr Ser Glu Asn Ala Gly Phe Cys Ile Pro
        275                 280                 285

Glu Gly Asn Cys Met Asp Ser Gly Val Leu Asn Ile Ser Ile Cys Lys
```

```
            290                 295                 300
Asn Gly Ala Pro Ile Ile Met Ser Phe Pro His Phe Tyr Gln Ala Asp
305                 310                 315                 320

Glu Lys Phe Val Ser Ala Ile Lys Gly Met His Pro Asn Lys Glu Glu
                325                 330                 335

His Glu Ser Phe Val Asp Ile Asn Pro Leu Thr Gly Ile Ile Leu Arg
                340                 345                 350

Gly Ala Lys Arg Phe Gln Ile Asn Thr Tyr Val Arg Lys Leu Asp Asp
                355                 360                 365

Phe Val Glu Thr Gly Asp Ile Arg Thr Met Val Phe Pro Val Met Tyr
            370                 375                 380

Leu Asn Glu Ser Val Leu Ile Asp Lys Glu Thr Ala Asn Gln Leu Lys
385                 390                 395                 400

Ser Val Ile Asn Thr Thr
                405

<210> SEQ ID NO 7
<211> LENGTH: 1437
<212> TYPE: DNA
<213> ORGANISM: Unknown
<220> FEATURE:
<223> OTHER INFORMATION: rat Limp-2

<400> SEQUENCE: 7
atggcccgat gctgcttcta cacggcgggg acactgtctc tgctgctgct ggtgaccagt    60
gtcacgctgc tagtggctcg agtctttcag aaggcagtgg accagacgat cgagaagaat   120
atggtattac aaaatggtac caaggtcttt gattcctggg agaagccccc tctacctgtg   180
tacatccagt tttatttctt caatgtcacc aatccagagg gatcctcca aggagaaatc    240 cccctgctag aagaagtggg gccgtacacc tacagggagc tcaggaacaa ggcaaacgtt   300
cagtttggag aaaatggaac aaccatatct gccgtcacca ataaggcata ttttttgaa    360 cgaaaccagt ctgttggaga ccctaccgtt gacttgatta gaacaataaa tattcctctg   420
ttgactgttg tggaaatggc ccagcagccc ttcctcaggg agatcatcga ggccatgctg   480
aaagcttatc agcagacgct gtttgtcact cacactgtac atgaactgct ctggggctac   540
aaagatgagg tcttgtcgct cgtccatatt ttcagacctg acgtctcccc taactttggc   600
ctgttctatg agagaaatgg aactaatgat ggggagtatg ttttttctga ctggagaggac   660 aattacctga actttacaaa aattgtggag tggaatggaa aaacgtcgct ggactggtgg   720
acgacggaca cgtgcaatat gatcaacggg acagacggag attcttttca cccattaata   780
agcaaggatg agaccctgta catcttccca tctgacttct gcaggtccgt ctatataact   840
ttcagtagct ttgagaacgt agaaggactg cctgcttttc ggtataaggt gcctgcagaa   900
atactagcca attcctccga aaacgctggc ttctgtatac ccgagggaaa ctgcatggac   960
gcgggagtgc tgaacgtcag catttgcaag aatggtgcgc ccattatcat gtcttcccca  1020
cacttttacc aagccgacga gaagttcgtt tcggccataa aaggcatgcg tccaaacaag  1080
gaagaacatg agtcatttgt ggacattaat ccttttgacag gaattatttt aagaggggcc  1140
aagagattcc aaatcaacac gtacgttaag aagctggatg actttgtgga acgggaaac   1200 attaggacta tggttttccc agtgatgtat ctcaatgaga gtgttctcat tgacaaagag  1260
actgcaagtc aactgaagtc tgtgattaac acaactttga ttgtcaccaa catacccctac  1320 atcatcatgg cactgggcgt gttctttggc ttgattttca cgtggctggc gtgtcgagga  1380
```

```
cagggqtcta cggatgaggg aactgcagat gaaagggcac ccctcatacg gacctaa    1437
```

<210> SEQ ID NO 8
<211> LENGTH: 406
<212> TYPE: PRT
<213> ORGANISM: Unknown
<220> FEATURE:
<223> OTHER INFORMATION: rat Limp-2 lumenal domain

<400> SEQUENCE: 8

```
Arg Val Phe Gln Lys Ala Val Asp Gln Thr Ile Glu Lys Asn Met Val
 1               5                  10                  15

Leu Gln Asn Gly Thr Lys Val Phe Asp Ser Trp Glu Lys Pro Pro Leu
            20                  25                  30

Pro Val Tyr Ile Gln Phe Tyr Phe Asn Val Thr Asn Pro Glu Glu
        35                  40                  45

Ile Leu Gln Gly Glu Ile Pro Leu Leu Glu Glu Val Gly Pro Tyr Thr
    50                  55                  60

Tyr Arg Glu Leu Arg Asn Lys Ala Asn Val Gln Phe Gly Glu Asn Gly
 65                  70                  75                  80

Thr Thr Ile Ser Ala Val Thr Asn Lys Ala Tyr Ile Phe Glu Arg Asn
                85                  90                  95

Gln Ser Val Gly Asp Pro Thr Val Asp Leu Ile Arg Thr Ile Asn Ile
            100                 105                 110

Pro Leu Leu Thr Val Val Glu Met Ala Gln Gln Pro Phe Leu Arg Glu
        115                 120                 125

Ile Ile Glu Ala Met Leu Lys Ala Tyr Gln Gln Thr Leu Phe Val Thr
    130                 135                 140

His Thr Val His Glu Leu Leu Trp Gly Tyr Lys Asp Glu Val Leu Ser
145                 150                 155                 160

Leu Val His Ile Phe Arg Pro Asp Val Ser Pro Asn Phe Gly Leu Phe
                165                 170                 175

Tyr Glu Arg Asn Gly Thr Asn Asp Gly Glu Tyr Val Phe Leu Thr Gly
            180                 185                 190

Glu Asp Asn Tyr Leu Asn Phe Thr Lys Ile Val Glu Trp Asn Gly Lys
        195                 200                 205

Thr Ser Leu Asp Trp Trp Thr Thr Asp Thr Cys Asn Met Ile Asn Gly
    210                 215                 220

Thr Asp Gly Asp Ser Phe His Pro Leu Ile Ser Lys Asp Glu Thr Leu
225                 230                 235                 240

Tyr Ile Phe Pro Ser Asp Phe Cys Arg Ser Val Tyr Ile Thr Phe Ser
                245                 250                 255

Ser Phe Glu Asn Val Glu Gly Leu Pro Ala Phe Arg Tyr Lys Val Pro
            260                 265                 270

Ala Glu Ile Leu Ala Asn Ser Ser Glu Asn Ala Gly Phe Cys Ile Pro
        275                 280                 285

Glu Gly Asn Cys Met Asp Ala Gly Val Leu Asn Val Ser Ile Cys Lys
    290                 295                 300

Asn Gly Ala Pro Ile Ile Met Ser Phe Pro His Phe Tyr Gln Ala Asp
305                 310                 315                 320

Glu Lys Phe Val Ser Ala Ile Lys Gly Met Arg Pro Asn Lys Glu Glu
                325                 330                 335

His Glu Ser Phe Val Asp Ile Asn Pro Leu Thr Gly Ile Ile Leu Arg
            340                 345                 350

Gly Ala Lys Arg Phe Gln Ile Asn Thr Tyr Val Lys Lys Leu Asp Asp
```

```
                      355                 360                 365
Phe Val Glu Thr Gly Asn Ile Arg Thr Met Val Phe Pro Val Met Tyr
                  370                 375                 380

Leu Asn Glu Ser Val Leu Ile Asp Lys Glu Thr Ala Ser Gln Leu Lys
385                 390                 395                 400

Ser Val Ile Asn Thr Thr
                405

<210> SEQ ID NO 9

<400> SEQUENCE: 9

000

<210> SEQ ID NO 10
<211> LENGTH: 1218
<212> TYPE: DNA
<213> ORGANISM: Unknown
<220> FEATURE:
<223> OTHER INFORMATION: hamster Limp-2 lumenal domain

<400> SEQUENCE: 10
cgagtcttcc agaaggcggt ggaccagacg atcgagaaga gtatggtgtt aagaaatggt      60
actgaggtct tgactcctg ggagaaaccc cctctacctg tgtacaccca gttctacttc     120
ttcaatgtca ccaatccaga ggagatcctc aaggagaaa tcccatact tcaagaagtg      180 ggaccataca catacaggga atcaggaac aaggcaaaca tccaatttgg agagaatgga     240
acaaccatat cggctgttag caataaggca tatgttttg aacgaaacca atctgttggc     300
gacactaatg ttgacttgat tagaacgata aatattcctc tgttgactgt tgtggaactg    360
acccagctgc ccctgcttaa ggaaatcatt gaggccatgc tgaaaaccta ccagcagaag    420
ctgtttgtga ctcacacagt gcacgagctg ctctggggct ataaagatga gatcttgtcc    480
ctcgtccatg ttttcaagcc tggaatctcc cctaactttg gcctgttcta cgaaaaaaat    540
ggaactaatg atggagatta tgtttttccta actggagaag acaattacct caactttaca   600
aaaattgtgg agtggaatgg taaaacgtca ctggactggt ggaccacaga cgaatgcaat    660
atgattaacg ggacagatgg agattctttt catccactga taaccaagga tgaagtcctc    720
tatgtgttcc cgtctgactt ctgcaggtca gtacatataa cttccagtgg ttttgagact    780
gtggagggtt tgcctgctt tcggtataag gtgcctgcag aaatactagc caacacctct    840
gaaaatgcag gcttctgcat ccctgaagga aactgcatgg actcgggagt gttgaatgtc    900
agcatctgca agaacggtgt accgattatc atgtctttcc cacactttta ccaagctgat   960
gaaaagttcg tttctgccat aaaaggcatg caccccaaaca aggaagagca tgagacattt  1020
gtggacatta tcctttgac tggaattatt ttaagagcag ccaagagatt ccaaatcaac    1080
acttatgtta aaaaaataga tggctttgtt gaaatgggaa acattaggac tatggttttc   1140
ccagtgatgt atctcaatga gagtgttctc attgacaaag agactgcaag tcgattgaag   1200
tccgtgacta acacgact                                                1218

<210> SEQ ID NO 11
<211> LENGTH: 536
<212> TYPE: PRT
<213> ORGANISM: Unknown
<220> FEATURE:
<223> OTHER INFORMATION: imiglucerase

<400> SEQUENCE: 11
```

```
Met Glu Phe Ser Ser Pro Ser Arg Glu Glu Cys Pro Lys Pro Leu Ser
  1               5                  10                  15

Arg Val Ser Ile Met Ala Gly Ser Leu Thr Gly Leu Leu Leu Leu Gln
             20                  25                  30

Ala Val Ser Trp Ala Ser Gly Ala Arg Pro Cys Ile Pro Lys Ser Phe
         35                  40                  45

Gly Tyr Ser Ser Val Val Cys Val Cys Asn Ala Thr Tyr Cys Asp Ser
     50                  55                  60

Phe Asp Pro Pro Thr Phe Pro Ala Leu Gly Thr Phe Ser Arg Tyr Glu
 65                  70                  75                  80

Ser Thr Arg Ser Gly Arg Arg Met Glu Leu Ser Met Gly Pro Ile Gln
                 85                  90                  95

Ala Asn Asn Thr Gly Thr Gly Leu Leu Leu Thr Leu Gln Pro Glu Gln
             100                 105                 110

Lys Phe Gln Lys Val Lys Gly Phe Gly Gly Ala Met Thr Asp Ala Ala
         115                 120                 125

Ala Leu Asn Ile Leu Ala Leu Ser Pro Pro Ala Gln Asn Leu Leu Leu
     130                 135                 140

Lys Ser Tyr Phe Ser Glu Glu Gly Ile Gly Tyr Asn Ile Ile Arg Tyr
145                 150                 155                 160

Pro Met Ala Ser Cys Asp Phe Ser Ile Arg Thr Tyr Thr Tyr Ala Asp
                 165                 170                 175

Thr Pro Asp Asp Phe Gln Leu His Asn Phe Ser Leu Pro Glu Glu Asp
             180                 185                 190

Thr Lys Leu Lys Ile Pro Leu Ile His Arg Ala Leu Gln Leu Ala Gln
         195                 200                 205

Arg Pro Val Ser Leu Leu Ala Ser Pro Trp Thr Ser Pro Thr Trp Leu
     210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                 245                 250                 255

Asp Ala Tyr Ala Glu His Lys Leu Gln Phe Trp Ala Val Thr Ala Glu
             260                 265                 270

Asn Glu Pro Ser Ala Gly Leu Leu Ser Gly Tyr Pro Phe Gly Cys Leu
         275                 280                 285

Gly Phe Thr Pro Glu His Gln Arg Asp Phe Ile Ala Arg Asp Leu Gly
     290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                 325                 330                 335

Asp Pro Glu Ala Ala Lys Tyr Val His Gly Ile Ala Val His Trp Tyr
             340                 345                 350

Leu Asp Phe Leu Ala Pro Ala Lys Ala Thr Leu Gly Glu Thr His Arg
         355                 360                 365

Leu Phe Pro Asn Thr Met Leu Phe Ala Ser Glu Ala Cys Val Gly Ser
     370                 375                 380

Lys Phe Trp Glu Gly Ser Val Arg Leu Gly Ser Trp Asp Arg Gly Met
385                 390                 395                 400

Gln Tyr Ser His Ser Ile Ile Thr Asn Leu Leu Tyr His Val Val Gly
                 405                 410                 415
```

```
Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535
```

```
<210> SEQ ID NO 12
<211> LENGTH: 25
<212> TYPE: RNA
<213> ORGANISM: Unknown
<220> FEATURE:
<223> OTHER INFORMATION: Limp-2 RNAi

<400> SEQUENCE: 12
gaaagccaaa cuaggagaca cgaaa                                              25

<210> SEQ ID NO 13
<211> LENGTH: 25
<212> TYPE: RNA
<213> ORGANISM: Unknown
<220> FEATURE:
<223> OTHER INFORMATION: Limp-2 RNAi

<400> SEQUENCE: 13
ccaaagagag augcaaccua uuugu                                              25

<210> SEQ ID NO 14
<211> LENGTH: 25
<212> TYPE: RNA
<213> ORGANISM: Unknown
<220> FEATURE:
<223> OTHER INFORMATION: Limp-2 RNAi

<400> SEQUENCE: 14
gauggagagg cugacaucau gauca                                              25

<210> SEQ ID NO 15
<211> LENGTH: 19
<212> TYPE: RNA
<213> ORGANISM: Unknown
<220> FEATURE:
<223> OTHER INFORMATION: Limp-2 RNAi

<400> SEQUENCE: 15
cgagaagagu auguguua                                                      19

<210> SEQ ID NO 16
<211> LENGTH: 19
<212> TYPE: RNA
<213> ORGANISM: Unknown
<220> FEATURE:
<223> OTHER INFORMATION: Limp-2 RNAi
```

-continued

```
<400> SEQUENCE: 16
gaacaaggca aacauccaa                                                  19

<210> SEQ ID NO 17
<211> LENGTH: 19
<212> TYPE: RNA
<213> ORGANISM: Unknown
<220> FEATURE:
<223> OTHER INFORMATION: Limp-2 RNAi

<400> SEQUENCE: 17
uaaggugccu gcagaaaua                                                  19

<210> SEQ ID NO 18
<211> LENGTH: 19
<212> TYPE: RNA
<213> ORGANISM: Unknown
<220> FEATURE:
<223> OTHER INFORMATION: Limp-2 RNAi

<400> SEQUENCE: 18
guucguuucu gccauaaaa                                                  19

<210> SEQ ID NO 19
<211> LENGTH: 19
<212> TYPE: RNA
<213> ORGANISM: Unknown
<220> FEATURE:
<223> OTHER INFORMATION: Limp-2 RNAi

<400> SEQUENCE: 19
agacauuugu ggacauuaa                                                  19

<210> SEQ ID NO 20
<211> LENGTH: 13
<212> TYPE: PRT
<213> ORGANISM: Unknown
<220> FEATURE:
<223> OTHER INFORMATION: amino acid 382-394 of mouse Limp-2

<400> SEQUENCE: 20

Arg Phe Gln Ile Asn Thr Tyr Val Arg Lys Leu Asp Asp
 1               5                  10

<210> SEQ ID NO 21
<211> LENGTH: 15
<212> TYPE: PRT
<213> ORGANISM: Unknown
<220> FEATURE:
<223> OTHER INFORMATION: amino acid 464-478 of mouse Limp-2

<400> SEQUENCE: 21

Met Asp Glu Gly Thr Ala Asp Glu Arg Ala Pro Leu Ile Arg Thr
 1               5                  10                  15

<210> SEQ ID NO 22
<211> LENGTH: 14
<212> TYPE: PRT
<213> ORGANISM: Unknown
<220> FEATURE:
<223> OTHER INFORMATION: c terminal 14 amino acid of human 22c-
      adrenergic receptor

<400> SEQUENCE: 22

Lys His Ile Leu Phe Arg Arg Arg Arg Arg Gly Phe Arg Gln
```

-continued

```
1               5                   10
```

<210> SEQ ID NO 23
<211> LENGTH: 41
<212> TYPE: PRT
<213> ORGANISM: Unknown
<220> FEATURE:
<223> OTHER INFORMATION: human Limp-2 coiled coil region

<400> SEQUENCE: 23

```
Val Leu Thr Val Ile Glu Trp Ser Gln Val His Phe Leu Arg Glu Ile
1               5                   10                  15

Ile Glu Ala Met Leu Lys Ala Tyr Gln Gln Lys Leu Phe Val Thr His
                20                  25                  30

Thr Val Asp Glu Leu Leu Trp Gly Tyr
        35                  40
```

<210> SEQ ID NO 24
<211> LENGTH: 41
<212> TYPE: PRT
<213> ORGANISM: Unknown
<220> FEATURE:
<223> OTHER INFORMATION: macaca Limp-2 coiled coil region

<400> SEQUENCE: 24

```
Val Leu Thr Val Ile Glu Trp Ser Gln Val His Phe Leu Arg Glu Ile
1               5                   10                  15

Ile Glu Ala Met Leu Lys Ala Tyr Gln Gln Lys Leu Phe Val Thr His
                20                  25                  30

Thr Val Asp Glu Leu Leu Trp Gly Tyr
        35                  40
```

<210> SEQ ID NO 25
<211> LENGTH: 41
<212> TYPE: PRT
<213> ORGANISM: Unknown
<220> FEATURE:
<223> OTHER INFORMATION: chimpanzee Limp-2 coiled coil region

<400> SEQUENCE: 25

```
Val Leu Thr Val Ile Glu Trp Ser Gln Val Arg Phe Leu Arg Glu Ile
1               5                   10                  15

Ile Glu Ala Met Leu Lys Ala Tyr Gln Gln Lys Leu Phe Val Thr His
                20                  25                  30

Thr Val Asp Glu Leu Leu Trp Gly Tyr
        35                  40
```

<210> SEQ ID NO 26
<211> LENGTH: 40
<212> TYPE: PRT
<213> ORGANISM: Unknown
<220> FEATURE:
<223> OTHER INFORMATION: dog Limp-2 coiled coil region

<400> SEQUENCE: 26

```
Val Thr Ala Met Glu Trp Ala His Leu His Phe Phe Arg Glu Leu Ile
1               5                   10                  15

Glu Ala Leu Leu Lys Ala Tyr Gln Gln Thr Leu Phe Val Thr His Thr
                20                  25                  30

Val Asp Glu Leu Leu Trp Gly Tyr
        35                  40
```

```
<210> SEQ ID NO 27
<211> LENGTH: 40
<212> TYPE: PRT
<213> ORGANISM: Unknown
<220> FEATURE:
<223> OTHER INFORMATION: cattle Limp-2 coiled coil region

<400> SEQUENCE: 27

Leu Thr Ala Met Glu Trp Thr Gln Leu Pro Leu Leu Arg Asp Ile Ile
1               5                   10                  15

Glu Ala Leu Leu Lys Ala Tyr Arg Gln Lys Leu Phe Val Thr His Thr
            20                  25                  30

Val Asp Glu Leu Leu Trp Gly Tyr
        35                  40

<210> SEQ ID NO 28
<211> LENGTH: 41
<212> TYPE: PRT
<213> ORGANISM: Unknown
<220> FEATURE:
<223> OTHER INFORMATION: rat Limp-2 coiled coil region

<400> SEQUENCE: 28

Leu Leu Thr Val Val Glu Met Ala Gln Gln Pro Phe Leu Arg Glu Ile
1               5                   10                  15

Ile Glu Ala Met Leu Lys Ala Tyr Gln Gln Thr Leu Phe Val Thr His
            20                  25                  30

Thr Val His Glu Leu Leu Trp Gly Tyr
        35                  40

<210> SEQ ID NO 29
<211> LENGTH: 41
<212> TYPE: PRT
<213> ORGANISM: Unknown
<220> FEATURE:
<223> OTHER INFORMATION: mouse Limp-2 coiled coil region

<400> SEQUENCE: 29

Leu Leu Thr Val Val Asp Leu Ala Gln Leu Thr Leu Leu Arg Glu Leu
1               5                   10                  15

Ile Glu Ala Met Leu Lys Ala Tyr Gln Gln Lys Leu Phe Val Ile His
            20                  25                  30

Thr Val His Glu Leu Leu Trp Gly Tyr
        35                  40

<210> SEQ ID NO 30
<211> LENGTH: 406
<212> TYPE: PRT
<213> ORGANISM: Unknown
<220> FEATURE:
<223> OTHER INFORMATION: consensus sequence of Limp-2 lumenal domain

<400> SEQUENCE: 30

Arg Val Phe Gln Lys Ala Val Asp Gln Thr Ile Glu Lys Asn Met Val
1               5                   10                  15

Leu Arg Asn Gly Thr Lys Val Phe Asp Ser Trp Glu Lys Pro Pro Leu
            20                  25                  30

Pro Val Tyr Thr Gln Phe Tyr Phe Asn Val Thr Asn Pro Glu Glu
        35                  40                  45

Ile Leu Gln Gly Glu Ile Pro Leu Leu Glu Glu Val Gly Pro Tyr Thr
    50                  55                  60

Tyr Arg Glu Leu Arg Asn Lys Ala Asn Ile Gln Phe Gly Glu Asn Gly
```

```
            65                  70                  75                  80
        Thr Thr Ile Ser Ala Val Ser Asn Lys Ala Tyr Val Phe Glu Arg Asn
                        85                  90                  95
        Gln Ser Val Gly Asp Pro Asn Val Asp Leu Ile Arg Thr Ile Asn Ile
                        100                 105                 110
        Pro Leu Leu Thr Val Val Glu Leu Ala Gln Leu Pro Leu Leu Arg Glu
                        115                 120                 125
        Ile Ile Glu Ala Met Leu Lys Ala Tyr Gln Gln Lys Leu Phe Val Thr
                        130                 135                 140
        His Thr Val His Glu Leu Leu Trp Gly Tyr Lys Asp Glu Ile Leu Ser
        145                 150                 155                 160
        Leu Val His Ile Phe Lys Pro Asp Ile Ser Pro Asn Phe Gly Leu Phe
                        165                 170                 175
        Tyr Glu Lys Asn Gly Thr Asn Asp Gly Asp Tyr Val Phe Leu Thr Gly
                        180                 185                 190
        Glu Asp Asn Tyr Leu Asn Phe Thr Lys Ile Val Glu Trp Asn Gly Lys
                        195                 200                 205
        Thr Ser Leu Asp Trp Trp Thr Thr Asp Thr Cys Asn Met Ile Asn Gly
        210                 215                 220
        Thr Asp Gly Asp Ser Phe His Pro Leu Ile Ser Lys Asp Glu Val Leu
        225                 230                 235                 240
        Tyr Val Phe Pro Ser Asp Phe Cys Arg Ser Val His Ile Thr Phe Ser
                        245                 250                 255
        Ser Phe Glu Asn Val Glu Gly Leu Pro Ala Phe Arg Tyr Lys Val Pro
                        260                 265                 270
        Ala Glu Ile Leu Ala Asn Thr Ser Glu Asn Ala Gly Phe Cys Ile Pro
                        275                 280                 285
        Glu Gly Asn Cys Met Asp Ser Gly Val Leu Asn Val Ser Ile Cys Lys
                        290                 295                 300
        Asn Gly Ala Pro Ile Ile Met Ser Phe Pro His Phe Tyr Gln Ala Asp
        305                 310                 315                 320
        Glu Lys Phe Val Ser Ala Ile Lys Gly Met His Pro Asn Lys Glu Glu
                        325                 330                 335
        His Glu Ser Phe Val Asp Ile Asn Pro Leu Thr Gly Ile Ile Leu Arg
                        340                 345                 350
        Ala Ala Lys Arg Phe Gln Ile Asn Thr Tyr Val Lys Lys Leu Asp Asp
                        355                 360                 365
        Phe Val Glu Thr Gly Asn Ile Arg Thr Met Val Phe Pro Val Met Tyr
                        370                 375                 380
        Leu Asn Glu Ser Val Leu Ile Asp Lys Glu Thr Ala Ser Arg Leu Lys
        385                 390                 395                 400
        Ser Val Ile Asn Thr Thr
                        405

<210> SEQ ID NO 31
<211> LENGTH: 478
<212> TYPE: PRT
<213> ORGANISM: Unknown
<220> FEATURE:
<223> OTHER INFORMATION: hamster Limp-2

<400> SEQUENCE: 31

Met Gly Arg Cys Cys Phe Tyr Thr Ala Gly Thr Leu Ser Leu Leu Leu
1               5                   10                  15

Leu Val Ala Ser Val Thr Leu Leu Val Ala Arg Val Phe Gln Lys Ala
```

```
                   20                  25                  30
    Val Asp Gln Thr Ile Glu Lys Ser Met Val Leu Arg Asn Gly Thr Glu
                35                  40                  45
    Val Phe Asp Ser Trp Glu Lys Pro Pro Leu Pro Val Tyr Thr Gln Phe
                50                  55                  60
    Tyr Phe Asn Val Thr Asn Pro Glu Glu Ile Leu Gln Gly Glu Ile
65                      70                  75                  80
    Pro Ile Leu Gln Glu Val Gly Pro Tyr Thr Tyr Arg Glu Ile Arg Asn
                    85                  90                  95
    Lys Ala Asn Ile Gln Phe Gly Glu Asn Gly Thr Thr Ile Ser Ala Val
                   100                 105                 110
    Ser Asn Lys Ala Tyr Val Phe Glu Arg Asn Gln Ser Val Gly Asp Thr
                   115                 120                 125
    Asn Val Asp Leu Ile Arg Thr Ile Asn Ile Pro Leu Leu Thr Val Val
                   130                 135                 140
    Glu Leu Thr Gln Leu Pro Leu Leu Lys Glu Ile Ile Glu Ala Met Leu
145                     150                 155                 160
    Lys Thr Tyr Gln Gln Lys Leu Phe Val Thr His Thr Val His Glu Leu
                   165                 170                 175
    Leu Trp Gly Tyr Lys Asp Glu Ile Leu Ser Leu Val His Val Phe Lys
                   180                 185                 190
    Pro Gly Ile Ser Pro Asn Phe Gly Leu Phe Tyr Glu Lys Asn Gly Thr
                   195                 200                 205
    Asn Asp Gly Asp Tyr Val Phe Leu Thr Gly Glu Asp Asn Tyr Leu Asn
                   210                 215                 220
    Phe Thr Lys Ile Val Glu Trp Asn Gly Lys Thr Ser Leu Asp Trp Trp
225                     230                 235                 240
    Thr Thr Asp Glu Cys Asn Met Ile Asn Gly Thr Asp Gly Asp Ser Phe
                   245                 250                 255
    His Pro Leu Ile Thr Lys Asp Glu Val Leu Tyr Val Phe Pro Ser Asp
                   260                 265                 270
    Phe Cys Arg Ser Val His Ile Thr Phe Ser Gly Phe Glu Thr Val Glu
                   275                 280                 285
    Gly Leu Pro Ala Phe Arg Tyr Lys Val Pro Ala Glu Ile Leu Ala Asn
                   290                 295                 300
    Thr Ser Glu Asn Ala Gly Phe Cys Ile Pro Glu Gly Asn Cys Met Asp
305                     310                 315                 320
    Ser Gly Val Leu Asn Val Ser Ile Cys Lys Asn Gly Val Pro Ile Ile
                   325                 330                 335
    Met Ser Phe Pro His Phe Tyr Gln Ala Asp Glu Lys Phe Val Ser Ala
                   340                 345                 350
    Ile Lys Gly Met His Pro Asn Lys Glu Glu His Glu Thr Phe Val Asp
                   355                 360                 365
    Ile Asn Pro Leu Thr Gly Ile Ile Leu Arg Ala Ala Lys Arg Phe Gln
                   370                 375                 380
    Ile Asn Thr Tyr Val Lys Lys Ile Asp Gly Phe Val Glu Met Gly Asn
385                     390                 395                 400
    Ile Arg Thr Met Val Phe Pro Val Met Tyr Leu Asn Glu Ser Val Leu
                   405                 410                 415
    Ile Asp Lys Glu Thr Ala Ser Arg Leu Lys Ser Val Thr Asn Thr Thr
                   420                 425                 430
    Leu Ile Val Thr Asn Ile Pro Tyr Ile Ile Met Ala Leu Gly Val Phe
                   435                 440                 445
```

```
Phe Gly Leu Val Phe Thr Trp Leu Ala Cys Arg Gly Gln Gly Pro Met
    450                 455                 460
Asp Glu Gly Thr Ala Asp Glu Arg Ala Pro Leu Ile Arg Thr
465                 470                 475
```

<210> SEQ ID NO 32
<211> LENGTH: 477
<212> TYPE: PRT
<213> ORGANISM: Unknown
<220> FEATURE:
<223> OTHER INFORMATION: human Limp-2

<400> SEQUENCE: 32

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335
```

```
Met Ser Phe Pro His Phe Tyr Gln Ala Asp Glu Arg Phe Val Ser Ala
                340                 345                 350

Ile Glu Gly Met His Pro Asn Gln Glu Asp His Glu Thr Phe Val Asp
            355                 360                 365

Ile Asn Pro Leu Thr Gly Ile Leu Lys Ala Ala Lys Arg Phe Gln Ile
        370                 375                 380

Asn Ile Tyr Val Lys Lys Leu Asp Asp Phe Val Glu Thr Gly Asp Ile
385                 390                 395                 400

Arg Thr Met Val Phe Pro Val Met Tyr Leu Asn Glu Ser Val His Ile
                405                 410                 415

Asp Lys Glu Thr Ala Ser Arg Leu Lys Ser Met Ile Asn Thr Thr Leu
            420                 425                 430

Ile Ile Thr Asn Ile Pro Tyr Ile Ile Met Ala Leu Gly Val Phe Phe
        435                 440                 445

Gly Leu Val Phe Thr Trp Leu Ala Cys Lys Gly Gln Gly Ser Met Asp
    450                 455                 460

Glu Gly Thr Ala Asp Glu Arg Ala Pro Leu Ile Arg Thr
465                 470                 475

<210> SEQ ID NO 33
<211> LENGTH: 478
<212> TYPE: PRT
<213> ORGANISM: Unknown
<220> FEATURE:
<223> OTHER INFORMATION: mouse Limp-2

<400> SEQUENCE: 33

Met Gly Arg Cys Cys Phe Tyr Thr Ala Gly Thr Leu Ser Leu Leu Leu
1                   5                   10                  15

Leu Val Thr Ser Val Thr Leu Leu Val Ala Arg Val Phe Gln Lys Ala
                20                  25                  30

Val Asp Gln Thr Ile Glu Lys Asn Met Val Leu Gln Asn Gly Thr Lys
            35                  40                  45

Val Phe Asn Ser Trp Glu Lys Pro Pro Leu Pro Val Tyr Ile Gln Phe
        50                  55                  60

Tyr Phe Phe Asn Val Thr Asn Pro Glu Glu Ile Leu Gln Gly Glu Ile
65                  70                  75                  80

Pro Leu Leu Glu Glu Val Gly Pro Tyr Thr Tyr Arg Glu Leu Arg Asn
                85                  90                  95

Lys Ala Asn Ile Gln Phe Gly Glu Asn Gly Thr Thr Ile Ser Ala Val
            100                 105                 110

Thr Asn Lys Ala Tyr Val Phe Glu Arg Asn Gln Ser Val Gly Asp Pro
        115                 120                 125

Asn Val Asp Leu Ile Arg Thr Ile Asn Ile Pro Leu Leu Thr Val Val
130                 135                 140

Asp Leu Ala Gln Leu Thr Leu Leu Arg Glu Leu Ile Glu Ala Met Leu
                145                 150                 155                 160

Lys Ala Tyr Gln Gln Lys Leu Phe Val Ile His Thr Val His Glu Leu
            165                 170                 175

Leu Gln Gly Tyr Lys Asp Glu Ile Leu Ser Leu Val His Ile Phe Lys
        180                 185                 190

Pro Asp Val Ser Pro Asn Phe Gly Leu Phe Tyr Glu Arg Asn Gly Thr
    195                 200                 205

Asn Asp Gly Glu Tyr Val Phe Leu Thr Gly Glu Asp Asn Tyr Leu Asn
    210                 215                 220
```

```
Phe Ser Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
                245                 250                 255

His Pro Leu Ile Ser Lys Asp Glu Val Leu Tyr Leu Phe Pro Ser Asp
            260                 265                 270

Leu Cys Arg Ser Val His Ile Thr Phe Ser Ser Phe Glu Asn Val Glu
        275                 280                 285

Gly Leu Pro Ala Phe Arg Tyr Lys Val Pro Ala Glu Ile Leu Ala Asn
    290                 295                 300

Thr Ser Glu Asn Ala Gly Phe Cys Ile Pro Glu Gly Asn Cys Met Asp
305                 310                 315                 320

Ser Gly Val Leu Asn Ile Ser Ile Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Lys Gly Met His Pro Asn Lys Glu Glu His Glu Ser Phe Val Asp
        355                 360                 365

Ile Asn Pro Leu Thr Gly Ile Ile Leu Arg Gly Ala Lys Arg Phe Gln
    370                 375                 380

Ile Asn Thr Tyr Val Arg Lys Leu Asp Asp Phe Val Glu Thr Gly Asp
385                 390                 395                 400

Ile Arg Thr Met Val Phe Pro Val Met Tyr Leu Asn Glu Ser Val Leu
                405                 410                 415

Ile Asp Lys Glu Thr Ala Asn Gln Leu Lys Ser Val Ile Asn Thr Thr
            420                 425                 430

Leu Val Val Thr Asn Ile Pro Tyr Ile Ile Met Ala Leu Gly Val Phe
        435                 440                 445

Phe Gly Leu Val Phe Thr Trp Leu Ala Cys Arg Gly Gln Gly Ser Met
    450                 455                 460

Asp Glu Gly Thr Ala Asp Glu Arg Ala Pro Leu Ile Arg Thr
465                 470                 475

<210> SEQ ID NO 34
<211> LENGTH: 479
<212> TYPE: PRT
<213> ORGANISM: Unknown
<220> FEATURE:
<223> OTHER INFORMATION: rat Limp-2

<400> SEQUENCE: 34

Met Ala Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Thr Ile Glu Lys Asn Met Val Leu Gln Asn Gly Thr Lys
        35                  40                  45

Val Phe Asp Ser Trp Glu Lys Pro Pro Leu Pro Val Tyr Ile Gln Phe
    50                  55                  60

Tyr Phe Phe Asn Val Thr Asn Pro Glu Glu Ile Leu Gln Gly Glu Ile
65                  70                  75                  80

Pro Leu Leu Glu Glu Val Gly Pro Tyr Thr Tyr Arg Glu Leu Arg Asn
                85                  90                  95

Lys Ala Asn Val Gln Phe Gly Glu Asn Gly Thr Thr Ile Ser Ala Val
            100                 105                 110
```

```
Thr Asn Lys Ala Tyr Ile Phe Glu Arg Asn Gln Ser Val Gly Asp Pro
            115                 120                 125

Thr Val Asp Leu Ile Arg Thr Ile Asn Ile Pro Leu Leu Thr Val Val
130                 135                 140

Glu Met Ala Gln Gln Pro Phe Leu Arg Glu Ile Ile Glu Ala Met Leu
145                 150                 155                 160

Lys Ala Tyr Gln Gln Thr Leu Phe Val Thr His Thr Val His Glu Leu
            165                 170                 175

Leu Trp Gly Tyr Lys Asp Glu Val Leu Ser Leu Val His Ile Phe Arg
            180                 185                 190

Pro Asp Val Ser Pro Asn Phe Gly Leu Phe Tyr Glu Arg Asn Gly Thr
            195                 200                 205

Asn Asp Gly Glu Tyr Val Phe Leu Thr Gly Glu Asp Asn Tyr Leu Asn
            210                 215                 220

Phe Thr Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
            245                 250                 255

His Pro Leu Ile Ser Lys Asp Glu Thr Leu Tyr Ile Phe Pro Ser Asp
            260                 265                 270

Phe Cys Arg Ser Val Tyr Ile Thr Phe Ser Ser Phe Glu Asn Val Glu
            275                 280                 285

Gly Leu Pro Ala Phe Arg Tyr Lys Val Pro Ala Glu Ile Leu Ala Asn
            290                 295                 300

Ser Ser Glu Asn Ala Gly Phe Cys Ile Pro Glu Asn Gly Asn Cys Met
305                 310                 315                 320

Asp Ala Gly Val Leu Asn Val Ser Ile Cys Lys Asn Gly Ala Pro Ile
            325                 330                 335

Ile Met Ser Phe Pro His Phe Tyr Gln Ala Asp Glu Lys Phe Val Ser
            340                 345                 350

Ala Ile Lys Gly Met Arg Pro Asn Lys Glu Glu His Glu Ser Phe Val
            355                 360                 365

Asp Ile Asn Pro Leu Thr Gly Ile Ile Leu Arg Gly Ala Lys Arg Phe
            370                 375                 380

Gln Ile Asn Thr Tyr Val Lys Lys Leu Asp Asp Phe Val Glu Thr Gly
385                 390                 395                 400

Asn Ile Arg Thr Met Val Phe Pro Val Met Tyr Leu Asn Glu Ser Val
            405                 410                 415

Leu Ile Asp Lys Glu Thr Ala Ser Gln Leu Lys Ser Val Ile Asn Thr
            420                 425                 430

Thr Leu Ile Val Thr Asn Ile Pro Tyr Ile Ile Met Ala Leu Gly Val
            435                 440                 445

Phe Phe Gly Leu Ile Phe Thr Trp Leu Ala Cys Arg Gly Gln Gly Ser
            450                 455                 460

Thr Asp Glu Gly Thr Ala Asp Glu Arg Ala Pro Leu Ile Arg Thr
465                 470                 475

<210> SEQ ID NO 35
<211> LENGTH: 478
<212> TYPE: PRT
<213> ORGANISM: Unknown
<220> FEATURE:
<223> OTHER INFORMATION: consensus sequence of Limp 2

<400> SEQUENCE: 35
```

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Thr Ile Glu Lys Asn Met Val Leu Arg Asn Gly Thr Lys
                35                  40                  45

Val Phe Asp Ser Trp Glu Lys Pro Leu Pro Val Tyr Thr Gln Phe
50                  55                  60

Tyr Phe Phe Asn Val Thr Asn Pro Glu Glu Ile Leu Gln Gly Glu Ile
65                  70                  75                  80

Pro Leu Leu Glu Glu Val Gly Pro Tyr Thr Tyr Arg Glu Leu Arg Asn
                85                  90                  95

Lys Ala Asn Ile Gln Phe Gly Glu Asn Gly Thr Thr Ile Ser Ala Val
                100                 105                 110

Ser Asn Lys Ala Tyr Val Phe Glu Arg Asn Gln Ser Val Gly Asp Pro
            115                 120                 125

Asn Val Asp Leu Ile Arg Thr Ile Asn Ile Pro Leu Leu Thr Val Val
            130                 135                 140

Glu Leu Ala Gln Leu Pro Leu Leu Arg Glu Ile Ile Glu Ala Met Leu
145                 150                 155                 160

Lys Ala Tyr Gln Gln Lys Leu Phe Val Thr His Thr Val His Glu Leu
                165                 170                 175

Leu Trp Gly Tyr Lys Asp Glu Ile Leu Ser Leu Val His Ile Phe Lys
                180                 185                 190

Pro Asp Ile Ser Pro Asn Phe Gly Leu Phe Tyr Glu Lys Asn Gly Thr
            195                 200                 205

Asn Asp Gly Asp Tyr Val Phe Leu Thr Gly Asp Asn Tyr Leu Asn
            210                 215                 220

Phe Thr Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
                245                 250                 255

His Pro Leu Ile Ser Lys Asp Glu Val Leu Tyr Val Phe Pro Ser Asp
            260                 265                 270

Phe Cys Arg Ser Val His Ile Thr Phe Ser Ser Phe Glu Asn Val Glu
            275                 280                 285

Gly Leu Pro Ala Phe Arg Tyr Lys Val Pro Ala Glu Ile Leu Ala Asn
            290                 295                 300

Thr Ser Glu Asn Ala Gly Phe Cys Ile Pro Glu Gly Asn Cys Met Asp
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Lys Gly Met His Pro Asn Lys Glu Glu His Glu Ser Phe Val Asp
                355                 360                 365

Ile Asn Pro Leu Thr Gly Ile Ile Leu Arg Ala Ala Lys Arg Phe Gln
            370                 375                 380

Ile Asn Thr Tyr Val Lys Lys Leu Asp Asp Phe Val Glu Thr Gly Asn
385                 390                 395                 400

Ile Arg Thr Met Val Phe Pro Val Met Tyr Leu Asn Glu Ser Val Leu
                405                 410                 415
```

-continued

```
Ile Asp Lys Glu Thr Ala Ser Arg Leu Lys Ser Val Ile Asn Thr Thr
            420                 425             430

Leu Ile Val Thr Asn Ile Pro Tyr Ile Ile Met Ala Leu Gly Val Phe
        435             440                 445

Phe Gly Leu Val Phe Thr Trp Leu Ala Cys Arg Gly Gln Gly Ser Met
        450             455                 460

Asp Glu Gly Thr Ala Asp Glu Arg Ala Pro Leu Ile Arg Thr
465                 470                 475
```

METHODS OF PRODUCING A SECRETED PROTEIN

RELATED APPLICATIONS

This application is the U.S. National Stage of International Application No. PCT/US2008/005942, filed May 9, 2008, which designates the U.S., published in English, and claims the benefit of U.S. Provisional Application No. 60/967,415, filed on Sep. 4, 2007 and U.S. Provisional Application No. 60/928,907, filed on May 11, 2007. The entire teachings of the above applications are incorporated herein by reference.

BACKGROUND OF THE INVENTION

Lysosomal enzymes are synthesized as soluble or membrane-integrated glycoproteins in the rough endoplasmic reticulum (ER). In mammalian cells mannose 6-phosphate receptors (MPRs) mediate the transport of the majority of lysosomal enzymes to lysosomes. Mannose 6-phosphate (Man-6-P) terminal residues are recognized in the trans-Golgi network (TGN) by two MPRs which mediate the sorting of lysosomal enzymes from the secretory pathway and deliver them to a prelysosomal compartment from where the receptors return to the TGN and the ligands are forwarded to dense lysosomes (reviewed in (Kornfeld, 1992; Kornfeld and Mellman, 1989; Ludwig et al., 1995)). The physiological importance of the MPR-dependent transport of lysosomal enzymes is illustrated by I-cell disease (ICD). In this disorder, the deficiency of the phosphotransferase responsible for catalyzing the addition of Man-6-P results in the synthesis of lysosomal enzymes that lack Man-6-P residues leading to a failure to bind to MPRs and a strongly increased secretion of most of the lysosomal enzymes (Neufeld, 1991). Although fibroblasts of these patients have a marked deficiency of lysosomal enzymes, liver, spleen, kidney and brain tissues have nearly normal levels of lysosomal hydrolases (Kornfeld, 1986; Kornfeld and Sly, 1985). It was therefore proposed that in addition to MPR-dependent mechanisms, MPR-independent mechanisms are likely to exist for the transport of newly synthesized lysosomal enzymes to lysosomes (Ahn et al., 2002; Ginsel and Fransen, 1991; Glickman and Kornfeld, 1993; Rijnboutt et al., 1991; Tanaka et al., 2000). Also in MPR-deficient mice an ICD-like phenotype with increase of lysosomal enzymes in serum and normal activities in some tissues has been described (Dittmer et al., 1999).

In fibroblasts of ICD patients the lysosomal hydrolase β-glucocerebrosidase (βGC) has been shown to be intracellularly retained suggesting that signals other than Man-6-P are responsible for targeting this enzyme (Aerts et al., 1988; van Dongen et al., 1985). Mutations within the gene coding for human βGC are the cause of the most common lysosomal storage disorder, Gaucher Disease, in which the defective enzyme leads to an accumulation of glucosylceramide (GlcCer) (Beutler, 1991, 2006). Although the clinical course of this disease has been well described and an efficient treatment option, enzyme replacement therapy, is available little is known about how GlcCer accumulation in lysosomes leads to cellular pathology. Also the mechanism by which βGC is targeted from its site of synthesis in the ER to lysosomes is not well understood.

Thus, a greater understanding of the mechanism by which β-GC is targeted from its site of synthesis in the endoplasmic reticulum to lysosomes could lead to improved methods of treating lysosomal storage disorders such as Gaucher Disease.

SUMMARY OF THE INVENTION

β-glucocerebrosidase, the enzyme defective in Gaucher disease, is targeted to the lysosome independently of a mannose 6-phosphate receptor. The invention is based, in part, on the identification of a protein that interacts with β-glucocerebrosidase, which has elucidated the targeting pathway of β-glucocerebrosidase. Affinity chromatography experiments revealed that the lysosomal integral membrane protein LIMP-2 is a specific binding partner of β-glucocerebrosidase and that this interaction involves a coiled coil domain within the lumenal domain. β-glucocerebrosidase activity and protein levels were severely decreased in LIMP-2 knockout mouse tissues. Analysis of fibroblasts and macrophages isolated from these mice indicated that a majority of β-glucocerebrosidase was secreted or partially retained in the ER. Missorting of β-glucocerebrosidase was also evident in vivo since protein and activity levels were significantly higher in sera from LIMP-2-deficient mice compared to wild type. Reconstitution of LIMP-2 in LIMP-2-deficient fibroblasts led to a rescue of β-glucocerebrosidase levels and distribution. LIMP-2 expression also led to lysosomal transport of a β-glucocerebrosidase endoplasmic reticulum retention mutant. These data support a role for LIMP-2 as the mannose 6-phosphate-independent trafficking receptor for β-glucocerebrosidase.

Accordingly, the invention is directed to methods of producing a polypeptide or a variant thereof, wherein the polypeptide or variant thereof is dependent on LIMP-2 for trafficking, localization, stabilization and/or sorting of the polypeptide in the cell. In general, the methods comprise culturing a lysosomal integral membrane protein II (LIMP-2) deficient cell which expresses the polypeptide or the variant thereof under conditions in which the polypeptide or the variant thereof is produced.

The invention is also directed to methods of producing a polypeptide or variant thereof for secretion, wherein the polypeptide or variant thereof is dependent on LIMP-2 for trafficking, localization, stabilization and/or sorting of the polypeptide in the cell. The method comprises culturing a LIMP-2 deficient cell or animal (e.g., a LIMP-2 knockout animal) which expresses the polypeptide under conditions in which the polypeptide is secreted from the cell into the extracellular environment, or the cells of animals into the sera.

In one embodiment, the invention is directed to a method of producing β-glucocerebrosidase or a variant thereof, comprising culturing a lysosomal integral membrane protein II (LIMP-2) deficient cell which expresses β-glucocerebrosidase or the variant thereof under conditions in which β-glucocerebrosidase or the variant thereof is produced, thereby producing β-glucocerebrosidase or the variant thereof. In a particular embodiment, the β-glucocerebrosidase or a variant thereof is secreted from the cell.

In a particular embodiment, the invention is directed to a method of producing human β-glucocerebrosidase or a variant thereof, comprising culturing a lysosomal integral membrane protein II (LIMP-2) deficient Chinese Hamster Ovary (CHO) cell which expresses β-glucocerebrosidase or the variant thereof under conditions in which β-glucocerebrosidase or the variant thereof is secreted from the CHO cell, thereby producing human β-glucocerebrosidase or the variant thereof.

Also described herein are the hamster LIMP-2 nucleotide and amino acid sequences. Thus, the invention is directed to an isolated hamster LIMP-2 nucleic acid molecule. In one embodiment, the hamster LIMP-2 nucleic acid molecule comprises SEQ ID NO: 1. In another embodiment, the nucleic acid molecule comprises a nucleotide sequence that encodes SEQ ID NO: 31.

The invention is also directed to a hamster LIMP-2 polypeptide. In one embodiment, the polypeptide has an amino acid sequence comprising SEQ ID NO: 31.

Also encompassed by the invention are expression constructs comprising the hamster LIMP-2 sequences described herein, and host cells comprising the expression constructs. Methods of producing hamster LIMP-2 using the host cells described herein, and the hamster LIMP-2 produced by the methods, are also provided.

An antibody or antigen binding fragment thereof that specifically binds to all or a portion of a hamster LIMP-2 protein is also provided. In a particular embodiment, the antibody or antigen binding fragment thereof specifically binds to all or a portion of a hamster LIMP-2 protein having the amino acid sequence of SEQ ID NO: 31.

Also encompassed by the invention is an siRNA molecule which knocks down expression of a nucleic acid that encodes a hamster LIMP-2 protein having the amino acid sequence of SEQ ID NO: 31, wherein the siRNA comprises a double stranded sequence. In the method, one strand of the siRNA molecule has sufficient sequence complementarity to a hamster LIMP-2 RNA sequence to knock down expression of the nucleic acid that encodes the hamster LIMP-2 protein.

An expression construct comprising the siRNA molecules and a host cell comprising the expression constructs are also encompassed by the invention.

The invention is also directed to a method of altering trafficking of a lysosomal polypeptide that is dependent on a LIMP-2 polypeptide for trafficking to a lysosome comprising culturing a LIMP-2 deficient cell which expresses the lysosomal polypeptide under conditions in which the trafficking of the lysosomal polypeptide to the lysosome is altered.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Affinity Chromatography: The arrowhead indicates the migration of the 75 kD GC binding protein. (FIG. 1B) Binding behavior of the 75 kD GC binding protein (LIMP-2) in the presence of soluble glucocerebrosidase competition. Buffer (not shown) or total detergent soluble murine liver extract was mixed with either BSA-agarose resin (BSA) or GC-agarose resin (GC). In some reactions a four-fold molar excess of either soluble BSA or GC was added as a negative control for competition (mock) or specific competition (comp), respectively. A lane showing the total starting liver extract used in these reactions is also shown (extract). The arrowhead indicates the 75 kDa binding protein, whereas the "*" depicts βGC co-eluted from the column. (FIG. 1C) The 75 kD GC binding protein in the presence (+) or absence (−) of PNGaseF. (FIG. 1D) βGC bound the lumenal domain of LIMP-2 but not of CD36. Purified recombinant fusion tagged lumenal domain of either LIMP-2 (L2LD) or CD36 (36LD) was mixed with a fusion tag specific affinity resin either on its own as a positive control for tag-based pull-down, or co-mixed with soluble βGC (GC) and the tag-specific affinity resin to assess specific interaction with βGC. Following extensive washing bound proteins were eluted and analyzed. Left panel: The migration of the purified GC used in the experiment is shown. Half the total load amount for each reaction is shown. Middle panel: The results for the binding of GC alone (GC) and tagged L2LD alone (L2LD) to the tag-specific affinity resin are shown as negative and positive controls for capture, respectively; the co-capture of GC in the presence of tagged L2LD is shown in the rightmost lane (L2LD+GC). Right panel: The results for the binding of βGC alone (GC) and those for binding of tagged L2LD alone (L2LD) and tagged 36LD alone (36LD) are shown as negative and positive controls for tagged-based capture, respectively; no co-capture of GC is seen in the presence of 36LD (36LD+GC). (FIG. 1E) The effect of pH on the association of βGC and the lumenal domain of LIMP-2. Affinity binding reactions were set up in a series of buffers ranging from pH 4.5 to 8.5. Following incubation, the GC affinity resin was washed in buffer of the same pH as used in each respective binding reaction, then any bound L2LD protein was eluted in Laemmli buffer, and analyzed by SDS-PAGE and Coomassie staining. The arrowhead indicates the migration of L2LD.

(FIG. 2A) βGC activity was determined in tissue extracts from wild type and LIMP-2-deficient liver, spleen, brain and lung from 4 month old mice (n=4 each). A strongly decreased enzyme activity was observed in LIMP-2$^{-/-}$ tissues. The percentage of activity in the knockout tissues relative to wild type (100%) is presented. (FIG. 2B) α-galactosidase (α-GAL) activity was determined in tissue extracts from wild type and LIMP-2-deficient liver, spleen, brain and lung from the same samples as used in FIG. 2A. α-GAL activities were unchanged, or elevated in the case of spleen, in LIMP-2-deficient tissue samples. (FIG. 2C) Severely decreased expression level of βGC revealed by immunoblot analysis in LIMP-2-deficient kidney and liver samples. Total homogenates were prepared from samples from four wild type and four LIMP-2 knockout animals, normalized loads of these total protein homogenates were resolved by SDS-PAGE, blotted to PVDF and probed with an antibody specific to GC. (FIG. 2D) Northern blot analysis of βGC transcript levels in liver, kidney and MEF samples (upper panel). As a loading control the same blot was rehybridized with a probe detecting mouse glyceraldehyde phosphate dehydrogenase mRNA levels (GAPDH; lower panel). No differences in βGC transcript levels were seen between wild type and LIMP-2 knockout tissues. (FIG. 2E) Immunohistology for LIMP-2, βGC and Lamp Associated Protein 1 (LAMP1) in liver from a control (a,c,e) and a 3 month old LIMP-2-deficient mouse (b,d,f). Staining for LIMP-2 shows complete absence of immunoreactivity in LIMP-2-deficient liver (b) as compared to wild type liver (a). βGC (GC) was predominantly expressed in hepatocytes in the vicinity of the portal vein (pv) in wild type liver (c). In LIMP-2-deficient liver (d) the GC expression was almost completely lost. LAMP1 staining shows lysosomal structures in wild type (e) and LIMP-2-knockout liver (f). Insets show magnification of merged images of GC and LAMP1 staining demonstrating lysosomal localization of GC in wild type but not in LIMP-2 KO hepatocytes. Bars: 50 μm. (FIG. 2F) Specific βGC activity (mU/mg protein) was determined in extracts of two independent wild type (+/+) and LIMP-2 KO (−/−) MEF cell lines. (FIG. 2G) Top panel: Decreased βGC levels in four independent LIMP-2 KO MEF cell lines as compared to wild type cells. Middle panel: tubulin expression as a loading control. Lower panel: LIMP-2 expression. (FIG. 2H) Immunofluorescence labeling of LAMP-2 (in red) and βGC (in green) in wild type (a,b) and LIMP-2 KO (c,d) MEF cells. A merged image is presented. Right panels show magnified views of boxed regions in a and c. Bars in a,c: 10 µm; in b,d: 1 µm. βGC is absent from lysosomes lacking LIMP-2.

(FIG. 3A) Specific βGC activity (mU/mg protein) was determined in two independent wild type (+/+) and LIMP-2-deficient (−/−) MEF cell lines. LIMP-2-knockout cell extracts showed only about 10% of the activity found in wild type cell extracts. (FIG. 3B) Severely decreased βGC levels in four independent LIMP-2-deficient MEF cell lines as compared to wild type cells. The middle panel shows tubulin expression to demonstrate equal protein loading. The lower panel shows the absence of LIMP-2 in the knockout MEF extracts. (FIG. 3C) Immunofluorescence labeling of LAMP-2 (in red) and βGC (in green) in wild type (a,b) and LIMP-2-deficient (c,d) MEF cells. A merged image is presented. The right panels show magnified views of the boxed regions in a and c. Bars in a,c: 10 µm; in b,d: 1 µm. βGC was absent from lysosomes lacking LIMP-2.

FIGS. 4A-4H: Reconstituted transport of β-glucocerebrosidase to lysosomes after re-expression of LIMP-2 in LIMP-2-deficient MEF cells. LIMP-2-deficient MEF cells were transiently transfected with a myc-tagged mouse ΔIMII-2 expression vector. (FIG. 4A) LIMP-2 staining, (FIG. 4B) βGC staining, (FIG. 4C) a merged image shows an almost complete colocalization of LIMP-2 and GC. * indicates knockout MEFs which were not transfected and showed only trace amount of GC. (FIGS. 4D-4G) Triple labeling experiment showing the rescue of βGC lysosomal localization. (FIG. 4D) LIMP-2 labeling, (FIG. 4E) βGC labeling, (FIG. 4F) LAMP-2 labeling. Bars in FIGS. 4A-4F: 10 µm; (FIG. 4G) A merged image of FIGS. 4D-4E shows colocalization of βGC and LAMP-2/LIMP-2 in a transfected cell. Bar: 5 µm. (FIG. 4H) Mouse LIMP-2 (mLIMP-2) was transfected (+) in wild type (+/+) and LIMP-2 KO (−/−) MEF cells and compared to non-transfected (−) cells by immunoblot analysis. βGC, mLIMP-2 and α-tubulin (loading control) expression are presented.

(FIG. 5A) Secretion of βGC in the serum of LIMP-2-deficient mice. Immunoblot analysis of βGC in normalized total protein loads of serum samples taken from four 6 month old wild type and four 6 month old LIMP-2 knockout mice. The lower panel shows equal protein loading (Coomassie stain). (FIG. 5B) Activity of βGC in the sera of wild type mice and LIMP-2-knockout mice. There was an 11 fold increase in βGC activity in the LIMP-2-deficient samples. (FIG. 5C) Primary macrophages from wild type and LIMP-2 knockout mice were immunoblotted for βGC (upper panel) and LIMP-2 (lower panel). Strongly reduced levels of βGC in cell extracts and an increased secretion into the culture supernatant as compared to wild type cells was observed. (FIG. 5D) Densitometric quantification of the experiment in FIG. 5C representing the percentage of βGC secreted into the culture medium. (FIG. 5E) Immunoblot analysis: MEF cell extracts were treated with EndoH or PNGaseF. Immunoblot analysis revealed that the majority of βGC (upper panel) is EndoH resistant in wild type MEF cells but EndoH sensitive in LIMP-2$^{-/-}$ MEFs. Blotting the same membrane for tubulin (lower panel) shows equal loading. (FIG. 5F) Pulse-chase analysis of βGC-expression in metabolically labeled Hela cells with and without LIMP-2 specific siRNA. a Autoradiograph of βGC cell extract immunoprecipitates (upper panel) treated with (+) or without (−) EndoH. b Increased secretion of βGC after 480 min chase in the cell culture medium. c Quantification of the data presented in a and b. Immunofluorescence (d) and immunoprecipitation (e) of LIMP-2 demonstrates it is downregulated following siRNA.

(FIG. 6A) βGC sorting in the presence of LIMP-2 and absence of MPRs. The preferential binding of βGC to LIMP-2 (binding complex highlighted in inset) at more neutral pH suggests these two proteins could associate in secretory compartments as early as the ER or Golgi apparatus from where they would then progress to distal, more acidic prelysosomal compartments (LE, late endosome) and eventually, to dense lysosomes (LYSO). At the lower pH of these late compartments βGC may dissociate from LIMP-2. Yellow arrows: LIMP-2 pathway. M6P-receptor pathway (white arrows) shown for comparison. βGC trafficking was unaffected by the absence of MPRs unlike other lysosomal enzymes which are consequently missorted. (FIG. 6B) βGC missorted in the absence of LIMP-2. In contrast to the scenario seen when MPRs are absent or in I-cell disease in which a population of lysosomal enzymes other than βGC is mis-targeted, when LIMP-2 was absent βGC was mis-targeted. It is possible that the absence of LIMP-2 may also result in the destabilization and subsequent degradation of a percentage of the missorted βGC.

(FIGS. 7A-7B) Cells were stained using antibodies against mouse-β-glucocerobrosidase (FITC-green labeling) and the lysosomal membrane protein type 1 (LAMP-1; PE-red labeling). A merged image is presented where yellow labeling indicates colocalization of β-glucocerobrosidase and LAMP-1. Insets in "a" represent higher magnification of the boxed areas in A and B. Insets in "b" show staining for the CI-MPR and in "c" of the CD-MPR, both which are absent in MPR$^{-/-}$ MEF cells. In MPR deficient MEFs (MPR$^{-/-}$) β-glucocerobrosidase was delivered normally to LAMP-1 containing late endocytic compartments. (FIGS. 7C, 7D) In contrast the lysosomal aspartylproteinase cathepsin-D (FITC-green labeling) was missorted in MPR$^{-/-}$ MEF cells (FIG. 7D) suggesting a mannose-6 phosphate dependent delivery to LAMP-1-(PE-red labeling) containing lysosomes. Insets in "a" represent higher magnification of the boxed areas in FIGS. 7C and 7D. Bars: 10 µm. (FIG. 7E) β-glucocerobrosidase activity was determined in cell extracts and supernatants of wild type (+/+) and MPR$^{-/-}$ MEF cells. The activity of the enzyme was comparable between both cell types and no difference in β-glucocerebrosidase secretion was observed. The data presented are a mean out of 4 experiments (+/−SD).

FIGS. 10A-10I: Overexpression of β-GC resulted in localization to the endoplasmic reticulum when LIMP-2 was absent. Hela cells (FIGS. 10A, 10D, 10G) were transfected with murine β-GC and stained for β-GC (FIG. 10A) or LAMP-2 (FIG. 10D). The merged image (FIG. 10G) shows that the expressed β-GC localizes to the lysosomal compartment. In contrast β-GC expression in LIMP-2 deficient MEF cells (FIGS. 10B, 10C, 10E, 10F, 10H, 10I) led to the retention of β-GC in the endoplasmic reticulum as revealed by co-staining with β-GC (FIG. 10B) and an antibody against KDEL (FIG. 10E). The merged image (FIG. 10H) reveals a significant co-localization of β-GC and the ER-marker (antibody against KDEL). Co-staining with β-GC (FIG. 10C) and LAMP-2 (FIG. 10F) shows that β-GC does not reach the lysosomal compartment in LIMP-2 deficient MEF cells (FIG. 10I). Bars represent 10 μm.

FIG. 12: LIMP-2 deficiency in mouse embryonic fibroblasts (MEF cells) led to decreased intracellular β-GC levels and increased secretion of the enzyme. Two independent experiments with two wildtype and two LIMP-2 knockout MEF cell lines are presented. MEF cells of wild type and LIMP-2 knockout mice were immunoblotted for LIMP-2 (upper panel), β-GC (middle panels) and tubulin (lower panel) as a loading control. Strongly reduced levels of β-GC in cell extracts and an increased secretion into the culture supernatant were observed. Quantification of the experiment representing the percentage of β-GC secreted into the culture medium is presented in the graphs below the blot images.

FIGS. 15A-15C show the alignment of the hamster (SEQ ID NO: 1), human (SEQ ID NO: 3), mouse (SEQ ID NO: 5) and rat (SEQ ID NO: 7) LIMP-2 nucleotide sequences.

FIGS. 16A-16B show the alignment of the hamster (SEQ ID NO: 2), human (SEQ ID NO: 4), mouse (SEQ ID NO: 6), rat (SEQ ID NO: 8) and consensus (SEQ ID NO: 30) LIMP-2 luminal domain amino acid sequences and FIGS. 16C-16E show the alignment of the hamster (SEQ ID NO: 31), human (SEQ ID NO: 32), mouse (SEQ ID NO: 33), rat (SEQ ID NO: 34) and consensus (SEQ ID NO: 35) LIMP-2 amino acid sequences.

FIGS. 17A-17B show the amino acid sequence (amino acids R27-T432; 406 amino acids total) (SEQ ID NO: 2) and nucleotide sequence (base pairs 79-1296; 1218 nucleotides total) (SEQ ID NO: 10) of the hamster LIMP-2 lumenal domain.

(FIG. 21A) Results were obtained exactly as described for FIG. 20. Here, transfection with a different LIMP-2 specific siRNA ("si976") was also done, and RNA was analyzed at 72 hours and 96 hours post-transfection. (FIG. 21B) For each transfection condition, upon reaching 80% confluence cells were incubated for 24 hours in either of two serum-free base media. At the end of this 24-hour period, cells were harvested for RNA analysis; the harvest was at 96 hours post-transfection for all transfected samples and at 72 hours for untransfected cells.

In FIG. 22C, a lipid only control ("Lipid") was also included.

FIG. 23 is the amino acid sequence of imiglucerase (SEQ ID NO: 11).

FIG. 24A-24G: Mis-targeting of LIMP-2 alters the localization of β-glucocerebrosidase. COST-cells (24A-24F) were co-transfected with LIMP-2-myc and βGC-HA expression constructs and after transfection stained with anti-myc-antibodies to detect LIMP-2 wildtype protein (24A) or the LIMP-2 mutant containing a strong ER retention motif (24B) or with an anti-HA antibody to detect the tagged βGC protein (24C, 24D). (24E, 24F): Merged images. * indicates non-transfected cells. Bars in 24E and 24F: 10 μμm. (24G) LIMP-2-myc (L2) or LIMP-2-myc containing an ER retention signal (L2ret) were expressed in COST cells. Pulldown with anti-myc (LIMP-2) antibodies (+) led to co-immunoprecipitation of βGC; (−) pulldown in the absence of LIMP-2 antibodies; upper panel: anti-myc (LIMP-2 detection); lower panel: anti-human βGC detection (cross reacts with endogenous βGC).

FIG. 25A-25F: Analysis of LIMP-2 and β-glucocerebrosidase binding. (25A) Rescue of lysosomal βGC expression after transfection of wild type (wt) LIMP-2 which demonstrates high coiled-coil probability from amino acid 150 to 167 (inset) in LIMP-2 KO MEFs. (25B) Multiple species sequence alignment of LIMP-2. The grey box highlights the conserved coiled-coil domain and a-g indicate the residues in the helix with hydrophobic residues presented in bold. (25C, 25D) No rescue of lysosomal βGC expression after transfection of LIMP-2 ΔΔcc (25C) or LIMP-2-L160P (25D) in LIMP-2 KO MEFs. Disruption of the coiled-coil probability is shown in the insets. Single labeling is shown in the black and white images. Merged images of LIMP-2 and βGC staining are shown in colored images of 25A, 25C, 25D. Bars in 25A, 25C, 25D: 10 μμm. (25E) Co-immunoprecipitation analysis after pull down with anti-myc (LIMP-2) antibodies. After transfection of myc-tagged LIMP-2 and LIMP-2 mutants (LIMP-2Δcc, LIMP-2-L160P and LIMP-2 ERret; lower panel) binding to endogenous βGC (upper panel) was analyzed. (25F) βGC mutant (L444P) is retained in the ER after transfection in COS7 cells (a). Coexpression of LIMP-2 leads to the lysosomal transport of this mutant (b,c,d). Colored images (a,d) present the merge of βGC and LIMP-2 stainings. b,c: single stainings. * untransfected cells. Bars: 10 μm.

FIG. 26A-26B: Co-immunoprecipitation of over-expressed LIMP-2 and βGC and mistargeting of β-glucocerebrosidase after co-expression of a secreted luminal LIMP-2 in COS7 cells. (26A) Co-immunoprecipitation of βGC after pulldown of LIMP-2 with anti-myc antibodies. COS-7 cells were (co)transfected with LIMP-2-myc, mouse βGC, or eGFP as a negative control. Samples with (+) and without (−) immunoprecipitatation and the total starting lysates (lys.) were separated on a SDS-PAGE, blotted, and then probed for LIMP-2-myc (myc; upper panel) or mouse βGC (lower panel). Immunoglobulin fragments are indicated by an (*). (26B) Expression of the LIMP-2 lumenal domain (LIMP-2 (ld)) leads to increased βGC secretion (supernatants) when co-expressed with βGC in COS7 cells. Upper panel: expression of LIMP-2 detected with an anti-myc antibody. Lower panel: expression of βGC detected with an antibody specific for mouse βGC.

FIG. 27A-27B: Binding of clinical βGC mutants to LIMP-2 and analysis of co-transport of β-glucocerebrosidase (P415R) to lysosomes. (27A) Analysis of in vitro binding of βGC mutants to LIMP-2. Purified recombinant fusion tagged lumenal domain of LIMP-2 was mixed with fusion tag specific affinity resin on its own or after being co-mixed with purified soluble wildtype, or G202R, or N370S or L444P βGC protein. The binding reactions were washed, eluted, and analyzed as in FIG. 1D. Similarly to wildtype βGC, all three of the mutants bound to the LIMP-2 lumenal domain. (27B) Expression of wild type βGC (a) or the clinical mutant (P415R; Ron, I., Horowitz, M. Hum Mol. Genet. 2005 14:2387-2398.) (e) in COS7 cells. The majority of the expressed βGC is retained in the ER. Coexpression of LIMP-2 led to a complete lysosomal localization of wildtype βGC (d:merged image; b: βGC staining, c: LIMP-2 staining). However, LIMP-2 expression did not alter the endoplasmic reticulum localization of βGC mutant P415R indicating that the mutation directly or indirectly influences the binding to LIMP-2 (h: merged image; f: βGC staining, g: LIMP-2 staining). Bars: 10 μm.

FIG. 34: Analysis of βGC and transferrin endocytosis in wildtype and LIMP-2-deficient MEF cells. Human holotransferrin (Sigma) and mouse β-glucocerebrosidase (Genzyme) were labelled with 125I using Iodogen (Pierce, Germany). Labelled proteins were diluted in endocytosis medium (DMEM+0.05% BSA). Cells were washed three times with PBS and starved in DMEM+0.05% BSA. After one hour the medium was replaced by the endocytosis medium containing the desired labelled protein. Transferrin endocytosis: For the negative uptake control cells were incubated with label medium containing a hundredfold excess of unlabeled transferrin. Uptake of transferrin was achieved by incubating the cells with the iodinated protein for half an hour at 37° C. βGC endocytosis: For the negative uptake control wildtype cells were chilled on ice in the cold room, cold label medium were added to cells and the cells were kept on ice for three hours. Uptake of βGC was achieved by incubating the cells for three hours at 37° C. After the desired incubation times the label medium was removed from all cells, the cells were transferred on ice and washed five times with cold PBS, two times for five minutes with cold acid washbuffer (0.5 M NaCl, 0.2 M acetic acid, pH 2.5) and two times with cold PBS. Cells were harvested, the radiation counted and the counts normalized to the protein content.

DETAILED DESCRIPTION OF THE INVENTION

Figure 1A:
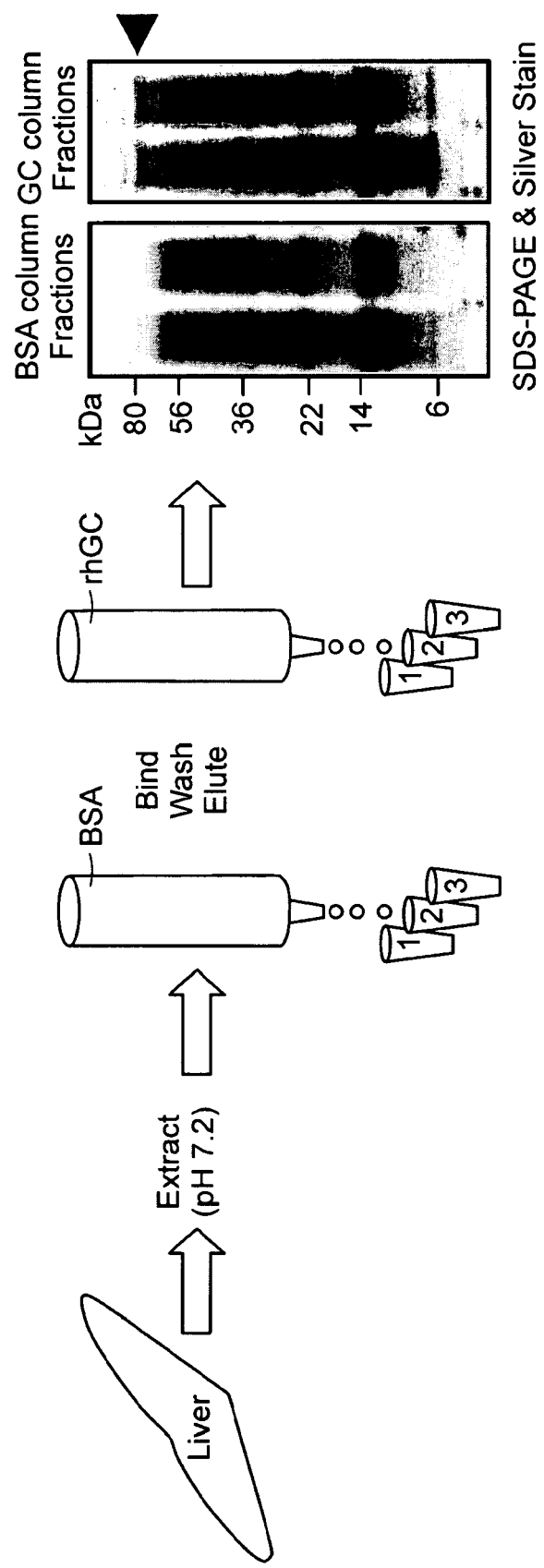
FIGS. 1A-1E: The lysosomal integral membrane protein-2 (LIMP-2) bound specifically to recombinant β-glucocerebrosidase.

As described herein, using pull-down experiments with purified β-GC the lysosomal integral membrane protein type-II (LIMP-2) has been identified as a specific binding partner for β-GC. In vitro and in vivo evidence showed that LIMP-2 acted as a receptor to bind β-GC, and that the β-GC-LIMP-2 complex was transported to the lysosomal compartment in an MPR-independent pathway.

Specifically, fractionation of tissue homogenates by affinity chromatography and subsequent mass spectrometry analysis identified LIMP-2 as a specific binding partner of β-GC. Biochemical characterization of the LIMP-2/β-GC interaction revealed the region in LIMP-2 involved in this association. Analysis and comparison of β-GC enzyme activity in tissues from wild type (WT) and LIMP-2 knockout mice indicated that that activity of the endogenous β-GC was decreased in the knockout mice and that this change directly correlated with a decrease in β-GC protein levels detected by immunoblot. Immunocytochemical staining of mouse embryonic fibroblasts (MEFs) isolated from LIMP-2 knockout mice corroborated the data. It was found that although significantly less β-GC was detected in knockout versus WT tissue homogenates, β-GC protein levels were much higher in the sera from LIMP-2 knockout mice compared to WT, and β-GC activity levels in these samples were increased over WT indicating that β-GC was missorted from cells in the absence of LIMP-2. Introduction of WT LIMP-2 into LIMP-2 knockout MEFs resulted in the rescue of β-GC protein levels and the normal localization of β-GC in these cells. Since endogenous β-GC trafficks independently of the mannose-6-phosphate receptor the data showed a role for LIMP-2 as a mannose-6-phosphate independent trafficking receptor for β-GC.

The findings described herein, particularly those relating to the missorting of β-GC in the absence of LIMP-2, provide for methods of producing a polypeptide or a variant thereof, wherein the polypeptide or variant thereof is dependent on LIMP-2 for trafficking, localization, stabilization and/or sorting of the polypeptide in the cell. In general, the methods comprise culturing a lysosomal integral membrane protein II (LIMP-2) deficient cell which expresses the polypeptide or the variant thereof under conditions in which the polypeptide or the variant thereof is produced.

As shown herein, expression of the polypeptide in a LIMP-2 deficient cell altered the localization (missorts) the polypeptide compared to the localization of the same polypeptide that was expressed in a normal or wild type cell. For example, the polypeptide can be retained in the endoplasmic reticulum of the LIMP-2 deficient cell and/or secreted from the LIMP-2 deficient cell.

Therefore, in a particular embodiment, the invention provides methods of producing a polypeptide or variant thereof for secretion (a secreted polypeptide or a variant thereof), wherein the polypeptide or variant thereof is dependent on LIMP-2 for trafficking, localization, stabilization and/or sorting of the polypeptide in the cell. The method comprises culturing a LIMP-2 deficient cell or animal (e.g., a LIMP-2 knockout animal) which expresses the polypeptide under conditions in which the polypeptide is secreted from the cell, or from the cells of the animal into the sera. Thus, in this embodiment, the method can be performed in vitro wherein the secreted protein can be obtained from the supernatant of a cell, or in vivo wherein the secreted protein can be obtained from the sera of a LIMP-2 deficient animal.

The method can be used for the production of any polypeptide (protein), referred to as a LIMP-2 ligand or LIMP-2 binding partner, that is dependent on LIMP-2 for trafficking, localization, stabilization, sorting or a combination thereof in a cell. The polypeptide can bind to all or a portion (e.g., a domain such as the lumenal domain) of LIMP-2. In another embodiment, the protein is β-glucocerebrosidase (βGC, β-GC, GC, acid β-glucocerebrosidase, acid β-glucosidase, glucosylceramidase, β-D-glucosyl-N-acylsphingosine glucohydrolase, EC 3.2.1.45) or a variant thereof. β-GC is used to treat Gaucher Disease. Thus, in one embodiment, the invention is directed to a method of producing β-GC or a variant thereof, comprising culturing a LIMP-2 deficient cell or animal (e.g., a LIMP-2 knockout animal) which expresses β-GC or the variant thereof under conditions in which β-GC or the variant thereof is produced, thereby producing β-GC or the variant thereof. In a particular embodiment, the method comprises culturing a LIMP-2 deficient cell or animal which expresses β-GC under conditions in which the β-GC is secreted from the cell. In another embodiment, the method further comprises purifying the β-GC secreted from the cell (e.g. from the supernatant of the cell) or animal (e.g., from the sera of the animal).

A variant of β-GC includes a protein having an amino acid sequence that is at least 90% identical to an amino acid sequence of β-GC (e.g., SEQ ID NO: 11). In one embodiment, the variant of β-GC is imiglucerase (the active ingredient in Cerezyme®, Genzyme Corporation, Cambridge, Mass.). Imiglucerase is an oligosaccharide-modified human β-glucocerebrosidase made using recombinant cells and is used to treat patients with Gaucher disease, a rare and devastating genetic disorder caused by a deficiency or malfunction of the β-glucocerebrosidase (see, e.g., Furbish et al., Biochim. Biophys. Acta 673:425-434 (1981); U.S. U.S. Pat. No. 5,549,892 which are incorporated herein by reference).

The methods described herein can further comprise isolating and/or further manipulating or modifying the polypeptide produced by the LIMP-2 deficient cell. For example, the method can further comprise purifying (e.g., substantially purifying), concentrating, and/or remodeling the polypeptide using techniques well known to those of skill in the art. Examples of such techniques include filtration, centrifugation, chromatography (e.g., gel electrophoresis, size exclusion, ion exchange, affinity, high pressure liquid chromatography, gas chromatography), mass spectrometry, oligosaccharide remodeling (Furbish et al., Biochim. Biophys. Acta 673:425-434 (1981); U.S. Pat. No. 5,549,892) and/or lyophilization.

In a particular embodiment, the invention is directed to a method of producing β-GC or a variant thereof, comprising culturing a LIMP-2 deficient cell which expresses β-GC or the variant thereof under conditions in which β-GC or the variant thereof is produced, thereby producing β-GC or the variant thereof. The method further comprises purifying and remodeling the carbohydrate chains of the β-GC or variant thereof produced. Methods for purifying and remodeling β-GC or a variant thereof are known in the art (e.g., see U.S. Pat. No. 5,549,892 which is incorporated herein by reference).

LIMP-2 is a heavily N-glycosylated 478 residue type-III transmembrane protein (Fujita, H., et al., *Biochem Biophys Res Commun* 178, 444-452 (1991)) comprised of an approximately 400 amino acid lumenal domain, two transmembrane domains and a cytoplasmic domain of 20 amino acids. Based on homology, LIMP-2 has been defined as a member of the CD36 family of scavenger receptor proteins (Febbraio, M., et al., *J Clin Invest* 108, 785-791 (2001); Krieger, M., *J Clin Invest* 108, 793-797 (2001)) which also includes CLA-1 (CD36-LIMP-2 Analogous-1/Scavenger Receptor BI) (Calvo, D., and Vega, M. A., *J Biol Chem* 268, 18929-18935 (1993)) and the *Drosophila* melanogaster proteins Croquemort, (Franc, N. C., et al., *Immunity* 4, 431-443 (1996)) and epithelial membrane protein, emp (Hart, K., and Wilcox, M., *J Mol Biol* 234, 249-253 (1993)). It has been recently shown that over-expression of LIMP-2 caused an enlargement of early endosomes and late endosomes/lysosomes and an impairment of endocytic membrane traffic out of the enlarged compartments (Kuronita, T., et al., *J Cell Sci* 115, 4117-4131 (2002); Kuronita, T., et al., *Traffic* 6, 895-906 (2005)). A deficiency of LIMP-2 in mice caused ureteric pelvic junction obstruction, deafness and peripheral neuropathy (Gamp, A., et al., *Hum Mol Genet.* 12, 631-646 (2003)) associated with an impaired vesicular trafficking and distribution of apically expressed proteins (Knipper, M., et al., *J Physiol* 576, 73-86 (2006)).

A number of LIMP-2 genes have been described in the art including human (Fujita, H., et al., *Biochem. Biophys. Res. Comm.*, 184(2):604-611 (1992)) mouse (Tabuchi, N., et al., *J. Biochem.*, 122(4):756-763 (1997)) and rat (Vega, M. A., et al., *J. Biol. Chem.*, 266(25):16818-16824 (1991)) LIMP-2 genes.

As described herein, the isolation and characterization of the hamster LIMP-2 nucleotide and amino acid sequences have now been provided. Thus, the invention is also directed to a nucleic acid molecule comprising the nucleotide sequence of hamster LIMP-2 (SEQ ID NO: 1). In one embodiment, the nucleic acid molecule encodes an amino acid sequence comprising SEQ ID NO: 31. Accordingly, the invention is also directed to an isolated polypeptide having an amino acid sequence of hamster LIMP-2 (SEQ ID NO: 31).

Expression constructs comprising the nucleotide hamster sequence as well as host cells comprising such expression constructs are also provided herein. In addition, the expression constructs and/or host cells of the invention can be used to produce hamster LIMP-2. Thus, the invention includes methods of producing hamster LIMP-2 comprising culturing a host cell comprising an isolated hamster LIMP-2 nucleic acid described herein under conditions in which the hamster LIMP-2 polypeptide is produced. The method can further comprise isolating the hamster LIMP-2 polypeptide from the cell. The present invention also relates to an isolated hamster LIMP-2 polypeptide produced by the method.

The availability of the hamster LIMP-2 nucleotide and amino acid sequences provides for methods of identifying an agent that alters (e.g., inhibits, enhances) interaction of a hamster LIMP-2 polypeptide with a LIMP-2 binding partner (e.g., β-GC). In one embodiment, the agent inhibits (e.g., partially, completely) the interaction of a hamster LIMP-2 polypeptide with a binding partner. In another embodiment, the agent enhances the interaction of a hamster LIMP-2 polypeptide with a binding partner. Such method can comprise, for example, contacting a hamster LIMP-2 polypeptide having an amino acid sequence comprising SEQ ID NO: 2 with β-GC under conditions in which the hamster LIMP-2 interacts with the β-GC, with an agent to be assessed. The extent to which the hamster LIMP-2 interacts with the β-GC in the presence of the agent to be assessed is determined, wherein if the extent to which hamster LIMP-2 interacts with β-GC is altered in the presence of the agent compared to the extent to which hamster LIMP-2 interacts with β-GC in the absence of the agent, then the agent alters interaction of a hamster LIMP-2 polypeptide with β-GC. Alternatively, the method can comprise contacting a host cell which comprises isolated nucleic acid that encodes a hamster LIMP-2 polypeptide having an amino acid sequence comprising SEQ ID NO: 31 wherein the LIMP-2 polypeptide, when expressed, interacts with β-GC in the cell, with an agent to be assessed. The secretion of β-GC from the host cell can then be assessed, wherein an altered secretion of β-GC from the host cell compared to secretion of β-GC from a control cell indicates that the agent alters interaction of a hamster LIMP-2 polypeptide with β-GC.

Example of agents (modulators) for use in the methods include nucleic acids (e.g., antisense RNA, siRNA, shRNA) peptides, peptidomimetics, small molecules such as small organic molecules or other drugs which bind to a hamster LIMP-2 polypeptide and/or inhibit or enhance (partially, completely) hamster LIMP-2 expression or activity.

Determining the ability of a hamster LIMP-2 polypeptide to bind to or interact with a binding partner can be accomplished using methods described herein and known to those of skill in the art. Moreover, in the methods of the invention, the hamster LIMP-2 polypeptide or its binding partner can be immobilized to facilitate separation of complexed from uncomplexed forms of one or both of the polypeptides, as well as to accommodate automation of the assay. Binding of an agent to a hamster LIMP-2, or interaction of a hamster LIMP-2 polypeptide with a binding partner in the presence and absence of an agent to be assessed, can be accomplished using, for example, columns, resins, microtitre plates, test tubes, and micro-centrifuge tubes.

In addition, the availability of the hamster LIMP-2 protein provides for an antibody or antigen binding fragment thereof that specifically binds to all or a portion of a hamster LIMP-2 protein having the amino acid sequence of SEQ ID NO: 31. That is, the antibody can bind to all of the hamster LIMP-2 protein of from about 8 amino acids to about 450 amino acids of the hamster LIMP-2 protein. In particular embodiments, the antibody can bind to about 10, 25, 50, 75, 100, 125, 150, 175, 200, 225, 250, 275, 300, 325, 350, 375, 400, or 425 amino acids of the LIMP-2 protein.

As used herein, the term "specific" when referring to an antibody-antigen interaction, is used to indicate that the antibody can selectively bind to hamster LIMP-2. In one embodiment, the antibody inhibits the activity of the hamster LIMP-2. In another embodiment, the antibody inhibits binding of LIMP-2 to β-glucocerebrosidase or a variant thereof. In yet another embodiment, the antibody specifically binds to all or a portion of a lumenal domain of β-glucocerebrosidase or a variant thereof.

An antibody that is specific for hamster LIMP-2 is a molecule that selectively binds to hamster LIMP-2 but does not substantially bind to other molecules in a sample, e.g., in a biological sample that contains hamster LIMP-2. The term "antibody," as used herein, refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, humanized, human, single-chain, chimeric, synthetic, recombinant, hybrid, mutated, conjugated and CDR-grafted antibodies. The term "antigen-binding site" refers to the part of an antibody molecule that comprises the area specifically binding to or complementary to, a part or all of an antigen. An antigen-binding site may comprise an antibody light chain variable region (VL) and an antibody heavy chain variable region (VH). An antigen-binding site may be provided by one or more antibody variable domains (e.g., an Fd antibody fragment consisting of a VH domain, an Fv antibody fragment consisting of a VH domain and a VL domain, or an scFv antibody fragment consisting of a VH domain and a VL domain joined by a linker). The term "anti-hamster LIMP-2 antibody," or "antibody against hamster LIMP-2," refers to any antibody that specifically binds to at least one epitope of LIMP-2.

The various antibodies and portions thereof can be produced using known techniques (Kohler and Milstein, Nature 256:495-497 (1975); Current Protocols in Immunology, Coligan et al., (eds.) John Wiley & Sons, Inc., New York, N.Y. (1994); Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1; Newman, R. et al., BioTechnology, 10: 1455-1460 (1992); Ladner et al., U.S. Pat. No. 4,946,778; Bird, R. E. et al., Science, 242: 423-426 (1988)).

As used herein a "LIMP-2 deficient cell" or "LIMP-2 deficient animal" includes a cell or animal in which the expression and/or function (activity) of LIMP-2 is completely or partially downregulated (blocked, inhibited, disrupted). Functions of LIMP-2 include the ability of LIMP-2 to associate with one or more of its ligands, such as β-GC. Whether LIMP-2 expression and/or function in a cell is deficient can be determined using a variety of techniques described herein and known in the art such as enzyme activity assays, gel electrophoresis, immunochemistry, quantitative polymerase chain reaction (PCR) (e.g., detect mRNA levels) and mass spectrometry. The results can also be compared to the results obtained from a suitable control, e.g., a wild type cell of the same, or from a different species, as the LIMP-2 deficient cell.

Examples of methods for obtaining or producing a LIMP-2 deficient cell or animal are described herein and are known in the art. For example, a LIMP-2 deficient cell can be obtained from a LIMP-2 deficient animal (Gamp, A., et al., *Hum Mol Genet.* 12, 631-646 (2003)). In addition, a LIMP-2 deficient cell or animal can be produced by introducing one or more targeted mutations specific for LIMP-2 into a cell, or into the cells of an animal to produce a LIMP-2 knockout animal (Gamp, A., et al., *Hum Mol Genet.* 12, 631-646 (2003)). In one embodiment, the mutated LIMP-2 polypeptide comprises a motif that alters localization of LIMP-2. An examples of such a motif is an endoplasmic reticulum retention motif.

Alternatively, a dominant negative mutant can be introduced into a cell or animal to render the cell or animal LIMP-2 deficient. For example, a LIMP-2 mutant protein that competitively binds to a ligand of LIMP-2 (e.g., β-GC) can be introduced into a cell. The LIMP-2 mutant protein can have enhanced binding properties such that the LIMP-2 ligand(s) preferentially binds to the LIMP-2 mutant protein rather than to the wild type LIMP-2 present in the cell. In another embodiment, a LIMP-2 fragment (a LIMP-2 peptide) comprising, or consisting essentially of, a region of LIMP-2 that competitively binds to a LIMP-2 ligand, can be introduced into the cell.

Moreover, treatment of cells with one or more small molecule inhibitors or antibodies that disrupt the association of LIMP-2 and a LIMP-2 ligand can also be used to produce a LIMP-2 deficient cell.

Antisense nucleic acid molecules, that is, molecules which are complementary to a sense nucleic acid encoding a LIMP-2 polypeptide (e.g., complementary to the coding strand of a double-stranded cDNA LIMP-2 molecule or complementary to an mRNA LIMP-2 sequence) can also be used to render a cell LIMP-2 deficient. The antisense nucleic acid can be complementary to an entire LIMP-2 coding strand, or to only a portion thereof, e.g., all or part of the protein coding region (or open reading frame). An antisense nucleic acid molecule can be antisense to a noncoding region of the coding strand of a nucleotide sequence encoding LIMP-2. The noncoding regions (5' and 3' untranslated regions) are the 5' and 3' sequences which flank the coding region and are not translated into amino acids. The antisense nucleic acid molecule can be complementary to the entire coding region of LIMP-2 mRNA, but more preferably is an oligonucleotide which is antisense to only a portion of the coding or noncoding region of LIMP-2 mRNA. An antisense oligonucleotide can be, for example, about 5, 10, 15, 20, 25, 30, 35, 40, 45 or 50 nucleotides in length. An antisense nucleic acid of the invention can be constructed using procedures known in the art (e.g., using chemical synthesis and enzymatic ligation reactions).

In a particular embodiment, RNA interference (RNAi) can be used to produce a LIMP-2 deficient cell or animal (e.g., using short interfering RNA (siRNA) or short hairpin RNA (shRNA)). As known in the art RNAi is a mechanism of post-transcriptional gene silencing directed by double stranded RNA (dsRNA) (Meister G, Tuschl T., *Nature.* 431, 343-9, (2004)). Exogenous dsRNA molecules that have sufficient sequence complementarity to a particular mRNA sequence, are introduced into a cell to destroy a particular mRNA, thereby diminishing or abolishing expression of the mRNA sequence. The exogenous dsRNA molecules introduced into the cells are processed by the RNase III enzyme Dicer into duplexes of 21-25 nucleotides (nt) containing 5' monophosphates and 2-nt 3' overhangs referred to as small interfering RNAs (siRNAs) (Bernstein, E., et al., *Nature.* 409, 363-6 (2001); Elbashir, S. M., et al., *Genes Dev.* 15, 188-200 (2001)). The siRNAs are incorporated into a multi-protein RNA-induced silencing complex (RISC) that degrades RNAs with sequences complementary to the siRNA (Tomari, Y., Zamore, P. D., *Genes Dev.* 19, 517-29 (2005)).

Thus, one or more siRNA or shRNA that degrades a LIMP-2 RNA sequence can be introduced into a cell or animal to render the cell or animal LIMP-2 deficient. Algorithms for designing siRNA directed to a particular sequence and methods for producing such siRNA sequences are well known to those of skill in the art (e.g., Reynolds et al., *Nature Biotechnology*, 22(3):326-330 (2004); Takasaki, S., et al., *Computational Biology and Chemistry*, 30, 169-178 (2006)). In particular embodiments, the one or more siRNA or shRNA molecules are targeted to one or more domains of LIMP-2 (e.g., a transmembrane domain, a cytoplasmic domain, a lumenal domain). In a particular embodiment, the siRNA or shRNA is targeted to the lumenal domain of LIMP-2.

Thus, the invention is also directed to an siRNA molecule which knocks down expression of a nucleic acid that encodes a hamster LIMP-2 protein having the amino acid sequence of SEQ ID NO: 31, wherein the siRNA comprises a double stranded sequence and one strand of the siRNA molecule has sufficient sequence complementarity to a hamster LIMP-2 RNA sequence to knock down expression of the nucleic acid that encodes the hamster LIMP-2 protein. In one embodiment, the one strand of the siRNA molecule has sufficient sequence complementarity to a LIMP-2 RNA sequence which encodes all or a portion of a lumenal domain of the hamster LIMP2 protein. In another embodiment, the LIMP-2 RNA sequence encodes all or a portion of SEQ ID NO: 2. In yet another embodiment, the one strand of the siRNA molecule comprises SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or a combination thereof.

In particular embodiments, the siRNA molecules of the present invention can result in at least about 50%, 55%, 60%, 65%, 70%, 75%, 80%, 85%, 90%, 95% or 99% knockdown of LIMP-2 protein expression.

The invention also provides an expression construct which comprises the siRNA or shRNA molecules described herein. In addition, host cells comprising such expression constructs are provided.

Appropriate siRNA or shRNA for use in the methods of the present invention can be obtained using, for example, the methods described herein or obtained from commercial sources (e.g., Ambion, Inc; Invitrogen). In one embodiment, the siRNA is double stranded and can comprise a sequence that is from about 17 nucleotides to about 35 nucleotides. In particular embodiments, the siRNA is double stranded and one or both strands (e.g., sense, antisense) can comprise a sequence of about 16, 17, 18, 19, 20, 21, 22, 23, 24, 25, 26, 27, 28, 29, 30, 31, 32, 33, 34 or 35 nucleotides. The siRNA is generally comprised of RNA, and in some embodiments, can include DNA base pairs, either at the end of or within one or more of the strands of the siRNA.

Conditions under which LIMP-2 deficient cells are maintained so that a polypeptide or variant thereof that is dependent on LIMP-2 for trafficking, localization, stabilization and/or sorting is produced, are apparent to those of skill in the art (e.g., see *Basic Techniques for Mammalian Cell Tissue Culture*, Mary C. Phelan, 2003, Juan S. Bonifacino, et al. (eds.), *Current Protocols in Cell Biology*, John Wiley & Sons, Inc). In the particular embodiment in which β-GC is produced, examples of conditions under which LIMP-2 deficient cells are maintained so that β-GC is produced are provided in Furbish et al., Biochim. Biophys. Acta 673:425-434 (1981) and U.S. Pat. No. 5,549,892.

The cells for use in the methods of the invention can include plant or animal cells. As used herein, the term "animal" includes mammals, as well as other animals, vertebrate and invertebrate (e.g., birds, fish, reptiles, insects (e.g., *Drosophila* species), mollusks (e.g., Aplysia). In a particular embodiment, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include primates (e.g., humans, monkeys, chimpanzees), rodents (e.g., rats, mice, guinea pigs), ruminents (e.g., cows, pigs, horses) felines and canines. In particular embodiment, the cell is a fibroblast or a macrophage.

Specific examples of suitable animal cells include, but are not limited to, the Chinese Hamster Ovary (CHO) cell line, including those designated CHO-K1, DG44, DUKX (also called DXB11), and CHO-S (commercially available from Invitrogen) and the hamster cell line BHK-21; the murine cell lines designated NIH3T3, NS0, C127, the simian cell lines COS, Vero; and the human cell lines HeLa, HEK293 (also called 293), PER.C6 (commercially available from Crucell) U-937 and Hep G2.

As described herein, expression of the polypeptide in a LIMP-2 deficient cell alters the localization of (missorts) the polypeptide compared to the localization of the same polypeptide that is expressed in a normal or wild type cell. Thus, the present invention is also directed to a method of altering trafficking of a lysosomal polypeptide that is dependent on a LIMP-2 polypeptide for trafficking to a lysosome. The method comprises culturing a LIMP-2 deficient cell which expresses the lysosomal polypeptide under conditions in which the trafficking of the lysosomal polypeptide to the lysosome is altered. In one embodiment, the altered trafficking results in increased secretion of the lysosomal polypeptide from the LIMP-2 deficient cell. In another embodiment, secretion of the lysosomal polypeptide is increased at least about 1.5-fold to about 20-fold, about 3-fold to about 18-fold, about 5-fold to about 15-fold and about 8-fold to about 10-fold, compared to secretion of the lysosomal polypeptide in a control cell. In a particular embodiment, secretion of the lysosomal polypeptide is increased at least about 11-fold compared to a control cell. Any suitable control cell can be used in the method. For example, the control can be a wild type cell of the same, or from a different species, as the LIMP-2 deficient cell.

The following Examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXPERIMENTATION

Example 1

LIMP-2 is a Receptor for Lysosomal Mannose 6-Phosphate Independent Targeting of β-GC In the study described herein, the lysosomal integral membrane protein type-II (LIMP-2) has been identified as a specific binding partner for βGC. LIMP-2 is a heavily N-glycosylated 478 residue type-III transmembrane protein (Fujita et al., 1991) comprised of a ~400 amino acid lumenal domain, two transmembrane domains and a cytoplasmic domain of 20 amino acids. Based on homology, LIMP-2 has been defined as a member of the CD36 family of scavenger receptor proteins (Febbraio et al., 2001; Krieger, 2001). It was recently shown that over-expression of LIMP-2 caused an enlargement of early endosomes and late endosomes/lysosomes and an impairment of endocytotic membrane traffic out of the enlarged compartments (Kuronita et al., 2002; Kuronita et al., 2005). A deficiency of LIMP-2 in mice caused ureteric pelvic junction obstruction, deafness and peripheral neuropathy (Gamp et al., 2003) associated with an impaired vesicular trafficking and distribution of apically expressed proteins (Knipper et al., 2006).

Presented herein is in vitro and in vivo evidence that LIMP-2 acts as a receptor to bind βGC and that the βGC-LIMP-2 complex is transported to the lysosomal compartment in an MPR-independent pathway.

Experimental Procedures

Materials

Restriction enzymes and other reagents for molecular biology were purchased from New England BioLabs (Beverly, Mass.) and Fermentas (Burlington, Canada). SDS-PAGE gels and protein standards were obtained from Invitrogen (Carlsbad, Calif., USA). BCA protein assay kits and western blotting reagents were purchased from Pierce (Rockford, Ill., USA).

Cell Lines and Mice

Mouse embryonic fibroblasts from LIMP-2-deficient and wild type mice were generated from E12.5 embryos and primary cell lines between passage 3 and 6 were used for the experiments. For rescue experiments cells were transiently transfected using Fugene 6 (Roche; Mannheim, Germany). Primary macrophages were isolated from mice 4 days after peritoneal injection of 4% thioglycolate (Huynh et al., 2007). Wild type and LIMP-2-deficient mice (C57B6×129SV) (Gamp et al., 2003) were maintained in a conventional animal facility. All experiments were performed with approval of the National Animal Care and Use Committee of Germany.

Antibodies and Antibody Generation

The following primary antibodies were used: rat anti-mouse LAMP-2 (ABL93), rat anti-mouse LAMP-1 (1D4B), mouse anti-tubulin (E7) (Developmental Studies Hybridoma Bank; Iowa City, Iowa, USA), mouse anti-protein disulphide isomerase (1D3, a gift of Stephen Fuller at EMBL, Germany), anti-mouse actin (SIGMA, Steinheim, Germany), anti-mouse cathepsin-D (Pohlmann, R., et al., *J Biol Chem*, 270:27311-27318 (1995)), anti-KDEL (Stressgene, Victoria, BC, Canada), anti human glucocerebrosidase antibody 8E4 (kind gift of J. M Aerts, University of Amsterdam). Antibody to the HPC4-epitope fusion tag was obtained from Roche Applied Science (Indianapolis, Ind., USA). Antibodies to the HA-epitope (3F10) were from Roche (Mannheim, Germany), antibodies against the myc-epitope tag were obtained from Abcam (Cambridge, UK).

Polyclonal antibodies to human LIMP-2 were raised in rabbits at Pine Acres Rabbit Farm antibody service facility (Norton, Mass.) using purified recombinant LIMP-2 (R27-T432) as antigen. The resulting antiserum was affinity purified over CNBr-activated agarose resin (Sigma Chemical Co.) covalently coupled with LIMP-2 (R27-T432). Anti-mouse LIMP-2 antibodies were raised in specific pathogen free rabbits at Eurogentec (Seraing, Belgium) against 2 peptides (C-RFQINTYVRKLDD (AS-382-394 of mLIMP-2) (SEQ ID NO: 20) and C-MDEGTADERAPLIRT (AS-464-478 of mLIMP-2) (SEQ ID NO: 21)). The resulting antiserum was affinity purified over a mixture of ACH- and CNBr-sepharose covalently coupled with the aforementioned peptides: Secondary conjugated antibodies for immunoblotting and immunofluorescence studies were obtained from Sigma Chemical. Co. (St. Louis, Mo.) and Molecular Probes (Carlsbad, Calif.), respectively. Polyclonal antibodies to murine β-glucocerebrosidase were raised in rabbits by plasmid injection followed by a boost with purified recombinant antigen (Aldevron Inc., Fargo, N. Dak.). The resulting antisera were affinity purified on recombinant antigen covalently coupled to NHS-activated sepharose.

Expression Plasmid Generation cDNA clones encoding full length human LIMP-2 was obtained from the ATCC (Manassas, Va.). The sequences encoding LIMP-2 (R27-T432) or CD36 (G30-K437) were amplified by PCR using primers which generated 5' EcoRI and 3' HindIII sites at their ends. The 5' primers also included the sequences encoding the honeybee mellitin signal peptide and the 3' primers included sequences encoding the HPC4 epitope fusion tag in the case of LIMP-2, or a tandem 6× his-HPC4 fusion tag in the case of CD36. The resulting products were subcloned into the pFastBac-1 expression vector, and introduced into the Bac-to-Bac baculovirus expression vector (BEV) system following the manufacturer's protocols (Invitrogen, Carlsbad, Calif.). The sequence encoding recombinant human β-glucocerebrosidase was amplified by PCR from the cDNA sequences encoding the human placental isoform using primers to generate a 5' NheI site and a 3' ClaI site. This product was subcloned into the pFastBac-1 expression vector (Invitrogen, Carlsbad, Calif.). The β-glucocerebrosidase N370S, G202R, and L444P mutants were derived from the wildtype construct using the Quickchange II mutagenesis kit according to the manufacturer's protocol (Stratagene, La Jolla, Calif.). Plasmid harboring the cDNA for full length murine β-glucocerebrosidase was purchased from Invitrogen and the coding sequences amplified by PCR using primers to generate a 5' EcoRI site and a C-terminal tandem 8× his+hpc4 tag flanked by a Not I site at the 3' end. This product was subcloned into the Invitrogen pENTR1A entry vector and an expression plasmid generated using the Gateway system to transfer the coding sequences into the pDEST 8 destination vector for use in BEV system.

cDNA clones encoding the full length murine LIMP-2 (mLIMP-2) and βGC (mGC) were obtained from RZPD (Heidelberg, Germany). The sequences encoding mLIMP-2 and mGC were amplified by PCR and subcloned into the eukaryotic expression vector pFrog3 derived from pcDNA3 (Invitrogen) (Gunther, W., et al., *Proc. Natl. Acad. Sci, USA*, 95:8075-8080 (1998)). The myc-epitope was inserted after the last amino acid of mLIMP-2. All recombinant sequences were determined to be free of PCR errors by nucleotide sequence analysis (Sequegen Inc. or MWG-Biotech AG). Murine LIMP-2 (Δcc and L160P, soluble LIMP-2) mutants and GC (P415R and L444P) mutants were derived from the respective wild type constructs using fusion PCR based site directed mutagenesis. The coding sequences for the C-terminally HPC4-tagged human LIMP-2 mutants, L160P and L177), were ordered from DNA 2.0 (Menlo Park, Calif.), then transferred into the pFastBac1 insect cell expression vector using the Invitrogen Gateway system. To generate LIMP-2 with a strong ER-retention signal the C-terminal 14 amino acids of the human α2C-adrenergic receptor (-KHILFR-RRRRGFRQ) (SEQ ID NO: 22) (Zerangue, N., et al., *Proc. natl. Acad. Sci, USA*, 97:3591-3595 (2000)) were fused to the C-terminus of LIMP-2 using PCR techniques.

Plasmids, Expression and Purification of Recombinant Proteins

Expression plasmids for LIMP-2 and βGC were generated as described in the Experimental Procedures. For protein expression in the BEV system Tn-5 cells (Expression Systems, CA) were infected with recombinant virus at an MOI=1. Conditioned medium was harvested 48 hr post-infection by centrifugation at 500 g and 0.22 μm filtered. Proteins expressed as fusions to the 12 amino acid HPC4 epitope tag were purified from the medium as described by (Rezaie et al., 1992). Recombinant human βGC was purified according to the method we previously described (Sawkar et al., 2006).

Affinity Chromatography and Binding Assays

Purified recombinant βGC was covalently coupled to CNBr-activated Sepharose 4B (Sigma Chemical Co., St. Louis, Mo.) as described by (Reczek et al., 1997) or coupled using the AminoLink immobilization kit (Pierce). Mouse tissue extracts were prepared from frozen tissues (Pel-Freeze Biologicals, Rogers, Ark.) and small-scale affinity chromatography experiments performed essentially as described (Reczek et al., 1997). For large-scale affinity chromatography, bound proteins were eluted from the coupled resin in 50 mM sodium acetate pH 4.7, 1M sodium chloride. Antibody-based pull down experiments were done using a monoclonal antibody to the HPC4 epitope covalently coupled to NHS-activated Sepharose 4 Fast Flow agarose support resin (AP-Biotech). Resin was incubated with solutions of HPC4-epitope tagged proteins, or non-epitope tagged proteins as controls, or with a mixture of epitope tagged protein and proteins to be tested for binding by co-capture in buffers containing 1 mM calcium chloride to allow for the calcium dependent HPC4 epitope-antibody interaction. 5-10 μg of each protein was used per reaction. Following extensive washing in the presence of 1 mM calcium chloride, HPC4-tagged and co-captured proteins were eluted in buffer containing 5 mM EDTA in place of calcium chloride and sample analyzed by SDS-PAGE followed by Coomassie staining.

Enzyme Activity Assays, PNGase-F, EndoH Treatment, and GL1-Substrate Analysis

The 4MU-based activity or colorimetric assay for βGC and alpha galactosidase and the quantitation of tissue glucosylceramide levels were performed using methods described previously (Marshall et al., 2002). PNGase F and EndoH treatment of LIMP-2 or βGC were performed using kits from New England Biolabs (Beverly, Mass.) and Roche (Mannheim, Germany) respectively.

LIMP2-siRNA in Hela Cells and Pulse-Chase-Analysis

HeLa cells were transfected with 60 pmol each of the LIMP2-RNAi-Duplexes (SCARB2 Stealth Select 3 RNAi; GAAAGCCAAACUAGGAGACACGAAA (SEQ ID NO: 12); CCAAAGAGAGAUGCAACCUAUUUGU (SEQ ID NO: 13); AUGGAGAGGCUGACAUCAUGAUCA (SEQ ID NO: 14)) using Lipofectamine 2000 (Invitrogen, Paisley, UK). After 2 days, cells were pulsed for 2 hours with 250 μCi 35S-Methionine/Cysteine ([35S]Met-label, Hartmann Analytic GmbH, Braunschweig, Germany) and chased for different time periods in DMEM containing 2% FCS. Medium was collected and cells were lysed and immunoprecipitated using mAb 8E4 anti-hβGC or anti-LIMP-2 Ab and Protein-A-Agarose (Pierce, Rockford, USA). βGC was released from Protein-A-agarose by boiling for 5 min with 100 mM citrate, 1% SDS, 0.1% β-mercaptoethanol and incubated for 16 h with 15 mU of endoglycosidase H (Roche, Mannheim, Germany). Proteins were separated on a 10% SDS-Gel and exposed for 3 days to a BAS-MP Imaging Plate (Fuji, Tokyo, Japan). The Imaging Plate was analyzed with the Fuji FLA-5000 (Fuji, Tokyo, Japan) using AIDA Version 3.10 and Multigauge.

Analysis of β-GC membrane Association

Cos7 cells were transfected with expression vectors for β-GC, LIMP-2myc or eGFP. 48 h after transfection cells were harvested in 0.5 ml PBS including protease inhibitors, sonicated and centrifuged at 1200 g. The post nuclear supernatants were either adjusted to 1% Triton X100 (cell extract) or further centrifuged at 45,000 g for 45 min. The resulting supernatants represent the soluble fraction and were used for SDS-PAGE analysis. The pellet (membrane fraction) was resuspended in RIPA buffer (150 mM NaCl, 50 mM Tris-Cl pH 7.4, 5 mM EDTA, 0.1% SDS, 1% NP40, 0.5% deoxycholate, proteinase inhibitors), sonicated, centrifuged for 10 min at 100,000 g and the resulting supernatant was used for SDS-PAGE analysis.

SDS-PAGE and Immunoblotting

Laemmli-SDS-PAGE gels were stained with Coomassie brilliant blue R-250, or stained using the Silver Stain kit from Owl Separation Systems (Portsmouth, N.H.). For immunoblots, proteins were transferred to polyvinylidene fluoride (PVDF) membranes (Millipore Corp, Bedford, Mass.) using a semi-dry electroblotter (Biorad, Hercules, Calif.). All blots were developed using an enhanced chemiluminescent detection system (Pierce). Immunoblots were blocked in 10% milk in PBS or TBS containing 0.1% Tween-20, then probed with 0.2 µg/mL affinity purified anti-LIMP-2, anti-βGC, anti-LAMP-2, anti-cathepsin-D, or anti-tubulin antibodies in 1% milk or 1% BSA, followed by 0.1 µg/mL of an appropriate peroxidase conjugated secondary IgG in 1% milk or 1% BSA.

Immunostaining and Immunohistochemistry on Tissue Sections

For immunostaining cells were grown on glass coverslips, fixed in 4% paraformaldehyde in phosphate-buffered saline (PBS) for 30 min, and permeabilized with PBS/0.2% saponin. The primary and secondary antibodies were diluted in PBS/3% BSA/0.2% saponin and incubated on cells for 1 h. Alexa Fluor 350-, 488-, or 594-conjugated secondary antibodies were from Molecular Probes (Eugene, Oreg.). Cells were embedded in Mowiol containing Dabco (Sigma Aldrich, Steinheim, Germany) as an antifading agent.

Spleen and liver of WT and LIMP-2 KO mice (n=2, each genotype) perfused with 4% paraformaldehyde (PFA) in 0.1M phosphate buffer (PB) were incubated in 30% sucrose in 0.1M phosphate buffer (PB)≥24 h before preparing free-floating cryo-sections (50 µm) at a Leica microtome. For immunohistochemistry, sections were rinsed in 0.1M PB and blocked in 0.1M PB with 0.2% BSA, 4% normal goat serum, 0.5% Triton-X-100 for 2 hrs at RT. After incubation with first antibody, sections were rinsed with 0.1M PB/0.5% Triton-X-100 and incubated with secondary fluorescent antibodies (Alexa fluor 488 and 594, Molecular Probes, 1:1000). Primary antibodies used: LAMP-1 (1:500, Pharmingen); LIMP-2 (1:500), β-GC (1:250). DAPI (1:1000) was used to stain nuclei. Samples were examined and photographed with a Zeiss Axiovert 200M fluorescence microscope equipped with an Apotome to generate optical sections and an Axiocam MRm Rev. 2D camera, using Axiovision Software Rel 4.2 (Zeiss; Göttingen, Germany).

Northern Blotting

Total RNA of kidney, liver and fibroblasts were prepared using RNAeasy columns from Qiagen (Hilden, Germany). Total RNA samples were separated in a formaldehyde agarose gel and blotted on Nylon filters. Filters were hybridized overnight with a mouse βGC or mouse glyceraldehyde dehydrogenase (GAPDH) cDNA probe, washed, exposed to an imaging plate and developed with the Fuji FLA-5000-Phosphoimager (Fujifilm, Japan) using AIDA software (version 3.10).

Mass Spectroscopy

LIMP-2 affinity purified from murine liver extract was resolved by SDS-PAGE, stained with Coomassie brilliant blue R-250, excised from the gel, in-gel digested with trypsin, and the resulting peptides analyzed by nano-LC/MS/MS to obtain peptide sequence data. These data were used to query the National Center for Biotechnology Information (Bethesda, Md.) non-redundant database using the Mascot program (Matrix Science Inc, Boston Mass.).

Proteasomal Inhibition Experiments

Hela cells or MEF cells were treated for 8 h with 15 µM MG-132 (Merck, Darmstadt, Germany) and 25 µM ALLN (Merck, Darmstadt, Germany) in normal cell culture or in $^{35}$S-Met/Cys medium for metabolic labeling. For metabolic labeling, MG-312 and ALLN were present throughout the labelling and the chase period. Proteasomal inhibition was confirmed by the accumulation of high-molecular weight Ubiquitin-aggregates (detected by an mouse-anti-polyUbiquitin, clone FK1, Biotrend, Cologne, Germany).

Analysis of Coiled-Coil Probability

Coiled-coil probabilities within LimpII wild-type and respective mutants were determined with the program COILS (www.ch.embnet.org).

Results

Figure 1B:
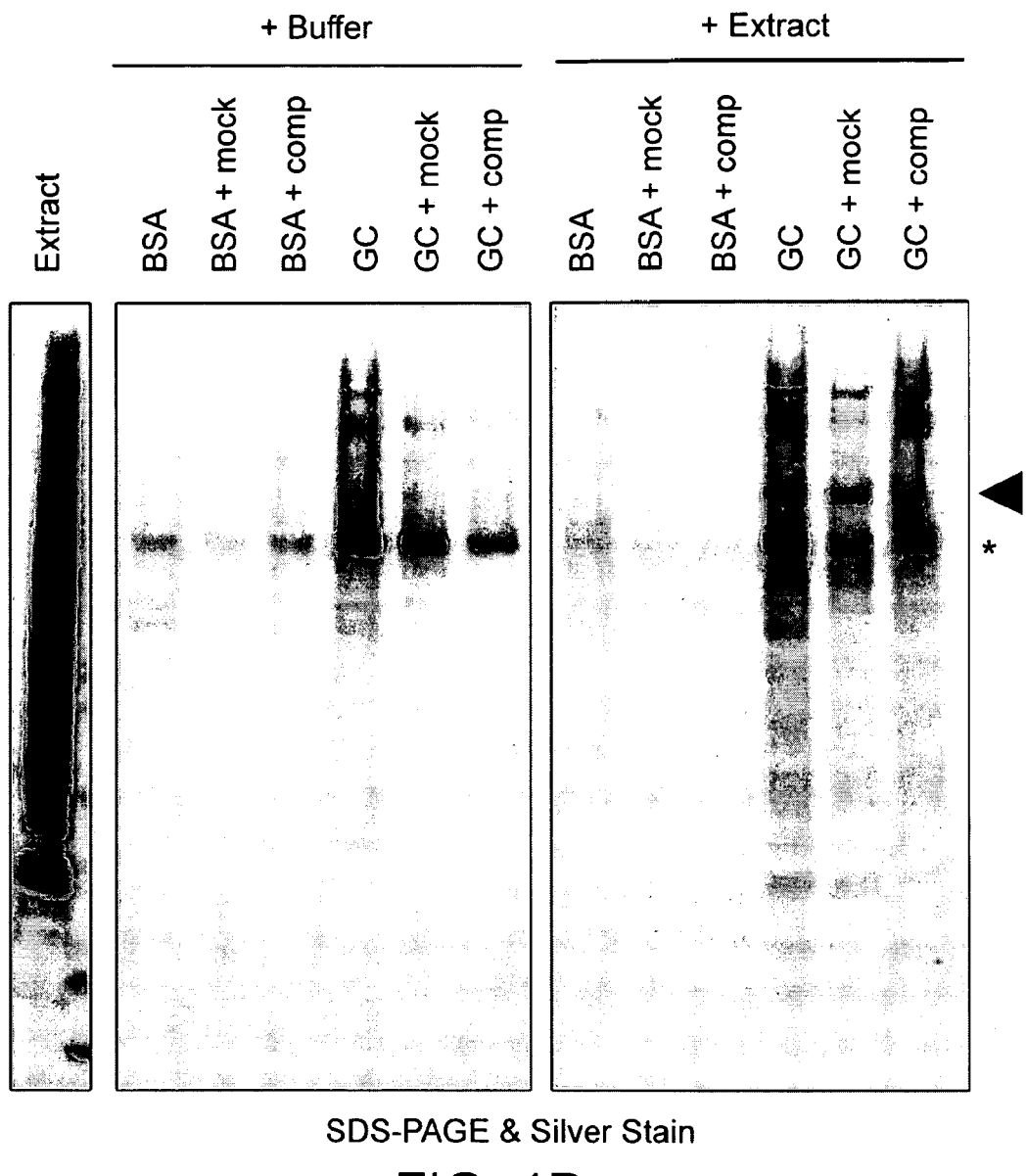
Figure 1C:
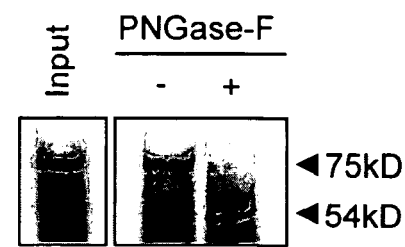

Isolation and Identification of LIMP-2 as a β-Glucocerebrosidase Interacting Protein The intracellular trafficking and enzymatic activity of βGC, unlike that of most lysosomal hydrolases, was unaffected in mouse embryonic fibroblasts doubly deficient for both MPRs (FIGS. 7A-7E). In an attempt to identify proteins involved in the intracellular trafficking of βGC an affinity chromatography approach was employed. A total detergent soluble extract of murine liver was passed over recombinant βGC affinity resin and, following extensive washing of the resin, bound proteins were eluted using pH 4.7 acetate buffer, collected and then analyzed by SDS-PAGE and silver staining (FIG. 1A). A sample of the same extract was also passed over a control resin to which an equimolar amount of bovine serum albumin (BSA) had been coupled to monitor non-specific background binding of proteins to the resin. A careful comparison of the eluates from the two columns revealed that a polypeptide with an apparent mass of 75 kD was present in the fractions eluted from the βGC resin but not the control resin (FIG. 1A). To further evaluate the specificity of this binding candidate for βGC a series of small-scale affinity binding reactions was run in the presence of excess soluble βGC or BSA. Competition with a four-fold molar excess of soluble βGC prevented binding of the 75 kD to the βGC resin (FIG. 1B). Molar excess of BSA had no effect on 75 kD polypeptide binding. These results further substantiated that the 75 kD polypeptide was binding specifically to βGC. To determine the identity of this protein, fractions from the large-scale βGC affinity column enriched in the 75 kD polypeptide were resolved by SDS-PAGE and the band of interest excised, in-gel digested with trypsin and sequenced using nano-LC-MS/MS. Based on the amino acid sequences obtained the polypeptide was identified as the lysosomal integral membrane protein, LIMP-2. PNGase-F treatment resulted in a mobility shift of this polypeptide from 75 kD to 54 kD (FIG. 1C) which was the molecular mass calculated for de-glycosylated LIMP-2.

Figure 1D:
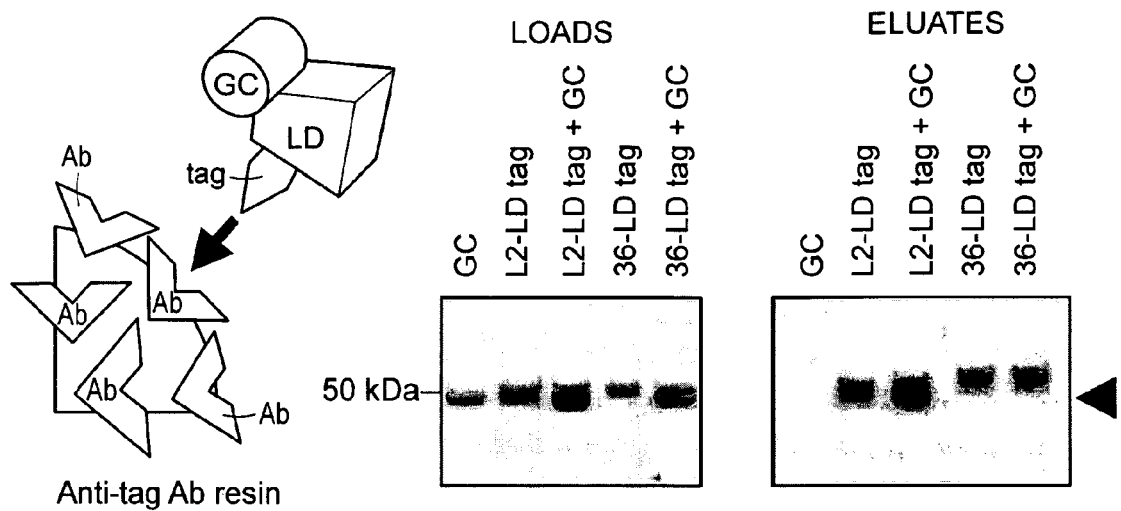

The Lumenal Domain of LIMP-2 is Required for Association with β-Glucocerebrosidase βGC resides in lysosomes as a protein associated with the lumenal membrane (Rijnboutt et al., 1991). Topologically, the lumenal portion of the LIMP-2 polypeptide was postulated to be in close proximity to this membrane (Okazaki et al., 1992). Therefore, whether this region in LIMP-2 might be responsible for the association with βGC (FIG. 1D) was investigated. Recombinant fusion-tagged LIMP-2 lumenal domain protein (L2LD) encompassing residues 27-432 was expressed as a soluble protein, purified and then used in an in vitro pull down assay with βGC (FIG. 1D). βGC bound specifically to L2LD indicating that the lumenal domain of LIMP-2 was sufficient for the interaction and that the binding between these two proteins was direct. When a similar in vitro pull down assay was performed using recombinant fusion-tagged LIMP-2 cytoplasmic domain protein or the isolated N- or C-terminal halves of the lumenal domain (residues 27-155 or 155-432) no binding of βGC was detected (data not shown). Also investigated was whether the corresponding lumenal region of CD36 (CD36LD) had the capacity to bind βGC in this assay since CD36 and LIMP-2 share ~34% overall sequence identity, the majority of which is found across the lumenal domain (FIG. 1D). No binding of CD36LD was detected indicating that the interaction of βGC with LIMP-2 likely depends on features unique to the LIMP-2 lumenal domain. These data support a scenario in which domains of LIMP-2 and βGC interact within the lumen of some or all of the secretory compartments in which they co-exist.

Figure 1E:
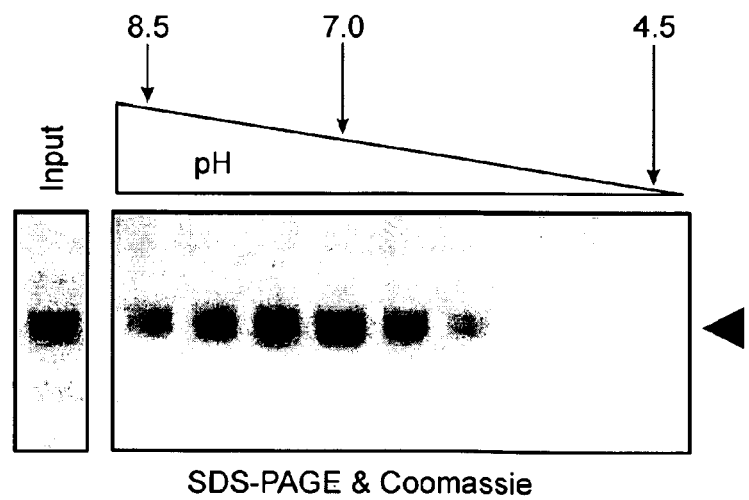

The efforts described herein to isolate and identify LIMP-2 from tissue extracts revealed that full length endogenous LIMP-2 could be released effectively from βGC affinity resin by elution with buffers at lysosomal pH. βGC passes through intracellular compartments of varying pH en route from its point of synthesis in the ER to its final destination in lysosomes. To determine compartments in which the association or dissociation of LIMP-2 and βGC may occur, the ability of βGC affinity resin to bind L2LD over a range of pH was tested via small-scale in vitro binding reactions (FIG. 1E). Binding of L2LD to the βGC resin was favored at neutral pH and attenuated as pH approached that typical of the lysosomal lumen. This indicated the most probable points of βGC and LIMP-2 association were prelysosomal, beginning in compartments is early as the ER or Golgi apparatus.

Figure 2A:
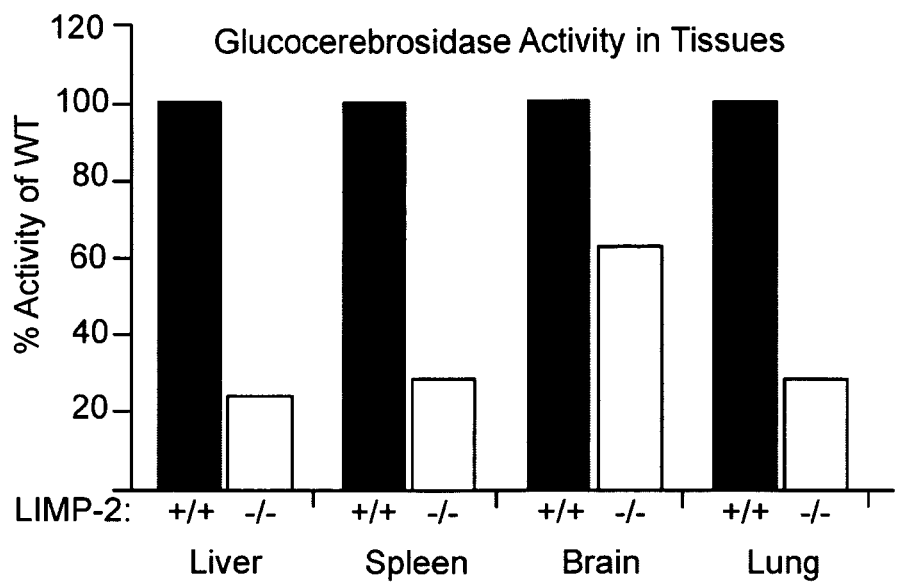
FIGS. 2A-2H: Decreased β-glucocerebrosidase activity and protein expression in LIMP-2-deficient mice.
Figure 2B:
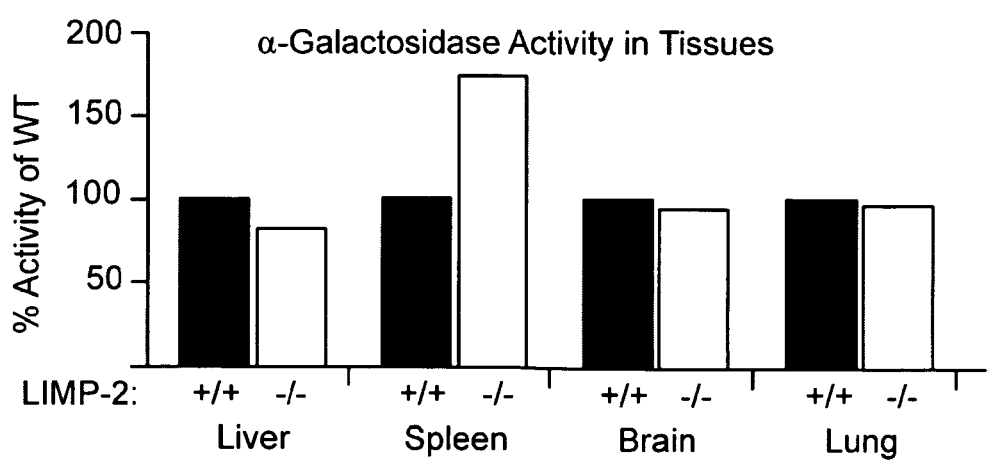
Figure 2C:
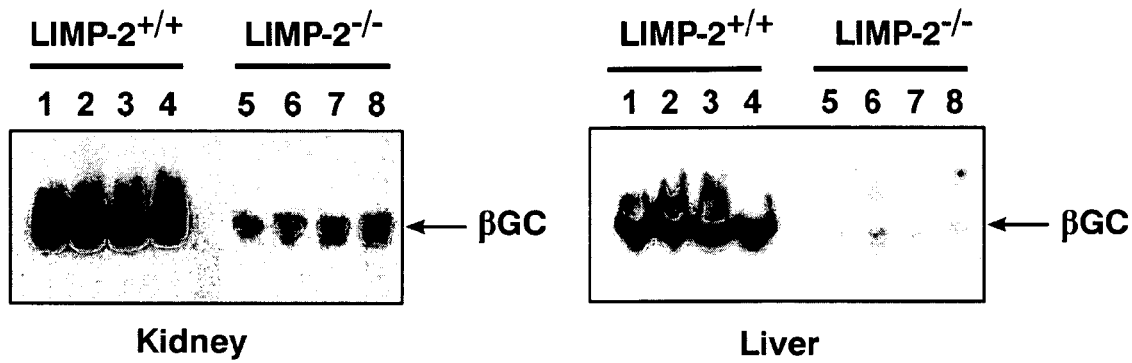
Figure 2D:
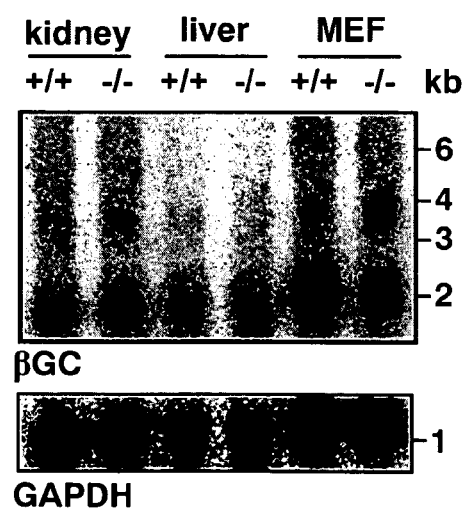

Effects of LIMP-2 Deficiency on β-Glucocerebrosidase Activity, Levels, and Localization The in vitro binding data provided herein support a situation in which βGC and LIMP-2 interact directly within intracellular trafficking compartments of cells. The effects of LIMP-2 deficiency in the LIMP-2 knockout mouse were explored to determine whether there might be βGC-specific consequences. This was started by evaluating βGC activity levels in total tissue homogenates from wild type and LIMP-2 knockout mice (FIG. 2A). The activity of another lysosomal hydrolase, α-galactosidase, which does not bind the lumenal domain of LIMP-2 in in vitro assays (data not shown), was also assayed for comparison (FIG. 2B). βGC activity was significantly decreased in all of the knockout tissue samples relative to wild type; this difference was most notable in liver where the average decrease was greater than 75% (FIG. 2A). In contrast, such a reduction was not seen when the activity of alpha-galactosidase was measured in the same samples. Immunoblotting revealed a very significant and consistent decrease in the levels of βGC protein in each of four knockout liver samples compared to wild type (FIG. 2C, right panel). Anti-βGC immunoblots of kidney homogenates prepared from these same animals yielded identical results (FIG. 2C, left panel). To determine if the reduced expression level was due to changes at the transcription level a Northern blot analysis of RNA derived from liver and kidney of wild type and LIMP-2 knockout mice was performed. The βGC transcript levels were not significantly different between the two genotypes (FIG. 2D) indicating that the decrease in βGC protein expression was due to post-transcriptional events.

Figure 2E:
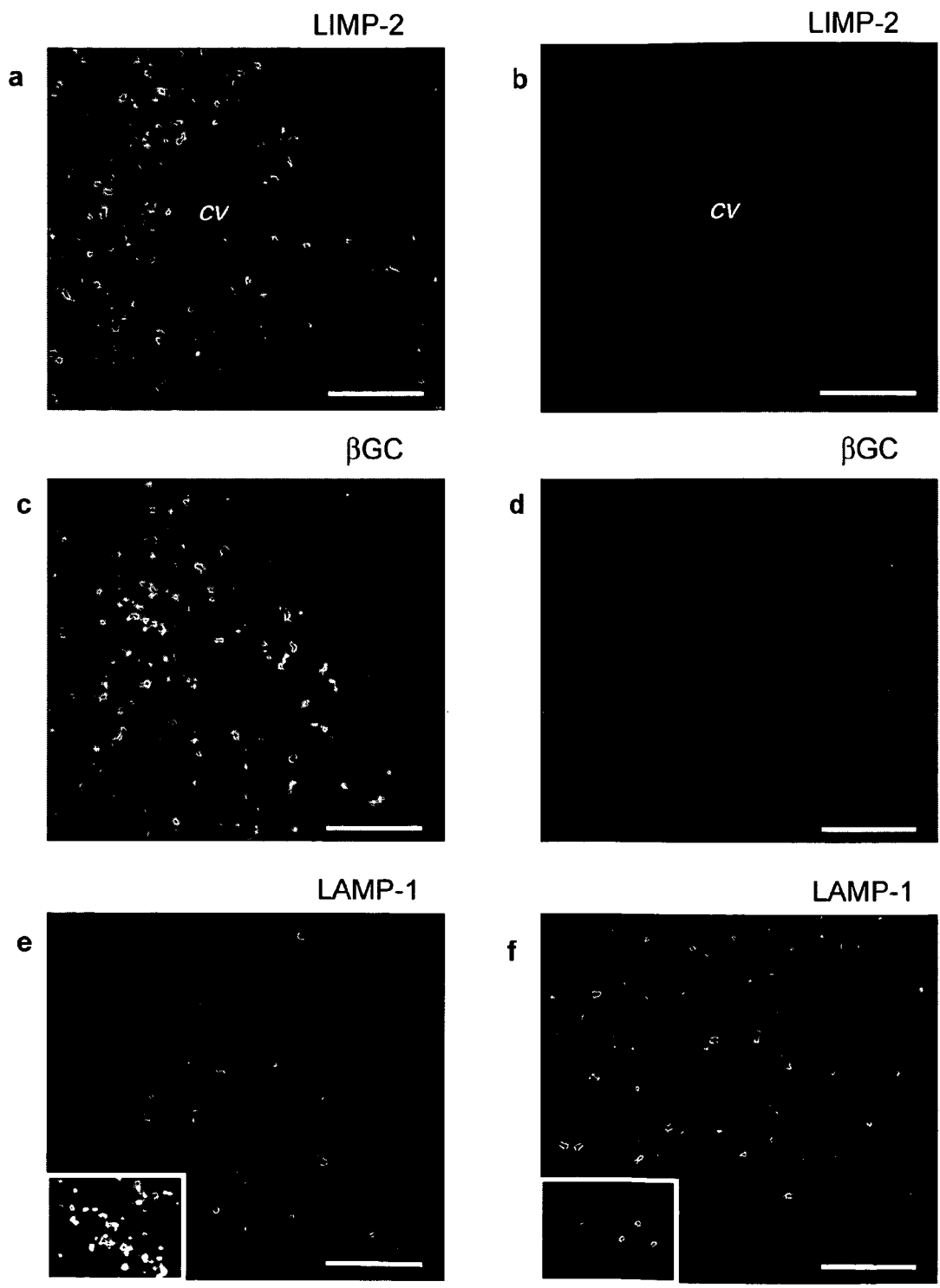
Figure 2F:
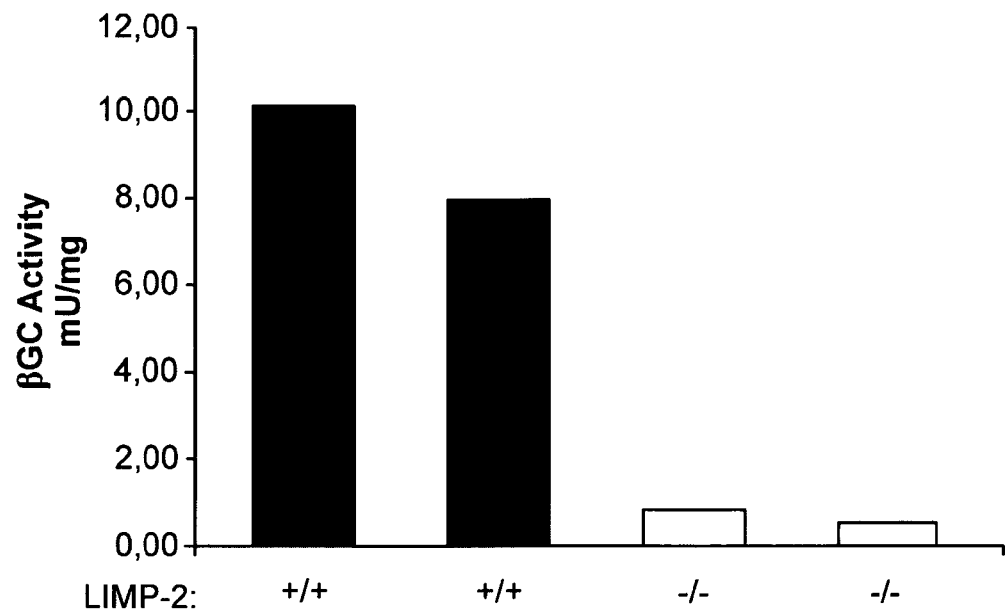
Figure 2G:
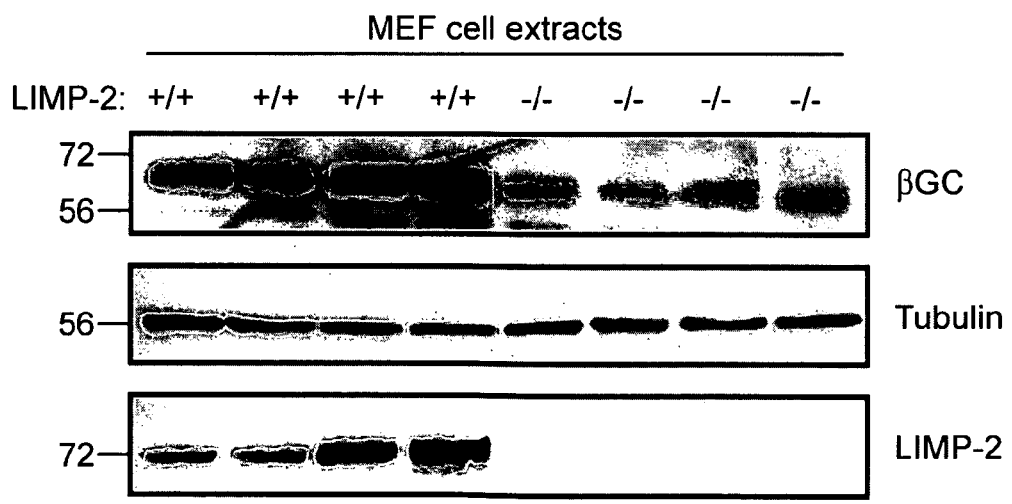
Figure 2H:
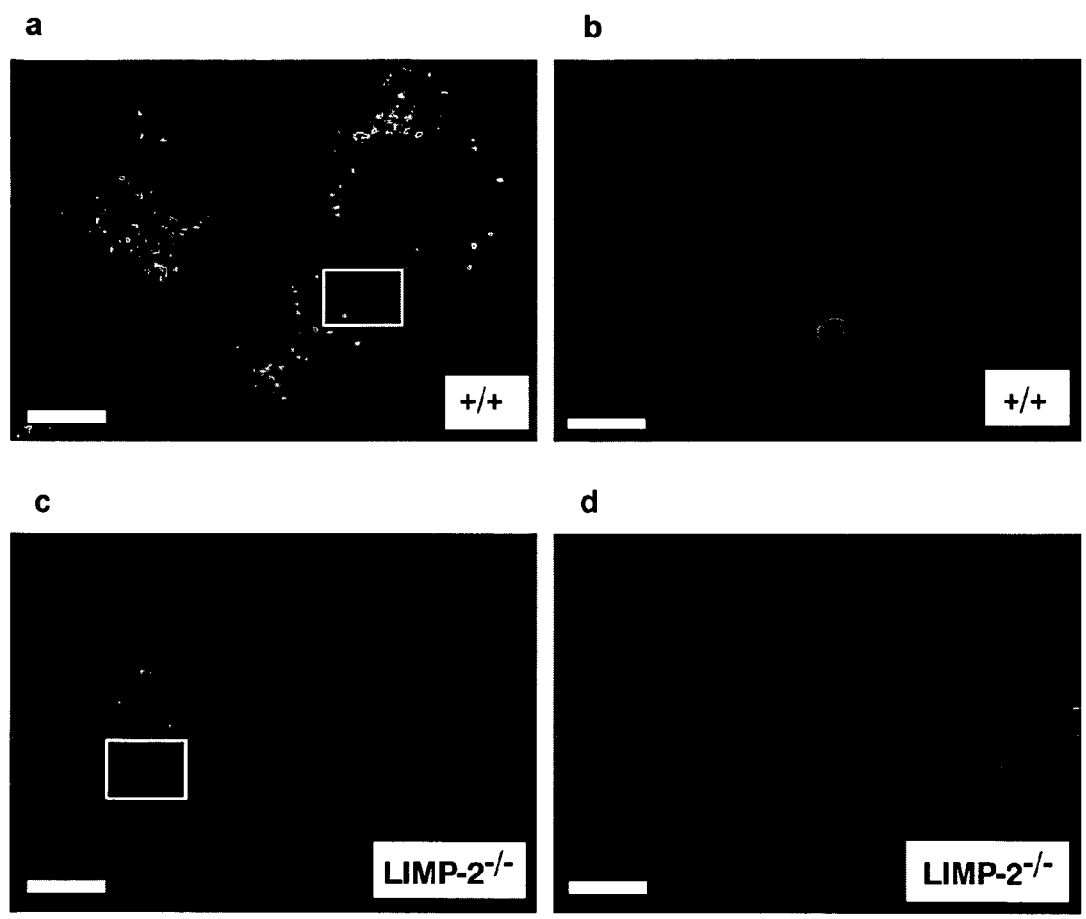
Figure 8:
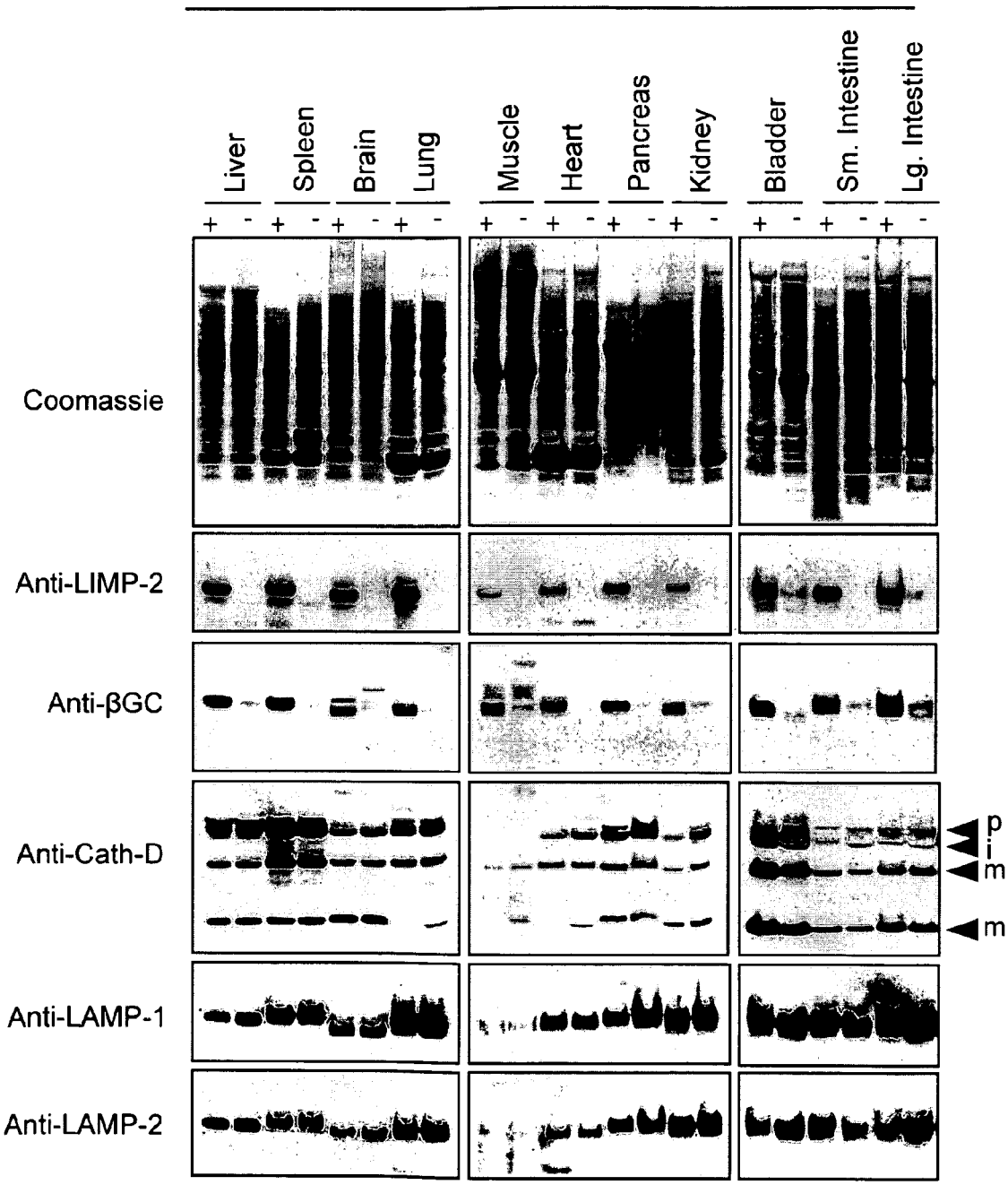
FIG. 8: Multiple tissue immunoblot showing the effect of LIMP-2 deficiency on the levels of LIMP-2, β-glucocerobrosidase, cathepsin-D, LAMP-1 and LAMP-2. Normalized loads of tissue homogenates were resolved by SDS-PAGE, blotted to PVDF and probed with antibodies specific to the proteins of interest. As a loading control Coomassie stained protein samples are shown (upper panel). β-glucocerobrosidase levels were strongly decreased in all analyzed tissues. Cathepsin-D levels and the levels of the lysosomal membrane proteins LAMP-1 and LAMP-2 were not changed. p, i, and m indicate the precursor, intermediate and mature forms of cathepsin-D
Figure 9A:
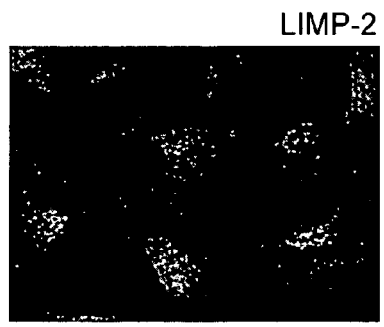
FIGS. 9A-9H: Downregulation of endogenous LIMP-2 expression by siRNA in Hela cells leads to a decrease in β-GC protein levels. Hela cells were transfected either with non-specific scrambled siRNA (FIGS. 9A, 9C, 9E, 9G) or with siRNA oligonucleotides specific for human LIMP-2 (FIGS. 9B, 9D, 9F, 9H). 3 days after transfection cells were analyzed for LIMP-2 expression (FIGS. 9A, 9B) and β-GC expression (FIGS. 9C, 9D). Nuclei were stained with DAPI (FIGS. 9E, 9F). Merged images are shown in G and H. Cells with a successful knockdown of LIMP-2 expression were indicated with an "*"; in these cells β-GC immunoreactivity was also dramatically reduced. Bars: 15 μm.
Figure 9B:
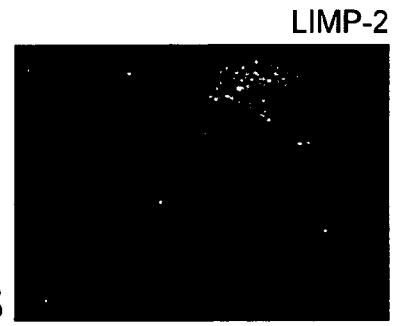
Figure 9C:
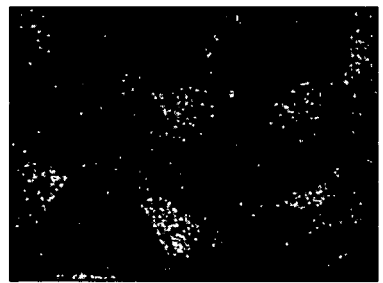
Figure 9D:
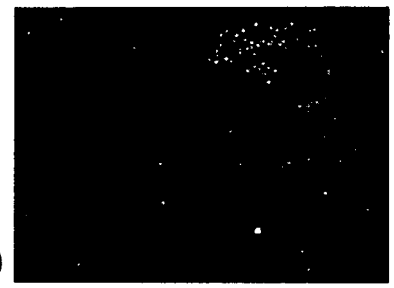
Figure 9E:
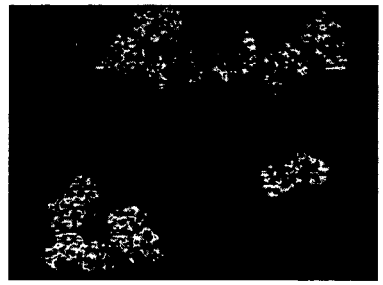
Figure 9F:
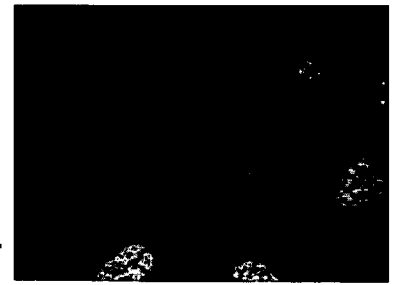
Figure 9G:
Figure 9H:
Figures 1, 10J:
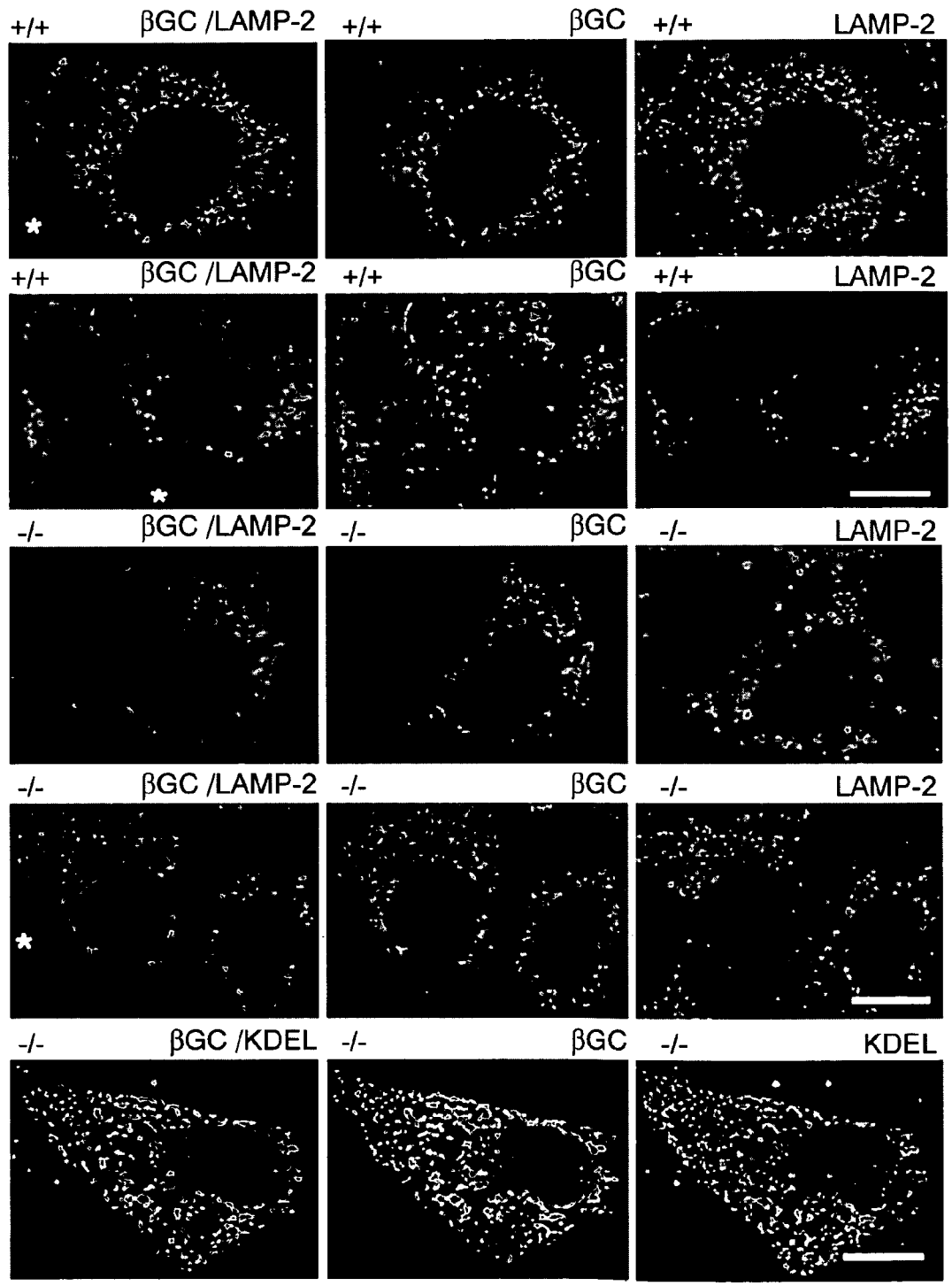
FIG. 10J: Wildtype (+/+) mouse embryonic fibroblasts (A) and LIMP-2 deficient MEF cells (B,C) were transfected with βGC and stained for βGC (middle panel) or LAMP-2 (right panel in A & B). The merged images (left panel) indicate that expressed βGC partially localizes to the lysosomal compartment in wildtype cells (A) but that in LIMP-2 knockout cells lysosomal delivery of the expressed βGC is not seen as evidenced by the lack of colocalization with LAMP-2 (B). βGC expression in LIMP-2 deficient MEF cells leads to the retention of βGC in the endoplasmic reticulum as revealed by co-staining with βGC (C: middle panel) and an antibody against KDEL (C:right panel). The merged image (C: left panel) reveals a significant co-localization off βGC and the ER-marker. Co-staining with βGC and LAMP-2 (B) shows that βGC does not reach the lysosomal compartment in LIMP-2 deficient MEF cells. Non transfected cells are marked by an *. Bars represent 10 μm. (D) Immunoblotting shows comparable transfection levels in wild type and LIMP-2 deficient MEF cells. A loading control (α-tubulin) is presented in the middle panel and LIMP-2 deficiency is confirmed in the lower panel. (E) In an additional experiment LIMP-2 deficient MEF cells were either left untransfected, transfected with □GC alone or transfected with βGC and LIMP-2 in different ratios. To determine the level of βGC remaining in the ER under each condition, a portion of each cell extract was incubated in the presence (+) or absence (−) of Endoglycosidase H (EndoH). In the upper panel it is revealed that when βGC is expressed alone almost all the protein is EndoH sensitive and therefore likely to reside in the ER. Transfection of βGC/LIMP-2 in a 1:1 ratio leads to a significant increase in βGC expression but also to an almost exclusive post-ER (lysosome) EndoH resistant form of βGC. Increasing the amount of LIMP-2 three fold did not further increase the βGC level or the βGC post-ER form. LIMP-2 expression is shown in the middle panel and a loading control is presented in the lower panel.
Figure 10J:
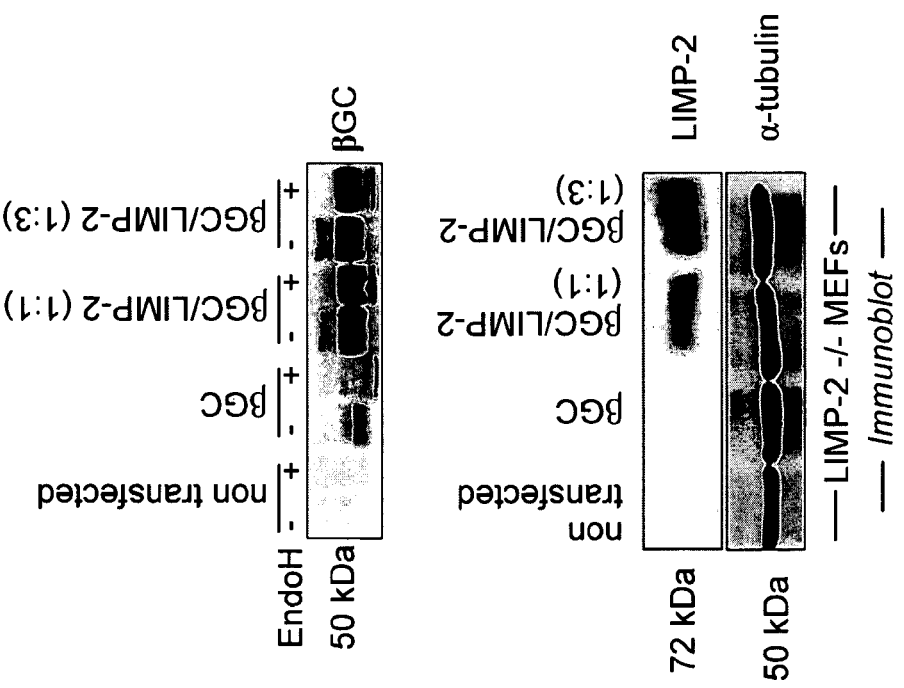
Figure 2:
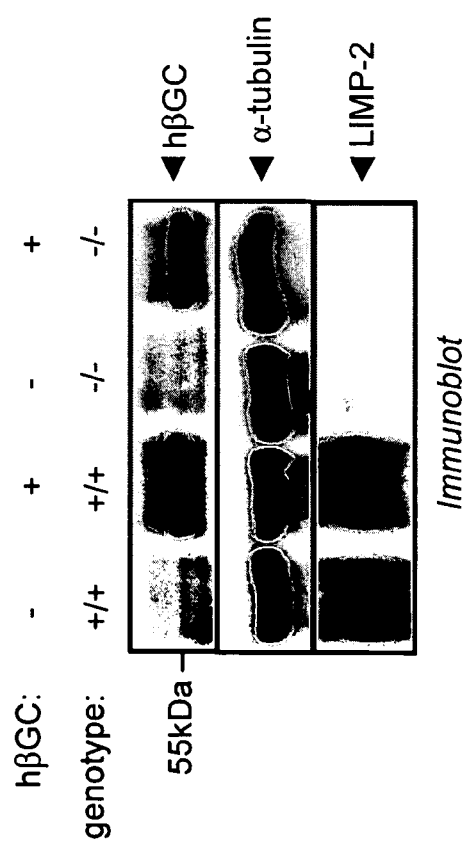
Figure 11A:
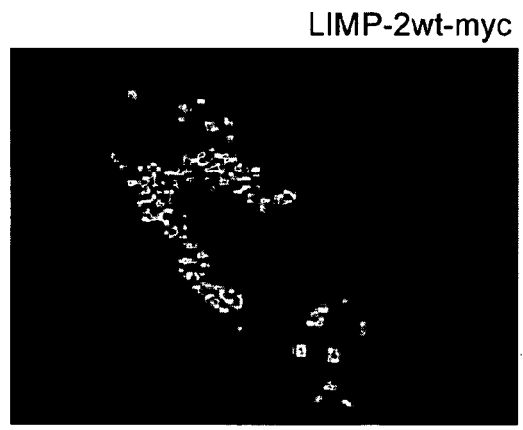
FIGS. 11A-11F: LIMP-2 was needed for efficient β-GC trafficking to the lysosomal compartment. COST-cells were co-transfected with LIMP-2 and β-GC expression constructs and 48 h after transfection fixed and stained with anti-myc-antibodies recognizing the tagged LIMP-2 wildtype protein (FIG. 11A) or the LIMP-2 mutant containing a strong ER retention motif (FIG. 11B) or with an anti-HA antibody detecting the tagged β-GC protein (FIGS. 11C, 11D). Merged images are presented in FIGS. 11E and 11F. The ER retention of LIMP-2 led to trapping of β-GC in the endoplasmic reticulum and prevented further transport to the vesicular lysosomal compartment. * indicates non transfected cells. Bars in FIGS. 11E and 11F: 10 μm.
Figure 11B:
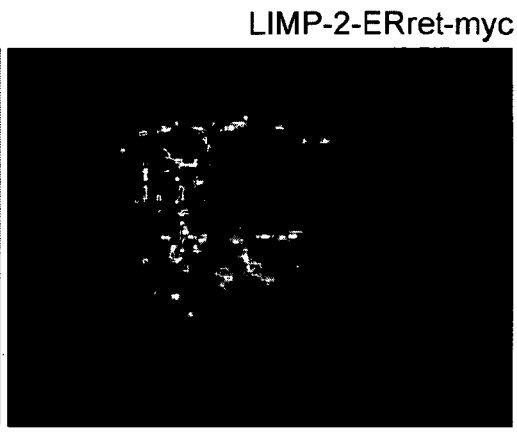
Figure 11C:
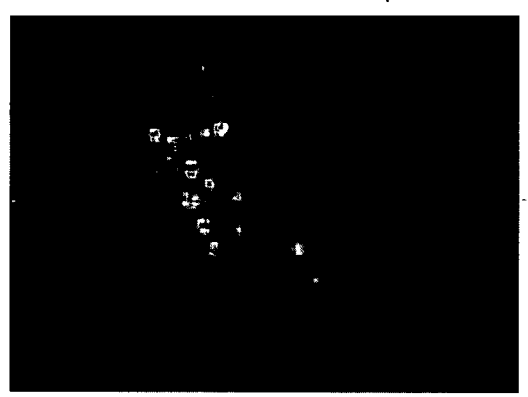
Figure 11D:
Figure 11E:
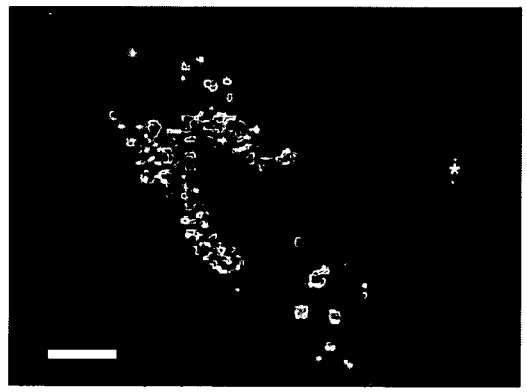
Figure 11F:
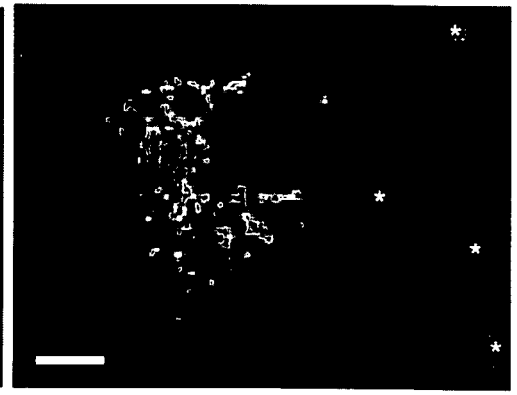

The differences in βGC enzyme activity detected between LIMP-2 wild type and knockout tissues were almost certainly a reflection of the drop in total βGC protein levels, a conclusion that was further substantiated by immunohistochemical staining (FIG. 2E). Spleen (not shown) and liver sections of WT and LIMP-2 KO mice were stained for LIMP-2 (FIG. 2E a,b), βGC (FIG. 2E c,d) and LAMP-1 (FIG. 2E e,f). In wild type tissues as exemplified by liver, LIMP-2 and βGC colocalized with LAMP-1 in lysosomes whereas in LIMP-2 KO tissue neither LIMP-2 nor βGC staining was visible. However, the levels and subcellular distribution of LAMP-1 in KO tissue appeared normal indicating that the integrity of the lysosomal compartment was maintained in LIMP-2-deficient tissue. In a wide spectrum of tissues a tight correlation between the relative levels of βGC and LIMP-2 protein was detected such that in samples in which LIMP-2 was absent βGC was deficient but in samples in which LIMP-2 was present βGC was readily detectable (FIG. 8).

Reduction of lysosomal βGC levels has been found to correlate with an increase in the βGC substrate glucosylceramide (GlcCer) in Gaucher disease (Brady et al., 1965; Nilsson et al., 1985; Nilsson and Svennerholm, 1982). Analysis of GlcCer levels in tissues isolated from wild type and LIMP-2 knockout mice revealed an almost two-fold increase of GlcCer in the liver and lung from LIMP-2-deficient animals (Table 1) compared to normal.

LIMP-2-Deficient Lysosomes are Depleted of β-Glucocerebrosidase

Figure 3A:
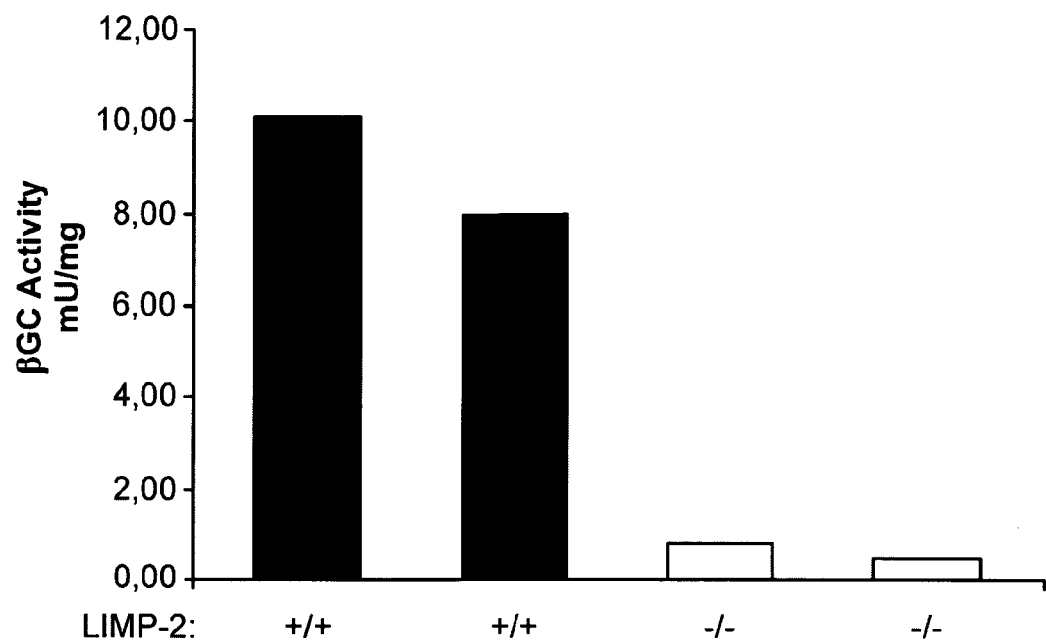
FIGS. 3A-3C: LIMP-2-deficient mouse embryonic fibroblasts were depleted of lysosomal βGC.
Figure 3B:
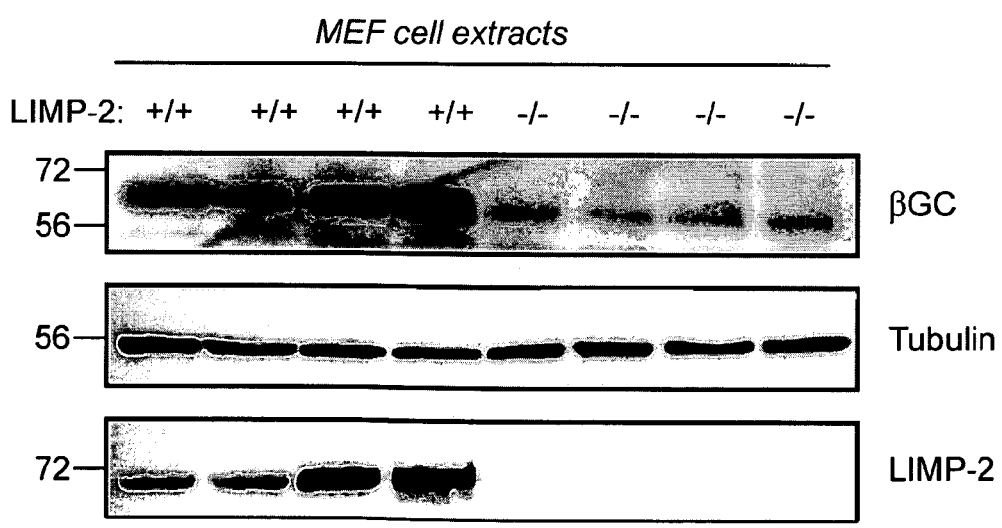
Figure 3C:
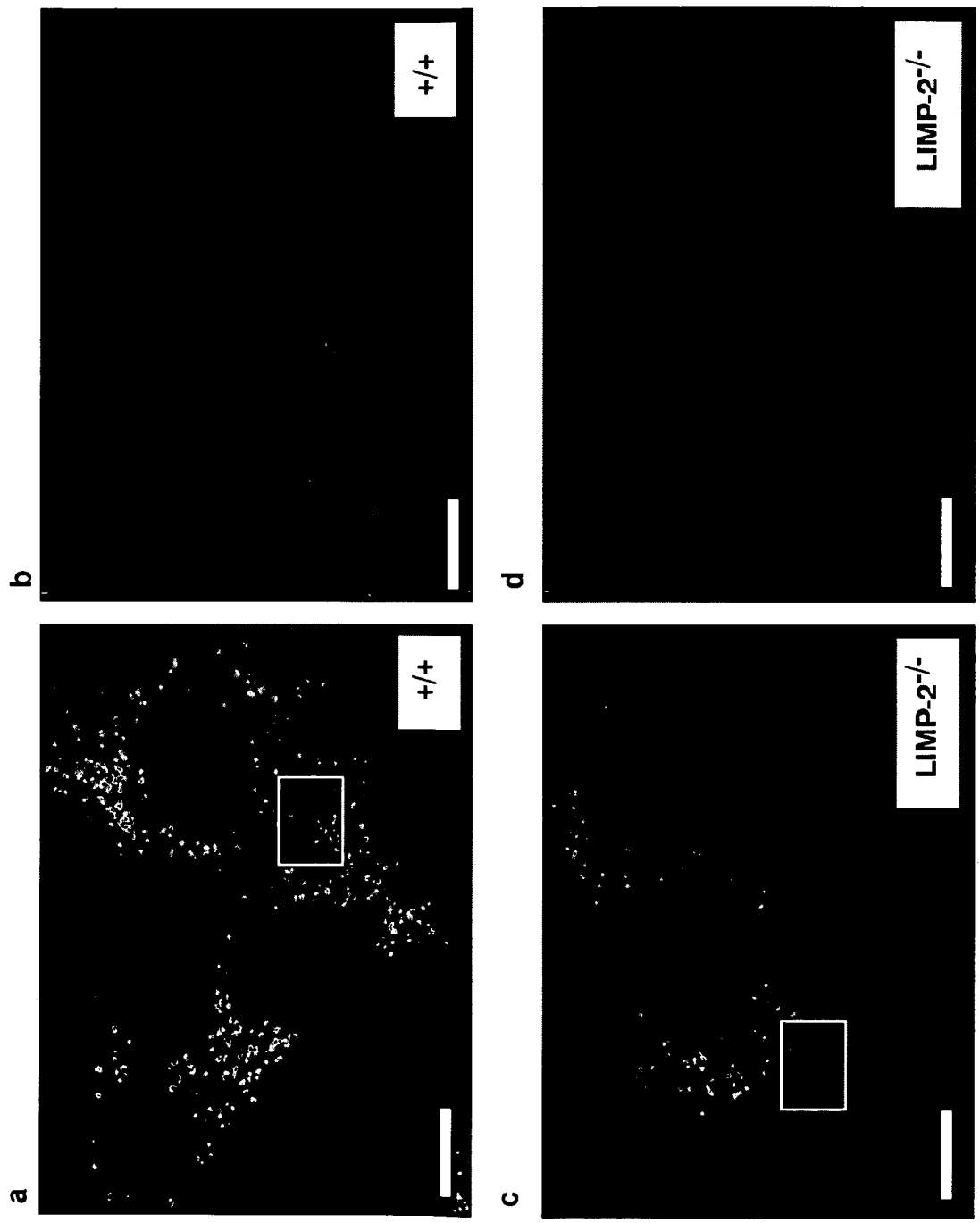

To more precisely define the molecular events leading to the reduction in βGC activity levels in LIMP-2-deficient tissues we examined the status of βGC in mouse embryonic fibroblast (MEF) cells derived from wild type and LIMP-2-deficient embryos. Both the activity (FIG. 3A) and the level of βGC protein (FIG. 3B) were dramatically reduced in the extracts from LIMP-2-deficient MEF cells. Immunostaining for βGC in the MEFs revealed that in WT cells βGC localized in LAMP-2 positive lysosomal compartments whereas in LIMP-2-deficient MEF cells (FIG. 3C) or Hela cells with an siRNA-mediated downregulation of LIMP-2 (FIGS. 9A-9H) almost no lysosomal βGC could be detected. Although in a minority of LIMP-2-deficient MEF cells a very weak lysosomal βGC staining was still detectable (not shown), in the majority of these cells it appeared that most if not all the βGC had been degraded and/or secreted. Overexpression of βGC in LIMP-2-deficient cells revealed that βGC was retained in the ER and unable to be delivered to the lysosomal compartment (FIGS. 10A-10I).

Figure 4G:
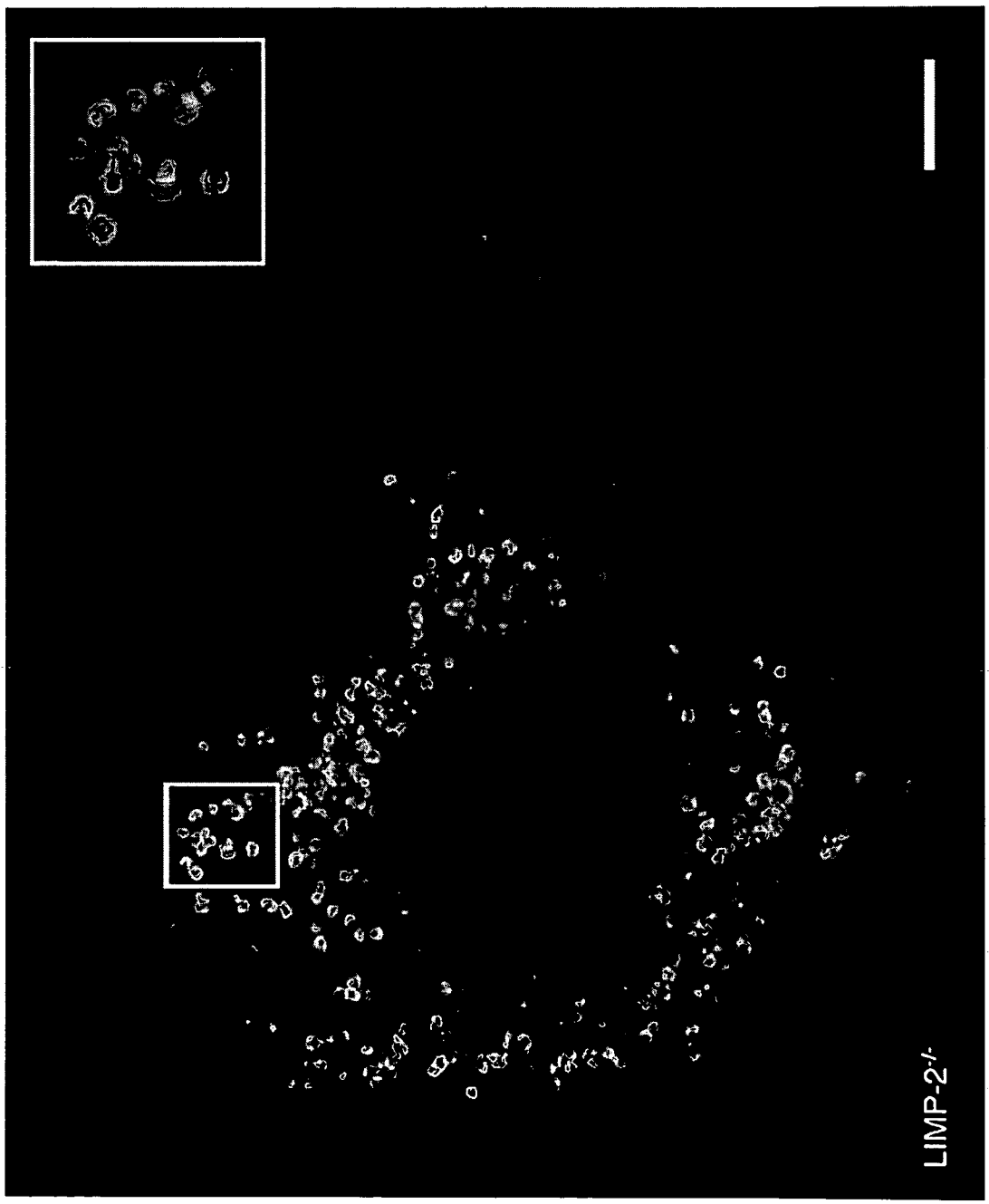
Figure 4H:
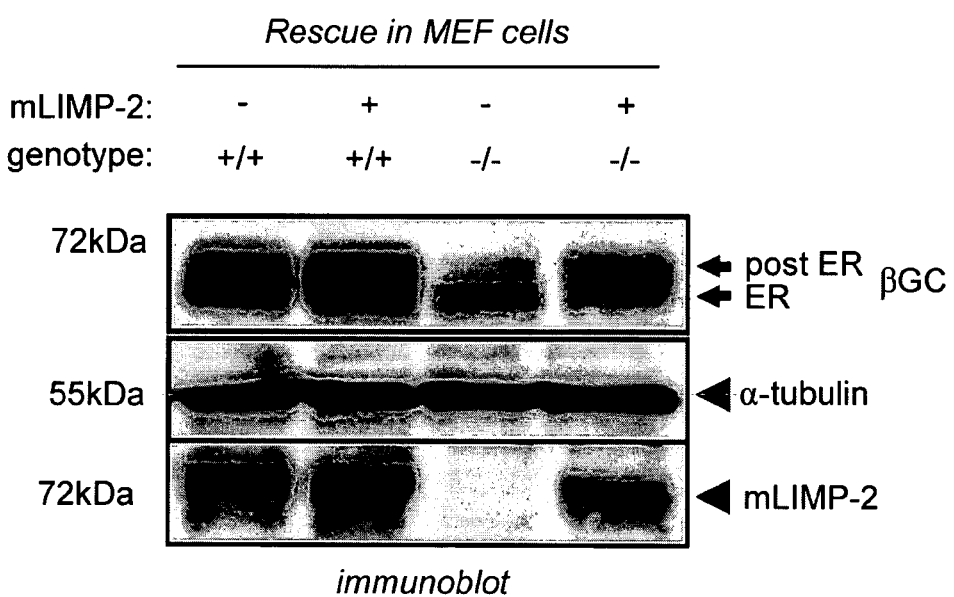

Given the dramatic effects of LIMP-2 deficiency on the status of βGC in cells whether LIMP-2 was directly required for the correct lysosomal localization of βGC was investigated. For this myc-tagged murine LIMP-2 was transfected into LIMP-2-deficient MEF cells and assessed whether LIMP-2 expression could rescue the mis-localization of βGC. Transfected cells were identified by staining with antibodies against the lumenal domain of LIMP-2 (not shown) or against the myc-epitope (FIG. 4A-C). In 95% of the LIMP-2 transfected cells, but not in LIMP-2 KO cells transfected with another lysosomal membrane protein (LAMP-2), the βGC expression levels were rescued to wild-type levels (see FIG. 3Ca) and βGC colocalized with LIMP-2 in lysosomal compartments (FIG. 4C). The juxta-membrane localization of both LIMP-2 and βGC was demonstrated by their ring-like staining pattern in the intracellular vesicles. A triple staining with LIMP-2, βGC and LAMP-2 (FIGS. 4D-4G) confirmed the correct lysosomal sorting of βGC after LIMP-2 re-expression. The requirement of LIMP-2 for the lysosomal localization of βGC was also supported by an additional experiment where LIMP-2 and βGC were co-expressed in Cos7 cells. Whereas LIMP-2 expression allows βGC to be delivered efficiently to the lysosomal compartment, the fusion of LIMP-2 to a strong ER retention motif (Zerangue et al., 2000) prevented the transport of βGC out of the ER (FIGS. 11A-11F). Immunoblot analysis after transient transfection of LIMP-2 in KO MEF cells confirmed the microscopical results. Expression of LIMP-2 led to an increase in the general βGC level and in the mature, most likely lysosomal, form of βGC (FIG. 3H).

Figure 26A:
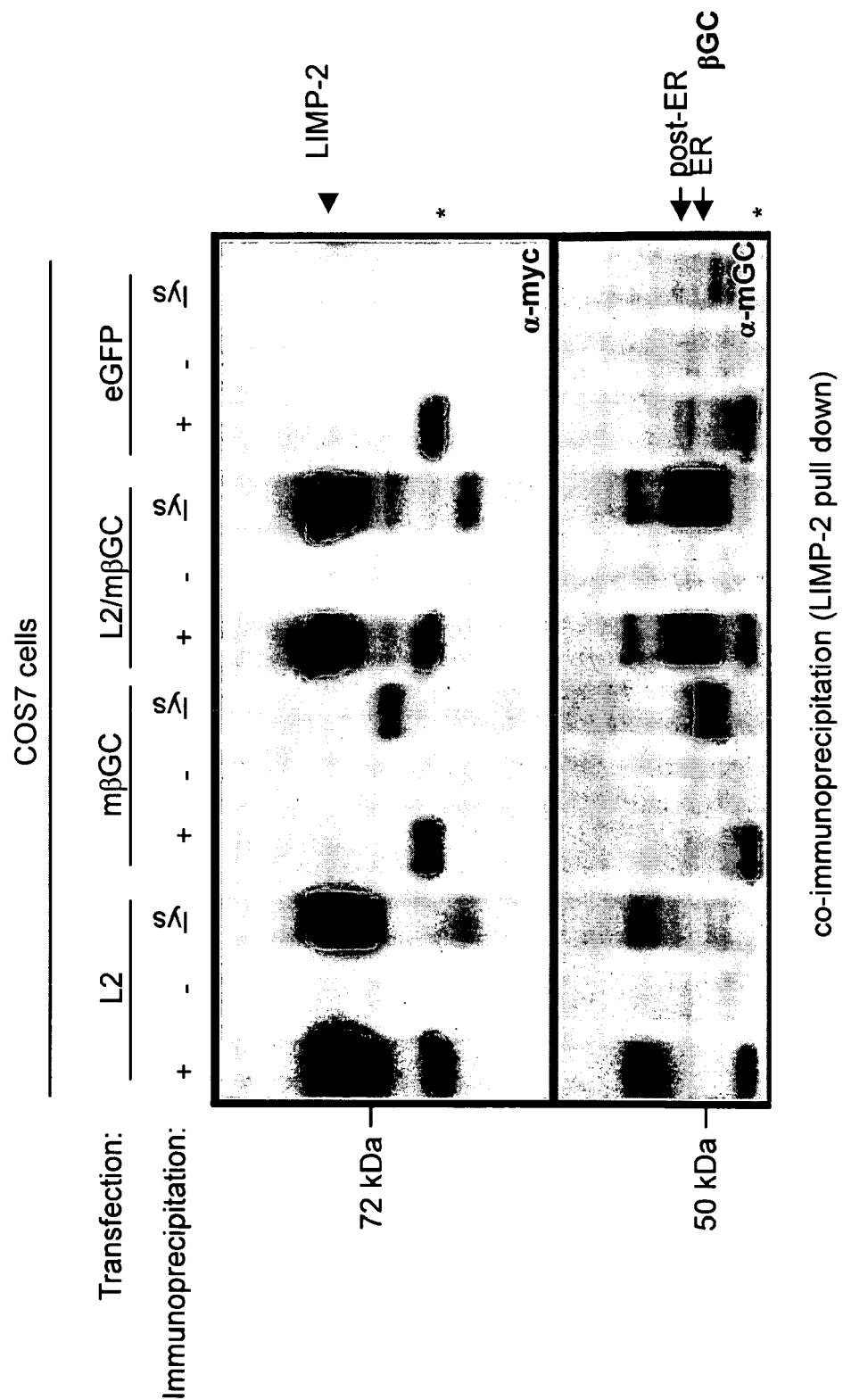

The requirement of LIMP-2 for the lysosomal localization of βGC was also supported by an additional experiment in COS cells in which LIMP-2 expression enabled the efficient delivery of βGC to the lysosomal compartment, but the fusion of LIMP-2 to a strong ER retention motif (Zerangue et al., 2000) prevented the transport of βGC out of the ER (FIG. 24A-24F). Co-immunoprecipitation confirmed the association of LIMP-2 and βGC as well as the association of the LIMP-2-ER retention mutant with βGC (FIG. 24G and FIG. 26A) again suggesting that binding of these proteins can occur in compartments as early as the endoplasmic reticulum. Also tested was the expression in COS cells of a truncated version of LIMP-2 (LIMP-2 (Id)) in which the lumenal domain was fused to the βGC signal peptide to target it to the extracellular space. LIMP-2 (Id) was found to be secreted. Coexpression of this LIMP-2 construct with βGC led to a dramatic increase in the amount of βGC secreted compared to that seen upon the expression of βGC on its own (FIG. 26B). Such an increase was not seen when wild type LIMP-2 was co-expressed with βGC. These data provided additional evidence for the association of these proteins.

Figure 25A:
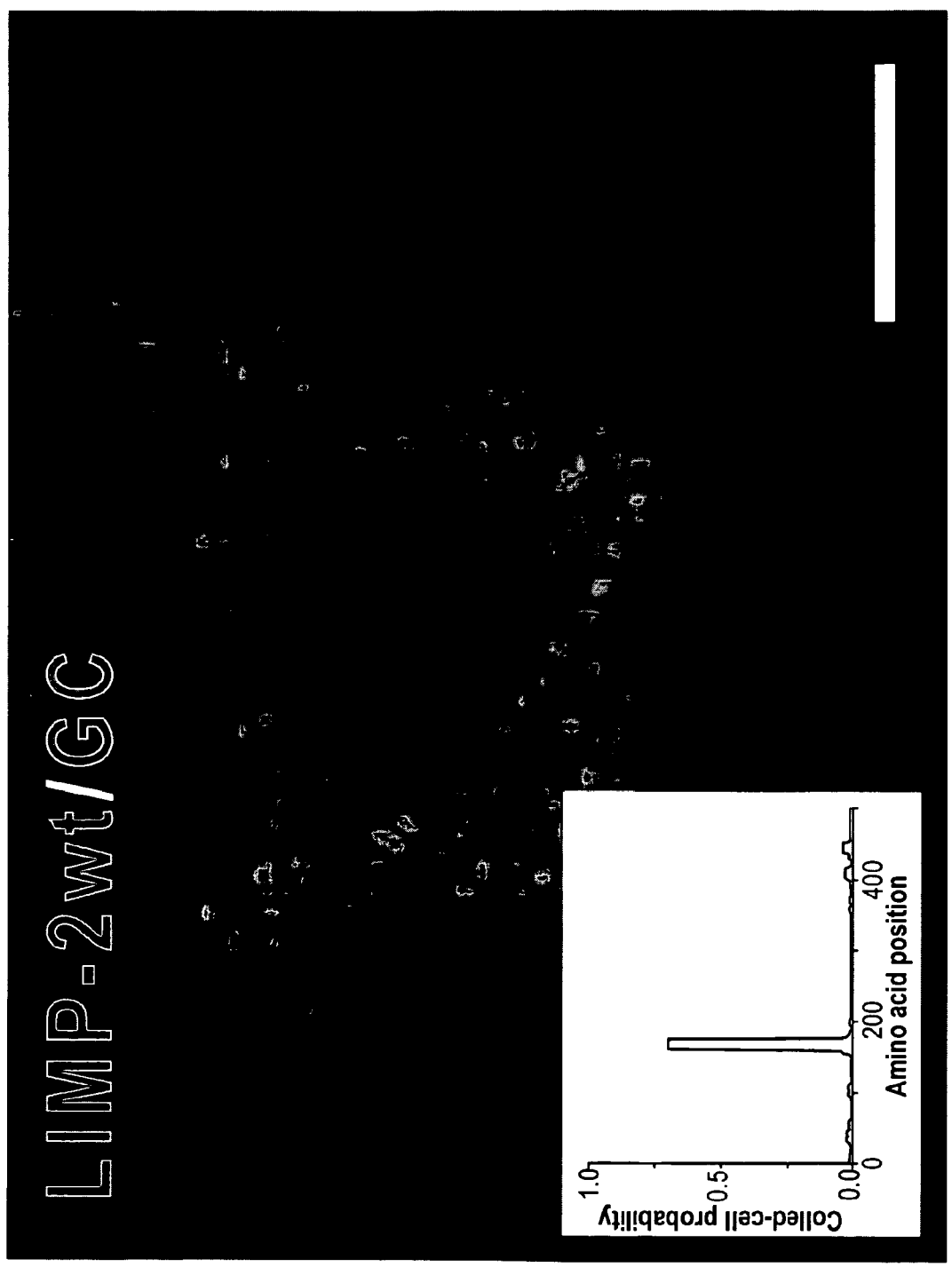
Figure 25C:
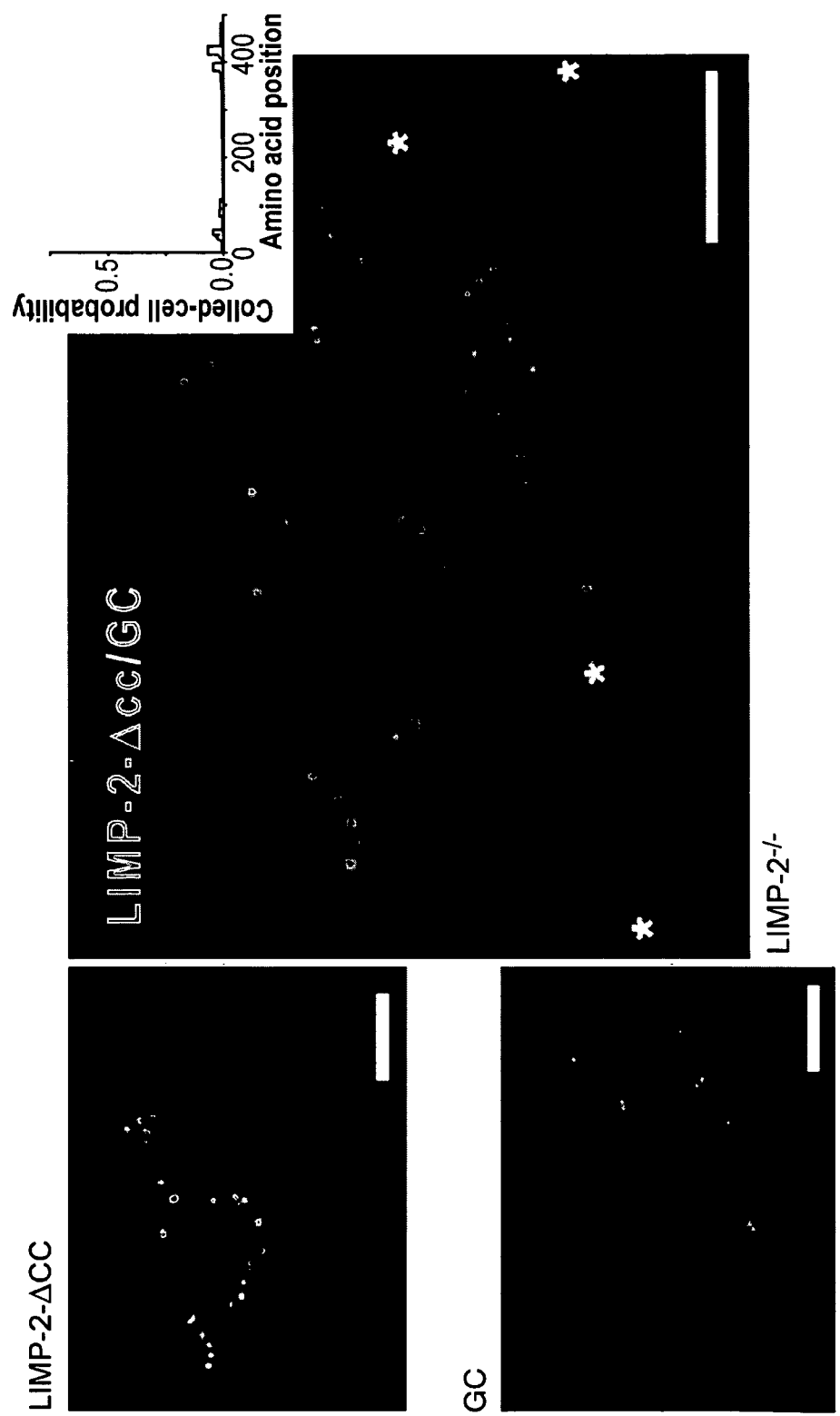
Figure 25D:
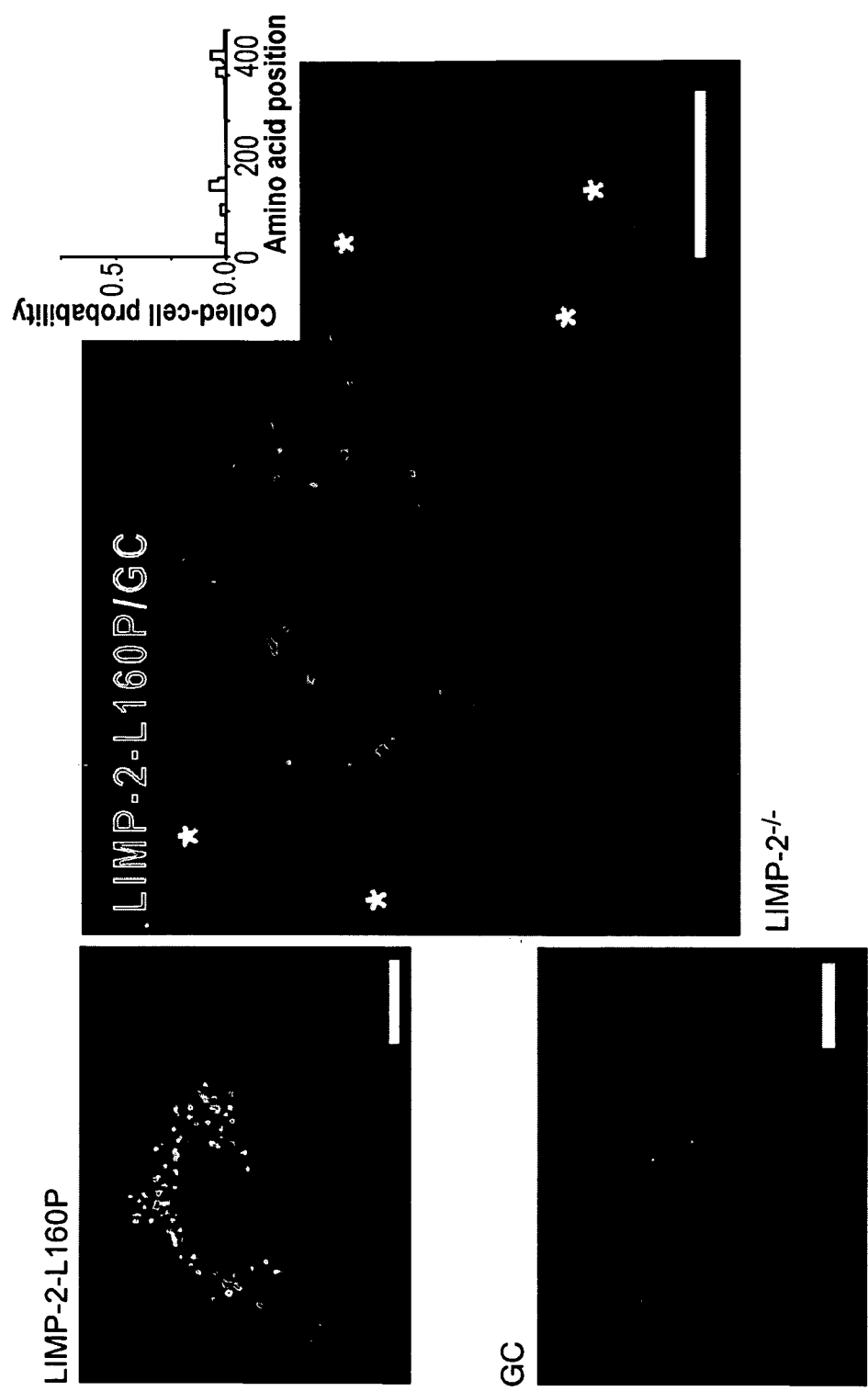

A Coiled-Coil Motif within the Lumenal Domain of LIMP-2 is Needed for □-Glucocerebrosidase Binding The isolated halves of the LIMP-2 lumenal domain (residues 27-155 and 155-432) do not bind βGC (data not shown). This suggested to us that a region around amino acid residue 155 might be required for the βGC-LIMP-2 association. Exploring this hypothesis, a conserved coiled-coil domain LIMP-2 from amino acid residue 150-167 (FIG. 25A, 25B) was discovered. When the putative coil-coiled domain was disrupted by deleting this region (LIMP-2Δcc) or by replacing a leucine to a proline at amino acid position 160 (LIMP-2-L160P), the resultant mutants failed to rescue lysosomal βGC expression in LIMP-2 deficient MEF cells despite the fact that both mutants were, like wildtype LIMP-2 (FIG. 25A), delivered normally to the lysosomal compartment (FIG. 25C, 25D). Co-immunoprecipitation analysis indicated that the physical interaction between endogenous βGC and LIMP-2 was lost in the case of both mutants (FIG. 25E). In vitro pull down experiments using purified recombinant proteins further confirmed the lack of βGC binding to the LIMP-2 L160P mutant (data not shown). Taken together, these results strongly suggest that the LIMP-2 region from residues 150-167 is crucially involved in the binding of LIMP-2 to βGC.

Figure 25F:
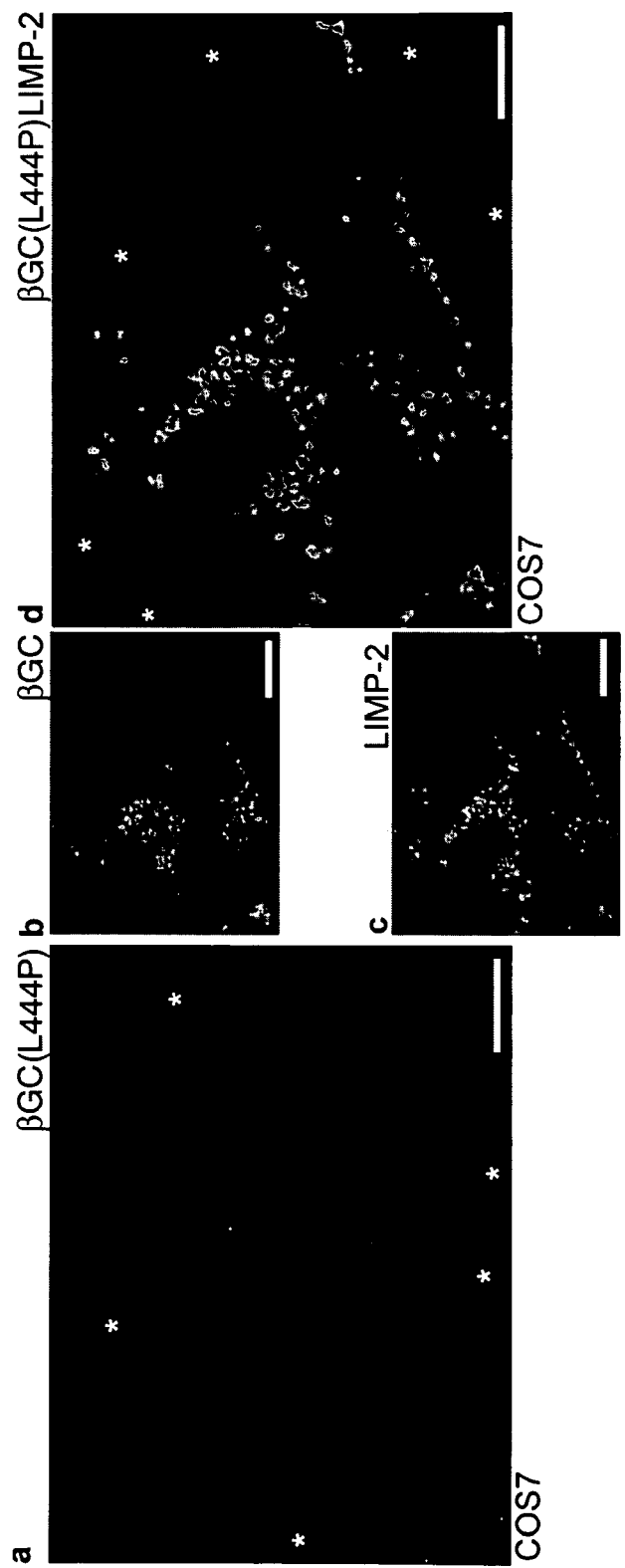
Figure 27B:
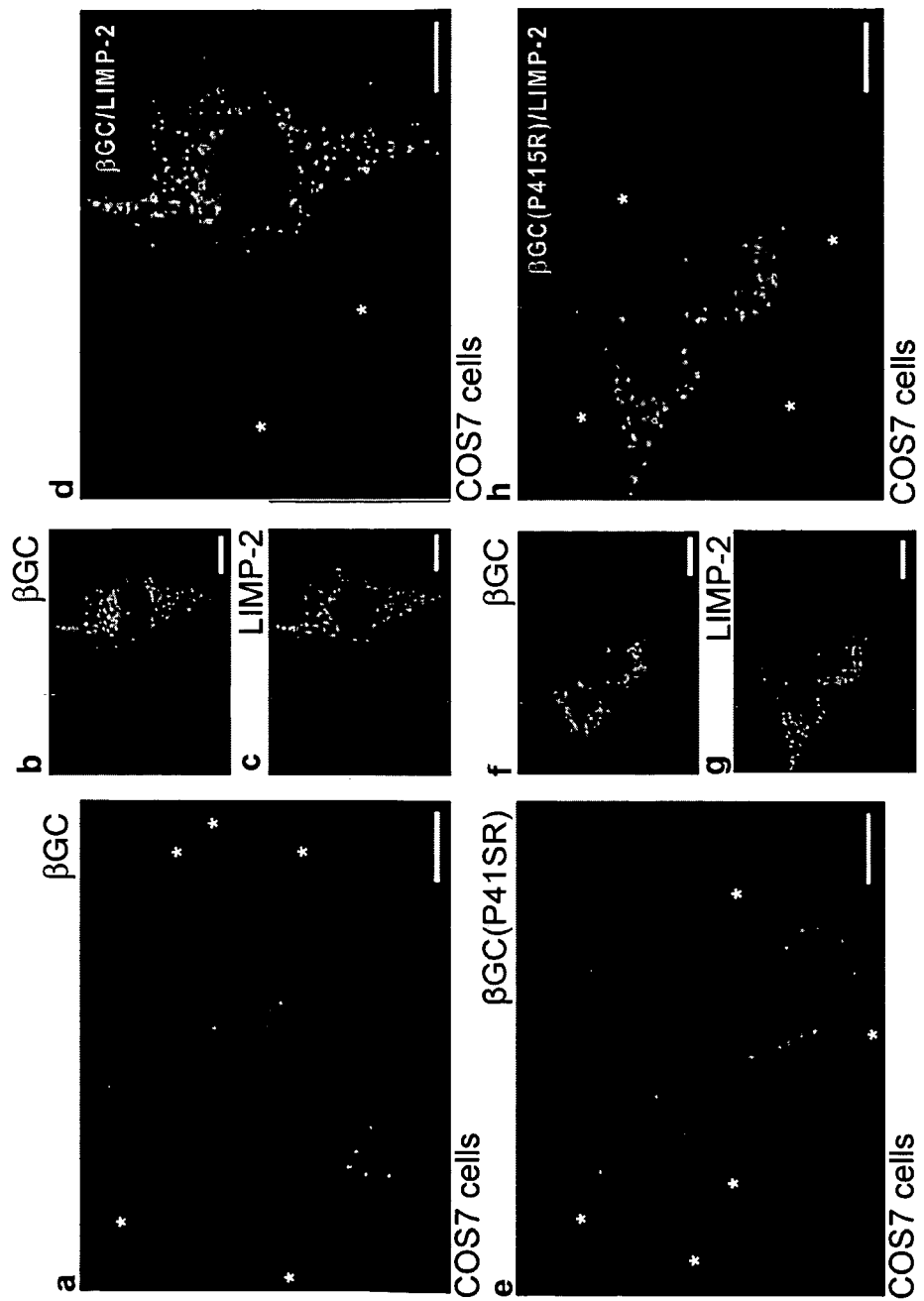

LIMP-2 Expression Leads to Lysosomal Localization of a Clinical Glucocerebrosidase Mutant Normally Retained in the Endoplasmic Reticulum To analyze if any of the more common clinical mutations within βGC affected binding to LIMP-2, βGC N370S, G202R and L444P were expressed, and interaction of LIMP-2 and these mutant proteins were analyzed in an in vitro binding assay. None of these mutations in βGC abrogated the binding to LIMP-2 (FIG. 27A-27B). Interestingly however, it was observed that LIMP-2 expression led to transport of βGC L444P, a known ER retention mutant (Schmitz et al., 2005), to the lysosomal compartment (FIG. 25F) suggesting that LIMP-2 can bind βGC within the endoplasmic reticulum and that an increase in LIMP-2 expression may be sufficient to overcome the ER retention of specific Gaucher mutants. Interestingly, the ER localization of another clinical βGC mutant, P415R, was not altered after overexpression of LIMP-2 (FIG. 27B) suggesting a direct or indirect effect of this mutation on binding to LIMP-2.

β-Glucocerebrosidase is Mis-Targeted In Vitro and In Vivo

Figure 5A:
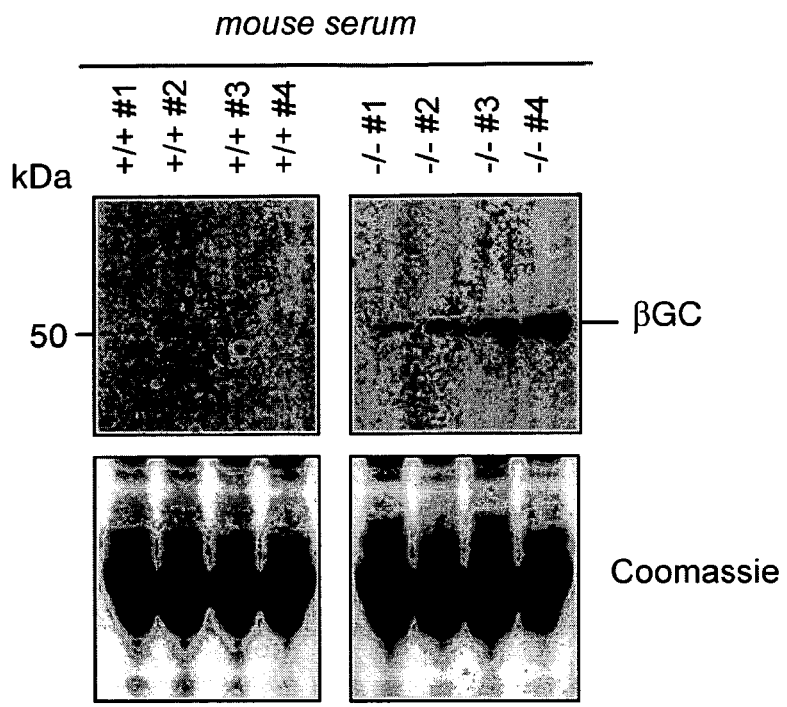
FIGS. 5A-5F: Missorting of β-glucocerebrosidase in the absence of LIMP-2.
Figure 5B:
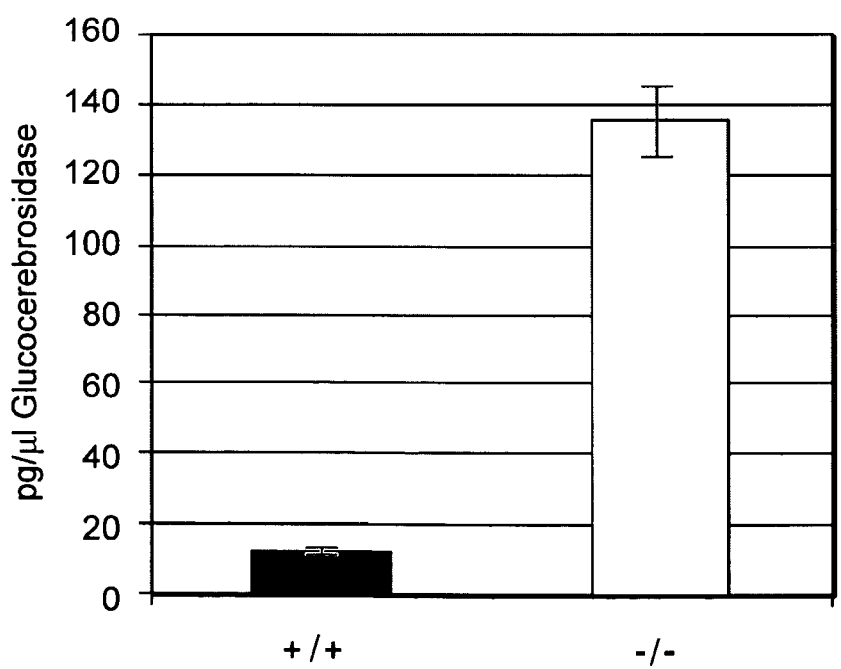
Figure 5C:
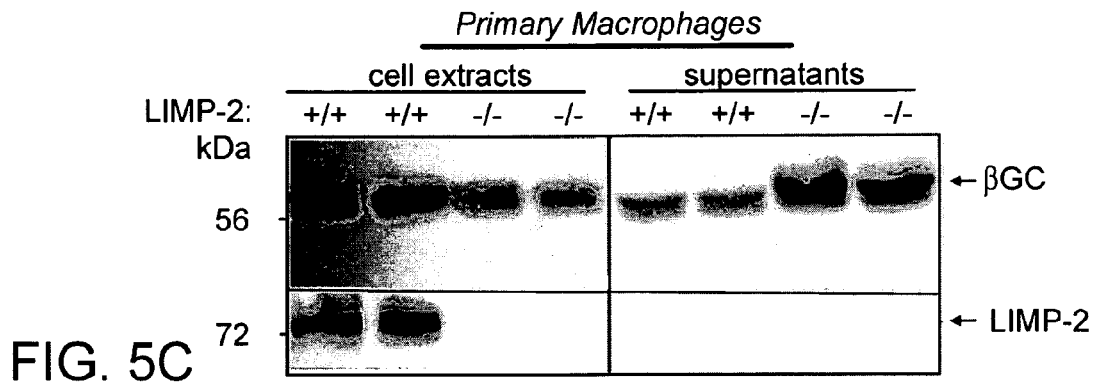
Figure 5D:
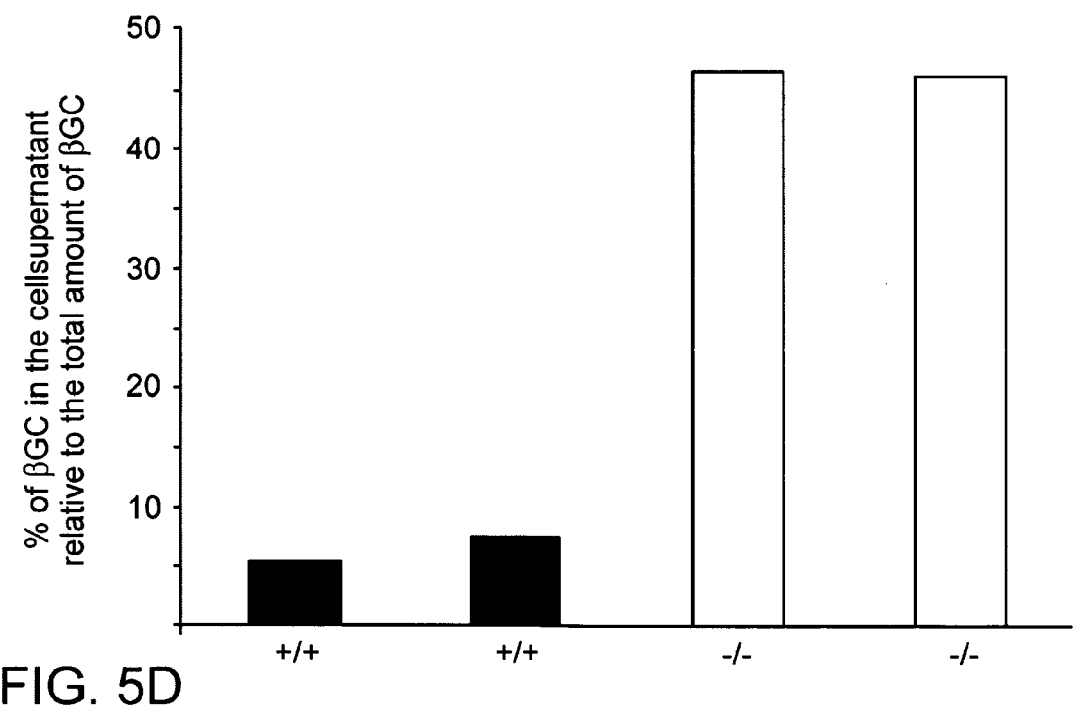
Figure 5E:
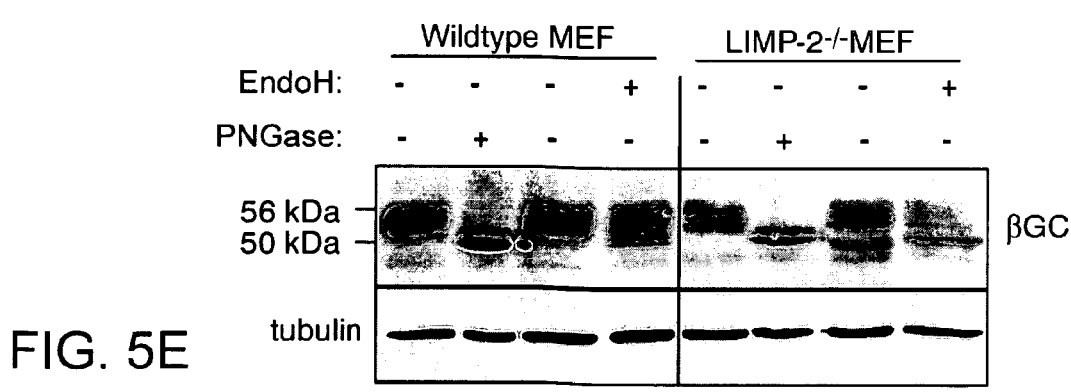

Since MPR-deficient mice and I-cell disease patients show an increased level of several lysosomal enzymes in their serum, whether an analogous observation might be made for βGC in the serum of LIMP-2-deficient mice was examined. Sera from wild type and LIMP-2-deficient mice were collected and total normalized protein samples analyzed for βGC levels by immunoblot. Whereas no βGC was found in the sera of wild type mice a significant level of βGC was observed in the serum from LIMP-2-deficient mice (FIG. 5A). This observation corresponded with an approximately 11 fold increase in βGC activity in the sera from LIMP-2-deficient animals (FIG. 5B) compared to that in wild type mice. These results provided in vivo evidence that a lack of LIMP-2 led to the mis-targeting of βGC to the extracellular space. To investigate this mis-targeting in isolated LIMP-2 knockout cells wild type and LIMP-2-deficient macrophage preparations were incubated in serum free medium for 24 hours and analyzed βGC levels in cell extracts and culture supernatants (FIG. 5C). In agreement with the in vivo observations described herein, a significant increase in βGC protein levels in the culture supernatants of LIMP-2-deficient macrophages was observed. In wild type cells only about 5-7% of the total βGC was found to be secreted. In LIMP-2-deficient macrophages between 46-47% of total βGC was found in the medium (FIG. 5D). Similar findings were made in MEF cells which also showed a large increase in the secretion of βGC in the absence of LIMP-2 (FIG. 12). Using PNGase F digestion it was observed that the molecular weight of intracellular βGC was reduced from 54 kDa to about 50 kDa in both wild type and LIMP-2-deficient MEF cells (FIG. 5E). EndoH treatment, which does not affect glycosylated proteins that have passed the Golgi apparatus, revealed that in wild type MEF cells more than 90% of the βGC was EndoH resistant, indicating that it had left the ER. In contrast, the same EndoH treatment in LIMP-2-deficient MEF cells, despite a lower overall βGC protein level, led to a complete digestion of the βGC carbohydrates suggesting that residual βGC in the absence of LIMP-2 was trapped in the ER.

Figures 1, 5F:
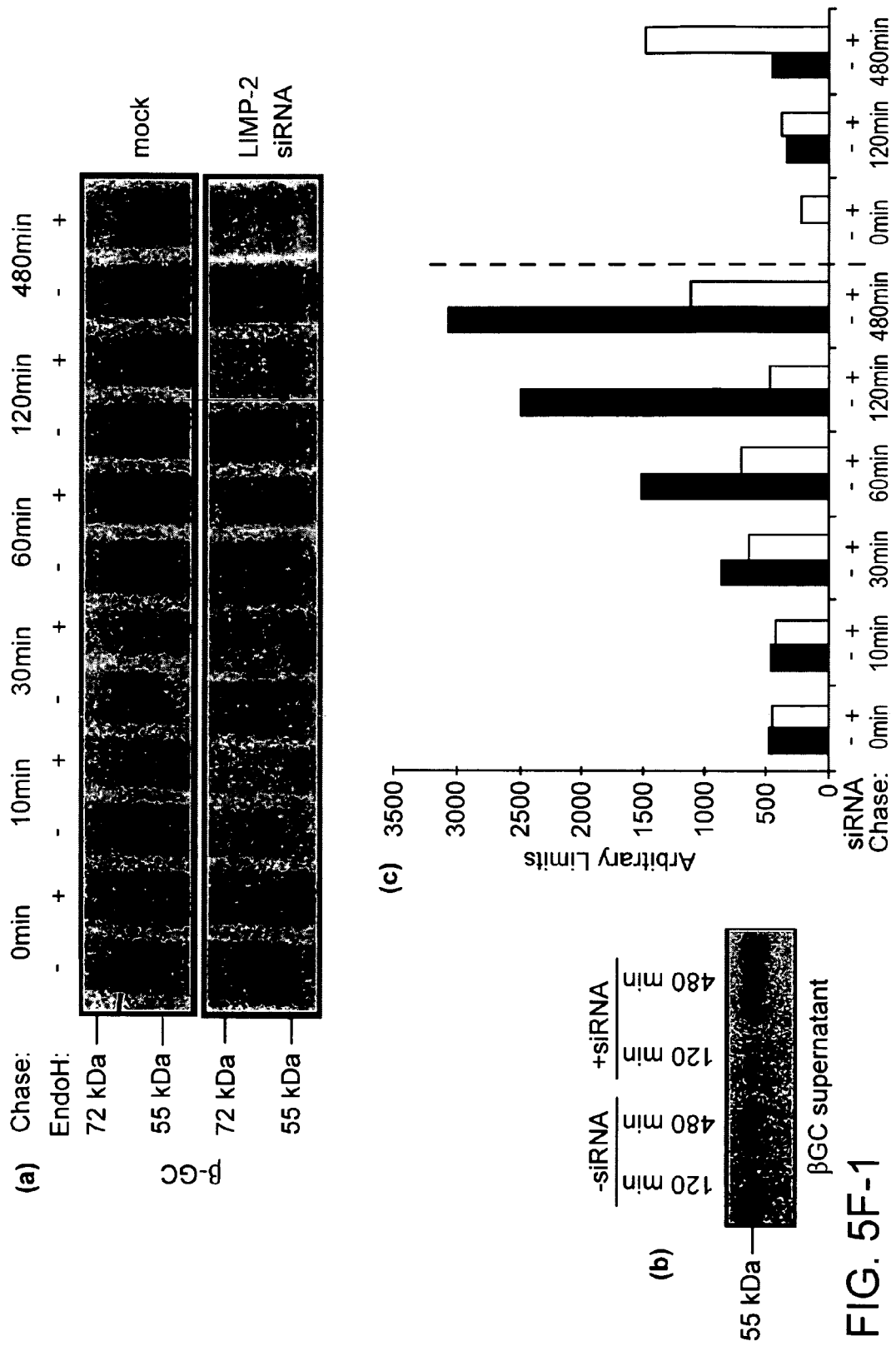
Figure 13:
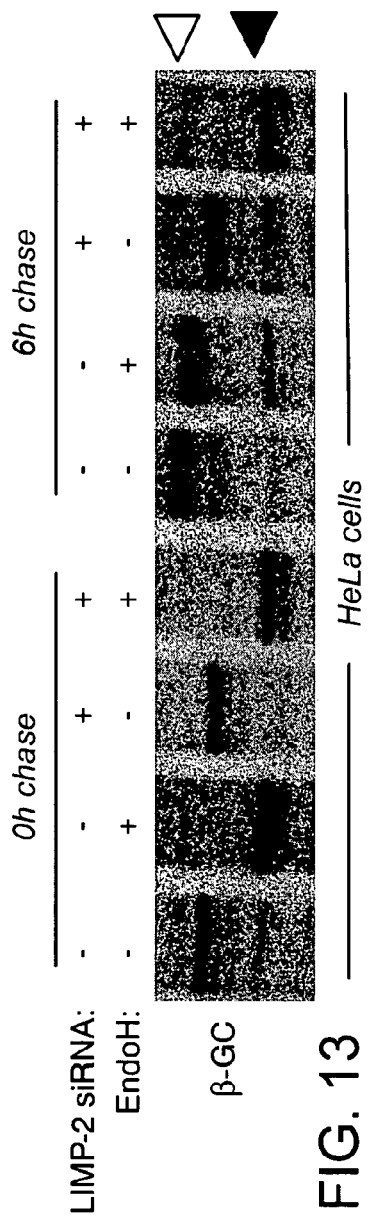
FIG. 13: ER retention of β-GC in cells with a downregulation of LIMP-2. Immunoprecipitation of β-GC in Hela cells which were metabolically labeled for 2 hr and chased for 0 h and 6 h, respectively. Cells transfected with a LIMP-2 specific siRNA show reduced levels of β-GC and the remaining β-GC was almost completely sensitive (black arrowhead) to EndoH digestion (ER localization) after 0 h and 6 h chase whereas the β-GC in untreated Hela cells has left the ER as indicated by the resistance to EndoH digestion after 6 h of chase (red arrowhead).
Figure 28A:
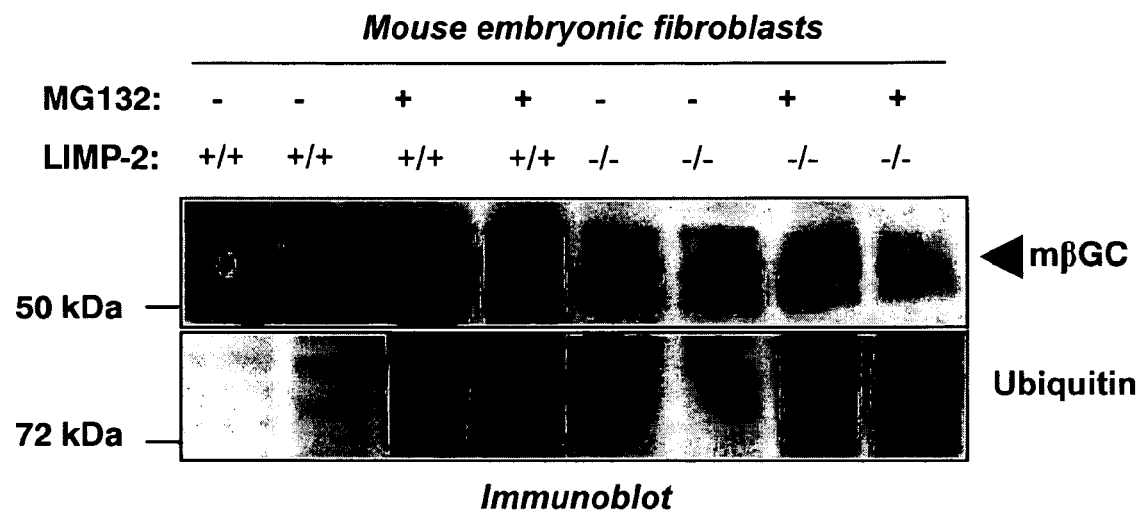
FIG. 28A-28C: Proteasomal inhibition does not show an effect on β-glucocerebrosidase expression. (28A) Wild type and LIMP-2 deficient mouse embryonic fibroblasts were treated for 8 h with 15 μM MG-132 (Merck, Darmstadt, Germany) in normal cell culture medium. Endogenous βGC expression was detected by immunoblot analysis. Incubation of the cells with the inhibitor did not increase the level of βGC in LIMP-2 deficient cells. Proteasomal inhibition was confirmed by the accumulation of high-molecular weight Ubiquitin-aggregates using mouse-anti-polyUbiquitin (28B) A similar treatment of LIMP-2 deficient cells using MG132 and 25 μM ALLN (Merck, Darmstadt, Germany) did not result in increased lysosomal levels of βGC as shown by immunofluorescense analysis after staining with anti-βGC antibodies (left panel). Immunofluorescense detection of ubiquitin after staining with anti-ubiquitin antibodies is shown as a positive control. Bars: 10 μm. (28C) Pulse-chase. For metabolic labelling, ALLN and MG-312 were present throughout the labelling and the chase period. No increase in βGC levels was observed after proteasomal inhibition. Immunofluorescense analysis following staining for LIMP-2 confirmed the successful downregulation of LIMP-2 after siRNA in Hela cells (lower panel). Immunoblot analysis, immunocytochemistry and metabolic labelling/immunoprecipitation were performed as described in the Materials and Methods section.
Figure 28B:
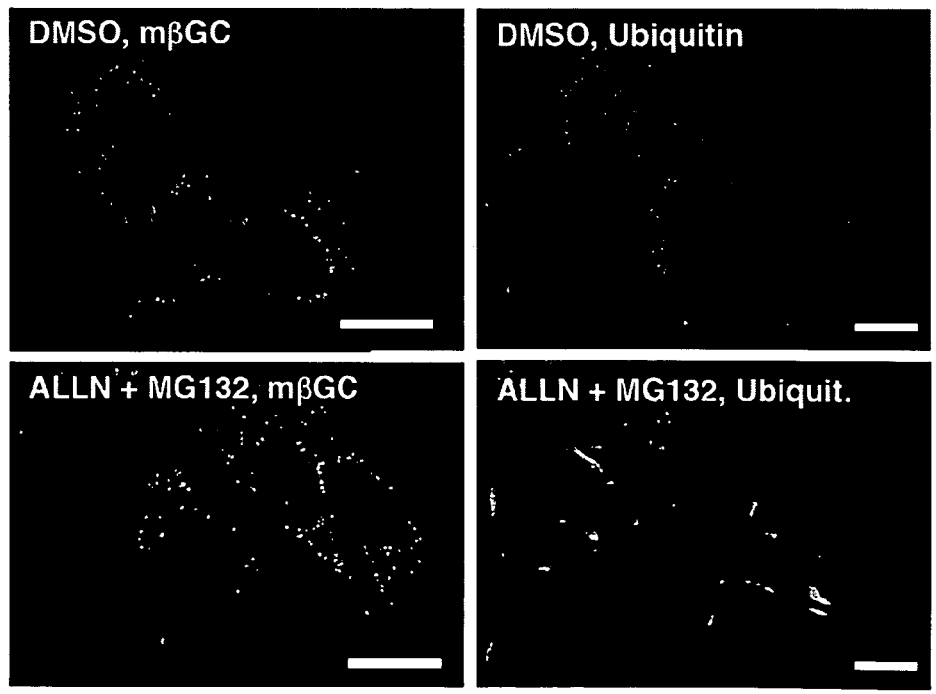
Figure 28C:
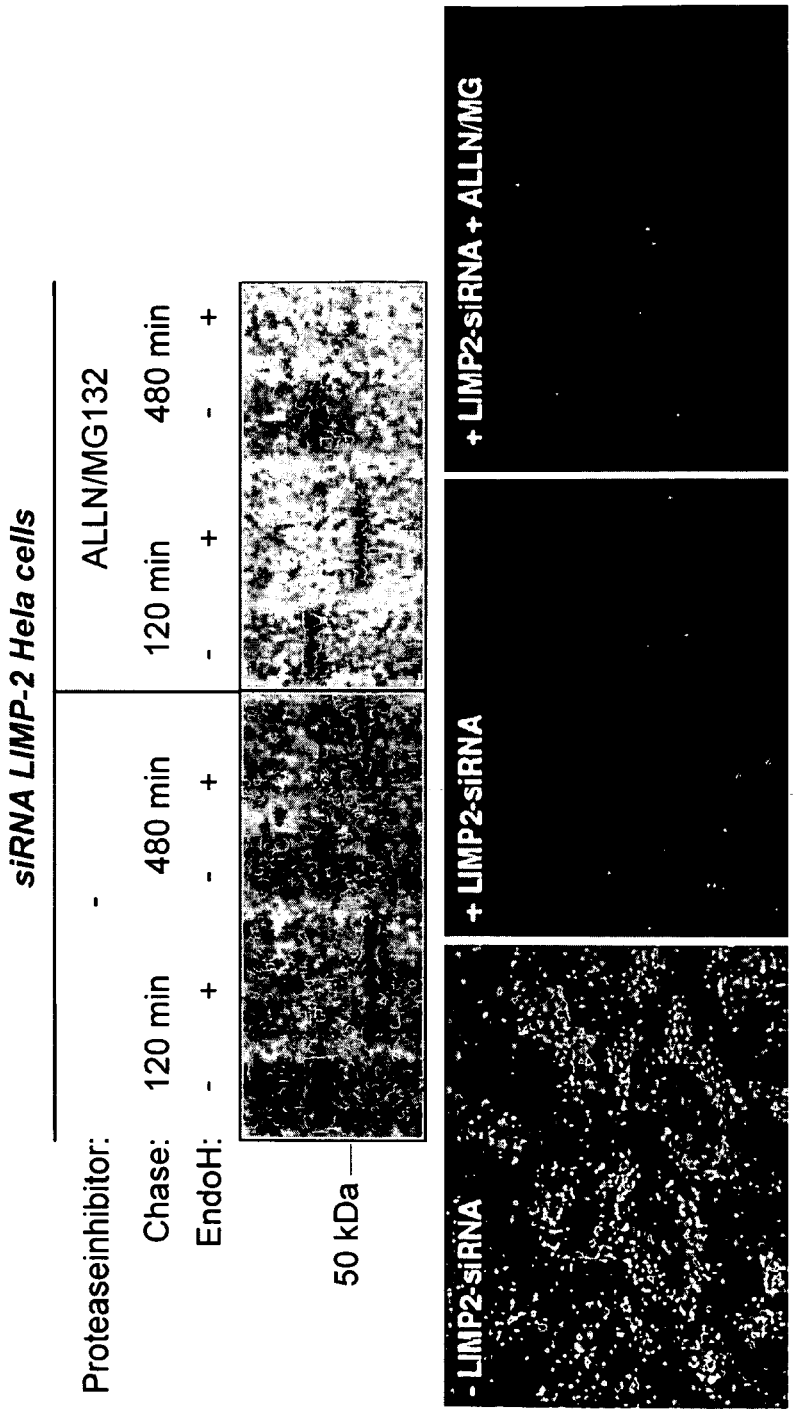
Figure 29:
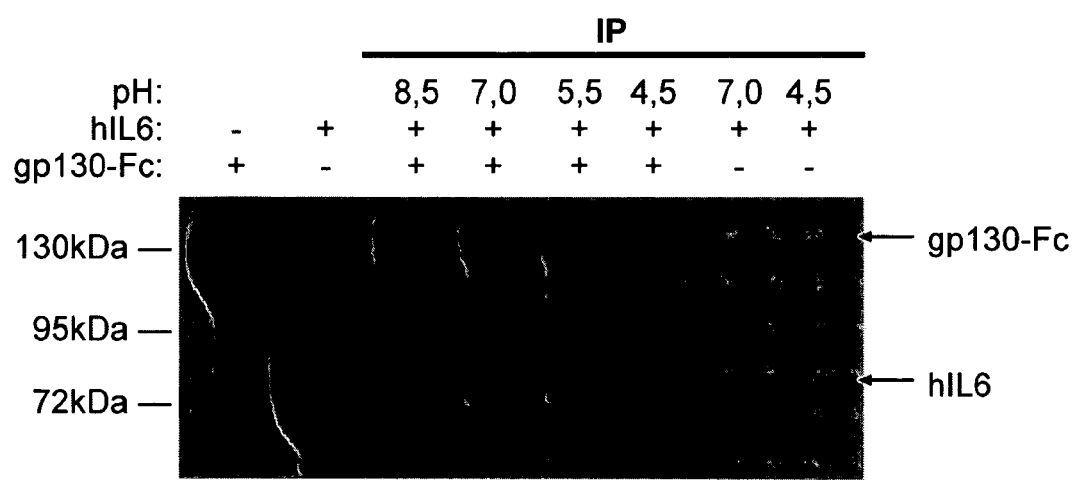
FIG. 29: Control experiment for FIG. 1E. No pH effect on the association of hIL6 and its Fc-tagged receptor gp130. Recombinant hIL6 and gp130-FC were incubated with protein A sepharose (Pierce) in a series of buffers ranging from pH 4.5 to pH 8.5. Subsequently, the sepharose was washed in buffer with the same pH as used in each respective binding reaction and as used in FIG. 1E. Bound proteins were eluted with Laemmli buffer and analyzed by SDS-PAGE and Coomassie stain. Binding of hIL6 to its receptor is stable under neutral and acidic pH. Incubation of hIL6 alone with protein A sepharose shows, that no non-specific binding of the protein to the sepharose occurs. Correct size of the binding partners was confirmed by loading each protein separately (lane 1 and 2).
Figure 30:
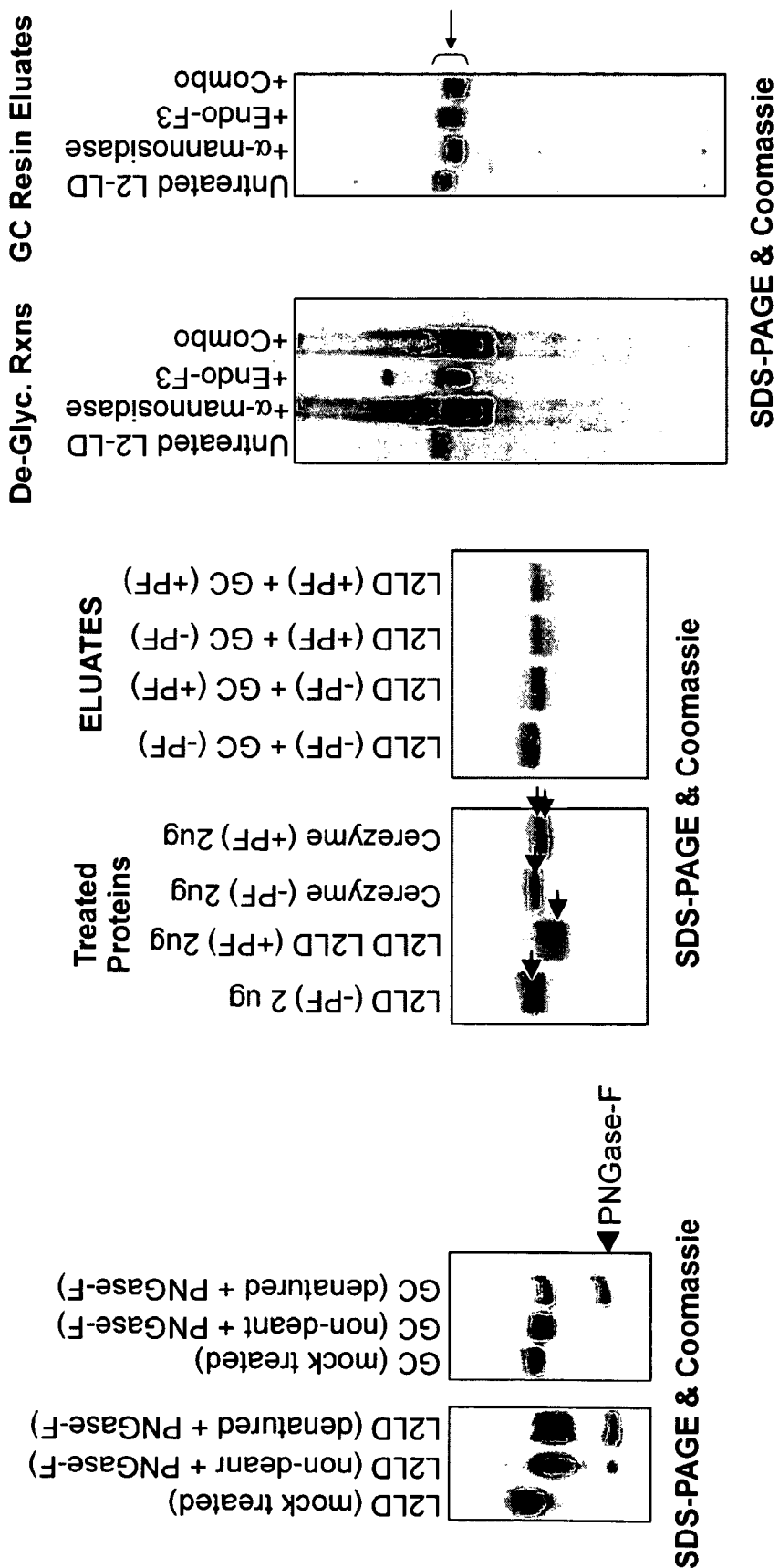
FIG. 30: Modulation of carbohydrates has no effect on βGC-LIMP-2 binding. Left panels: PNGase-F treatment. Samples of purified LIMP-2 lumenal domain and βGC proteins were treated or mock treated with PNGase-F under native or denaturing conditions (to compare efficiency of sugar removal under each condition) then resolved by SDS-PAGE and Coomassie stained. Middle Panels: In vitro binding reactions using PNGase-F treated proteins. Samples of LIMP-2 lumenal domain and βGC PNGase-F treated under native conditions (representative loads shown at left) were tested for binding using the in vitro pull down assay described in FIG. 1D. The eluates from each reaction are shown at right (Coomassie stained gel). (−PF, untreated; +PF, PNGase-F treated). The results suggest that at least partially N-linked de-glycosylated βGC and the fusion tagged LIMP-2 lumenal can still interact following the treatments described. Right Panels: In vitro binding reactions using α-mannosidase or Endoglycosidase-F3 or α-mannosidase+Endoglycosidase-F3 treated LIMP-2 lumenal domain. Samples of purified LIMP-2 lumenal domain were mock treated (untreated) or treated with α-mannosidase or Endoglycosidase-F3 or a combination of α-mannosidase+Endoglycosidase-F3 to remove N-linked sugar moieties and then tested for binding to a Cerezyme affinity resin using a method similar to that described for FIGS. 1A and 1B. Representative loads of the de-glycosylation reactions used in each binding reaction are shown at left (contain enzymes and LIMP-2). The eluates from the affinity binding reactions are shown at right. LIMP-2 lumenal domain still binds βGC following these treatments.
Figure 31:
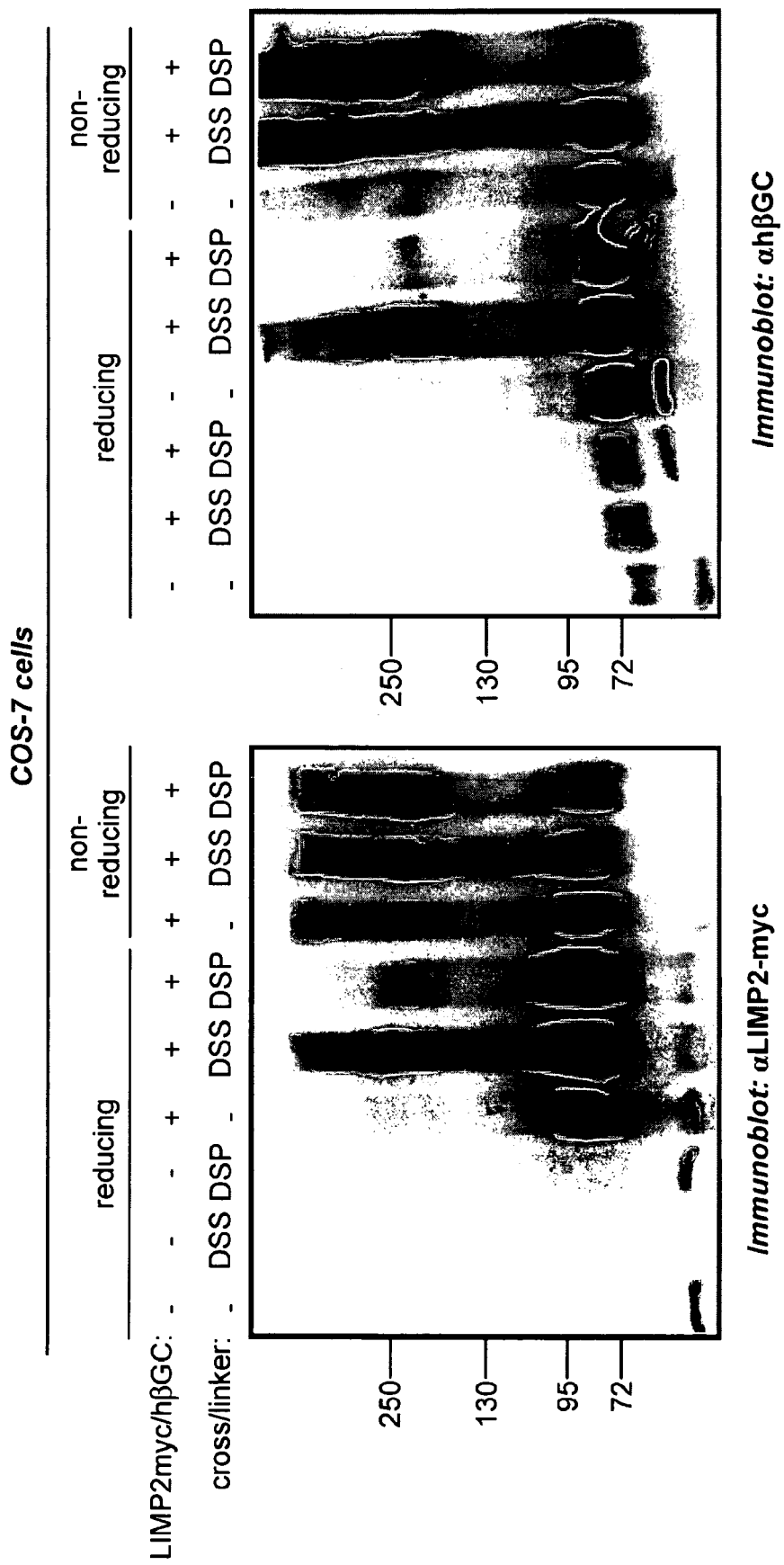
FIG. 31: Crosslink of LIMP-2/βGC complex suggest an approx. 250 kDa protein complex of LIMP-2 and βGC. COST-cells were transfected with LIMP2-myc and hβGC. Confluent cells were incubated with either 0.6 mM DSS (disuccinimidyl suberate) or 0.6 mM DSP (Dithiobis[succinimidylpropionate]) in EBSS/10 mM Hepes pH 7.0 for 30 min at 37° C. The reaction was stopped by addition of 20 mM ethanolamine (Sigma Aldrich, Steinheim, Germany) in EBSS/10 mM Hepes pH 7.0. Cells were harvested and processed for Western Blot as described in the material and method section. Samples were prepared in reducing (+20 mM DTT) and non-reducing sample buffer (−DTT). Cross-linkage reveals a protein complex with an approximate size of 250 kDa containing both LIMP2 and βGC. The DSP-complex is unstable under reducing conditions, due to disruption of the disulfide-bridge in the cross-linker. The exact stochiometry of the complex needs to be determined. A complex of 2 LIMP2-molecules with one or two βGC-molecules seems to be possible. Those complexes would have a calculated size of about 220 kDa or 280 kDa.
Figure 32:
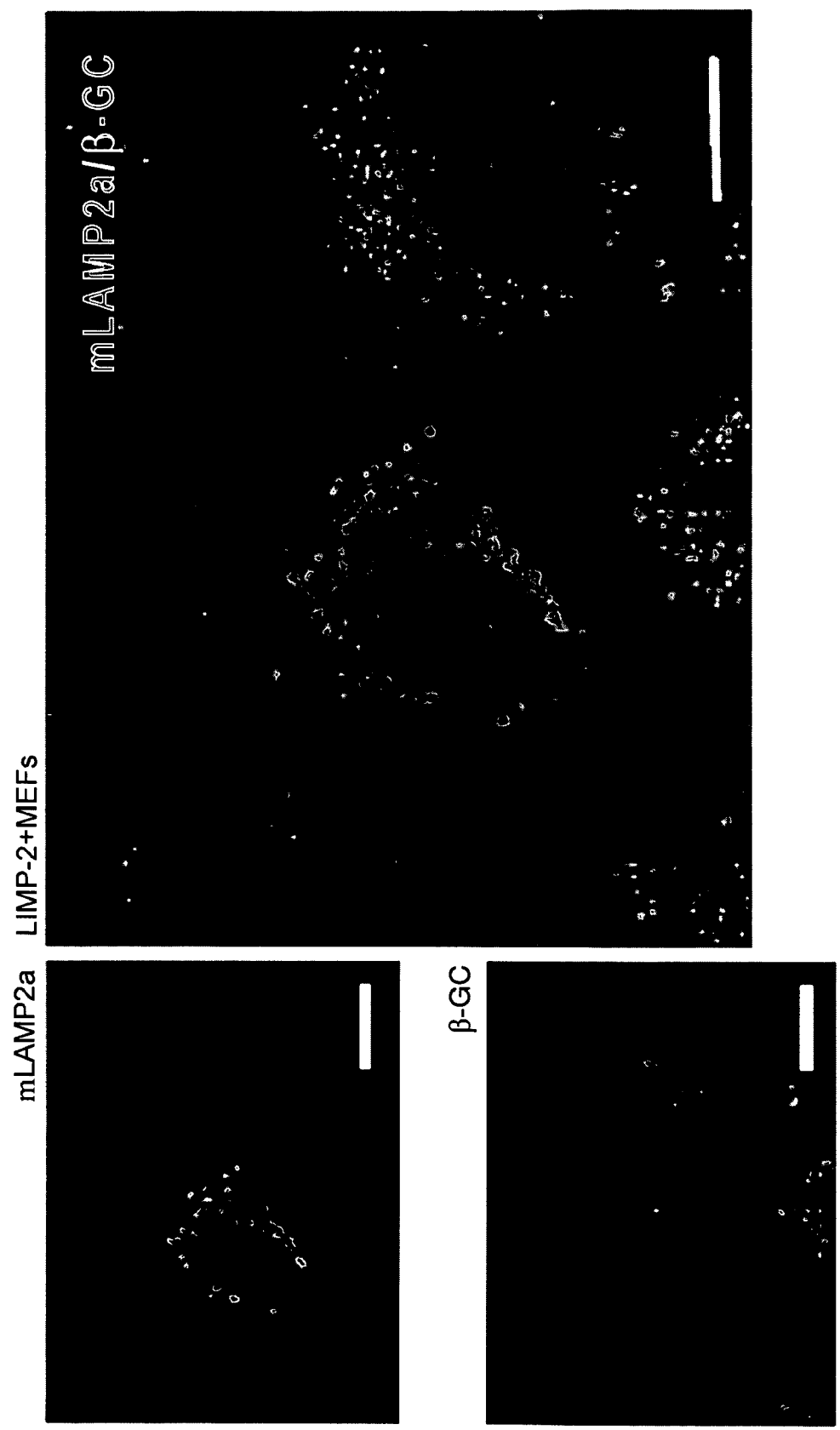
FIG. 32: No rescue of βGC expression in LIMP-2 knockout MEFs after overexpression of LAMP-2. LIMP-2 deficient MEF cells were transfected with murine LAMP-2 (C-terminal tagged with a HA-epitope) and co-stained for βGC and LAMP2a by using the 3F10 antibody (Roche) against the HA-epitope. In contrast to the successful rescue after expression of LIMP-2 (FIG. 3) expression of LAMP-2 did not change the low expression level of βGC in cells lacking LIMP-2.
Figure 33:
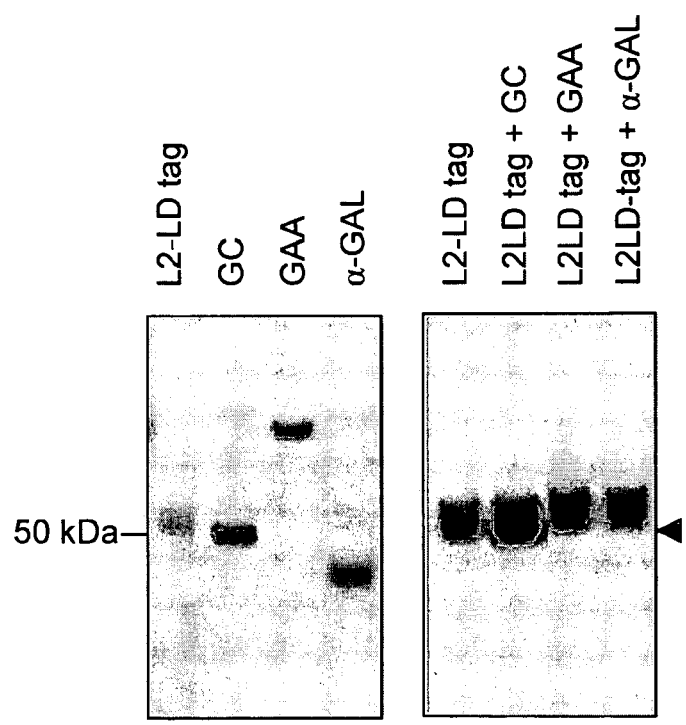
FIG. 33: Acid alpha-glucosidase and alpha-galactosidase do not bind to LIMP-2. Samples of purified βGC, acid alpha-glucosidase or alpha-galactosidase were tested and compared for binding to LIMP-2 lumenal domain using the fusion tag specific affinity resin in vitro pull down assay described in FIG. 1D. Left panel: Samples of the purified proteins used in the reactions are shown. Right panel: Eluates from the pull down reactions indicated. The "L2LD tag" reaction is a positive control for the pull down of fusion tagged LIMP-2 lumenal domain on the tag-specific affinity resin. βGC binds to the LIMP-2 lumenal domain whereas acid alpha-glucosidase and alpha-galactosidase do not.

Pulse-chase experiments in HeLa cells depleted of LIMP-2 using siRNA allowed examination of the fate of βGC under conditions of LIMP-2 deficiency over time. (FIG. 5F). Whereas in mock transfected cells βGC starts to become EndoH resistant after 30-60 min, and after 8 h almost all βGC was EndoH resistant, indicating it had left the ER, LIMP-2 siRNA treatment led to a partial ER retention (FIG. 13) until 120 min of chase and a dramatic reduction in intracellular βGC between 120 min and 480 min (FIG. 5F a, d). This drop was correlated with missorting of βGC into the cell culture supernatant between 120 min and 480 min was also seen at 24 hr (FIG. 5F b, d). In contrast, the processing and secretion of cathepsin D was not affected by the downregulation of LIMP-2 (data not shown). Proteasomal degradation of βGC in the absence or down-regulation of LIMP-2 was excluded since inhibition of the proteasome did not alter βGC protein levels (FIG. 28A-28C).

Taken together, these experiments show that LIMP-2 was required for the intracellular retention of βGC and a failure to bind LIMP-2 led to mis-targeting and a marked increase in the secretion of βGC with residual intracellular βGC localized to the ER or degraded.

Discussion

In the present study a novel role for LIMP-2 as a sorting receptor required for the delivery of glucocerebrosidase to lysosomes has been identified. The Man-6-P receptor pathway has been very well characterized as a major route for the sorting of lysosomal enzymes, however the mechanism for the intracellular targeting of βGC to lysosomes has been unclear until now.

Figure 6A:
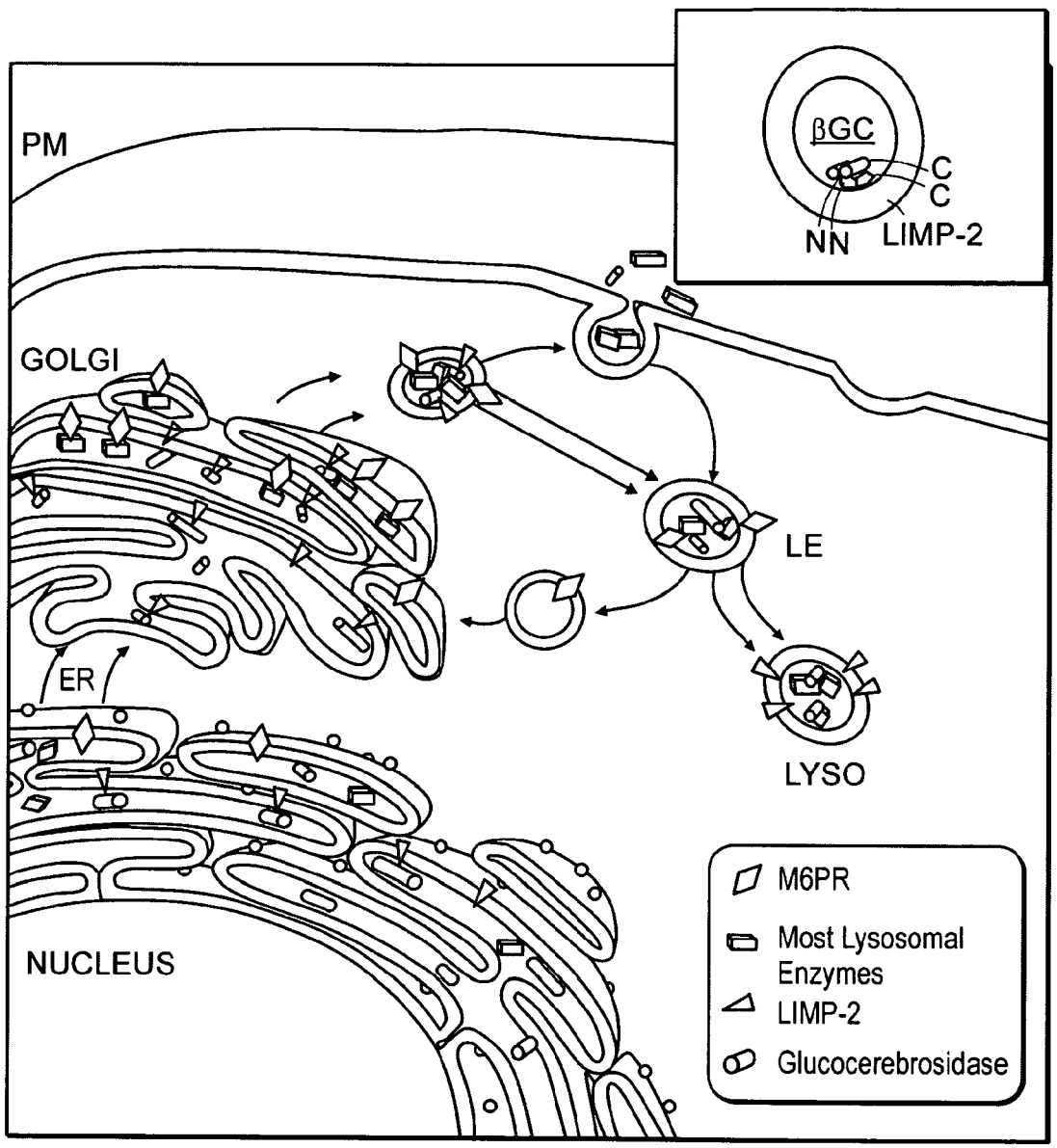
FIGS. 6A-6B: Model for the lysosomal sorting of β-glucocerebrosidase in the presence or absence of LIMP-2.
Figure 6B:
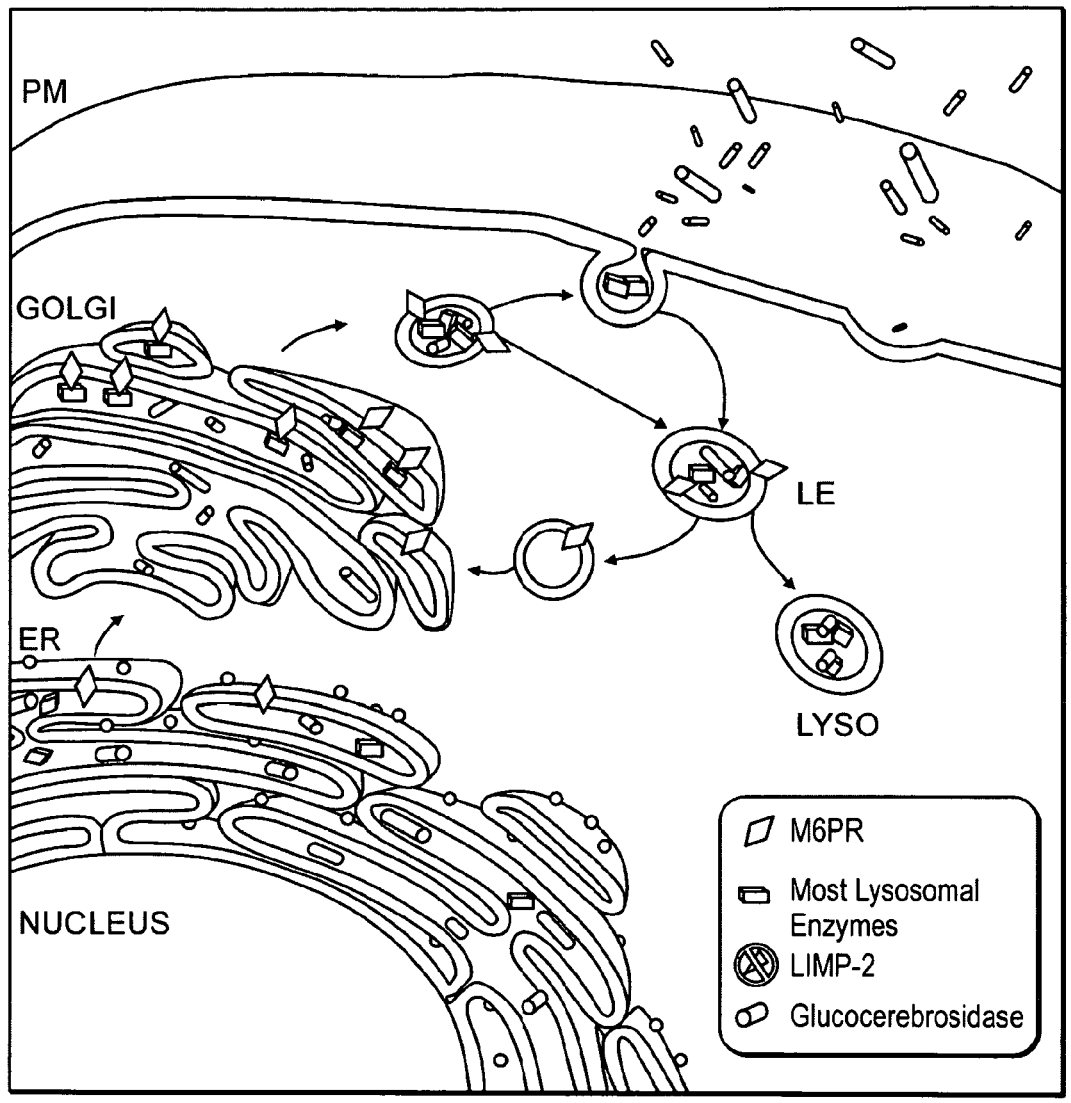
Figure 7A:
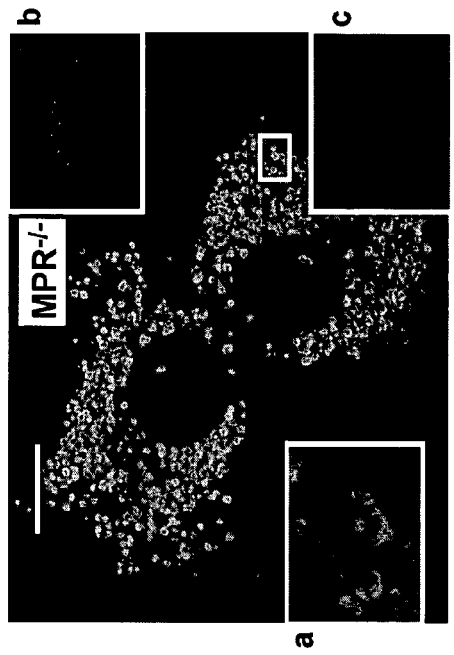
FIGS. 7A-7E: β-glucocerobrosidase was transported independently of the mannose-6 phosphate receptor in MEFs. Mouse embryonic fibroblasts derived from control mice (FIGS. 7A, 7C) and mice with a combined deficiency of both mannose-6 phosphate receptors (CD-MPR, CI-MPR) (FIGS. 7B, 7D) were analyzed by immunofluorescence.
Figure 7B:
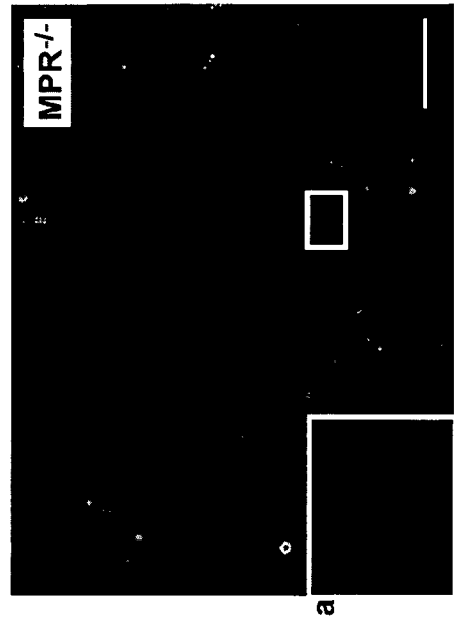
Figure 7C:
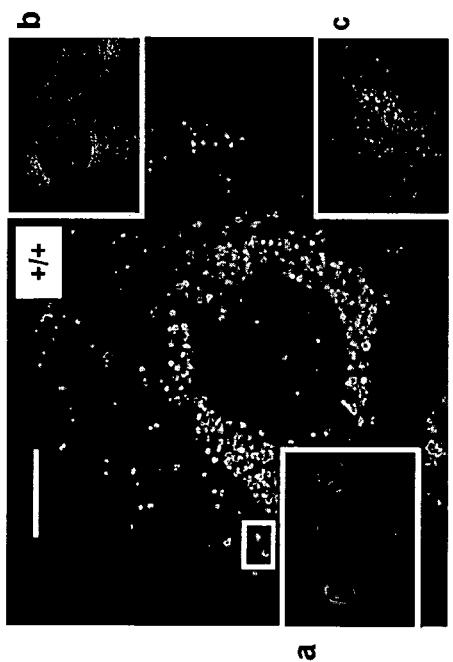
Figure 7D:
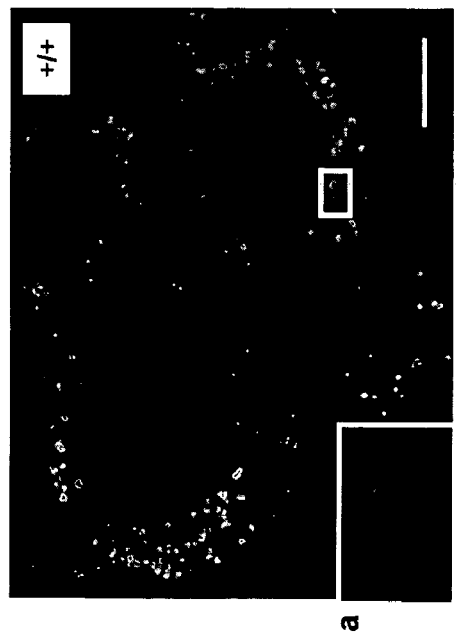
Figure 7E:
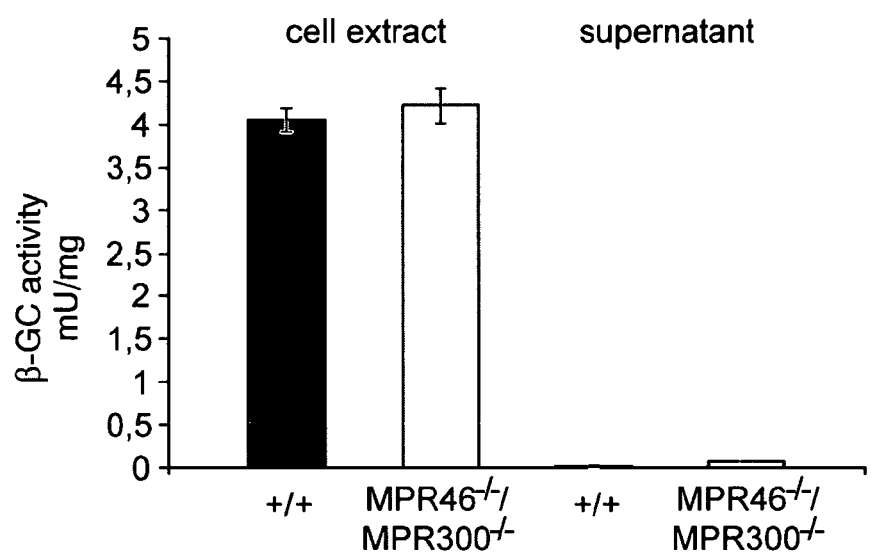

A role for LIMP-2 in the maintenance and biogenesis of lysosomes has been suggested based on overexpression studies in cultured cells (Kuronita et al., 2005) and on the phenotypic analysis of LIMP-2 knockout mice (Gamp et al., 2003; Knipper et al., 2006). Based on the data presented herein, a number of features and qualities of LIMP-2 can be seen in the context of its role as a M6P-independent trafficking receptor for βGC. Lysosomal membrane proteins such as LIMP-2, in contrast to soluble M6PR-binding lysosomal proteins, are directed from the Golgi to lysosomes in a manner unique from that of soluble proteins destined for this same compartment. Rather than relying on the M6PR for sorting and delivery they are incorporated into clathrin coated vesicles by virtue of the interaction of distinct targeting motifs in their cytoplasmic tails with multimeric adaptor proteins; in the case of LIMP-2 the tandem leu-ile residues in its cytoplasmic domain have been suggested to mediate such an association with AP-3 (Honing et al., 1998; Le Borgne et al., 1998; Ogata and Fukuda, 1994; Sandoval et al., 1994; Tabuchi et al., 2002; Vega et al., 1991b) and AP-1 (Fujita et al., 1999)) and affect its targeting. The present findings that βGC associates with LIMP-2, that these proteins co-localize in intracellular vesicular compartments, and that the activity, levels and localization of βGC exhibit a dramatic correlation with the presence or absence of LIMP-2 described herein, reveal that βGC independence of M6P-based sorting mechanisms is almost certainly a consequence of its routing through the lysosomal membrane protein delivery pathway. However, when the status of βGC and LIMP-2 in AP-3 deficient cells from the mocha mouse was explored, missorting or altered βGC localization was not observed, indicating that there may be other targeting motifs in LIMP-2 that do not involve interactions with AP-3 (data not shown). Additionally, the deletion of the cytoplasmic-tail of LIMP-2 did not result in an altered localization of this LIMP-2 (data not shown) indicating that additional sorting motifs exist within the transmembrane or lumenal domain of this membrane protein. The evidence that the association of βGC and LIMP-2 was sensitive to changes in the range of pH values found within the intracellular compartments through which these proteins pass is also consistent with a model for LIMP-2 based trafficking (FIGS. 6A-6B). Preliminary crosslink experiments with LIMP-2 and βGC co-expressed in COS cells suggest that the protein-protein complex is about 250 kDa in size which would fit with a 2:2 βGC/LIMP-2 stoichiometry (FIG. 6A-6B). These data support a scenario in which LIMP-2 and βGC would associate in the ER or Golgi at more neutral pH and subsequently dissociate in the lysosome at more acidic pH (FIG. 6A). In this way LIMP-2 could capture and deliver its cargo of βGC in a pH-dependent manner analogous to the transport of M6P-tagged enzymes by the M6PR. It is also interesting to note that the missorting of βGC and the normal delivery of other lysosomal proteins such as cathepsin-D in LIMP-2-deficient cells is the converse of the situation seen in cells doubly deficient for the MPRs or in I-cell disease (FIG. 6B). An additional role for LIMP-2 in stabilizing βGC against proteolysis cannot be ruled out based on our current data.

Such an early association is supported by our co-immunoprecipitation experiments, in particular after expression of a LIMP-2 ER retention mutant. Interestingly, also observed was that a clinical mutant of βGC, L444P, which is usually retained in the ER, can be shifted to the lysosomal compartment after co-expression of LIMP-2. These data not only suggest that an increase in LIMP-2 levels may be of some therapeutic interest for selected βGC mutations but also support the other data demonstrating that interaction can occur in the endoplasmic reticulum. When the fate of newly synthesized βGC was monitored in the absence of LIMP-2 it was observed that βGC release from the ER was retarded before βGC was missorted and secreted suggesting that LIMP-2 binding to βGC is needed for efficient ER exit towards the lysosomal compartment. βGC secretion in the absence of LIMP-2 is also substantiated by our experiments with proteasomal inhibitors which did not affect the rapid intracellular loss of βGC (FIG. 28A-28C). In contrast to lysosomal delivery of M6PR-targeted proteins or proteins like the major histocompatibility complex II through the binding of the invariant chain (Trombetta and Mellman, 2005), where diversion from the constitutive secretory pathway occurs after leaving the trans Golgi network (Kornfeld, 1992) (FIG. 12), it appears that lysosomal βGC trafficking requires LIMP-2 binding already taking place in the ER. The observations described herein that modulation of carbohydrates has no effect on the association of both proteins (data not shown) also substantiates association in the ER. It is also conceivable that the early association of both proteins generates a signal for sorting within the TGN.

Figure 14:
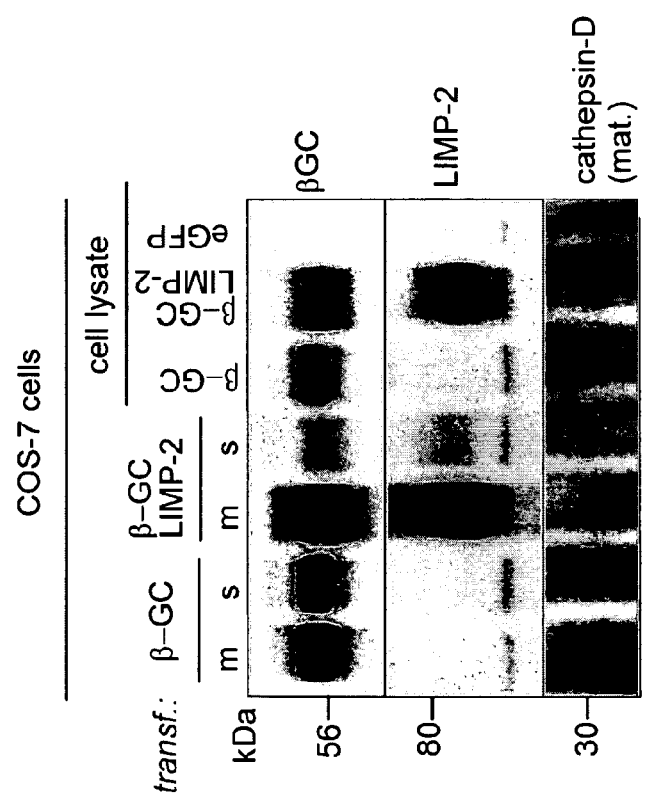
FIG. 14: Increased membrane association after co-expression of β-GC and LIMP-2 in Cos7 cells. 48 h after transfection of β-GC, β-GC and LIMP-2 or eGFP, cell lysates, membrane fractions (m) and soluble fractions (s) were prepared and analyzed by immunoblot for β-GC, LIMP-2 and cathepsin-D expression. Co-expression of β-GC and LIMP-2 led to an increase in membrane-associated β-GC. Analysis of the β-GC expression in total cell lysates indicated similar expression level of the enzyme as well as successful expression of LIMP-2. The mature form of cathepsin-D was found in the soluble fraction.

The in vitro binding studies described herein indicate that βGC interacts with the lumenal but not the cytoplasmic domain of LIMP-2. This region of LIMP-2 is in a context where it would encounter an intra-vesicular protein like βGC. βGC associates with membranes in a carbohydrate-independent manner (Aerts et al., 1988; Imai, 1988; Leonova and Grabowski, 2000) and this persists from the ER through lysosomes (Rijnboutt et al., 1991). Interestingly, it was found that overexpression of LIMP-2 in Cos7 cells significantly enhanced the membrane association of co-expressed βGC compared to the expression of βGC on its own (FIG. 14) further emphasizing the importance of the LIMP-2/βGC interaction in vesicular compartments. The data also revealed that the binding of LIMP-2 and βGC appeared to be stable during transport through the Golgi apparatus since expression of a secreted LIMP-2 mutant also led to a significant missorting and consequent increase of secreted βGC. Moreover, it seems unlikely that a defect in endocytosis of βGC underlies the increased extracellular levels of the enzyme since uptake of iodinated βGC in LIMP-2 KO cells is unimpaired (data not shown).

It is still unclear whether LIMP-2 might, similarly to the M6PR, also recycle back from endosomes to the Golgi apparatus, and we can not completely rule out the possibility that other lysosomal proteins might also bind to LIMP-2 at this point. The results from our affinity chromatography experiments with mouse liver extract and the lack of LIMP-2 association with β-galactosidase and β-glucosidase (data not shown) however, highlight a rather specific nature for the LIMP-2/βGC interaction. LIMP-2 is homologous to CD36 and defines it as a member of the CD36-scavenger receptor-like protein family (Vega et al., 1991). Despite the fact that LIMP-2 and CD36 share ~34% sequence identity over their lumenal domains we found that βGC did not bind to this region of CD36 under conditions in which it bound the corresponding region in LIMP-2. Thrombospondin-1 (TSP-1), however, has been demonstrated to bind both CD36 and LIMP-2 (Asch et al., 1987; Crombie and Silverstein, 1998).

The lumenal domain of LIMP-2 is homologous to CD36 and defines it as a member of the CD36-scavenger receptor-like protein family (Vega et al., 1991a). Members of this family have been shown to function in receptor roles in various cellular contexts. For example, CD36 acts at the cell surface to bind different ligands such as long chain fatty acids, modified low-density lipoproteins, thrombospondin-1 (TSP-1), and *Plasmodium falciparum* infected erythrocytes (Ge and Elghetany, 2005). Other members of this family such as CLA-1 and the *Drosophila* protein Croquemort function as a cell surface receptor for high density lipoproteins (Murao et al., 1997) and in embryogenesis as a monocyte receptor for apoptotic cells (Franc et al., 1996), respectively. Despite the fact that LIMP-2 and CD36 share ~34% sequence identity over their lumenal domains it was found that βGC did not bind to this region of CD36 under conditions in which it bound the corresponding region in LIMP-2. TSP-1, however, has been demonstrated to bind both CD36 and LIMP-2 (Asch et al., 1987; Crombie and Silverstein, 1998). The differing ability of these two family members to bind βGC indicates that as a ligand βGC has an apparently higher level of specificity for LIMP-2 than does TSP-1. Since LIMP-2 is predominantly localized on intracellular membrane bound compartments (Vega et al., 1991a) and exhibits only low levels of cell surface expression (Maeda et al., 1999; Okazaki et al., 1992; Suarez-Quian, 1987, 1988) it is possible that the interaction between LIMP-2 and TSP-1 does not predominate in the physiological setting, particularly given that TSP-1 is found in the matricellular environment. It may be that there are two subtypes to the CD36 family: proteins like LIMP-2 which function intracellularly, and others like CD36, CLA-1 and Croquemort that preferentially act at the plasma membrane.

The binding studies indicate that βGC interacts with a coiled-coil domain in the lumenal domain of LIMP-2. The disruption of the coiled-coil domain abolished interaction with βGC yet allowed normal expression and lysosomal transport of these LIMP-2 mutants. Coiled-coil domains have been shown to be involved in protein-protein interaction (Lupas et al., 1991) and the experiments revealed a critical role of this domain in LIMP-2 for βGC binding. A more detailed structural analysis however, will be necessary to completely resolve the nature of the binding of both proteins.

A large variety of mutations that occur in the gene encoding βGC result in the accumulation of its substrate glucosylceramide (GlcCer) and consequently lead to Gaucher disease in humans (for review see: (Sidransky, 2004)). Manifestation of this disease is typically due to a deficiency in enzyme activity, inappropriate βGC localization, decreased βGC stability, or a combination of these factors (Beutler and Kuhl, 1986; Liou et al., 2006; Schmitz et al., 2005; Zimmer et al., 1999). Given the significant decreases in βGC protein levels and activity that was detected in tissues of LIMP-2 knockout animals and that this was a consequence of the enzyme being mislocalized, LIMP-2 knockout mice were examined more closely for phenotypes that might correlate with Gaucher disease. It was found that the levels of GlcCer substrate were elevated in LIMP-2-deficient liver and lung but apparently unaffected in other tissues, namely, kidney, spleen and brain (data not shown). Such tissue-specific differences could result from differences in substrate availability or utilization in each tissue; alternatively they could be due to varying amounts of residual βGC activity still detectable in LIMP-2 deficient animal tissues which may be sufficient to prevent GlcCer accumulation to levels at which more significant Gaucher-like pathologies might be seen. Despite the absence of robust Gaucher-like phenotypes in LIMP-2 knockout mice it is nonetheless interesting to speculate that some of the diversity in Gaucher phenotypes observed in humans carrying identical βGC mutations might result from secondary mutations in the LIMP-2 pathway.

It was observed that in contrast to the more common βGC disease related mutant L444P which, like the N370S and G202R mutants, still bound to the LIMP-2 lumenal domain, the βGC mutant P415R could not be transported to lysosomes after co-expression with LIMP-2 suggesting that this mutation directly or indirectly affects the binding site for LIMP-2. Structural analyses of the LIMP-2/βGC complex will be required to evaluate the importance of this βGC region for LIMP-2 binding.

In conclusion, a novel function for LIMP-2 as a Man-6-P-independent trafficking receptor for βGC has been identified. The discovery of this function helps link together many of the details from previous studies of both LIMP-2 and βGC biology and, importantly, it helps clarify the role proposed for LIMP-2 in the biogenesis and maintenance of lysosomes. The nature of how the interaction between these two proteins is mediated, whether there are additional cargoes for LIMP-2, and how this finding plays into the realm of LIMP-2 and βGC related pathologies will be the exciting subjects for future studies.

TABLE 1

Analysis and comparison of glucosylceramide (GlcCer) substrate levels in tissues from wild type and LIMP-2 knockout mice.

| Tissue | LIMP-2 Genotype | GlcCer (ng/mg tissue) | Standard Deviation |
|---|---|---|---|
| Liver | WT | 47 | 11 |
|  | KO | 88 | 21 |
| Lung | WT | 53 | 11 |
|  | KO | 98 | 11 |

Samples of liver and lung tissue isolated from wild type and LIMP-2 knockout mice (n = 4 for each category) were analyzed for GlcCer substrate levels utilizing a mass-spectrometry based assay (see Materials and Methods). An average of an approximately 2-fold increase in GlcCer was apparent in liver and lung from knockout animals.

Example 2

Hamster LIMP-2 RNA Knockdown Experiments

Isolation of Hamster LIMP-2 (haLIMP-2) Open Reading Frame

Total RNA was prepared from the a CHO parental cell line and high fidelity reverse transcriptase (Stratagene) was used to synthesize cDNA from the RNA preparation. The resulting cDNA preparation was used as a template for PCR. Several forward and reverse PCR primers were designed based on the alignment of human, mouse, rat, and mucaca LIMP-2 cDNA sequences (FIGS. 15A, 15B, 16A, 16B). Upon routine optimization of reaction conditions, high fidelity Pfu DNA polymerase (Stratagene) was used to successfully PCR amplify the hamster LIMP2 open reading frame from the cDNA template. A PCR product of the predicted size (~1600 bp), based on the location of the primer sites in the mouse and rat open reading frames, was synthesized. The PCR product was gel purified and ligated into a Topo-Blunt DNA vector (Invitrogen), and the ligation products were transformed into E. coli. Five E. coli clones containing TOPO-Blunt/haLIMP-2 plasmid DNA (identified by restriction digest screen) were sequenced (see SEQ ID NOs: 1 and 2). Alignment of the five independent nucleotide sequences showed 100% consensus, as well as 88.5% homology with mouse LIMP-2 nucleotide sequence.

Generation of Reagents Using the haLIMP-2 Sequence
Plasmids for Mouse Injection

The haLIMP-2 open reading frame and the haLIMP-2 lumenal domain were each cloned into mammalian expression vectors. The full length open reading frame fragment was excised from the Topo-Blunt DNA vector and ligated into pcDNA3.1(−) (Invitrogen). A DNA fragment encoding the lumenal domain was PCR amplified to include a stop codon at the 3' end. The PCR product was gel purified and ligated into pENTR/GHSS (derived from Invitrogen pENTR™, with start codon/human growth hormone signal sequence, "GHSS" added). The GHSS/haLIMP-2 lumenal domain fragment was inserted into pcDNA-DEST40 (Invitrogen) by Gateway™ recombination.

siRNA Duplexes for RNAi Knockdown Experiments

Five siRNA duplexes were designed using an algorithm based on published reports (Reynolds et al., *Nature Biotechnology*, 22(3):326-330 (2004); Takasaki, S., et al., *Computational Biology and Chemistry*, 30, 169-178 (2006)). Specifically: The haLIMP-2 open reading frame sequence was analyzed using a computer program written to evaluate 19 base pair sections for potential use in siRNA duplexes. The rules utilized by the program were adapted from an established, frequently cited publication (Reynolds et al., *Nature Biotechnology*, 22(3):326-330 (2004)) and are summarized in Table 2. Note: the program did not predict hairpins, thus the third rule on the list was not incorporated.

TABLE 2

Criteria for designing siRNA duplexes

| Criterion | Score if True | Score if False |
|---|---|---|
| 30%-52% GC content | 1 | 0 |
| A or U at positions 15-19 | 5 (1 for each) | 0 |
| No internal repeats (predicted hairpin $T_m$ < 20° C.) | 1 | 0 |
| A at position 19 | 1 | 0 |
| A at position 13 | 1 | 0 |
| U at position 10 | 1 | 0 |
| A or U at position 19 | 0 | −1 |
| No G at position 13 | 0 | −1 |

In addition, an algorithm utilizing a scoring table derived from statistical analysis was used in a similar manner to evaluate blocks of the haLIMP-2 open reading frame for utility as siRNA duplexes. This scoring method was reported by Takasaki, S., et al., *Computational Biology and Chemistry*, 30, 169-178 (2006)). Use of the two scoring methods provided five candidate siRNA duplex sequences. Two sequences, si976 and si1182, were the top scoring sequences from the first algorithm (Reynolds, A., et al., *Nature Biotechnology*, 22(3), 326-330 (2004)). Sequence si376 received the top scoring from the second method (Takasaki, S., et al., *Computational Biology and Chemistry*, 30, 169-178 (2006)), based on both the scoring table and GC content. The final two sequences, si202 and si1135, were selected based on combinatorial analysis of the two sets of results, described below. Sequence si1135 was also near the top of the Reynolds et al. scoring (tied with 6 other sequences for 3rd best score).

Figure 18:
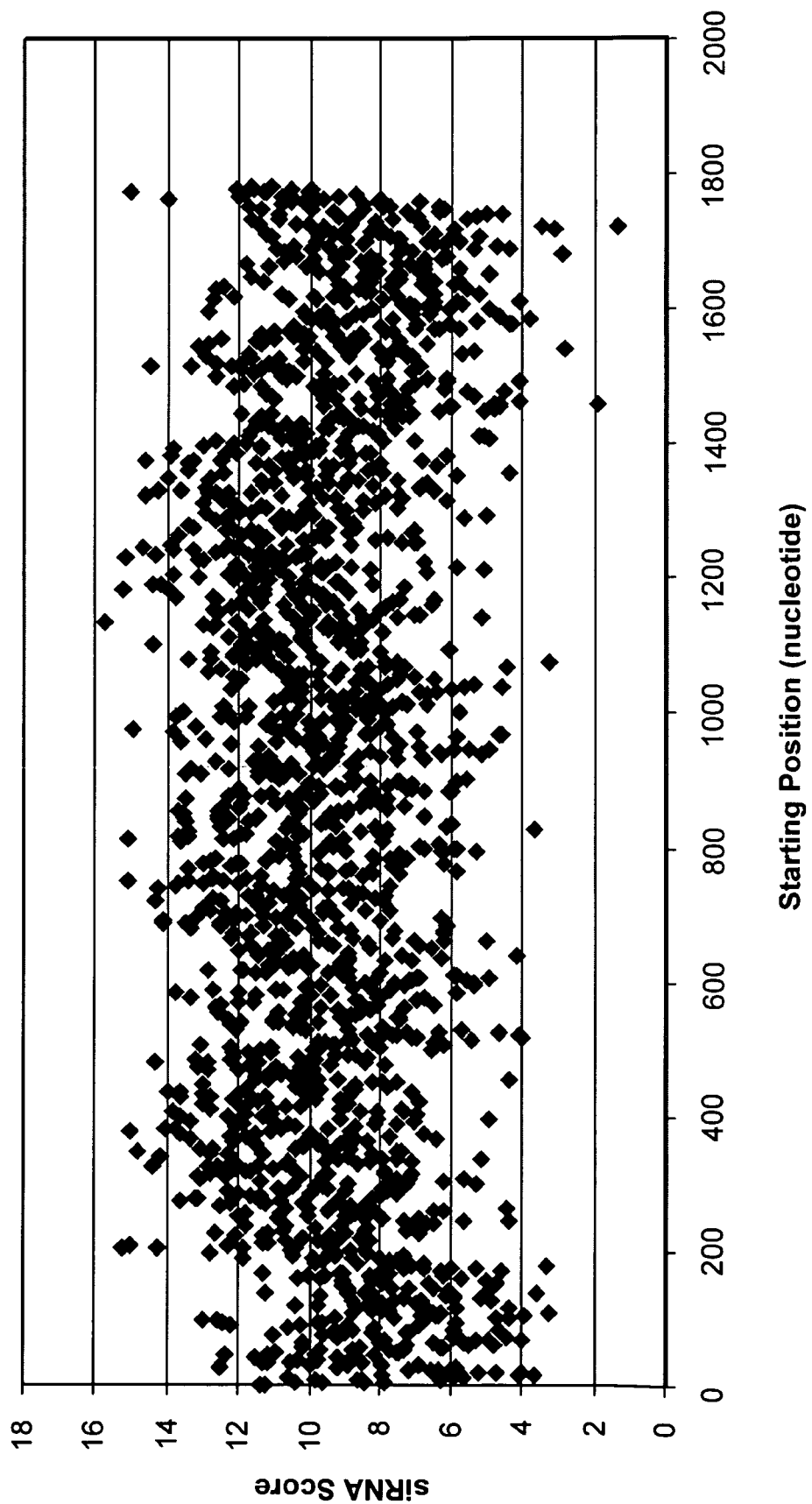
FIG. 18 shows the results of the scoring method by which results of algorithms for the design of siRNA duplexes were formatted to be compatible and then summed. In this method, a higher score was indicative of a more effective siRNA duplex.

FIG. 18 shows the results of the scoring method by which results of both algorithms were formatted to be compatible and then summed. In this method, a higher score was indicative of a more effective siRNA duplex.

Figure 19:
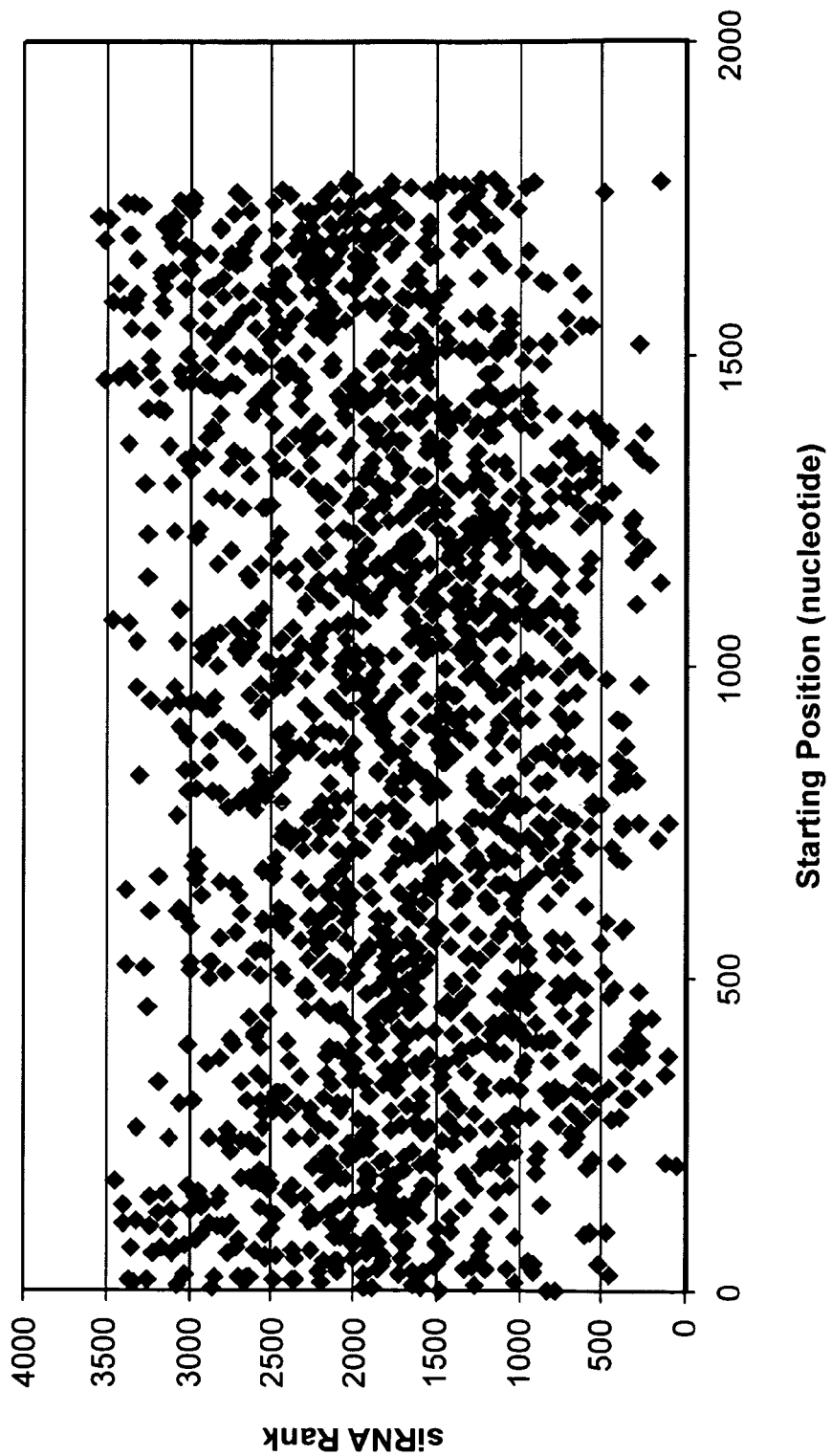
FIG. 19 shows the results of the scoring mechanism which used a numeric ranking of each sequence based on the results of each algorithm for the design of siRNA duplexes. In this method, a lower ranking was indicative of a more effective siRNA duplex.

FIG. 19 shows the results of the scoring mechanism which used a numeric ranking of each sequence based on the results of each algorithm. In this method, a lower ranking was indicative of a more effective siRNA duplex.

Five siRNA duplexes designed through use of these algorithms were ordered from Invitrogen (custom siRNA service); these and their sequences are in Table 3 below.

TABLE 3 siRNA Duplex Positions and Sequences

| Position | Sense Strand Sequence |
|---|---|
| 202 | 5'-CGAGAAGAGUAUGGUGUUA[dT][dT]-3' (SEQ ID NO: 15) |
| 376 | 5'-GAACAAGGCAAACAUCCAA[dT][dT]-3' (SEQ ID NO: 16) |
| 976 | 5'-UAAGGUGCCUGCAGAAAUA[dT][dT]-3' (SEQ ID NO: 17) |
| 1135 | 5'-GUUCGUUUCUGCCAUAAAA[dT][dT]-3' (SEQ ID NO: 18) |
| 1182* | 5'-AGACAUUUGUGGACAUUAA[dT][dT]-3' (SEQ ID NO: 19) |

The position indicated refers to the basepair index in the haLIMP-2 ORF corresponding to the first 5' base of the sense strand of the siRNA duplex. The [dT] designates the two deoxyribose thymines added to the 3' ends of both strands in each duplex.

TaqMan Primer/Probe Sets

Using Applied Biosystems Primer Express software, two optimal primer/probe sets for TaqMan quantitative PCR analysis were designed using the haLIMP-2 open reading frame sequence. The primers and probes were ordered from Integrated DNA Technologies.

Experimental Conditions

Optimal siRNA transfection conditions were initially determined for a stable recombinant human β-GC expressing CHO cell line using Lipofectamine™ 2000 (Invitrogen) and the BLOCK-iT™ fluorescent oligo (Invitrogen). Also, both TaqMan primer/probe sets successfully detected haLIMP-2 in cDNA samples from the cell line and one primer/probe set was chosen for use in all subsequent work.

All optimization experiments were done in 6-well plates. For each transfection, the CHO cell line was seeded at 3.0× $10^5$ cells/well in MEMα+GlutaMAX™-I medium with ribonucleosides and deoxyribonucleosides (Invitrogen) containing 10% fetal bovine serum (Invitrogen) and incubated overnight at 37° C., 5% CO2. Cells were transfected the next day, when they were approximately 30% confluent. The siRNA and the Lipofectamine™ 2000 were each diluted in OptiMem® medium (Invitrogen) then mixed and added to the cells. Within the scope of three experiments, siRNA transfection conditions were optimized for haLIMP-2 knockdown:

1) siRNA duplex concentrations of 50, 100, and 200 pmol per 2 ml medium (per well) were compared, keeping Lipofectamine™ 2000 concentration constant (7.5 ul per 2 ml medium) and assessing knockdown efficiency through 48 hours post-transfection;

2) Lipofectamine™ 2000 concentrations of 2.5, 5.0, and 7.5 ul per 2 ml medium were compared, keeping siRNA concentration constant (100 pmol) and assessing knockdown efficiency through 48 hours post-transfection 3) siRNA concentrations of 100 and 200 pmol per 2 ml medium were compared, keeping Lipofectamine™ 2000 concentration constant (7.5 ul per 2 ml medium) and assessing knockdown through 96 hours post-transfection (without a 24 hour time point).

In a particular embodiment, the conditions were 200 pmol siRNA and 7.5 ul Lipofectamine™ 2000 per 2 ml medium (per well of 6-well plate).

haLIMP-2 RNA Knockdown Results

To determine the degree of haLIMP-2 knockdown in the rhGC cell line, cells from an individual well of 6-well plate or from an individual T25 flask were harvested at 24, 48, 72, and/or 96 hours post-transfection (each time point from an individual well of 6-well plate). For T25 transfections, all conditions (cell number, medium volume, siRNA concentration, and lipid concentration) were scaled according to the increase in surface area from the 6-well plate experiments, and as noted previously, cells were approximately 30% confluent at the time of transfection. Two control conditions were also consistently done: 1) cells that were transfected with a non-specific siRNA (designed from huLIMP-2 3'UTR sequence that is not contained in the mouse, rat, and presumably, hamster sequence) and 2) untransfected cells. In one experiment, a lipid only control was also included (Lipofectamine™ 2000 diluted in OptiMem®). Total RNA was isolated from harvested cells using the illustra RNA Spin Mini kit (GE Healthcare), and cDNA was prepared from the RNA using the Ready-To-Go™ You-Prime First Strand Beads kit (Amersham). The cDNA samples were analyzed by TaqMan in two separate plates, one using the haLIMP-2 primers and probe to determine the LIMP-2 RNA level in each sample, and the other using elongation factor 1 (EF1) primers and probe to determine the RNA level of an internal standard. To illustrate the degree of knockdown obtained with siRNA treatment, the haLIMP-2 value was normalized to the EF1 value in each sample and the normalized values were graphed as a percentage of the untransfected control sample values.

Figure 20:
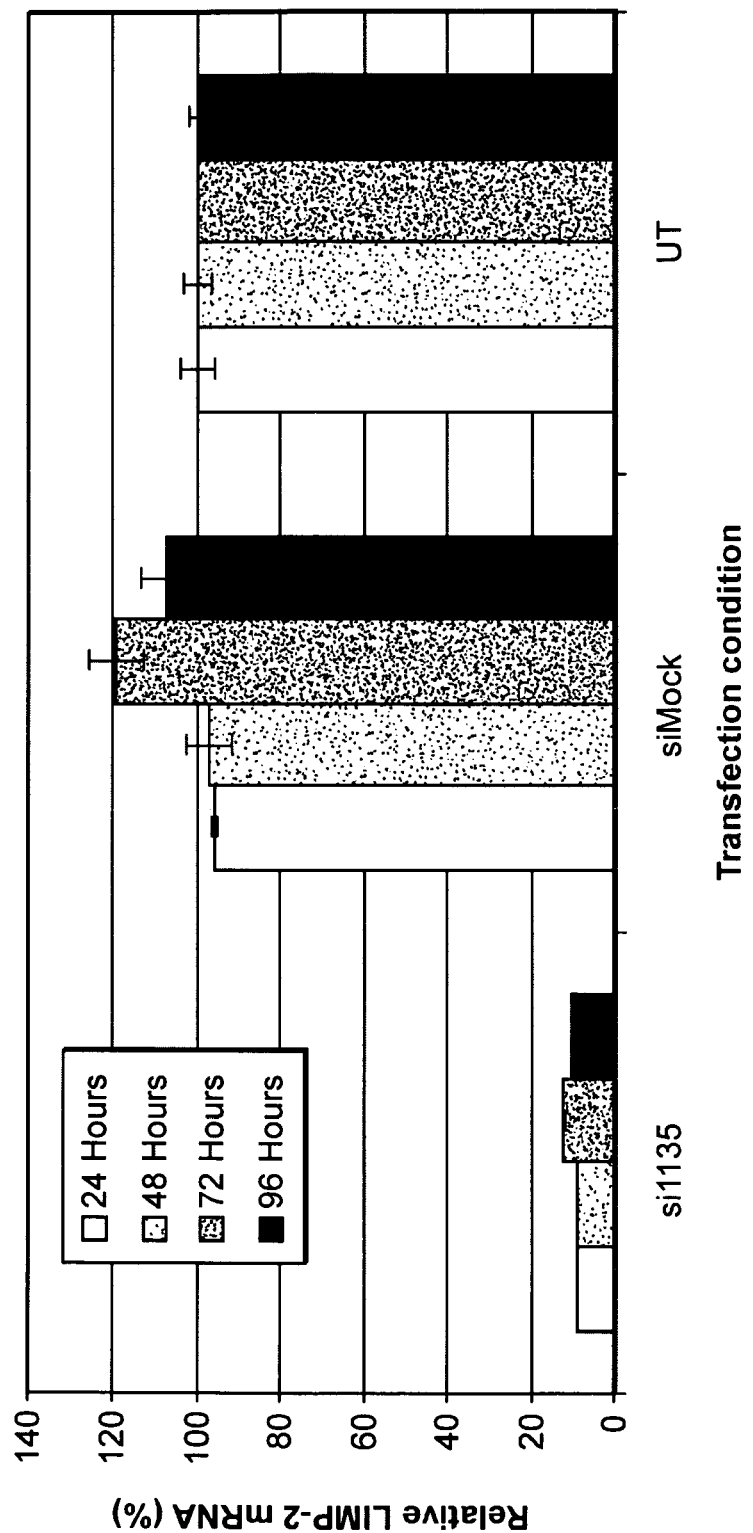
FIG. 20 is a graph showing the results of hamster LIMP-2 RNA knockdown in a stable recombinant human β-GC expressing CHO cell line, referred to herein as rhGC cells. rhGC cells in T25 flasks were transfected with the siRNA duplex specified on the x-axis, either a hamster LIMP-2 specific siRNA ("si1135") or a non-specific siRNA ("siMock"). Results for untransfected cells ("UT") are also shown. For each indicated time point post-transfection, the relative level of hamster LIMP-2 RNA (normalized to EF1 RNA for each sample) is shown as a percent of that in the untransfected samples. RNA levels were determined by quantitative PCR, and each bar shows the average of duplicate samples.
Figure 21A:
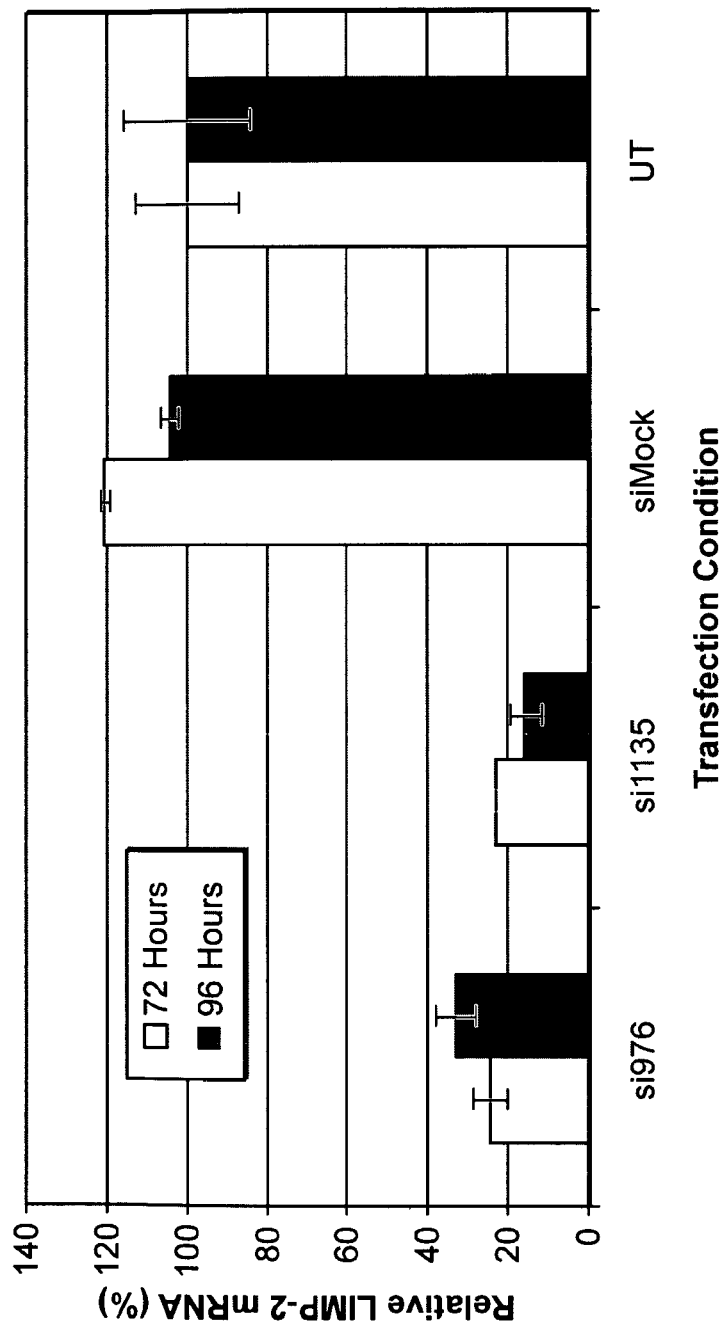
FIGS. 21A and 21B are graphs of the results of hamster LIMP-2 RNA knockdown in the rhGC cells.
Figure 21B:
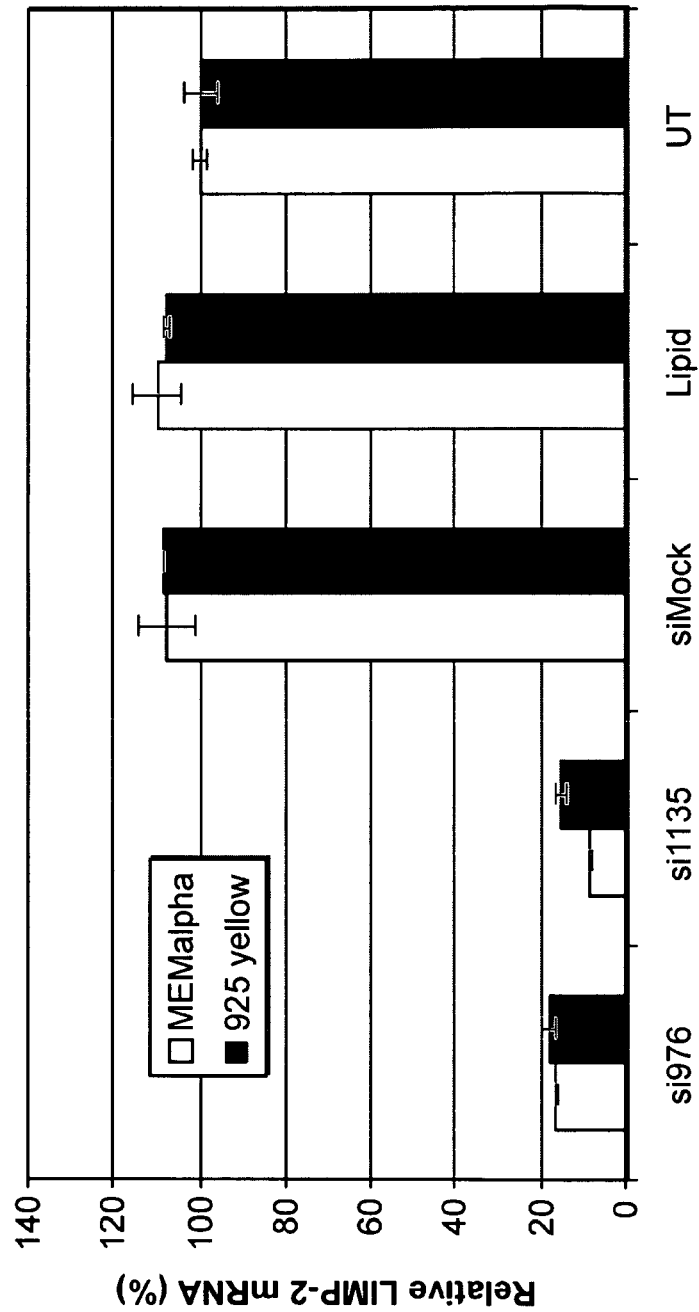

All five siRNAs resulted in haLIMP-2 RNA knockdown, ranging from approximately 60-80% knockdown. The most effective siRNAs were si976 and si1135, which reproducibly resulted in approximately ≥80% knockdown of haLIMP-2 RNA in an rhGC cell line. Results (FIGS. 20 and 21A-21B) demonstrate stable knockdown of LIMP-2 RNA levels through 96 hours post-transfection. Each transfection was done in duplicate and results are shown as the averages of the duplicate samples. "siMock" samples were transfected with the non-specific siRNA noted above, "UT" samples were untransfected cells, and "Lipid" samples were treated with lipid only as noted above. FIG. 21B demonstrates consistent LIMP-2 RNA knockdown after cells had completed a 24 hour conditioning period in serum-free media, where RNA was harvested from all samples 24 hours after cells had reached 80% confluence (such that RNA harvests were done at 96 hours post-transfection for all treated cells and at 72 hours for untransfected cells).

Results

GC Production Levels from LIMP-2 siRNA Treated rhGC Cells

Figure 22A:
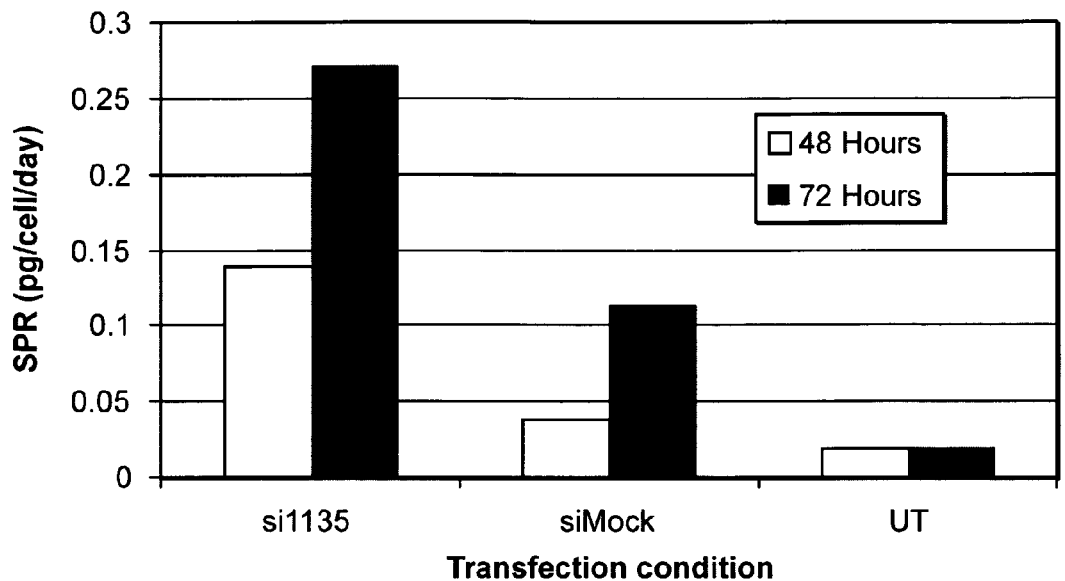
FIGS. 22A-22C are graphs of the results of rhGC specific production rates (SPRs) for the rhGC cells (in T25 flasks) that had been transfected as indicated on the x-axes of the graphs. For each sample, the cell culture was assessed for GC activity and the resulting values were normalized to total cell number. The cell culture was assessed over a 24 hour period beginning at either 48 or 72 hours port-transfection (FIG. 22A). Cell culture was assessed over a period of 24 hours beginning when the culture was at 80% confluence (FIG. 22B and FIG. 22C).
Figure 22B:
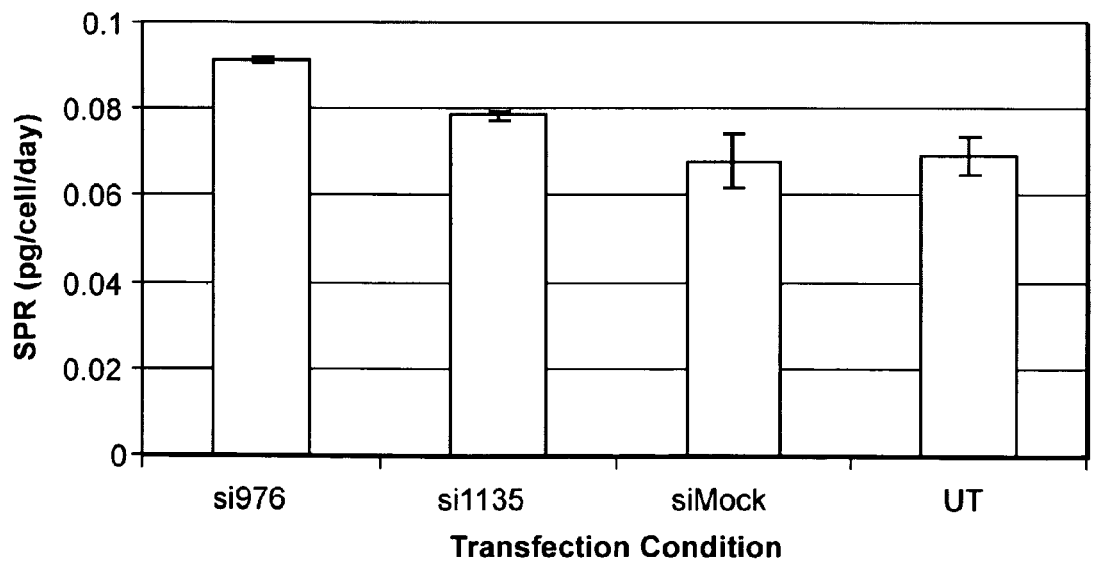
Figure 22C:
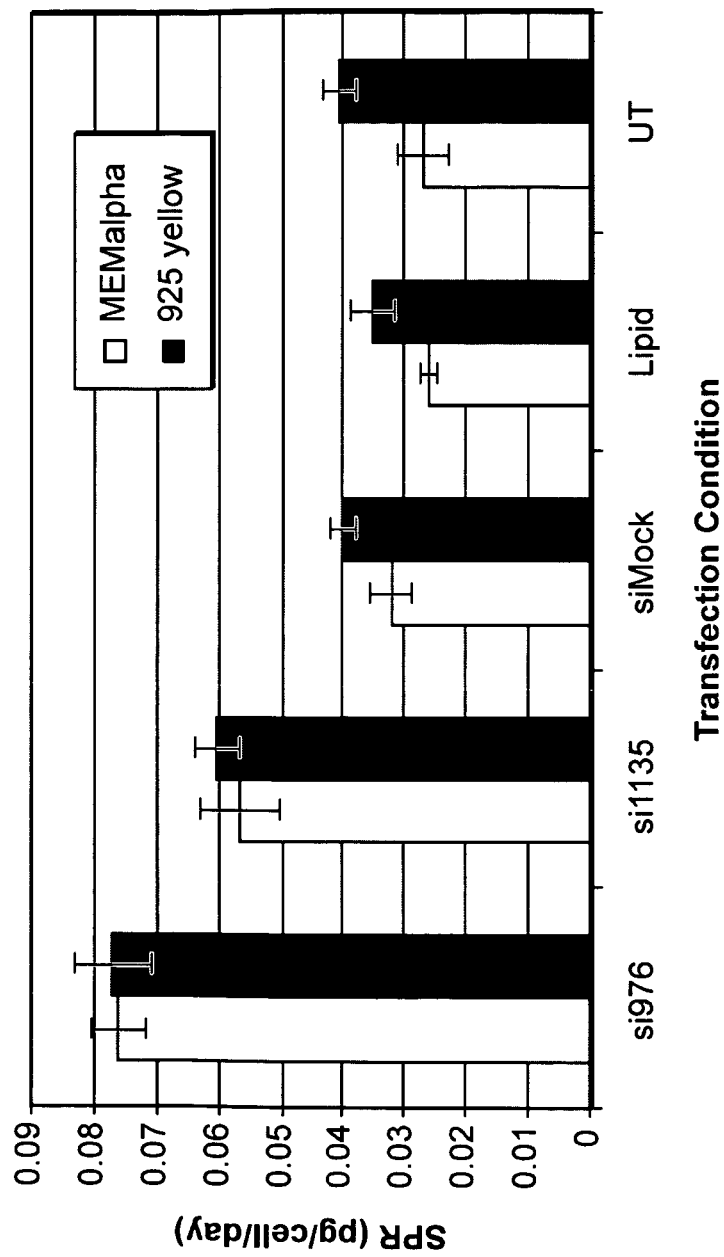
Figures 24A, 24B:
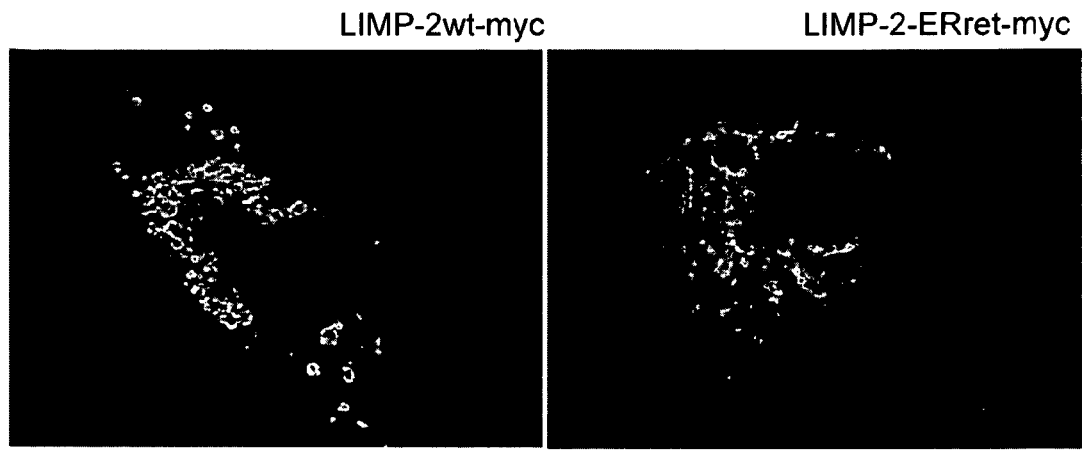
Figures 24C, 24D:
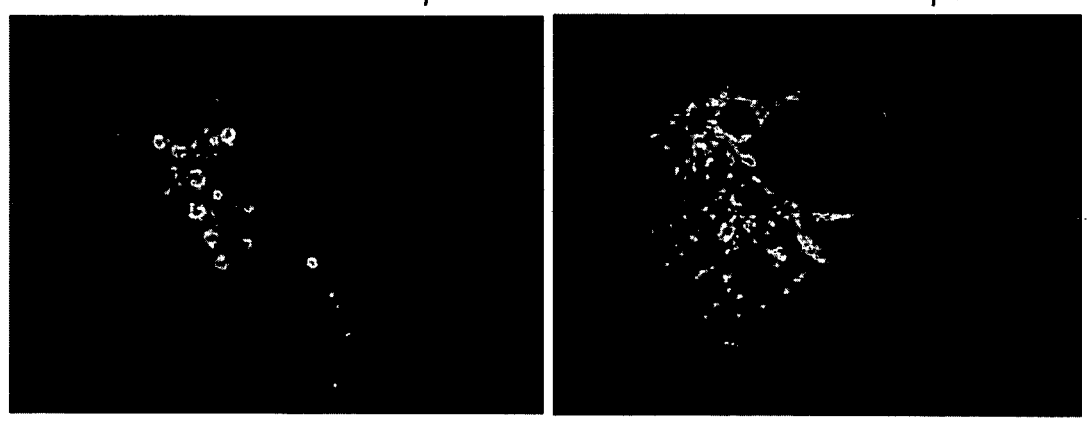
Figures 24E, 24F:
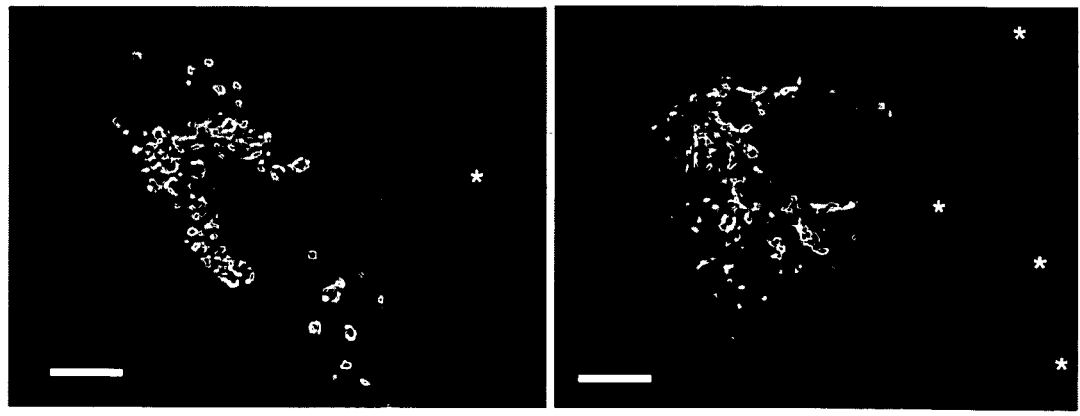

To assess GC production levels of the haLIMP-2 siRNA transfected rhGC cells and control cells, cells in T25 flasks were incubated in serum-free conditioning medium for 24 hours. Briefly, at a designated time point post-transfection (detailed below), growth medium was removed, cells were rinsed twice with phosphate buffered saline (PBS), and 1.5 ml serum-free conditioning medium was added to the cells. Cells were incubated for 24 hours at 37° C., 7.5% $CO_2$. GC activity levels in the conditioned media harvests were determined by a 4MU-βGlc activity assay (Marshall et al., 2002). Each resulting GC value was normalized to total cell number at the time of media harvest to calculate the specific production rate (SPR) for GC from each sample. FIGS. 22A-22C are graphs of the rhGC SPRs.

For FIG. 22A, as indicated above, cells were swapped into serum-free media (either 48 or 72 hours post transfection) and incubated for 24 hours, then assayed. In this experiment, the LIMP-2 siRNA treated samples ("si1135") showed a 2.5- to 3-fold increase in GC SPRs over the corresponding mock samples.

For FIG. 22B, as indicated above, cells were swapped into serum-free media when cells had reached 80% confluence, then incubated for 24 hours, then assayed. In this experiment, the LIMP-2 siRNA treated samples ("si976" and "si1135") showed a 1.2- to 1.3-fold increase in GC SPRs over the mock samples.

For FIG. 22C, as indicated above, cells were swapped into serum-free media when cells had reached 80% confluence, then incubated for 24 hours, then assayed. In this experiment, the cells were also harvested for RNA analysis at the end of the 24 hour incubation (the corresponding LIMP-2 RNA knockdown results are shown in FIG. 21B). In these experiments, the LIMP-2 RNA knockdown samples ("si976" and "si1135") showed a 1.8- to 2.4-fold increase in GC SPRs over the mock samples, and the LIMP-2 knockdown samples showed a 1.5- to 1.9-fold increase in GC SPRs over the mock samples, respectively.

REFERENCES

Aerts, J. M., Schram, A. W., Strijland, A., van Weely, S., Jonsson, L. M., Tager, J. M., Sorrell, S. H., Ginns, E. I., Barranger, J. A., and Murray, G. J. (1988). Glucocerebrosidase, a lysosomal enzyme that does not undergo oligosaccharide phosphorylation. Biochim Biophys Acta 964, 303-308.

Ahn, K., Yeyeodu, S., Collette, J., Madden, V., Arthur, J., Li, L., and Erickson, A. H. (2002). An alternate targeting pathway for procathepsin L in mouse fibroblasts. Traffic 3, 147-159.

Asch, A. S., Barnwell, J., Silverstein, R. L., and Nachman, R. L. (1987). Isolation of the thrombospondin membrane receptor. J Clin Invest 79, 1054-1061.

Beutler, E. (1991). Gaucher's disease. N Engl J Med 325, 1354-1360.

Beutler, E. (2006). Gaucher disease: multiple lessons from a single gene disorder. Acta Paediatr Suppl 95, 103-109.

Beutler, E., and Kuhl, W. (1986). Glucocerebrosidase processing in normal fibroblasts and in fibroblasts from patients with type I, type II, and type III Gaucher disease. Proc Natl Acad Sci USA 83, 7472-7474.

Brady, R. O., Kanfer, J. N., and Shapiro, D. (1965). Metabolism of Glucocerebrosides. Ii. Evidence of an Enzymatic Deficiency in Gaucher's Disease. Biochem Biophys Res Commun 18, 221-225.

Crombie, R., and Silverstein, R. (1998). Lysosomal integral membrane protein II binds thrombospondin-1. Structure-function homology with the cell adhesion molecule CD36 defines a conserved recognition motif. J Biol Chem 273, 4855-4863.

Dittmer, F. D., Ulbrich, E. J., Hafner, A., Schmahl, W., Meister, T., Pohlmann, R., and von Figura, K. (1999). Alternative mechanisms for trafficking of lysosomal enzymes in mannose 6-phosphate receptor-deficient mice are cell type-specific. J Cell Sci 112, 1591-1597.

Febbraio, M., Hajjar, D. P., and Silverstein, R. L. (2001). CD36: a class B scavenger receptor involved in angiogenesis, atherosclerosis, inflammation, and lipid metabolism. J Clin Invest 108, 785-791.

Franc, N. C., Dimarcq, J. L., Lagueux, M., Hoffmann, J., and Ezekowitz, R. A. (1996). Croquemort, a novel *Drosophila* hemocyte/macrophage receptor that recognizes apoptotic cells. Immunity 4, 431-443.

Fujita, H., Ezaki, J., Noguchi, Y., Kono, A., Himeno, M., and Kato, K. (1991). Isolation and sequencing of a cDNA clone encoding 85 kDa sialoglycoprotein in rat liver lysosomal membranes. Biochem Biophys Res Commun 178, 444-452.

Fujita, H., Saeki, M., Yasunaga, K., Ueda, T., Imoto, T., and Himeno, M. (1999). In vitro binding study of adaptor protein complex (AP-1) to lysosomal targeting motif (L1-motif). Biochem Biophys Res Commun 255, 54-58.

Gamp, A., Tanaka, Y., Lullmann-Rauch, R., Wittke, D., D'Hooge, R., De Deyn, P., Moser, T., Maier, H., Hartmann, D., Reiss, K., et al. (2003). LIMP-2/LGP85 deficiency causes ureteric pelvic junction obstruction, deafness and peripheral neuropathy in mice. Hum Mol Genet. 12, 631-646.

Ge, Y., and Elghetany, M. T. (2005). CD36: a multiligand molecule. Lab Hematol 11, 31-37.

Ginsel, L. A., and Fransen, J. A. (1991). Mannose 6-phosphate receptor independent targeting of lysosomal enzymes (a mini-review). Cell Biol Int Rep 15, 1167-1173.

Glickman, J. N., and Kornfeld, S. (1993). Mannose 6-phosphate-independent targeting of lysosomal enzymes in I-cell disease B lymphoblasts. J Cell Biol 123, 99-108.

Honing, S., Sandoval, I. V., and von Figura, K. (1998). A di-leucine-based motif in the cytoplasmic tail of LIMP-II and tyrosinase mediates selective binding of AP-3. Embo J 17, 1304-1314.

Huynh, K. K., Eskelinen, E. L., Scott, C. C., Malevanets, A., Saftig, P., and Grinstein, S. (2007). LAMP proteins are required for fusion of lysosomes with phagosomes. Embo J 26, 313-324.

Imai, K. (1988). A macrophage receptor for liver lysosomal beta-glucosidase. Cell Struct Funct 13, 325-332.

Knipper, M., Claussen, C., Ruttiger, L., Zimmermann, U., Lullmann-Rauch, R., Eskelinen, E. L., Schroder, J., Schwake, M., and Saftig, P. (2006). Deafness in LIMP2-deficient mice due to early loss of the potassium channel KCNQ1/KCNE1 in marginal cells of the stria vascularis. J Physiol 576, 73-86.

Kornfeld, S. (1986). Trafficking of lysosomal enzymes in normal and disease states. J Clin Invest 77, 1-6.

Kornfeld, S. (0992). Structure and function of the mannose 6-phosphate/insulinlike growth factor II receptors. Annu Rev Biochem 61, 307-330. Kornfeld, S., and Mellman, I. (1989). The biogenesis of lysosomes. Annu Rev Cell Biol 5, 483-525.

Kornfeld, S., and Sly, W. S. (1985). Lysosomal storage defects. Hosp Pract (Off Ed) 20, 71-75, 78-82.

Krieger, M. (2001). Scavenger receptor class B type I is a multiligand HDL receptor that influences diverse physiologic systems. J Clin Invest 108, 793-797.

Kuronita, T., Eskelinen, E. L., Fujita, H., Saftig, P., Himeno, M., and Tanaka, Y. (2002). A role for the lysosomal membrane protein LGP85 in the biogenesis and maintenance of endosomal and lysosomal morphology. J Cell Sci 115, 4117-4131.

Kuronita, T., Hatano, T., Furuyama, A., Hirota, Y., Masuyama, N., Saftig, P., Himeno, M., Fujita, H., and Tanaka, Y. (2005). The NH(2)-terminal transmembrane and lumenal domains of LGP85 are needed for the formation of enlarged endosomes/lysosomes. Traffic 6, 895-906.

Le Borgne, R., Alconada, A., Bauer, U., and Hoflack, B. (1998). The mammalian AP-3 adaptor-like complex mediates the intracellular transport of lysosomal membrane glycoproteins. J Biol Chem 273, 29451-29461.

Leonova, T., and Grabowski, G. A. (2000). Fate and sorting of acid beta-glucosidase in transgenic mammalian cells. Mol Genet Metab 70, 281-294.

Liou, B., Kazimierczuk, A., Zhang, M., Scott, C. R., Hegde, R. S., and Grabowski, G. A. (2006). Analyses of variant acid beta-glucosidases: effects of Gaucher disease mutations. J Biol Chem 281, 4242-4253.

Ludwig, T., Le Borgne, R., and Hoflack, B. (1995). Roles for mannose-6-phosphate receptors in lysosomal enzyme sorting, IGF-II binding and clathrin-coat assembly. Trends Cell Biol 5, 202-206.

Maeda, H., Akasaki, K., Yoshimine, Y., Akamine, A., and Yamamoto, K. (1999). Limited and selective localization of the lysosomal membrane glycoproteins LGP85 and LGP96 in rat osteoclasts. Histochem Cell Biol 111, 245-251.

Marshall, J., McEachern, K. A., Kyros, J. A., Nietupski, J. B., Budzinski, T., Ziegler, R. J., Yew, N. S., Sullivan, J., A., S., van Rooijen, N., et al. (2002). Demonstration of feasibility of in vivo gene therapy for Gaucher disease using a chemically induced mouse model. Mol Ther 6, 179-189.

Murao, K., Terpstra, V., Green, S. R., Kondratenko, N., Steinberg, D., and Quehenberger, O. (1997). Characterization of CLA-1, a human homologue of rodent scavenger receptor BI, as a receptor for high density lipoprotein and apoptotic thymocytes. J Biol Chem 272, 17551-17557.

Neufeld, E. F. (1991). Lysosomal storage diseases. Annu Rev Biochem 60, 257-280.

Nilsson, O., Grabowski, G. A., Ludman, M. D., Desnick, R. J., and Svennerholm, L. (1985). Glycosphingolipid studies of visceral tissues and brain from type 1 Gaucher disease variants. Clin Genet. 27, 443-450.

Nilsson, O., and Svennerholm, L. (1982). Accumulation of glucosylceramide and glucosylsphingosine (psychosine) in cerebrum and cerebellum in infantile and juvenile Gaucher disease. J Neurochem 39, 709-718.

Ogata, S., and Fukuda, M. (1994). Lysosomal targeting of Limp II membrane glycoprotein requires a novel Leu-Ile motif at a particular position in its cytoplasmic tail. J Biol Chem 269, 5210-5217.

Okazaki, I., Himeno, M., Ezaki, J., Ishikawa, T., and Kato, K. (1992). Purification and characterization of an 85 kDa sialoglycoprotein in rat liver lysosomal membranes. J Biochem (Tokyo) 111, 763-769.

Reczek, D., Berryman, M., and Bretscher, A. (1997). Identification of EBP50: A PDZ-containing phosphoprotein that associates with members of the ezrin-radixin-moesin family. J Cell Biol 139, 169-179.

Rezaie, A. R., Fiore, M. M., Neuenschwander, P. F., Esmon, C. T., and Morrissey, J. H. (1992). Expression and purification of a soluble tissue factor fusion protein with an epitope for an unusual calcium-dependent antibody. Protein Expr Purif 3, 453-460.

Rijnboutt, S., Aerts, H. M., Geuze, H. J., Tager, J. M., and Strous, G. J. (1991). Mannose 6-phosphate-independent membrane association of cathepsin D, glucocerebrosidase, and sphingolipid-activating protein in HepG2 cells. J Biol Chem 266, 4862-4868.

Sandoval, I. V., Arredondo, J. J., Alcalde, J., Gonzalez Noriega, A., Vandekerckhove, J., Jimenez, M. A., and Rico, M. (1994). The residues Leu(Ile)475-Ile(Leu, Val, Ala) 476, contained in the extended carboxyl cytoplasmic tail, are critical for targeting of the resident lysosomal membrane protein LIMP II to lysosomes. J Biol Chem 269, 6622-6631.

Sasagasako, N., Kobayashi, T., Yamaguchi, Y., Shinnoh, N., and Goto, I. (1994). Glucosylceramide and glucosylsphingosine metabolism in cultured fibroblasts deficient in acid beta-glucosidase activity. J Biochem (Tokyo) 115, 113-119.

Sawkar, A., Schmitz, M., Zimmer, K. P., Reczek, D., Edmunds, D., Balch, T., and Kelly, J. (2006). Chemical Chaperones and Permissive Temperatures Alter Localization of Gaucher Disease Associated Glucocerebrosidase Variants. ACS Chem Biol 1, 235-251.

Schueler, U. H., Kolter, T., Kaneski, C. R., Zirzow, G. C., Sandhoff, K., and Brady, R. O. (2004). Correlation between enzyme activity and substrate storage in a cell culture model system for Gaucher disease. J Inherit Metab Dis 27, 649-658.

Sidransky, E. (2004). Gaucher disease: complexity in a "simple" disorder. Mol Genet Metab 83, 6-15.

Suarez-Quian, C. A. (1987). The distribution of four lysosomal integral membrane proteins (LIMPs) in rat basophilic leukemia cells. Tissue Cell 19, 495-504.

Suarez-Quian, C. A. (1988). Differential cell surface expression of four lysosomal integral membrane proteins (LIMPs) in normal rat kidney cells. Tissue Cell 20, 35-46.

Tabuchi, N., Akasaki, K., and Tsuji, H. (2002). Ile (476), a constituent of di-leucine-based motif of a major lysosomal membrane protein, LGP85/LIMP II, is important for its proper distribution in late endosomes and lysosomes. Biochem Biophys Res Commun 295, 149-156.

Tanaka, Y., Tanaka, R., and Himeno, M. (2000). Lysosomal cysteine protease, cathepsin H, is targeted to lysosomes by the mannose 6-phosphate-independent system in rat hepatocytes. Biol Pharm Bull 23, 805-809.

van Dongen, J. M., Willemsen, R., Ginns, E. I., Sips, H. J., Tager, J. M., Barranger, J. A., and Reuser, A. J. (1985). The subcellular localization of soluble and membrane-bound lysosomal enzymes in I-cell fibroblasts: a comparative immunocytochemical study. Eur J Cell Biol 39, 179-189.

Vega, M. A., Rodriguez, F., Segui, B., Cales, C., Alcalde, J., and Sandoval, I. V. (1991a). Targeting of lysosomal integral membrane protein LIMP II. The tyrosine-lacking carboxyl cytoplasmic tail of LIMP II is sufficient for direct targeting to lysosomes. J Biol Chem 266, 16269-16272.

Vega, M. A., Segui-Real, B., Garcia, J. A., Cales, C., Rodriguez, F., Vanderkerckhove, J., and Sandoval, I. V. (1991b). Cloning, sequencing, and expression of a cDNA encoding rat LIMP II, a novel 74-kDa lysosomal membrane protein related to the surface adhesion protein CD36. J Biol Chem 266, 16818-16824.

Zerangue, N., Jan, Y. N., and Jan, L. Y. (2000). An artificial tetramerization domain restores efficient assembly of functional Shaker channels lacking T1. Proc Natl Acad Sci USA 97, 3591-3595.

Zimmer, K. P., le Coutre, P., Aerts, H. M., Harzer, K., Fukuda, M., O'Brien, J. S., and Naim, H. Y. (1999). Intracellular transport of acid beta-glucosidase and lysosome-associated membrane proteins is affected in Gaucher's disease (G202R mutation). J Pathol 188, 407-414.

Gunther, W., Luchow, A., Cluzeaud, F., Vandewalle, A., and Jentsch, T. J. (1998). ClC-5, the chloride channel mutated in Dent's disease, colocalizes with the proton pump in endocytotically active kidney cells. Proc Natl Acad Sci USA 95, 8075-8080.

Pohlmann, R., Wendland, M., Boeker, C., and von Figura, K. (1995). The two mannose 6-phosphate receptors transport distinct complements of lysosomal proteins. J Biol Chem 270, 27311-27318.

Zerangue, N., Jan, Y. N., and Jan, L. Y. (2000). An artificial tetramerization domain restores efficient assembly of functional Shaker channels lacking T1. Proc Natl Acad Sci USA 97, 3591-3595.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing β-glucocerebrosidase or a β-glucocerebrosidase variant wherein the β-glucocerebrosidase variant is at least 90% identical to SEQ ID NO: 11 and has β-glucocerebrosidase activity, comprising culturing a lysosomal integral membrane protein II (LIMP-2) deficient cell which expresses β-glucocerebrosidase or the β-glucocerebrosidase variant under conditions in which β-glucocerebrosidase or the β-glucocerebrosidase variant is produced, thereby producing β-glucocerebrosidase or the β-glucocerebrosidase variant, wherein the β-glucocerebrosidase or β-glucocerebrosidase variant is secreted from the cell in increased amount compared to LIMP-2 positive cells.

2. The method of claim 1 wherein the β-glucocerebrosidase is human β-glucocerebrosidase.

3. The method of claim 1 wherein the LIMP-2 deficient cell is deficient in LIMP-2 expression, LIMP-2 activity or a combination thereof, compared to a control cell.

4. The method of claim 3 wherein the LIMP-2 deficient cell is a cell in which all or a portion of the nucleic acid encoding LIMP-2 has been degraded.

5. The method of claim 4 wherein the portion of the nucleic acid encodes a LIMP-2 lumenal domain or a portion thereof.

6. The method of claim 4 wherein the nucleic acid encodes an amino acid sequence comprising SEQ ID NO: 2.

7. The method of claim 1 wherein the LIMP-2 deficient cell comprises a mutated LIMP-2 polypeptide.

8. The method of claim 1 wherein the LIMP-2 deficient cell is an animal cell.

9. The method of claim 8 wherein the animal cell is selected from the group consisting of: a fibroblast and a macrophage.

10. The method of claim 8 wherein the LIMP-2 deficient cell is a Chinese Hamster Ovary (CHO) cell.

11. The method of claim 8 wherein the LIMP-2 deficient cell is a human cell.

12. The method of claim 1 further comprising isolating the β-glucocerebrosidase or β-glucocerebrosidase variant secreted from the cells.

13. A method of producing human β-glucocerebrosidase or a β-glucocerebrosidase variant wherein the human β-glucocerebrosidase variant is at least 90% identical to SEQ ID NO: 11 and has β-glucocerebrosidase activity, comprising culturing a lysosomal integral membrane protein II (LIMP-2) deficient Chinese Hamster Ovary (CHO) cell which expresses the β-glucocerebrosidase or the β-glucocerebrosidase variant under conditions in which the β-glucocerebrosidase or the β-glucocerebrosidase variant is secreted from the CHO cell, thereby producing human β-glucocerebrosidase or the β-glucocerebrosidase variant.

14. The method of claim 13 further comprising isolating the β-glucocerebrosidase or the β-glucocerebrosidase variant secreted from the cells.

* * * * *